(12) United States Patent
Evans et al.

(10) Patent No.: US 7,408,065 B2
(45) Date of Patent: Aug. 5, 2008

(54) P2X₇ RECEPTOR ANTAGONISTS AND THEIR USE

(75) Inventors: Richard Evans, Loughborough (GB); Christine Eyssade, Loughborough (GB); Rhonan Ford, Loughborough (GB); Barrie Martin, Loughborough (GB); Toby Thompson, Loughborough (GB); Paul Willis, Loughborough (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/558,898

(22) PCT Filed: Jun. 1, 2004

(86) PCT No.: PCT/SE2004/000836

§ 371 (c)(1),
(2), (4) Date: Nov. 30, 2005

(87) PCT Pub. No.: WO2004/106305

PCT Pub. Date: Dec. 9, 2004

(65) Prior Publication Data
US 2006/0293337 A1 Dec. 28, 2006

(30) Foreign Application Priority Data
Jun. 2, 2003 (GB) .................... 0312609.1
Jun. 10, 2003 (SE) .................... 0301700

(51) Int. Cl.
C07D 453/02 (2006.01)
C07D 217/00 (2006.01)
C07D 215/00 (2006.01)

(52) U.S. Cl. .......... 546/134; 546/139; 546/152

(58) Field of Classification Search .......... 546/134, 546/139, 152
See application file for complete search history.

(56) References Cited

U.S. PATENT DOCUMENTS

| 3,464,998 | A | 9/1969 | Krimmel |
| 3,471,491 | A | 10/1969 | Venkatachala et al. |
| 4,751,292 | A | 6/1988 | Fox |
| 5,804,588 | A | 9/1998 | Dyke et al. |
| 6,949,539 | B2 | 9/2005 | Alcaraz et al. |
| 7,129,246 | B2 | 10/2006 | Alcaraz et al. |
| 2001/0003121 | A1 | 6/2001 | Baxter et al. |
| 2004/0236109 | A1 | 11/2004 | Van Straten et al. |

FOREIGN PATENT DOCUMENTS

| BE | 650919 | A | 7/1964 |
| DE | 1943404 | A | 12/1970 |
| EP | 0002065 | A1 | 5/1979 |
| EP | 0501656 | B1 | 9/1992 |
| EP | 0867436 | A1 | 9/1998 |
| EP | 0940391 | B1 | 9/1999 |
| WO | WO 95/04720 | | 2/1995 |
| WO | WO 97/19926 | | 6/1997 |
| WO | WO 99/26927 | | 6/1999 |
| WO | WO 99/29660 | | 6/1999 |
| WO | WO 99/29661 | | 6/1999 |
| WO | WO 00/61569 | | 10/2000 |
| WO | WO 00/73283 | | 12/2000 |
| WO | WO/2001/037826 | * | 5/2001 |
| WO | WO 01/94338 | | 12/2001 |
| WO | WO/03/080579 A1 | * | 3/2003 |
| WO | WO 03/042190 | | 5/2003 |
| WO | WO03045313 | | 6/2003 |
| WO | WO 03/080579 A1 | | 10/2003 |
| WO | WO 03080579 A1 | * | 10/2003 |
| WO | WO 2004/106305 | | 12/2004 |
| WO | WO 2005/009968 | | 2/2005 |
| WO | WO 2006/059945 | | 6/2006 |

OTHER PUBLICATIONS

STN International, file CHEMCATS, Accession No. 2002:1977776, Jul. 9, 2002, BAS 1098675, "Cyclopropanecarboxamide, N-(2-methyl-5-quinolinyl)-", CAS Registry No. 333432-34-1.

STN International, file CHEMCATS, Accession No. Jan. 11, 2001, Cyclopropanecarboxamide, N-(2,6-dimethyl-5-quinolinyl)-(9CI)(CA Index Name), CAS Registry No. 313479-89-9

Modena et al., "Plant Growth Regulating Activities of 2-[2-(Arylamino)-2-oxoethyl]benzoic acids", *Il Farmaco* 48(4):567-572 (1993).

Sharma et al., "Studies on Fused β-Lactams: Synthesis & Antibacterial Activity of Some Pyridyl/Quinolyl-2-azetidinones", *Indian Journal of Chemistry* 27B:494-497 (1988).

Alcaraz et al., Preparation of Adamantane Derivatives as P2X7 Receptor Antagonists, CAS Accession No. 2001:904155.

(Continued)

*Primary Examiner*—D. Margaret Seaman
*Assistant Examiner*—Nizal S Chandrakumar
(74) *Attorney, Agent, or Firm*—Fish & Richardson P.C.

(57) ABSTRACT

The invention provides compounds of formula (IA), processes for their preparation, pharmaceutical compositions containing them, and their use in therapy.

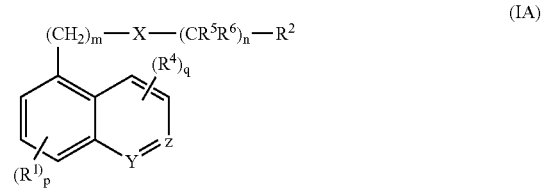

8 Claims, No Drawings

OTHER PUBLICATIONS

Alcaraz et al., "Novel P2X7 Receptor Antagonists"*Bioorganic and Medicinal Chemistry Letters*, 13:4043-4046 (2003).

Baxter et al., "Hit-to-Lead Studies: The Discovery of Potent Adamantane Amide P2X7 Receptor Antagonists," *Bioorganic and Medicinal Chemistry Letters*, 13:4047-4050 (2003).

Bourrie et al., "SSR125329A, A High Affinity Receptor Ligand with Potent Anti-Inflammatory Properties," *Eur. J. of Pharm.*, 456:123-131 (2002).

Costakis et al., "Synthesis of Some Adamantane Derivatives of 2-Aminobenzothiazoles", *Journal of Medicinal Chemistry* 14(12):1222-1223 (1971).

Ferrari et al., "Extracellular ATP Triggers IL-1β Release by Activating the Purinergic P2Z Receptor of Human Macrophages", *J. Immunol.* 159:1451-1458 (1997).

Ferrari et al., "Purinergic Modulation of Interleukin-1β Release from Microglial Cells Stimulated with Bacterial Endotoxin", *J. Exp. Med.* 185(3):579-582 (1997).

Henderson et al., "Inhibition of interleukin-1-induced synovitis and articular cartilage proteoglycan loss in the rabbit knee by recombinant human interleukin-1 receptor antagonist", *Cytokine* 3(3):246-249 (1991).

Ho et al., "Synthesis of a Peptidomimetic Tricyclic Tetrahydrobenzo[ij]quinoline as a VLA-4 Antagonist", *J. Org. Chem.* 65:6743-6748, p. 6745, scheme 5, (27) (2000).

Kadota et al., "Significance of IL-1β and IL-1 receptor antagonist (IL-1Ra) in bronchoalveolar lavage fluid (BALF) in patients with diffuse panbronchiolitis (DPB)", *Clin Exp. Immunol.* 103:461-466 (1996).

Khurana et al., "Clinical aspects of rheumatoid arthritis", Pathophysiology, vol. 12, Issue 3, Abstract (2005).

Kirkham, "Interleukin-1, Immune Activation Pathways, and Different Mechanisms in Osteoarthritis and Rheumatoid Arthritis", *Annals of the Rheumatic Diseases*, 50:395-400 (1991).

Li et al., "Should atherosclerosis be considered a cancer of the vascular wall?" *Medical Hypotheses*, 64:694-698 (2005).

Mackenzie et al., "Could rheumatoid arthritis have an infectious aetiology?" Drug Discovery Today: Disease Mechanism, vol. 2, Issue 3, Abstract (2005).

Otterness et al., "Possible Role of IL-1 in Arthritis: Effects of Prostaglandins in the Regulation of IL-1 Synthesis and Actions", Agent Act 39 (Suppl):109-120 (1993).

Richards et al., "Substituted 2-Phenyl-benzimidazole Derivatives: Novel Compounds that Suppress Key Markers of Allergy," Eur. J. of Medic. Chem., 41:950-969 (2006).

Sakito et al., "Interleukin 1β, Tumor Necrosis Factor Alpha, and Interleukin 8 in Bronchoalveolar Lavage Fluid of Patients with Diffuse Panbronchiolitis: A Potential Mechanism of Macrolide Therapy", *Respiration* 63:42-48 (1996).

STN International, File REGISTRY, see RN 405068-97-5, 405070-41-9, 405076-22-4, Apr. 14, 2002.

STN International, File REGISTRY, see RN 445032-09-7, Aug. 30, 2002.

STN International, File CHEMCATS, Accession No. 2001:48444, May 14, 2001, NS18552, 2-Quinolinecarboxamide, N-(tricycle[3.3.1.13,7]dec-1-ylmethyl), CAS Registry No. 313688-07-2.

STN International, File REGISTRY, see RN 401622-10-4, Mar., 24, 2002.

van den Berg, Lessons from animal models of osteoarthritis, *Curr. Opin. Rheumatol*, 13(5): 452-6 (2001).

Yu et al., "Inhibition of IL-1 Release from Human Monocytes and Suppression of Streptococcal Cell Wall and Adjuvant-induced Arthritis in Rats by an Extract of *Tripterygium wilfordii* Hook", *Gen. Pharmac.* 25(6):1115-1122 (1994).

Ayral-Kaloustian, Semiramis et al., "Preparation of 3-Hydroxycyclohexaneacetonitriles", *Journal of Organic Chemistry*, vol. 46, No. 24, (1981), pp. 4880-4885.

Biggs, D. F. et al., "Snythesis and Pharmacological Evaluation of Some ββ-Disubstituted Analogs of Acetylcholine", *Journal of Medicinal Chemistry*, vol. 15, No. 6, (1972), pp. 642-646.

Fülöp, Ferenc et al., "A Versatile Method For The Synthesis of *cis*-2-Aminoethylcyclanols", *Synthetic Communications*, vol. 28, No. 12, (1998), pp. 2303-2309.

Leonard, Nelson J. et al., "Small Charged Rings. II. The Synthesis of Aziridinium Salts", *Journal of the American Chemical Society*, vol. 84, (1962), pp. 4806-4813.

Picotin, Gerard et al., "Activation of Zinc by Trimethylchlorosilane: An Improved Procedure for the Preparation of β-Hydroxy Esters from Ethyl Bromoacetate and Aldehydes or Ketones (Reformatsky Reaction)", *Journal of Organic Chemistry*, vol. 52, (1987), pp. 4796-4798.

Whitehead, Calvert W. et al., "Diuretics. IV. 6-Chloro-3-substituted 7-Sulfamoyl-1,2,4-benzothiadiazine 1,1-Dioxides", *Journal of Organic Chemistry*, vol. 26, (1961), pp. 2809-2813.

STN International, File REGISTRY, Registry Copyright Jul. 14, 2006 ACS on STN RN: 892733-99-2, 1 page.

STN International, File REGISTRY, Registry Copyright Aug. 8, 2006 ACS on STN RN: 899526-58-0, 1 page.

* cited by examiner

P2X7 RECEPTOR ANTAGONISTS AND THEIR USE

CROSS-REFERENCE TO RELATED APPLICATIONS

This application is a national phase application under 35 U.S.C. § 371 of PCT International Application No. PCT/SE2004/000836, filed Jun. 1, 2004, which claims priority to Great Britain Application Serial No. 0312609.1, filed Jun. 2, 2003 and Swedish Application Serial No. 0301700-1, filed Jun. 10, 2003.

The present invention relates to certain heteroaryl amide derivatives, processes for their preparation, pharmaceutical compositions containing them, and their use in therapy.

The P2X$_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the P2X$_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis and L-selectin shedding (lymphocytes). P2X$_7$ receptors are also located on antigen-presenting cells (APC), keratinocytes, salivary acinar cells (parotid cells), hepatocytes and mesangial cells.

It would be desirable to make compounds effective as P2X$_7$ receptor antagonists for use in the treatment of inflammatory, immune or cardiovascular diseases, in the aetiologies of which the P2X$_7$ receptor may play a role.

The present invention provides a compound of formula (IA)

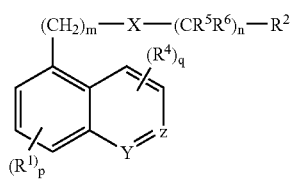

or a pharmaceutically acceptable salt, prodrug or solvate thereof, wherein p is 0, 1 or 2;

each $R^1$ independently represents halogen or $C_{1-6}$ alkyl optionally substituted by at least one substituent selected from hydroxyl, halogen and $C_{1-6}$ alkoxy;

q is 0, 1 or 2;

each $R^4$ independently represents halogen or $C_{1-6}$ alkyl optionally substituted by at least one substituent selected from hydroxyl, halogen and $C_{1-6}$ alkoxy;

m is 0, 1, 2 or 3;

X is —C(O)NH— or —NHC(O)—;

n is 0, 1, 2 or 3;

within each grouping $CR^5R^6$, $R^5$ and $R^6$ each independently represent hydrogen, $C_{1-6}$ alkyl or $R^5$ and $R^6$ together with the carbon atom to which they are both attached can form a 3- to 6-membered cycloalkyl ring;

$R^2$ represents a 4- to 9-membered cycloalkyl ring system, which cycloakyl ring system can be optionally substituted by at least one substituent independently selected from halogen, hydroxyl, —S(O)$_f$C$_{1-6}$alkyl, —NR$^7$R$^8$, —C(O)OR$^{12}$, —OC(O)R$^{13}$, —C(O)NR$^{14}$R$^{15}$, —SO$_2$NR$^{16}$R$^{17}$, —NR$^{18}$SO$_2$R$^{19}$, C$_{1-6}$ alkoxy, C$_{1-6}$ hydroxyalkyl or a C$_{1-6}$ alkyl group which C$_{1-6}$ alkyl group can be optionally substituted by at least one halogen; f is 0, 1 or 2;

one of Y or Z is nitrogen and the other is a group $CR^3$ wherein $R^3$ is a group of formula (IIA)

wherein $X^1$ represents an oxygen or sulphur atom, or a group >N—R$^{11}$ wherein R$^{11}$ is hydrogen or a C$_{1-5}$ alkyl group which can be optionally substituted by one or more substituents selected from hydroxy, halogen or C$_{1-6}$alkoxy; s is 0 or 1;

$R^9$ represents a bond or a C$_{1-5}$ alkylene group, which can be optionally substituted by at least one substituent selected from hydroxyl, halogen and C$_1$-C$_6$ alkoxy;

$R^{10}$ represents hydrogen, hydroxyl, carboxyl, —C(O)OR$^{20}$, —NR$^{21}$R$^{22}$, —C(O)NOH, or a group —WR$^{23}$;

or $R^{10}$ represents a 4- to 9-membered carbocyclic or heterocyclic ring, either of which may include bridging groups, which carbocyclic and heterocyclic ring can be optionally substituted by at least one substituent selected from halogen, hydroxyl, =O, carboxyl, cyano, C$_1$-C$_6$ alkyl, C$_1$-C$_6$ hydroxyalkyl, a group —W'R$^{24}$, —C(O)NOH, —(CH$_2$)$_t$NR$^{25}$R$^{26}$, —(CH$_2$)$_t$C(O)NR$^{27}$R$^{28}$, —(CH$_2$)$_t$R$^{29}$—(CH$_2$)$_t$NR$^{30}$C(O)R$^{31}$, —S(O)$_r$R$^{32}$, NR$^{33}$SO$_2$R$^{34}$, NR$^{35}$C(O)NR$^{36}$S(O)$_r$R$^{37}$, —S(O)$_r$(CH$_2$)$_t$NR$^{38}$R$^{39}$, —NR$^{40}$S(O)$_r$NR$^{41}$R$^{42}$, —S(O)$_r$(CH$_2$)$_t$C(O)OR$^{43}$, or -M(CH$_2$)$_t$C(O)OR$^{44}$ wherein M represents a bond, O, or a group >NR$^{45}$;

t is 0, 1, 2, 3, 4, 5 or 6;

r is 0, 1 or 2;

$R^{21}$ and $R^{22}$ are independently selected from hydrogen, C$_{2-7}$ alkenyl, C$_{1-6}$ alkylcarbonyl, —SO$_2$R$^{46}$, —C(O)NHSO$_2$R$^{47}$, a 3- to 8-membered carbocyclic or heterocyclic ring which carbocyclic or heterocyclic ring can be optionally substituted by at least one substituent selected from halogen, hydroxyl and carboxyl, or $R^{21}$ and $R^{22}$ may independently represent a C$_{1-7}$ alkyl group which C$_{1-7}$ alkyl group can be optionally substituted by at least one substituent independently selected from halogen, carboxyl, hydroxyl, —NH(CH$_2$)$_{2-4}$OH, C$_{1-6}$ alkoxy, C$_{1-6}$ alkylthio, C$_{1-6}$ alkoxycarbonyl, —NR$^{48}$R$^{49}$, —C(O)NR$^{50}$R$^{51}$, —NR$^{52}$COR$^{53}$, —NR$^{54}$SO$_2$$^{55}$ and —NR$^{67}$C(O)NR$^{68}$SO$_2$R$^{56}$;

W and W' independently represent a bond, O, S(O)$_p$, —NR$^{57}$C(O)—, —C(O)NR$^{58}$—, —SO$_2$NR$^{59}$, —NR$^{60}$SO$_2$—, >NR$^{61}$, C$_{1-6}$ alkylene, or a group —O(CH$_2$)$_{1-6}$—, —S(O)$_p$(CH$_2$)$_{1-6}$—, —NR$^{62}$(CH$_2$)$_{1-6}$—, —(CH$_2$)$_{1-3}$O(CH$_2$)$_{1-3}$—, —(CH$_2$)$_{1-3}$S(O)$_p$(CH$_2$)$_{1-3}$—, —$(CH_2)_{1-3}NR^{63}(CH_2)_{1-3}$—, —$(CH_2)_{1-3}NR^{64}C(O)(CH_2)_{0-3}$—, —$(CH_2)_{1-3}C(O)NR^{65}(CH_2)_{0-3}$—, or —$S(O)_p(CH_2)_{1-6}NR^{66}$—; p is 0, 1 or 2;

$R^{23}$ and $R^{24}$ independently represent a 3- to 10-membered carbocyclic or heterocyclic ring comprising from 1 to 5 heteroatoms independently selected from nitrogen, oxygen and sulphur, which carbocyclic or heterocyclic ring can be optionally substituted with at least one substituent selected from hydroxyl, =O, =S, nitro, cyano, amino, halogen, —$SO_2C_{1-6}$ alkyl, $C_{1-6}$ alkylcarbonyl, $C_{1-6}$ alkoxycarbonyl, $C_{1-6}$ alkylamino, di-$C_{1-6}$ alkylamino, and a $C_{1-6}$ alkyl group which $C_{1-6}$ alkyl group can be optionally substituted by at least one substituent selected from halogen and hydroxyl;

$R^7$, $R^8$, $R^{12}$, $R^{13}$, $R^{14}$, $R^{15}$, $R^{16}$, $R^{17}$, $R^{18}$ and $R^{19}$ each independently represent a hydrogen atom or $C_{1-6}$ alkyl group optionally substituted by at least one substituent selected from hydroxyl, halogen and $C_{1-6}$ alkoxy, or any of $R^7$ and $R^8$, $R^{14}$ and $R^{15}$, $R^{16}$ and $R^{17}$ together with the nitrogen atom to which they are both attached can form a 3- to 8-membered saturated heterocyclic ring;

$R^{20}$, $R^{34}$, $R^{37}$, $R^{46}$, $R^{47}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$ and $R^{68}$ each independently represent hydrogen or a $C_{1-6}$ alkyl group which can be optionally substituted by at least one substituent selected from halogen and hydroxyl;

$R^{25}$, $R^{26}$, $R^{27}$, $R^{28}$, $R^{30}$, $R^{31}$, $R^{32}$, $R^{33}$, $R^{35}$, $R^{36}$, $R^{38}$, $R^{39}$, $R^{40}$, $R^{41}$, $R^{42}$, $R^{43}$, $R^{44}$, $R^{45}$, $R^{48}$, $R^{49}$, $R^{50}$, $R^{51}$, $R^{52}$ and $R^{53}$ each independently represent a hydrogen atom or a $C_{1-6}$ alkyl, $C_{2-6}$ hydroxyalkyl or a $C_{3-8}$ cycloalkyl group, or any of $R^{25}$ and $R^{26}$, $R^{27}$ and $R^{28}$, $R^{38}$ and $R^{39}$, $R^{41}$ and $R^{42}$, $R^{48}$ and $R^{49}$, $R^{50}$ and $R^{51}$ together with the nitrogen atom to which they are both attached can form a 3- to 8-membered saturated heterocyclic ring; and $R^{29}$ is aryl.

Certain compounds of formula (IA) are capable of existing in stereoisomeric forms. It will be understood that the invention encompasses all geometric and optical isomers of the compounds of formula (IA) and mixtures thereof including racemates. Tautomers and mixtures thereof also form an aspect of the present invention.

As used herein, the term "halogen" includes fluorine, chlorine, bromine and iodine, and in particular is fluorine and chlorine. In the context of the present specification, unless otherwise indicated, an alkyl substituent or alkyl moiety in a substituent group may be linear or branched and may contain up to 10 carbon atoms. Examples of alkyl groups/moieties containing up to 7 carbon atoms include methyl, ethyl, n-propyl, isopropyl, n-butyl, isobutyl, tert-butyl, n-pentyl, n-hexyl and n-heptyl.

The term "cycloalkyl" refers to saturated alkyl rings, unless otherwise indicated containing from 3 to 9 and preferably from 4 to 7 carbon atoms. The term "heteroatom" includes oxygen, sulphur and nitrogen. The term "aryl" refers to aromatic groups such as phenyl or naphthyl, and in particular phenyl. "Carbocyclic" refers to saturated or unsaturated rings containing from 3 to 10 carbon atoms.

The expression "heterocyclic" includes saturated and unsaturated rings which unless otherwise indicated are of from 3 to 10 atoms, at least one of which is a heteroatom selected from oxygen, sulphur or nitrogen. The rings may be mono- or bicyclic, and saturated or unsaturated. Bicyclic rings may be fully or partially aromatic in character. Nitrogen heteroatoms will be substituted as necessary, and may also be in the form of N-oxides. Sulphur atoms may be in the form of S, S(O) or $S(O)_2$. In particular heterocyclic rings in compounds of formula (IA) and (IB) are saturated rings, such as piperidine, piperazine, pyrrolidine or homopiperidine.

A "hydroxyalkyl" substituent may contain one or more hydroxyl groups but preferably contains one hydroxyl group.

In formula (IA), each $R^1$ or $R^4$ independently represents halogen or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from hydroxyl, halogen (e.g. chlorine, fluorine, bromine or iodine) and $C_1$-$C_6$, preferably $C_1$-$C_4$, alkoxy (e.g. methoxy, ethoxy, n-propoxy or n-butoxy).

In an embodiment of the invention, in formula (IA) p is 0 or p is 1 and $R^1$ represents halogen, preferably chlorine, or $R^1$ represents methyl.

In an embodiment of the invention, in formula (IA) n is 1 or 2, preferably 1.

In an embodiment of the invention, in formula (IA) q is 0.

In an embodiment of the invention, in formula (IA) m is 1 or 0, preferably 0.

In formula (IA), within each grouping $CR^5R^6$, $R^5$ and $R^6$ each independently represent hydrogen, halogen (e.g. chlorine, fluorine, bromine or iodine) or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), or $R^5$ and $R^6$ together with the carbon atom to which they are both attached form a 3- to 6-membered cycloalkyl ring (e.g. cyclopropyl, cyclobutyl, cyclopentyl or cyclohexyl).

In an embodiment of the invention, in formula (IA) $R^5$ and $R^6$ each independently represent hydrogen, $C_1$-$C_4$ alkyl, preferably methyl, or $R^5$ and $R^6$ together with the carbon atom to which they are both attached form a cyclopropyl ring. Preferably each $R^5$ and $R^6$ is hydrogen.

In formula (IA), $R^2$ represents a 4- to 9-membered cycloalkyl ring system, which cycloakyl ring system can be optionally substituted by at least one substituent (e.g. one, two, three or four substituents independently) independently selected from halogen (e.g. chlorine, fluorine, bromine or iodine), hydroxyl, —$S(O)_fC_{1-6}$alkyl, —$NR^7R^8$, —C(O)OR$^{12}$, —OC(O)R$^{13}$, —C(O)NR$^{14}R^{15}$, —$SO_2NR^{16}R^{17}$, —NR$^{18}SO_2R^{19}$, $C_{1-6}$ alkoxy (e.g. methoxy, ethoxy, n-propoxy or n-butoxy), $C_{1-6}$ hydroxyalkyl (e.g. —$CH_2OH$, —$CH_2CH_2OH$, —$CH_2CH_2CH_2OH$ or —$CH(OH)CH_3$) or a $C_{1-6}$, preferably $C_{1-4}$, alkyl group (e.g. methyl, ethyl, n-propyl, isopropyl, n-butyl, isobutyl, tert-butyl, n-pentyl or n-hexyl) which $C_{1-6}$ alkyl group can be optionally substituted by at least one halogen (e.g. chlorine, fluorine, bromine or iodine); f is 0, 1 or 2.

In formula (IA), preferred 4- to 9-membered cycloalkyl ring systems $R^2$ include cyclobutyl, cyclopentyl, cyclohexyl, cycloheptyl and cyclooctyl.

In formula (IA), preferred substituents on the 4- to 9-membered cycloalkyl ring system $R^2$ include halogen, hydroxyl, —$S(O)_fC_{1-6}$alkyl and a $C_{1-6}$ alkyl group.

In formula (IA), examples of groups —$S(O)_fC_{1-6}$alkyl include methylthio, ethylthio, methylsulphinyl, ethylsulphinyl, methylsulphonyl and ethylsulphonyl.

In an embodiment of the invention, in formula (IA) $R^2$ represents a cyclopentyl or cyclohexyl ring optionally substituted with a $C_{1-4}$ alkyl group.

In formula (IA), one of Y or Z is nitrogen and the other is a group $CR^3$ wherein $R^3$ is a group of formula (IIA)

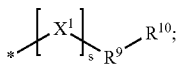 (IA)

wherein $X^1$ represents an oxygen or sulphur atom, or a group >N—$R^{11}$ wherein $R^{11}$ is hydrogen or a $C_{1-5}$, preferably $C_{1-4}$, alkyl group (e.g. methyl, ethyl, n-propyl, isopropyl, n-butyl, isobutyl, tert-butyl) which can be optionally substituted by one or more substituents (e.g. one, two, three or four substituents independently) selected from hydroxyl, halogen (e.g. chlorine, fluorine, bromine or iodine), or $C_{1-6}$, preferably $C_{1-4}$, alkoxy (e.g. methoxy, ethoxy, n-propoxy or n-butoxy); s is 0 or 1.

In an embodiment of the invention, in formula (IA) Y is nitrogen and Z is a group $CR^3$.

In formula (IIA), $R^9$ represents a bond or a $C_{1-5}$, preferably $C_{1-3}$, alkylene group (e.g. —$CH_2$—, —$CH_2CH_2$— or —$CH_2CH_2CH_2$—), which can be optionally substituted by at least one substituent (e.g. one, two, three or four substituents independently) selected from hydroxyl, halogen (e.g. chlorine, fluorine, bromine or iodine), or $C_{1-6}$, preferably $C_{1-4}$, alkoxy (e.g. methoxy, ethoxy, n-propoxy or n-butoxy).

In formula (IIA), $R^{10}$ represents hydrogen, hydroxyl, carboxyl, —C(O)$R^{20}$, —N$R^{21}R^{22}$, —C(O)NOH, or a group —W$R^{23}$;

or $R^{10}$ represents a 4- to 9-membered carbocyclic or heterocyclic ring, either of which may include bridging groups, which carbocyclic and heterocyclic ring can be optionally substituted by at least one substituent (e.g. one, two, three or four substituents independently) selected from halogen (e.g. chlorine, fluorine, bromine or iodine), hydroxyl, =O, carboxyl, cyano, $C_1$-$C_6$, preferably $C_{1-4}$, alkyl (e.g. methyl, ethyl, n-propyl, isopropyl, n-butyl, isobutyl, tert-butyl, n-pentyl), $C_{1-6}$, preferably $C_{1-4}$, hydroxyalkyl (e.g. —$CH_2OH$, —$CH_2CH_2OH$, —$CH_2CH_2CH_2OH$ or —CH(OH)$CH_3$), a group —W'$R^{24}$, —C(O)NOH, —$(CH_2)_tNR^{25}R^{26}$, —$(CH_2)_t$C(O)N$R^{27}R^{28}$, —$(CH_2)_tR^{29}$—$(CH_2)_tNR^{30}C(O)R^{31}$, —S(O)$_r$ $R^{32}$, —N$R^{33}SO_2R^{34}$, —N$R^{35}C(O)NR^{36}S(O)_rR^{37}$, —S(O)$_r(CH_2)_tNR^{38}R^{39}$, —N$R^{40}S(O)_rNR^{41}R^{42}$, —S(O)$_r(CH_2)_tC(O)OR^{43}$, or M$(CH_2)_tC(O)OR^{44}$ wherein M represents a bond, O, S(O)$_r$, or a group >N$R^{45}$.

In an embodiment of the invention, in formula (IIA) t is 0, 1 or 2, preferably 0.

In an embodiment of the invention, in formula (IIA) $R^9$ represents a $C_{1-5}$ alkylene group which can be optionally substituted by at least one hydroxyl; and $R^{10}$ represents hydrogen, hydroxyl, carboxyl, —C(O)$R^{20}$, —N$R^{21}R^{22}$, —C(O)NOH, or a group —W$R^{23}$.

In formula (IIA), when $R^{10}$ represents a 4- to 9-membered carbocyclic ring examples of preferred carbocyclic rings include cyclobutyl, cyclopentyl, cyclohexyl, most preferably cyclohexyl.

In formula (IIA), when $R^{10}$ represents a 4- to 9-membered heterocyclic ring, the heterocyclic ring preferably contains from 1 to 3, more preferably 1 to 2, heteroatoms selected from nitrogen, oxygen and sulphur, preferably nitrogen: examples of preferred heterocyclic rings $R^{10}$ in formula (IA) include pyrrolidinyl, piperidinyl, piperazinyl, homopiperazinyl and homopiperidinyl.

In formula (IIA), when $R^{10}$ represents a substituted 4-to 9-membered heterocyclic ring, examples of preferred substituents for the heterocyclic ring include hydroxyl, cyano, carboxyl, methyl, —$NH_2$, —$NHCH_3$, —$NHCH_2CH_2OH$, —$CH_2C(O)OH$, —$NHCH_2C(O)OH$, —$NHCH_2CH_2C(O)OH$, —$CH_2NHCH_3$, —$CH_2NHCH_2CH_2OH$, —$SO_2CH_2CH_2OH$, —$N(CH_2CH_2OH)C(O)OC(CH_3)_3$, —$NHSO_2CF_3$, —$NHC(O)NHSO_2CH_3$, tetrazolyl and groups of formula:

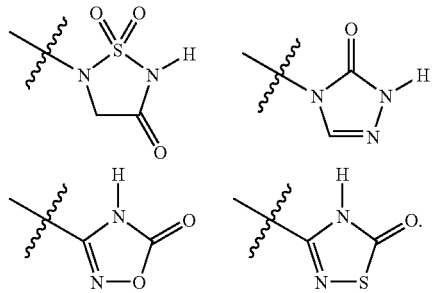

In an embodiment of the invention, in formula (IIA) s is 0; $R^9$ is a bond; and $R^{10}$ is an optionally substituted 4- to 9-membered carbocyclic or heterocyclic ring.

In an embodiment of the invention, when in formula (IIA) s is 0 and $R^9$ represents a bond, $R^{10}$ represents a pyrrolidinyl, piperidinyl, piperazinyl or homopiperidinyl group, which can be optionally substituted by at least one substituent selected from hydroxyl, cyano, carboxyl, methyl, —$NH_2$, —$NHCH_3$, —$NHCH_2CH_2OH$, —$CH_2C(O)OH$, —$NHCH_2C(O)OH$, —$NHCH_2CH_2C(O)OH$, —$CH_2NHCH_3$, —$CH_2NHCH_2CH_2OH$, —$SO_2CH_2CH_2OH$, —$N(CH_2CH_2OH)C(O)OC(CH_3)_3$, —$NHSO_2CF_3$, —$NHC(O)NHSO_2CH_3$.

In another embodiment of the invention, when in formula (IIA) s is 0 and $R^9$ represents a bond, $R^{10}$ represents a pyrrolidinyl, piperidinyl, piperazinyl or homopiperidinyl group, which can be optionally substituted by at least one substituent selected from tetrazolyl and groups of formula:

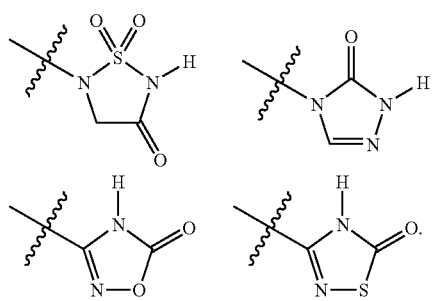

In formula (IIA), $R^{21}$ and $R^{22}$ are independently selected from hydrogen, $C_{2-7}$ alkenyl, $C_{1-6}$ alkylcarbonyl (e.g. methylcarbonyl or ethylcarbonyl), —$SO_2R^{46}$ (e.g. $SO_2CF_3$), —C(O)NHSO$_2R^{47}$ (e.g. —C(O)NHSO$_2CH_3$), a 3- to 8-membered carbocyclic or heterocyclic ring which carbocyclic or heterocyclic ring can be optionally substituted by at least one substituent (e.g. one, two, three or four substituents independently) selected from halogen, hydroxyl and carboxyl. When $R^{21}$ and/or $R^{22}$ represent a 3- to 8-membered heterocyclic ring, said ring preferably comprises from 1 to 3, more preferably 1 to 2, heretoatoms selected from nitrogen, oxygen and sulphur.

Alternatively, in formula (IIA) $R^{21}$ and $R^{22}$ may independently represent a $C_{1-7}$, preferably $C_{1-4}$ alkyl group (e.g. methyl, ethyl, n-propyl, isopropyl, n-butyl, isobutyl, tert-butyl, n-pentyl) which $C_{1-7}$ alkyl group can be optionally substituted by at least one substituent (e.g. one, two, three or four substituents independently) independently selected from halogen (e.g. chlorine, fluorine, bromine or iodine), carboxyl, hydroxyl, —NH(CH$_2$)$_{2-4}$OH, $C_{1-6}$, preferably $C_{1-4}$, alkoxy (e.g. methoxy, ethoxy, n-propoxy or n-butoxy), $C_{1-6}$ alkylthio (e.g. methylthio, ethylthio, n-propylthio or n-butylthio), $C_{1-6}$, preferably $C_{1-4}$, alkoxycarbonyl (e.g. methoxycarbonyl or ethoxycarbonyl), —NR$^{48}$R$^{49}$, —C(O)NR$^{50}$R$^{51}$, NR$^{52}$C(O)R$^{53}$, —NR$^{54}$SO$_2$R$^{55}$ and —NR$^{67}$C(O)NR$^{68}$SO$_2$R$^{56}$.

In an embodiment of the invention, in formula (IIA) when s is 1 and R$^9$ is a bond, R$^{10}$ is other than hydroxyl, carboxyl, —C(O)OR$^{20}$, —NR$^{21}$R$^{22}$, or C(O)NOH In formula (IIA) in the groups —WR$^{23}$ and —W'R$^{24}$, W and W' preferably independently represent a bond, O, S, SO, SO$_2$ or >NR$^{61}$, most preferably a bond.

In formula (IIA), R$^{23}$ and R$^{24}$ independently represent a 3- to 10-, preferably 5 to 6-membered carbocyclic or heterocyclic ring comprising from 1 to 5, preferably 2 to 4, heteroatoms independently selected from nitrogen, oxygen and sulphur, which carbocyclic or heterocyclic ring can be optionally substituted with at least one substituent (e.g. one, two or three substituents independently) selected from hydroxyl, =O, =S, nitro, cyano, amino, halogen (e.g. chlorine, fluorine bromine or iodine), —SO$_2$C$_{1-6}$ alkyl, C$_{1-6}$ alkylcarbonyl (e.g. methylcarbonyl or ethylcarbonyl), C$_{1-6}$ alkoxycarbonyl (e.g. methoxycarbonyl or ethyoxycarbonyl), C$_{1-6}$ alkylamino(e.g. methylamino or ethyl amino), di-C$_{1-6}$ alkylamino (e.g. dimethylamino) and a C$_{1-6}$ alkyl group (e.g. methyl, ethyl, n-propyl, isopropyl, n-butyl, isobutyl, tert-butyl, n-pentyl or n-hexyl) which C$_{1-6}$ alkyl group can be optionally substituted by at least one substituent (e.g. one, two or three substituents independently) selected from halogen (e.g. chlorine, fluorine bromine or iodine) and hydroxyl;

Examples of groups R$^{23}$ and R$^{24}$ that may be conveniently employed in the present invention in accordance with formula (IA) include:—
  (I) tetrazolyl;
  (II) a 5- to 6-membered carbocyclic or heterocyclic ring comprising from 1 to 4, preferably 1 to 3, heteroatoms selected from nitrogen, oxygen and sulphur, which carbocyclic or heterocyclic ring is substituted by at least one substituent (e.g. one, two or three substituents independently) selected from hydroxyl, =O, and =S and which carbocyclic or heterocyclic ring may further be optionally substituted by at least one substituent selected from halogen (e.g. chlorine, fluorine, bromine or iodine), nitro, cyano, —SO$_2$C$_{1-6}$ alkyl, C$_{1-6}$ alkylcarbonyl, C$_{1-6}$ alkoxycarbonyl, and a C$_{1-6}$, preferably C$_{1-4}$, alkyl group which C$_{1-6}$ alkyl group can be optionally substituted by at least one substituent (e.g. one, two or three substituents) selected from halogen (e.g. chlorine, fluorine, bromine or iodine), and hydroxyl;
  (III) a 1,2,3-triazolyl or 1,2,4 triazolyl group which triazolyl group can be optionally substituted by at least one substituent (e.g. one, two or three substituents) selected from halogen (e.g. chlorine, fluorine, bromine or iodine), nitro, cyano, —SO$_2$C$_{1-6}$ alkyl, C$_{1-6}$ alkylcarbonyl, C$_{1-6}$ alkoxycarbonyl and a C$_{1-6}$, preferably C$_{1-4}$, alkyl group which C$_{1-6}$ alkyl group can be optionally substituted by at least one substituent (e.g. one, two or three substituents) selected from halogen (e.g. chlorine, fluorine, bromine or iodine), and hydroxyl; and
  (IV) a phenyl group or a 5- to 6-membered unsaturated heterocyclic ring comprising from 1 to 2 nitrogen atoms, which phenyl group or heterocyclic ring is substituted by a group —NR$^{69}$SO$_2$NR$^{70}$R$^{71}$ or a group —SO$_2$R$^{72}$, wherein R$^{69}$, R$^{70}$, R$^{71}$ and R$^{72}$ each independently represent a hydrogen atom or a C$_{1-6}$, preferably C$_{1-4}$, alkyl group which C$_{1-6}$ alkyl group can be optionally substituted by at least one substituent (e.g. one, two or three substituents) selected from halogen (e.g. chlorine, fluorine, bromine or iodine), and hydroxyl.

When in formula (IIA) R$^{23}$ and/or R$^{24}$ represent a 5- to 6-membered heterocyclic ring substituted by at least one substituent selected hydroxyl, =O or =S, nitrogen heteroatoms in the heterocyclic ring may carry hydroxyl substituents and sulphur atoms in the heterocyclic ring may be in the form of S, S(O) (i.e. carrying one oxo substituent) or S(O)$_2$ (i.e. carrying two oxo substituents).

When in formula (IIA), R$^{23}$ and/or R$^{24}$ represent a 5 to 6-membered unsaturated heterocyclic ring comprising from 1 to 2 nitrogen atoms and substituted by a group —NR$^{69}$SO$_2$NR$^{70}$R$^{71}$ or a group —SO$_2$R$^{72}$, examples of preferred heterocyclic rings include pyridinyl, pyrimidinyl and imidazolyl.

In formula (IIA), examples of groups —R$^{23}$ and —R$^{24}$ include:

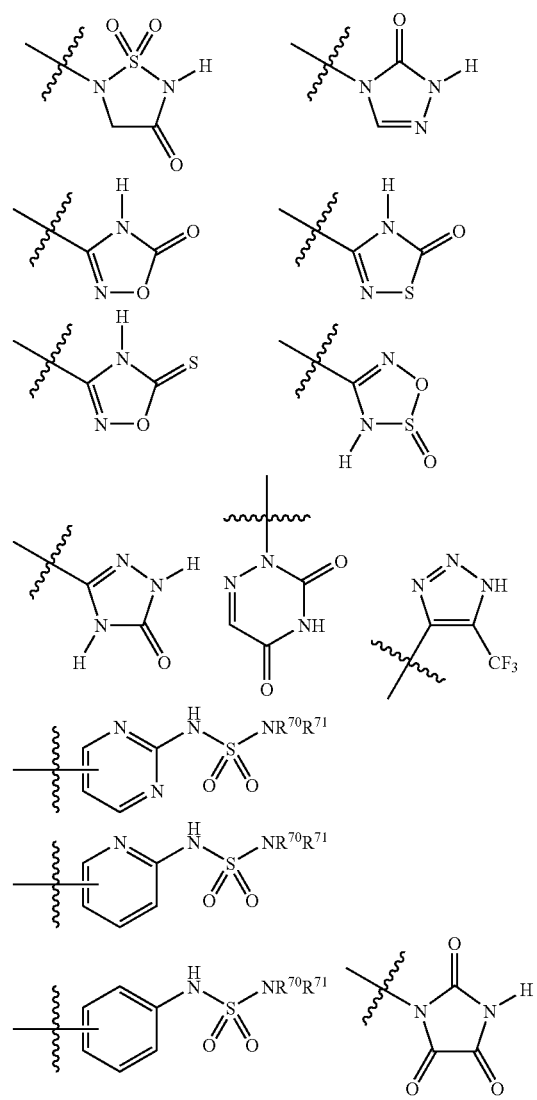

-continued

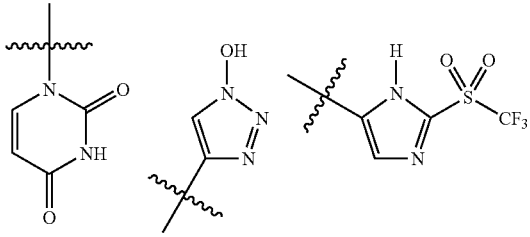

In an embodiment of the invention, in formula (IIA) $R^{10}$ represents —$WR^{23}$ or $R^{10}$ represents a 4- to 9-membered carbocyclic or heterocyclic ring, either of which may include bridging groups, which carbocyclic and heterocyclic ring is substituted by at least one substituent —$W'R^{24}$. In this embodiment W, W' $R^{23}$ and $R^{24}$ are as defined herein above.

In an embodiment of the invention, $R^{23}$ and $R^{24}$ are independently selected from tetrazolyl or a 5- to 6-membered carbocyclic or heterocyclic ring comprising from 1 to 3 heteroatoms selected from nitrogen, oxygen and sulphur, which carbocyclic or heterocyclic ring is substituted by at least one substituent selected from hydroxyl, =O, and =S. In a further aspect of this embodiment, W and W' represent a bond.

In formula (IA), $R^7$, $R^8$, $R^{12}$, $R^{13}$, $R^{14}$, $R^{15}$, $R^{16}$, $R^{17}$, $R^{18}$ and $R^{19}$ each independently represent a hydrogen atom or $C_{1-6}$, preferably $C_{1-4}$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents independently) selected from hydroxyl, halogen (e.g. chlorine, fluorine, bromine or iodine), and $C_{1-6}$, preferably $C_{1-4}$, alkoxy (e.g. methoxy, ethoxy, n-propoxy or n-butoxy), or any of $R^7$ and $R^8$, $R^{14}$ and $R^{15}$, $R^{16}$ and $R^{17}$ together with the nitrogen atom to which they are both attached can form a 3- to 8-membered saturated heterocyclic ring (e.g. a pyrollidine or piperazine ring).

In formula (IA), $R^{20}$, $R^{34}$, $R^{37}$, $R^{46}$, $R^{47}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$ and $R^{66}$ each independently represent hydrogen or a $C_{1-6}$, preferably $C_{1-4}$, alkyl (e.g. methyl, ethyl, n-propyl, isopropyl, n-butyl, isobutyl, tert-butyl, n-pentyl or n-hexyl) which can be optionally substituted by at least one substituent (e.g. one, two or three substituents independently) selected from halogen (e.g. chlorine, fluorine, bromine or iodine), and hydroxyl.

In formula (IA), $R^{25}$, $R^{26}$, $R^{27}$, $R^{28}$, $R^{30}$, $R^{31}$, $R^{32}$, $R^{33}$, $R^{35}$, $R^{36}$, $R^{38}$, $R^{39}$, $R^{40}$, $R^{41}$, $R^{42}$, $R^{43}$, $R^{44}$, $R^{45}$, $R^{48}$, $R^{49}$, $R^{50}$, $R^{51}$, $R^{52}$ and $R^{53}$ each independently represent a hydrogen atom or a $C_{1-6}$, preferably $C_{1-4}$, alkyl (e.g. methyl, ethyl, n-propyl, isopropyl, n-butyl, isobutyl, tert-butyl, n-pentyl), $C_{2-6}$, preferably $C_{1-4}$, hydroxyalkyl (e.g. —$CH_2CH_2OH$, —$CH_2CH_2CH_2OH$ or —$CH(OH)CH_3$), or a $C_{3-8}$, preferably $C_{4-6}$, cycloalkyl group (e.g. cyclobutyl, cyclopentyl and cyclohexyl), or any of $R^{25}$ and $R^{26}$, $R^{27}$ and $R^{28}$, $R^{38}$ and $R^{39}$, $R^{41}$ and $R^{42}$, $R^{48}$ and $R^{49}$, $R^{50}$ and $R^{51}$ together with the nitrogen atom to which they are both attached can form a 3- to 8-membered saturated heterocyclic ring (e.g. a pyrollidine or piperazine ring); $R^{29}$ is aryl (e.g. phenyl).

In formula (IIA), any hydroxyl groups will not normally be attached to a carbon atom adjacent a nitrogen atom. Further, when $R^9$ is other than a bond, the group $R^{10}$ may be attached to the $C_1$-$C_5$ alkyl moiety of $R^9$ at any suitable point; thus $R^{10}$ may be attached to an internal or terminal carbon atom of the $C_1$-$C_5$ alkyl moiety of $R^9$.

In a embodiment of the invention, there is provided a compound of formula (IA) or a pharmaceutically acceptable salt, prodrug or solvate thereof, wherein:

p is 0 or 1;

$R^1$ represents halogen or methyl;

q is 0;

X is —C(O)NH— or —NHC(O)—;

n is 0, 1, 2 or 3;

m is 0;

within each grouping $CR^5R^6$, $R^5$ and $R^6$ each independently represent hydrogen or a $C_{1-4}$ alkyl group or $R^5$ and $R^6$ together with the carbon atom to which they are both attached can form a cyclopropyl ring;

$R^2$ represents a 4- to 7-membered cycloalkyl ring optionally substituted with a $C_{1-4}$ alkyl group which alkyl group can be optionally substituted with 1 to 3 halogen atoms;

Y is nitrogen and Z is a group $CR^3$ wherein $R^3$ is a group of formula (IIA)

s is 0 or 1;

$X^1$ is a group >N—$R^{11}$ wherein $R^{11}$ is hydrogen or a $C_{1-4}$ alkyl group;

$R^9$ represents a bond or a $C_{1-5}$ alkylene group optionally substituted by hydroxyl;

$R^{10}$ represents hydrogen, hydroxyl, carboxyl, —C(O)O$R^{20}$, —NR$^{21}$R$^{22}$ or C(O)NOH, or $R^{10}$ represents a 4- to 9-membered carbocyclic or heterocyclic ring which heterocyclic ring comprises 1 or 2 nitrogen atoms and which carbocyclic or heterocyclic ring can be optionally substituted by at least one substituent selected from halogen, carboxyl, cyano, $C_1$-$C_6$ alkyl, $C_1$-$C_6$ hydroxyalkyl, —C(O)NOH, —(CH$_2$)$_t$NR$^{25}$R$^{26}$, —(CH$_2$)$_t$C(O)NR$^{27}$R$^{28}$, —(CH$_2$)$_t$R$^{29}$—(CH$_2$)$_t$NR$^{30}$C(O)R$^{31}$, NR$^{33}$SO$_2$R$^{34}$, NR$^{35}$C(O)NR$^{36}$S(O)$_r$R$^{37}$, —S(O)$_r$(CH$_2$)$_t$NR$^{38}$R$^{39}$, —S(O)$_r$(CH$_2$)$_t$C(O)OR$^{43}$, or M(CH$^?$)$_t$C(O)OR$^{44}$ wherein M represents a bond, O, or a group >NR$^{45}$;

t is 0, 1 or 2;

r is 0, 1 or 2;

$R^{21}$ and $R^{22}$ are independently selected from hydrogen, $C_{2-7}$ alkenyl, $C_{1-6}$ alkylcarbonyl, —SO$_2$R$^{46}$, —C(O)NHSO$_2$R$^{47}$, or $R^{21}$ and $R^{22}$ may independently represent a $C_{1-7}$ alkyl group which $C_{1-7}$ alkyl group can be optionally substituted by at least one substituent independently selected from halogen, carboxyl, hydroxyl, —NH(CH$_2$)$_{2-4}$OH, $C_{1-6}$ alkoxy, $C_{1-6}$ alkylthio, $C_{1-6}$ alkoxycarbonyl, —NR$^{48}$R$^{49}$, —C(O)NR$^{50}$R$^{51}$, NR$^{52}$COR$^{53}$, —NR$^{54}$SO$_2$R$^{55}$ and —NR$^{67}$C(O)NR$^{68}$SO$_2$R$^{56}$; and $R^{25}$, $R^{26}$, $R^{27}$, $R^{28}$, $R^{30}$, $R^{31}$, $R^{32}$, $R^{33}$, $R^{35}$, $R^{36}$, $R^{38}$, $R^{39}$, $R^{43}$, $R^{44}$, $R^{45}$, $R^{48}$, $R^{49}$, $R^{50}$, $R^{51}$, $R^{52}$ and $R^{53}$ each independently represent a hydrogen atom, a $C_{1-6}$ alkyl group or a $C_{2-6}$ hydroxyalkyl group; $R^{29}$ is aryl; and $R^{34}$, $R^{37}$, $R^{46}$, $R^{47}$, $R^{54}$, $R^{55}$, $R^{56}$, $R^{67}$ and $R^{68}$ each independently represent hydrogen or a $C_{1-6}$ alkyl group which can be optionally substituted by at least one substituent selected from halogen and hydroxyl.

In a further embodiment of the invention, there is provided a compound of formula (IA) or a pharmaceutically acceptable salt, prodrug or solvate thereof, wherein:

p is 0 or 1;

$R^1$ represents halogen or methyl;

q is 0;

X is —C(O)NH— or —NHC(O)—;

n is 0, 1, 2 or 3;

m is 0;

within each grouping $CR^5R^6$, $R^5$ and $R^6$ each independently represent hydrogen or a $C_{1-4}$ alkyl group or $R^5$ and $R^6$ together with the carbon atom to which they are both attached can form a cyclopropyl ring;

$R^2$ represents a 4- to 7-membered cycloalkyl ring optionally substituted with a $C_{1-4}$ alkyl group which alkyl group can be optionally substituted with 1 to 3 halogen atoms;

Y is nitrogen and Z is a group $CR^3$ wherein $R^3$ is a group of formula (IIA)

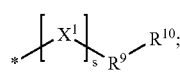

(IIA)

s is 0 or 1;

$X^1$ is a group >N—$R^{11}$ wherein $R^{11}$ is hydrogen or a $C_{1-4}$ alkyl group;

$R^9$ represents a bond or a $C_{1-5}$ alkylene group optionally substituted by hydroxyl;

$R^{10}$ represents a group —$WR^{23}$, or $R^{10}$ represents a 4- to 9-membered carbocyclic or heterocyclic ring which heterocyclic ring comprises 1 or 2 nitrogen atoms, and which carbocyclic or heterocyclic ring is substituted by at least one substituent —$W'R^{24}$ and may further be optionally substituted by at least one substituent selected from halogen or $C_1$-$C_6$ alkyl;

W and W' independently represent a bond; and $R^{23}$ and $R^{24}$ independently represent a group selected from: tetrazolyl;

a 5- to 6-membered carbocyclic or heterocyclic ring comprising from 1 to 3 heteroatoms selected from nitrogen, oxygen and sulphur, which carbocyclic or heterocyclic ring is substituted by at least one substituent selected from hydroxyl, =O, and =S and which carbocyclic or heterocyclic ring may further be optionally substituted by at least one substituent selected from halogen, nitro, cyano, —$SO_2C_{1-6}$ alkyl, $C_{1-6}$ alkylcarbonyl, $C_{1-6}$ alkoxycarbonyl, and a $C_{1-6}$ alkyl group which $C_{1-6}$ alkyl group can be optionally substituted by at least one substituent selected from halogen and hydroxyl;

a 1,2,3-triazolyl or 1,2,4 triazolyl group which triazolyl group can be optionally substituted by at least one substituent selected from halogen, nitro, cyano, —$SO_2C_{1-6}$ alkyl, $C_{1-6}$ alkylcarbonyl, $C_{1-6}$ alkoxycarbonyl and $C_{1-6}$ alkyl;

a phenyl group or a 5- to 6-membered unsaturated heterocyclic ring comprising from 1 to 2 nitrogen atoms, which phenyl group or heterocyclic ring is substituted by a group —$NR^{69}SO_2NR^{70}R^{71}$ or a group —$SO_2R^{72}$, wherein $R^{69}$, $R^{70}$, $R^{71}$ and $R^{72}$ each independently represent a hydrogen atom or a $C_{1-6}$, preferably $C_{1-4}$, alkyl group which $C_{1-6}$ alkyl group can be optionally substituted by at least one substituent (e.g. one, two or three substituents) selected from halogen (e.g. chlorine, fluorine, bromine or iodine), and hydroxyl.

In a further embodiment of the invention, there is provided a compound of formula (IA) or a pharmaceutically acceptable salt, prodrug or solvate thereof, wherein:

p is 0 or 1;

$R^1$ represents halogen or methyl;

q is 0;

X is —C(O)NH— or —NHC(O)—;

n is 1 or 2;

m is 0;

within each grouping $CR^5R^6$, $R^5$ and $R^6$ each independently represent hydrogen or a $C_{1-4}$ alkyl group;

$R^2$ represents a 5 or 6-membered cycloalkyl ring optionally substituted with a $C_{1-4}$ alkyl group;

Y is nitrogen and Z is a group $CR^3$ wherein $R^3$ is a group of formula (IIA)

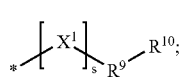

(IIA)

s is 0;

$R^9$ represents a bond; and $R^{10}$ represents a 4- to 9-membered heterocyclic ring, which heterocyclic ring comprises 1 or 2 nitrogen atoms, and which heterocyclic ring can be optionally substituted by at least one substituent selected from hydroxyl, cyano, carboxyl, methyl, —$NH_2$, —$NHCH_3$, —$NHCH_2CH_2OH$, —$CH_2C(O)OH$, —$NHCH_2C(O)OH$, —$NHCH_2CH_2C(O)OH$, —$CH_2NHCH_3$, —$CH_2NHCH_2CH_2OH$, —$SO_2CH_2CH_2OH$, —$N(CH_2CH_2OH)C(O)OC(CH_3)_3$, —$NHSO_2CF_3$, —NHC(O)NHSO_2CH_3$.

In a further embodiment of the invention the compound of formula (IA) is

N-[6-Chloro-2-(4-piperidinylmethyl)-5-quinolinyl]-cyclohexaneacetamide, dihydrochloride, N-[6-Chloro-2-(1-piperazinyl)-5-quinolinyl]-cyclohexaneacetamide, dihydrochloride, N-[6-Chloro-2-[methyl[3-(methylamino)propyl]amino]-5-quinolinyl]-cyclohexaneacetamide, dihydrochloride, 6-Chloro-N-(cyclohexylmethyl)-2-methyl-5-quinolinecarboxamide, hydrochloride, N-[6-Chloro-2-[(3-hydroxypropyl)amino]-5-quinolinyl]-cyclohexaneacetamide, hydrochloride, N-[6-Chloro-2-[[(2R)-2,3-dihydroxypropyl]amino]-5-quinolinyl]-cyclohexaneacetamide, 4-[[6-Chloro-5-[(cyclohexylacetyl)amino]-2-quinolinyl]amino]-butanoic acid, N-[6-Chloro-2-[methyl[3-(methylamino)propyl]amino]-5-quinolinyl]-4-(trifluoromethyl)-cyclohexaneacetamide, dihydrochloride, N-[6-Chloro-2-(1-piperazinyl)-5-quinolinyl]-4-(trifluoromethyl)-cyclohexaneacetamide, N-[6-Chloro-2-(hexahydro-1H-1,4-diazepin-1-yl)-5-quinolinyl]-cyclohexaneacetamide,
N-[6-Chloro-2-[(cis-3,5-dimethyl-1-piperazinyl]-5-quinolinyl]-cyclohexaneacetamide,
N-[6-Chloro-2-(4-methyl-1-piperazinyl)-5-quinolinyl]-cyclohexaneacetamide, dihydrochloride,
N-[6-Chloro-2-[(1S,4S)-2,5-diazabicyclo[2.2.1]hept-2-yl]-5-quinolinyl]-cyclohexaneacetamide, acetate,
N-[6-Chloro-2-[(3R)-3-pyrrolidinylamino]-5-quinolinyl]-cyclohexaneacetamide, dihydrochloride,
N-[2-[3-(Ethylamino)propyl]-6-methyl-5-quinolinyl]-cyclohexaneacetamide, dihydrochloride,
N-[6-Chloro-2-[3-(ethylamino)propyl]-5-quinolinyl]-cyclohexaneacetamide, dihydrochloride,
N-[6-Chloro-2-[[2-[(2-hydroxyethyl)amino]ethyl]amino]-5-quinolinyl]-cyclohexaneacetamide, dihydrochloride,
N-5-Quinolinyl-cyclohexaneacetamide,
1-Methyl-N-5-quinolinyl-cyclohexaneacetamide,
4-Methyl-N-5-quinolinyl-cyclohexaneacetamide,
N-5-Quinolinyl-cyclopentanepropanamide,
N-[6-Chloro-2-[3-[(3-hydroxypropyl)amino]propyl]-5-quinolinyl]-cyclohexaneacetamide,
N-[2-(3-Aminopropyl)-6-chloro-5-quinolinyl]-cyclohexaneacetamide,
N-[6-Chloro-2-[3-[[[(methylsulfonyl)amino]carbonyl]amino]propyl]-5-quinolinyl]-cyclohexaneacetamide,
N-[2-[3-(Butylamino)propyl]-6-chloro-5-quinolinyl]-cyclohexaneacetamide dihydrochloride,
N-[6-Chloro-2-[methyl[3-(methylamino)propyl]amino]-5-quinolinyl]-1-cyclohexyl-cyclopropanecarboxamide, hydrochloride,
N-[6-Chloro-2-(1-piperazinyl)-5-quinolinyl]-1-cyclohexyl-cyclopropanecarboxamide,
N-[6-Chloro-2-[(3R)-3-hydroxy-1-pyrrolidinyl]-5-quinolinyl]-cyclohexaneacetamide,
N-[6-Chloro-2-[(3S)-3-hydroxy-1-pyrrolidinyl]-5-quinolinyl]-cyclohexaneacetamide,
N-[2-[(3R)-3-Amino-1-pyrrolidinyl]-6-chloro-5-quinolinyl]-cyclohexaneacetamide,
N-[2-[(3S)-3-Amino-1-pyrrolidinyl]-6-chloro-5-quinolinyl]-cyclohexaneacetamide,
N-[2-(4-Amino-1-piperidinyl)-6-chloro-5-quinolinyl]-cyclohexaneacetamide,
N-[6-Chloro-2-[(3R)-3-(methylamino)-1-pyrrolidinyl]-5-quinolinyl]-cyclohexaneacetamide,
N-[6-Chloro-2-[(3R)-3-[(2-hydroxyethyl)amino]-1-pyrrolidinyl]-5-quinolinyl]-cyclohexaneacetamide,
N-[6-Chloro-2-[(3S)-3-(methylamino)-1-pyrrolidinyl]-5-quinolinyl]-cyclohexaneacetamide,
N-[6-Chloro-2-[(3S)-3-[(2-hydroxyethyl)amino]-1-pyrrolidinyl]-5-quinolinyl]-cyclohexaneacetamide,
N-[6-Chloro-2-[(3R)-3-hydroxy-1-piperidinyl]-5-quinolinyl]-cyclohexaneacetamide,
N-[2-[(3S)-3-Amino-1-pyrrolidinyl]-6-methyl-5-quinolinyl]-cyclohexaneacetamide,
N-[6-Methyl-2-(1-piperazinyl)-5-quinolinyl]-cyclohexaneacetamide,
N-[6-Chloro-5-[(cyclohexylacetyl)amino]-2-quinolinyl]-glycine,
N-[6-Chloro-5-[(cyclohexylacetyl)amino]-2-quinolinyl]-β-alanine,
6-Chloro-N-(cyclohexylmethyl)quinoline-5-carboxamide,
6-Chloro-N-(cyclohexylmethyl)-2-(1-piperazinyl)-5-quinolinecarboxamide, dihydrochloride,
2-[(3S)-3-Amino-1-pyrrolidinyl]-6-chloro-N-(cyclohexylmethyl)-5-quinolinecarboxamide,
6-Chloro-N-(cyclohexylmethyl)-2-[methyl[3-(methylamino)propyl]amino]-5-quinoline carboxamide, dihydrochloride,
6-Chloro-N-(cyclohexylmethyl)-2-[methyl[2-(methylamino)ethyl]amino]-5-quinolinecarboxamide, dihydrochloride,
6-Chloro-N-(cyclohexylmethyl)-2-[3-[(3-hydroxypropyl)amino]propyl]-5-quinolinecarboxamide,
2-[(3R)-3-Amino-1-pyrrolidinyl]-6-chloro-N-(cyclohexylmethyl)-5-quinolinecarboxamide, dihydrochloride,
N-(2-Amino-6-chloro-5-quinolinyl)-cyclohexaneacetamide, trifluoroacetate,
6-Chloro-N-(cyclohexylmethyl)-2-[(3S)-3-[(2-hydroxyethyl)amino]-1-pyrrolidinyl]-5-quinolinecarboxamide, hydrochloride,
2-[(3S)-3-Amino-1-piperidinyl]-6-chloro-N-(cyclohexylmethyl)-5-quinolinecarboxamide,
6-Chloro-N-(cyclohexylmethyl)-2-[(3S)-3-[(2-hydroxyethyl)amino]-1-piperidinyl]-5-quinolinecarboxamide, hydrochloride,
6-Chloro-N-(cyclohexylmethyl)-2-(3-hydroxy-1-azetidinyl)-5-quinolinecarboxamide,
2-[(3S)-3-Amino-1-pyrrolidinyl]-N-(cyclohexylmethyl)-5-quinolinecarboxamide,
6-Chloro-N-(cyclohexylmethyl)-2-[3-[(2-hydroxyethyl)amino]-1-azetidinyl]-5 quinolinecarboxamide,
[1-[6-Chloro-5-[(cyclohexylacetyl)amino]-2-quinolinyl]-3-pyrrolidinyl](2-hydroxyethyl)-carbamic acid 1,1-dimethylethyl ester,
N-(Cyclohexylmethyl)-6-methyl-5-quinolinecarboxamide,
2-[(3S)-3-Amino-1-pyrrolidinyl]-N-(cyclohexylmethyl)-6-methyl-5-quinolinecarboxamide, acetate,
N-[2-[[(3S)-3-Amino-1-pyrrolidinyl]methyl]-6-chloro-5-quinolinyl]-cyclohexaneacetamide,
N-[2-[(3S)-3-Amino-1-piperidinyl]-6-chloro-5-quinolinyl]-cyclohexaneacetamide,
N-[6-Chloro-2-[(3S)-3-[(2-hydroxyethyl)amino]-1-piperidinyl]-5-quinolinyl]-cyclohexaneacetamide,
N-[2-[(3S)-3-Amino-1-pyrrolidinyl]-6-chloro-5-quinolinyl]-cyclopentanepropanamide,
N-[6-Chloro-2-[(3S)-3-[(2-hydroxyethyl)amino]-1-pyrrolidinyl]-5-quinolinyl]-cyclopentanepropanamide,
N-[6-Chloro-2-[4-(1,5-dihydro-5-oxo-4H-1,2,4-triazol-4-yl)-1-piperidinyl]-5-quinolinyl]-cyclohexaneacetamide,
1-[6-Chloro-5-[(cyclohexylacetyl)amino]-2-quinolinyl]-D-proline, trifluoroacetate,
1-[6-Chloro-5-[(cyclohexylacetyl)amino]-2-quinolinyl]-4-piperidinecarboxylic acid, lithium salt,
6-Chloro-5-[(cyclohexylacetyl)amino]-2-quinolinebutanoic acid,
1-[6-Chloro-5-[(cyclohexylacetyl)amino]-2-quinolinyl]-4-piperidineacetic acid,
4-[6-Chloro-5-[(cyclohexylacetyl)amino]-2-quinolinyl]-1-piperazineacetic acid, lithium salt,
6-Chloro-5-[(cyclohexylacetyl)amino]-2-quinolinepentanoic acid, 1-[6-Chloro-5-[[(cyclohexylmethyl)amino]carbonyl]-2-quinolinyl]-D-proline,
1-[6-Chloro-5-[[(cyclohexylmethyl)amino]carbonyl]-2-quinolinyl]-L-proline, trifluoroacetate,
4-[6-Chloro-5-[[(cyclohexylmethyl)amino]carbonyl]-2-quinolinyl]-1-piperazineacetic acid, acetate,
1-[6-Chloro-5-[[(cyclohexylmethyl)amino]carbonyl]-2-quinolinyl]-4-piperidinecarboxylic acid, sodium salt,
1-[6-Chloro-5-[[(cyclohexylmethyl)amino]carbonyl]-2-quinolinyl]-4-piperidineacetic acid, trifluoroacetate,
1-[6-Chloro-5-[[(2-cyclohexylethyl)amino]carbonyl]-2-quinolinyl]-4-piperidinecarboxylic acid, 1-[6-Chloro-5-[(3-cyclopentyl-1-oxopropyl)amino]-2-quinolinyl]-4-piperidinecarboxylic acid,
1-[6-Chloro-5-[(3-cyclohexyl-1-oxopropyl)amino]-2-quinolinyl]-4-piperidinecarboxylic acid, potassium salt,
1-[6-Chloro-5-[[(1-methylcyclohexyl)acetyl]amino]-2-quinolinyl]-4-piperidinecarboxylic acid,
N-[6-Chloro-2-[3-[(2-hydroxyethyl)amino]-1-piperidinyl]-5-quinolinyl]-cyclohexaneacetamide,
N-[6-Chloro-2-[2-[[(2-hydroxyethyl)amino]methyl]-1-pyrrolidinyl]-5-quinolinyl]-cyclohexaneacetamide,
N-[6-Chloro-2-[3-(methylamino)-1-piperidinyl]-5-quinolinyl]-cyclohexaneacetamide,
N-[6-Chloro-2-[2-[(methylamino)methyl]-1-pyrrolidinyl]-5-quinolinyl]-cyclohexaneacetamide,
N-[2-[(3R)-3-Hydroxy-1-pyrrolidinyl]-6-methyl-5-quinolinyl]-cyclohexaneacetamide,
N-[(3S)-1-[6-Chloro-5-[(cyclohexylacetyl)amino]-2-quinolinyl]-3-pyrrolidinyl]-glycine,
N-[2-[(3S)-3-[(2-Hydroxyethyl)amino]-1-pyrrolidinyl]-6-methyl-5-quinolinyl]-cyclohexaneacetamide,
N-[(3S)-1-[6-Chloro-5-[(cyclohexylacetyl)amino]-2-quinolinyl]-3-pyrrolidinyl]-β-alanine,
N-[6-Chloro-2-[(3S)-3-[[(trifluoromethyl)sulfonyl]amino]-1-pyrrolidinyl]-5-quinolinyl]-cyclohexaneacetamide,
N-[6-Chloro-2-[(3S)-3-[[[(methylsulfonyl)amino]carbonyl]amino]-1-pyrrolidinyl]-5-quinolinyl]-cyclohexaneacetamide,
N-[2-[(3S)-3-Amino-1-pyrrolidinyl]-6-chloro-5-quinolinyl]-cyclohexanepropanamide,
N-[6-Chloro-2-[methyl[3-(methylamino)propyl]amino]-5-quinolinyl]-cyclohexanepropanamide,
N-[6-Chloro-2-(1-piperazinyl)-5-quinolinyl]-cyclohexanepropanamide,
N-[6-Chloro-2-[(3S)-3-[(2-hydroxyethyl)amino]-1-pyrrolidinyl]-5-quinolinyl]-cyclohexanepropanamide,
2-[(3S)-3-Amino-1-pyrrolidinyl]-6-chloro-N-(2-cyclohexylethyl)-5-quinolinecarboxamide, ditrifluoroacetate,
N-[6-Chloro-2-[(3S)-3-[(2-hydroxyethyl)sulfonyl]-1-pyrrolidinyl]-5-quinolinyl]-cyclohexaneacetamide,
N-[6-Chloro-2-[(3S)-3-cyano-1-pyrrolidinyl]-5-quinolinyl]cyclohexaneacetamide,
N-[1-[6-Chloro-5-[[(cyclohexylmethyl)amino]carbonyl]-2-quinolinyl]-3-azetidinyl]-β-alanine,
6-Chloro-N-(cyclohexylmethyl)-2-[3-(1H-tetrazol-5-yl)-1-azetidinyl]-5-quinolinecarboxamide,
N-[6-Chloro-2-[(3S)-3-(1H-tetrazol-5-yl)-1-pyrrolidinyl]-5-quinolinyl]-cyclohexaneacetamide,
N-[6-Chloro-2-[(3R)-3-(1H-tetrazol-5-yl)-1-pyrrolidinyl]-5-quinolinyl]-cyclohexaneacetamide,
N-[6-Chloro-2-[(3S)-3-[[2-(2H-tetrazol-5-yl)ethyl]amino]-1-pyrrolidinyl]-5-quinolinyl]-cyclohexaneacetamide,
N-[6-Chloro-2-[4-(4,5-dihydro-5-oxo-1,2,4-oxadiazol-3-yl)-1-piperidinyl]-5-quinolinyl]-cyclohexaneacetamide,
N-[6-Chloro-2-[4-(4,5-dihydro-5-oxo-1,2,4-thiadiazol-3-yl)-1-piperidinyl]-5-quinolinyl]-cyclohexaneacetamide,
N-[6-Chloro-2-[3-(1H-tetrazol-5-yl)propyl]-5-quinolinyl]-cyclohexaneacetamide, trifluoroacetate,
N-[6-Chloro-2-[4-(1H-tetrazol-5-yl)butyl]-5-quinolinyl]-cyclohexaneacetamide,
6-Chloro-N-(cyclohexylmethyl)-2-[4-(1H-tetrazol-5-yl)butyl]-5-quinolinecarboxamide,
N-[6-Chloro-2-[(3S)-3-[2-(1H-tetrazol-5-yl)ethoxy]-1-pyrrolidinyl]-5-quinolinyl]-cyclohexaneacetamide,
N-[6-Chloro-2-[(3S)-3-[2-(4,5-dihydro-5-oxo-1,2,4-oxadiazol-3-yl)ethoxy]-1-pyrrolidinyl]-5-quinolinyl]-cyclohexaneacetamide,
N-[6-Chloro-2-[4-(1H-tetrazol-5-yl)-1-piperidinyl]-5-quinolinyl]cyclohexane-acetamide,
6-Chloro-N-(cyclohexylmethyl)-2-[4-(1H-tetrazol-5-yl)-1-piperidinyl]-5-quinolinecarboxamide,
6-Chloro-N-(2-cyclohexylethyl)-2-[4-(1H-tetrazol-5-yl)-1-piperidinyl]-5-quinolinecarboxamide,
6-Chloro-N-(cyclohexylmethyl)-2-[(3S)-3-(1,1-dioxido-4-oxo-1,2,5-thiadiazolidin-2-yl)-1-pyrrolidinyl]-5-quinolinecarboxamide,
N-[6-Chloro-2-(4-cyano-1-piperidinyl)-5-quinolinyl]-cyclohexaneacetamide, or
N-[6-Chloro-2-[4-[[(trifluoromethyl)sulfonyl]amino]-1-piperidinyl]-5-quinolinyl]-cyclohexaneacetamide.

or a pharmaceutically acceptable salt, prodrug or solvate of anyone thereof.

Pharmaceutically acceptable salts of compounds of formula (IA) that may conveniently be employed include base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulphonate, fumarate, hydrochloride, hydrobromide, citrate, maleate and salts formed with phosphoric and sulphuric acid. There may be more than one cation or anion depending on the number of charged functions and the valency of the cations or anions. A preferred pharmaceutically acceptable salt is a hydrochloride or sodium salt.

Prodrugs of compounds of formula (IA) that may conveniently be employed are compounds which are hydrolysed in vivo to form compounds of formula (IA). Thus for example where compounds of formula (IA) include a carboxy group, these may be in the form of pharmaceutically acceptable esters or amides.

Pharmaceutically acceptable esters of formula (IA) for carboxyl groups include $C_{1-6}$alkyl esters, for example methyl or ethyl; $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; $C_{1-6}$alkoxycarbonyloxyethyl esters, for example 1-methoxycarbonyloxyethyl; aminocarbonylmethyl esters and mono- or di-N-($C_{1-6}$alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Pharmaceutically acceptable esters for hydroxy include $C_{1-6}$alkanoyl esters, for example acetyl esters; and benzoyl esters wherein the phenyl group may be substituted with aminomethyl or N-substituted mono- or di-$C_{1-6}$alkyl aminomethyl, for example 4-aminomethylbenzoyl esters and 4-N,N-dimethylaminomethylbenzoyl esters.

Pharmaceutically acceptable amides are similarly in-vivo hydrolysable to yield the parent acid, and include $C_{1-6}$alkylamides such as acetamide.

The present invention further provides a process for the preparation of a compound of formula (IA) as defined above, or a pharmaceutically acceptable salt, prodrug or solvate thereof, which comprises either:

(a) reacting a compound of formula (IVA)

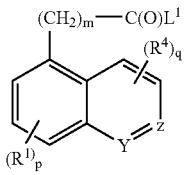
(IVA)

wherein $L^1$ represents a leaving group (e.g. hydroxyl or halogen) and Y, Z, $R^1$, $R^4$, m, p and q are as defined in formula (IA), with a compound of formula (VA), $$H_2N\text{—}(CR^5R^6)_n\text{—}R^2 \qquad (VA)$$

$R^2$, $R^5$, $R^6$ and n are as defined in formula (IA); or (b) reacting a compound of formula (VIA)

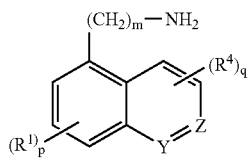
(VIA)

wherein Y, Z, $R^1$, $R^4$, m, p and q are as defined in formula (IA), with a compound of formula (VIIA)

$$L^2C(O)\text{—}(CR^5R^6)_n\text{—}R^2 \qquad (VIIA)$$

wherein $L^2$ represents a leaving group (e.g. hydroxyl or halogen) and $R^2$, $R^5$, $R^6$ and n are as defined in formula (IA); or (c) when Y is N and Z is $CR^3$, and $R^3$ represents a group of formula (IIA) above where s is 1 and X is $>NR^{11}$, reacting a compound of formula (VIIIA)

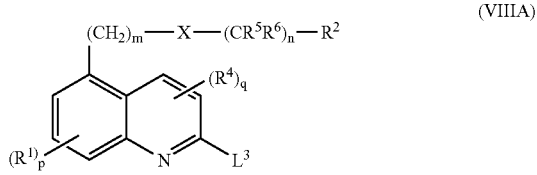
(VIIIA)

wherein $L^3$ is a leaving group (e.g. halogen, paratoluene sulphonate or methane sulphonate), and all other variables are as defined in relation to formula (IA), with a compound of formula (IXA), $H\text{—}N(R^{11})\text{—}R^9\text{-}R^{10}$, wherein $R^9$, $R^{10}$ and $R^{11}$ are as defined in formula (IIA); or (d) when Y is N and Z is $CR^3$, and $R^3$ is a group formula (IIA) wherein s is 0 and $R^9$ is a $C_1$-$C_5$ alkylene group which may be optionally substituted as defined herein above with respect to formula (IA), reacting a compound of formula (VIIIA) as defined in (c) above with a compound of formula (XA) or (XIA)

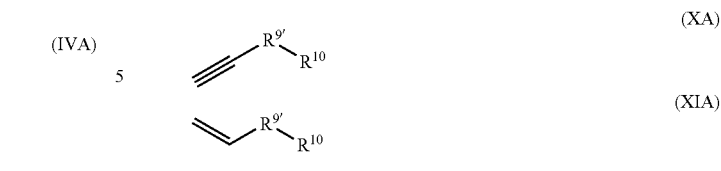

wherein wherein $R^{9'}$ is suitably defined such that saturation of the alkene or alkyne and combination with $R^{9'}$ gives a group of formula $R^9$ as defined in formula (IIA), optionally followed by a hydrogenation reaction; or (e) when Y is N and Z is $CR^3$, and $R^3$ is a group of formula (IIA) where s is 0, $R^9$ is $(CH_2)_2$ and $R^{10}$ is $\text{—}NR^{21}R^{22}$, reacting a compound of formula (VIIA) as defined in (c) above with a compound of formula (XIIA)

(XIIA)

wherein $L^4$ is a leaving group (eg. trialkyltin, dialkylboron or zinc), followed by reaction with a compound of formula (XIIIA), $HNR^{21}R^{22}$, wherein $R^{21}$ and $R^{22}$ are as defined above;

(f) when Y is N and Z is $CR^3$, and $R^3$ is a group of formula (IIA) where s is 0, $R^9$ is $(CH_2)$ and $R^{10}$ is $\text{—}NR^{19}R^{20}$, reacting a compound of formula (VIIIA) as defined in (c) above with a compound of formula (XIIA) as defined in (e) above, followed by an oxidation reaction and then by reaction with a compound of formula (XIIIA) as defined in (e) above under reductive amination conditions; or (g) when Y is N and Z is $CR^3$, and $R^3$ is a group of formula (IIA) where s is 0, reacting a compound of formula (VIIIA) as defined in (c) above with a compound of formula (XIVA)

(XIVA)

wherein $R^{9'}$ is suitably defined such that saturation of the alkene and combination with $R^{9'}$ gives a group of formula $R^9$ as defined in formula (IIA) and $R^{10}$ is as defined in formula (IIA), followed by removal of any protecting groups; or (h) when Y is N and Z=$CR^3$, and $R^{23}$ or $R^{24}$ represent tetrazolyl, reacting a compound of formula $IIA_1$ or $IIA_2$

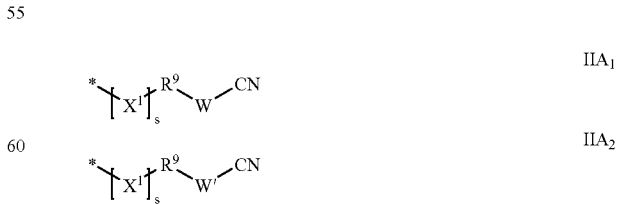

with a compound of formula $PN_3$ wherein P is sodium, a trialkylsilyl, an alkyltin or ammonium gives a group of formula $IIA_1$ or $IIA_2$ wherein $X^1$, $R^9$, W, W' are defined in IIA; or (i) when Y is N and Z=CR³, and R²³ or R²⁴ represent a group of formula (XVA)

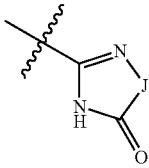
(XVA)

reacting a compound of formula IIA₁ or IIA₂ wherein IIA₁ or IIA₂ are as defined in (h) above with hydroxylamine, followed by treatment with 1,1'-thiocarbonyldiimidazole and subsequent treatment with silica gives a group of formula (XVA) wherein J is S, alternatively reacting a compound of formula IIA₁ or IIA₂ wherein IIA₁ or IIA₂ are as defined in (h) above with hydroxylamine, followed by treatment with a chloroformate gives a group of formula (XVA) wherein J is O; or (j) when Y is N and Z=CR³, and R²³ or R²⁴ represent a group of formula (XVIA)

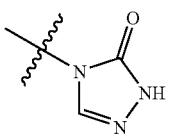
(XVIA)

reacting a compound of formula IIA₃ or IIA₄

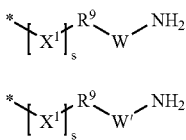
IIA₃

IIA₄ with a source of phosgene followed by treatment with formyl hydrazine and subsequent treatment with base; or (k) when Y is N and Z=CR³, and R²³ or R²⁴ represent a group of formula (XVIIA)

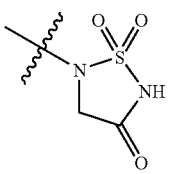
(XVIIA)

reacting a compound of formula IIA₃ or IIA₄ as defined above in (j) with ethyl chloroacetate, followed by reaction with (chlorosulfonyl)-carbamic acid, 1,1-dimethylethyl ester and subsequent treatment with acid and base gives the compound of formula (XVIIA);

(l) when Y is N, X is NHC(O) and m is 0, compounds of the formula (VIIIA) as defined above in (c) can be derived by reacting a compound of formula (XVIIIA)

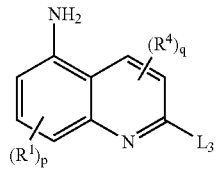
(XVIIIA)

with a suitable acid of formula (XIXA)

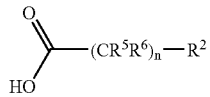
(XIXA)

wherein L³ is a leaving group (e.g. halogen, paratoluene sulphonate or methane sulphonate), and all other variables are as defined in relation to formula (IA); or (m) when Y is N, X is C(O)NH and m is 0, compounds of the formula (VIIIA) as defined above in (c) can be derived by reacting a compound of formula (XXA)

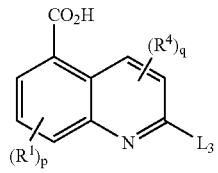
(XXA)

with a suitable amine of formula (XIXA)

$H_2N-(CR^5R^6)_n-R^2$ (XXIA)

wherein L³ is a leaving group (e.g. halogen, paratoluene sulphonate or methane sulphonate), and all other variables are as defined in relation to formula (IA); or (n) when Y is N, X is C(O)NH and m is 0, compounds of the formula (VIIIA) as defined above in (c) can be derived by reacting a compound of formula (XXIIA)

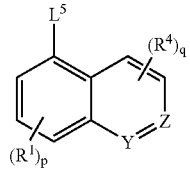
(XXIIA)

with a suitable amine of formula (XXIA), wherein L⁵ is a halogen (e.g. bromine or iodine) and all other variables are as defined in relation to formula (IA) with a suitable source of carbon monoxide and a suitable catalyst;

and optionally after (a), (b), (c), (d), (e), (f), (g), (h), (i), (j), (k), (l), (m) or (n) carrying out one or more of the following:
  converting the compound obtained to a further compound of the invention forming a pharmaceutically acceptable salt, prodrug or solvate of the compound.

In processes (a), (b), (l) and (m) the coupling reaction is conveniently carried out in an organic solvent such as dichloromethane, N,N-dimethylformamide or 1-methyl-2-pyrrolidinone.

If $L^1$ or $L^2$ represent a hydroxyl group, it may be necessary or desirable to use a coupling agent such as bromo-tris-pyrrolidino-phosphonium hexafluorophosphate (PyBroP). If $L^1$ or $L^2$ are chloride, such compounds may be conveniently prepared by treatment of the corresponding carboxylic acid derivative under standard conditions (such as thionyl chloride in dichloromethane with additional N,N-dimethylformamide) and used in a solvent such as acetone or dichloromethane with a suitable base such as potassium carbonate or triethylamine.

In process (c) the reaction may be performed in an organic solvent such as acetonitrile, N,N-dimethylformamide or 1-methyl-2-pyrrolidinone, and in the presence of a suitable base such as sodium hydride, triethylamine or potassium carbonate at a temperature in the range from, e.g. 50° C. to 150° C., in particular from 80° C. to 120° C., either in a microwave or conventional thermal conditions.

In process (d), if the compound of formula (VIIIA) is reacted with a compound of formula (XA), then the reaction is conveniently carried out in an organic solvent such as acetonitrile, e.g. at ambient temperature (20° C.), in the presence of catalytic bistriphenylphosphine dichloride palladium (0), copper (I) iodide and a base (e.g. triethylamine). The subsequent hydrogenation reaction may use hydrogen gas with a catalyst such as 5% rhodium on carbon in a solvent, for example, ethyl acetate or ethanol, and at a pressure of 3 bar.

Alternatively, if the compound of formula (VIIIA) is reacted with a compound of formula (XIA), then it is preferred if the compound of formula (XIA) is pre-treated by reaction with a hydroborating reagent (e.g. 9-borabicyclo[3.3.1]nonane or catecholborane) in an organic solvent such as diethyl ether or tetrahydrofuran at a temperature in the range from, e.g. 0° C. to 80° C., in particular from 60° C. to 70° C., for about 2 to 3 hours. The pre-treated compound is then reacted with the compound of formula (VIIIA) in the presence of a suitable base (e.g. sodium hydroxide or tri-potassium orthophosphate) and a palladium catalyst (e.g. dichloro[1,1'-bis(diphenylphosphino)ferrocene]palladium (II) dichloromethane adduct), typically at a temperature in the range from 25° C. to 90° C., particularly from 60° C. to 70° C., for about 2 to 24 hours.

In process (e), the reaction with the vinyl compound of formula (XIIA) may conveniently be carried out in a solvent such as N,N-dimethylformamide and in the presence of catalytic dichlorobis(triphenylphosphine)palladium, at elevated temperature, e.g. at about 70° C. The subsequent addition reaction with the compound of formula (XIIIA) may be performed under acidic or basic conditions, for example, in acetic acid in a solvent such as methanol or isopropanol at elevated temperature, e.g. at about 100° C.

In process (f), the reaction of the vinyl compound of formula (XVIIIA) may be performed by procedures analogous to those outlined in the previous paragraph on process (e). The subsequent oxidation reaction may be carried out under standard conditions, for example, by using ozone followed by treatment with dimethylsulfide or triphenylphosphine in a suitable solvent such as dichloromethane, or, by using osmium tetroxide and sodium periodate in a suitable solvent such as 1,4-dioxane and water. The reductive amination step may be conveniently carried out in the presence of a reducing agent such as sodium cyanoborohydride, triacetoxyborohydride or sodium borohydride, in a polar solvent such as methanol, ethanol or dichloromethane either alone or in combination with acetic acid.

In process (g), the compound of formula (XIVA) is pre-treated by reaction with a hydroborating reagent (such as 9-borabicyclo[3.3.1]nonane or catecholborane) in a solvent (such as diethyl ether or tetrahydrofuran) at a temperature in the range from 0° C. to 80° C. (in particular from 60° C. to 70° C.) for about 2 to 3 hours, then cooling the reaction mixture to room temperature and adding a solution of a base (such as sodium hydroxide in water or tri-potassium orthophosphate in water) followed by a solution of the compound of formula (VIIIA) in a solvent (such as N,N-dimethylformamide) and a palladium catalyst (such as tetrakis(triphenylphosphine)palladium (II)). The resulting reaction mixture is stirred at a temperature in the range from 25° C. to 90° C. (particularly from 60° C. to 70° C.) for about 2 to 24 hours to yield the desired compounds of formula (IA).

In process (h), the compound of formula $IIA_1$ or $IIA_2$ is treated with a compound of the formula $PN_3$ in a solvent (such as toluene, N,N-dimethylformamide or 1-methyl-2-pyrrolidinone) optionally in the presence of catalyst (such as dibutyltin oxide) at a temperature in the range from 70° C. to 120° C.

In process (i), the compound of formula $IIA_1$ or $IIA_2$ wherein $IIA_1$ or $IIA_2$ are defined as in (h) and J=O, is treated with hydroxylamine in a suitable solvent (such as methanol or ethanol) at a temperature in the range from 70° C. to 130° C. The resulting intermediate is treated with a suitable chloroformate (such as 2-ethylhexylchloroformate) in a suitable solvent (such as dichloromethane) and heated at a temperature in the range from 70° C. to 150° C. to give the desired compounds of the formula (IA). Alternatively, when J=S, treatment of the hydroxylamine adduct with 1,1'-thiocarbonyldiimidazole in a suitable solvent (such as tetrahydrofuran) and addition of silica yields the desired compounds of the formula (IA).

In process (j), the compound of formula $IIA_3$ or $IIA_4$ is treated with phosgene or a phosgene equivalent (such as triphosgene) in a suitable solvent (such as dichloromethane) with a suitable base (such as triethylamine). The resulting compound is further treated with formyl hydrazine and this subsequently with a base (such as potassium hydroxide) in a suitable solvent (such as methanol) at a temperature in the range from 50° C. to 130° C. to give the desired compounds of the formula (IA).

In process (k), the compound of formula $IIA_3$ or $IIA_4$ wherein $IIA_3$ or $IIA_4$ are as defined above in (j) is treated with ethyl chloroacetate in a suitable solvent (such as acetonitrile) with a suitable base (such as triethylamine) at a temperature in the range from 50° C. to 130° C. Treatment of this adduct with (chlorosulfonyl)-carbamic acid, 1,1-dimethylethyl ester in a suitable solvent (such as dichloromethane) and subsequent treatment with a suitable acid (such as trifluoroacetic acid) and a suitable base (such as sodium methoxide) to give the desired compounds of the formula (IA).

In process (n), suitable palladium catalysts include dichlorobis(triphenylphosphine)palladium(II) and the reaction may be carried out in an inert solvent such as N-methylpyrrolidinone, at a temperature between 25° C. and 150° C., preferably 100° C. and under a 1-15 bar pressure of carbon monoxide, preferably 6 bar to give the desired compounds of the formula (VIIIA).

Compounds of formulae (IVA), (VA), (VIA), (VIIA), (IXA), (XA), (XIA), (XIIA), (XIIIA), (XIVA), (XIXA), (XXIA) and (XXIIA) are either commercially available, are known in the literature or may be prepared using known techniques.

Compounds of formula (VIIIA) are novel compounds and form a further aspect of the invention. Examples of preparation methods for certain of these compounds are given hereinafter in the examples. Other examples can be prepared by analogous methods. In particular, compounds of formula (VIIIA) or analogues where Y is $CL^3$ and Z is N can be prepared by either (i) reacting a compound of formula (XVA)

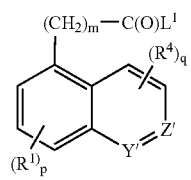

(XVA)

wherein $L^1$ represents a leaving group (e.g. hydroxyl or halogen) and $R^1$, $R^4$, m, p and q are as defined in formula (IA), and one of Y' or Z' is N and the other is a group $CL^3$ where $L^3$ is as defined in relation to formula (VIIIA), with a compound of formula (VA) as defined above;

(ii) reacting a compound of formula (XVIA)

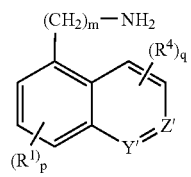

(XVIA)

wherein $R^1$, $R^4$, m, p and q are as defined in formula (IA), Y' and Z' are as defined in relation to formula (XVA) with a compound of formula (VIIA) as defined above. Reaction conditions analogous to those described above in relation to steps (a) and (b) are suitably employed.

Compounds of formula (XVA) and (XVIA) are either commercially available, are known in the literature or may be prepared using known techniques.

Compounds of formula (XVIIIA) are either known in the literature or may be prepared by nitration of the corresponding 2-chloroquinoline under standard conditions (such as nitric acid and sulfuric acid at a temperature in the range of 0° C. to 100° C.) followed by subsequent reduction to the corresponding aniline derivative under standard conditions (such as iron powder, acetic acid, hydrochloric acid, water and ethanol at a temperature in the range of 20° C. to 100° C.). Alternatively, a suitable nitro derivative with no substitution at the 2-position may be functionalised to compounds of formula (XVIIIA) by N-oxidation of the quinoline nitrogen under standard conditions (such as peracetic acid in acetic acid at a temperature in the range of 0° C. to 60° C.) and further conversion to its 2-chloro derivative by treatment with a suitable chlorinating agent (such as phosphorus oxychloride at a temperature in the range of 0° C. to 100° C.). 2-Hydroxy compounds may be similarly converted to the 2-chloro derivatives by treatment with similar chlorinating agents.

Compounds of formula (XXA) may be prepared from an appropriately substituted 5-bromo-2-halo-quinoline, such as 5-bromo-2,6-dichloroquinoline, by treatment with a Grignard reagent followed carbon dioxide. Suitable Grignard reagents include isopropylmagnesium chloride and the reaction may be carried out in an inert solvent such as tetrahydrofuran or diethyl ether, at a temperature from −30° C. to 30° C., but preferentially at 0° C. The reaction may be poured onto solid carbon dioxide or more preferably $CO_2$ gas may be bubbled through the reaction mixture.

The appropriately substituted 5-bromo-2-haloquinoline may be prepared by bromination of an appropriately substituted 2-haloquinoline such as 2,6-dichloroquinoline. The reaction may be carried by treatment with bromine in the presence of a Lewis acid such as aluminium trichloride at temperatures between −10° C. to 150° C., preferably at 120° C., in the absence of solvent.

Compounds of formula (VIIIA) where Y is N and Z is C-$L_3$, where $L_3$ is a leaving group such as halogen, $R^1$, $R^4$, p and q are as defined in formula (IA) and m is 0, may be prepared from an appropriately substituted 5-bromo-quinoline by treatment with an amine of formula (XXIA), where $R^5$, $R^6$, n and $R^2$ are as defined in formula (IA), in the presence of carbon monoxide and a palladium catalyst, followed by introduction of the 2-chlorine by treatment with an oxidising agent then a chlorinating agent. Suitable palladium catalysts include dichlorobis(triphenylphosphine)palladium (II) and the reaction may be carried out in an inert solvent such as N-methylpyrrolidinone, at a temperature between 25° C. and 150° C., preferably 100° C. and under a 1-15 bar pressure of carbon monoxide, preferably 6 bar. The 2-chlorine may be introduced by treatment with an oxidant such as hydrogen peroxide in a solvent such as acetic acid at 65° C. followed by treatment with a chlorinating agent such as thionyl chloride or preferably phosphorous oxychloride at a temperature of 120° C.

The appropriately substituted 5-bromo-quinolines may be prepared by literature methods (J Heterocyclic Chem., 1967, 4, 410, Khimiya Geterotsiklicheskikh Soedinenii, 1988, 8, 1084).

Compounds of formula (IA) can be converted into further compounds of formula (IA) using standard procedures. For example, compounds of formula (IA) in which $R^2$ represents a halogen atom may be converted to a corresponding compound of formula (IA) in which $R^2$ represents a $C_1$-$C_6$ alkyl group by reaction with an alkyl Grignard reagent (e.g. methyl magnesium bromide) in the presence of a catalyst such as [1,3-bis(diphenylphosphino) propane]dichloronickel (II) in a solvent such as tetrahydrofuran.

In a further example of the conversion of a compound of formula (IA) to another compound of formula (IA); a compound of formula (IA) where the group $NR^{13}R^{14}$ represents $NH_2$ may be converted into another compound of formula (IA) wherein $R^{13}$ represents H and $R^{14}$ is as defined in formula (IIIA), by treatment with an appropriate aldehyde (for example a suitably protected hydroxyl-acetaldehyde) in a reductive amination reaction. Suitable reducing agents include sodium cyanoborohydride, triacetoxyborohydride or sodium borohydride and the reaction may be carried out in a polar solvent such as methanol, ethanol or dichloromethane either alone or in combination with acetic acid.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (IA) above may involve, at various stages, the addition and removal of one or more protecting groups. The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (IA) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt. Other pharmaceutically acceptable salts, as well as prodrugs such as pharmaceutically acceptable esters and pharmaceutically acceptable amides may be prepared using conventional methods.

In a further aspect the invention provides a compound of formula (IB)

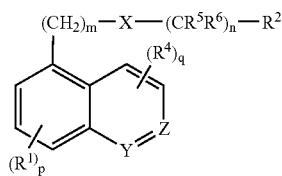

(IB)

or a pharmaceutically acceptable salt, prodrug or solvate thereof, wherein p is 0, 1 or 2;

each $R^1$ is independently selected from halogen, or optionally substituted $C_{1-6}$ alkyl, m is 0, 1, 2 or 3;

X is C(O)NH or NHC(O);

n is 0, 1, 2 or 3;

each $R^5$ and each $R^6$ are independently selected from hydrogen or $C_{1-3}$alkyl, or $R^5$ and $R^6$ together with the carbon atom to which they are both attached forms a $C_{3-6}$cycloalkyl ring, $R^2$ is an optionally substituted cycloalkyl group;

one of Y or Z is nitrogen and the other is a group $CR^3$ where $R^3$ is hydrogen, or a group $R^7$, $OR^7$, $SR^7$, $NR^7R^8$, where $R^7$ and $R^8$ are independently selected from hydrogen, optionally substituted $C_{1-10}$alkyl, an optionally substituted cycloalkyl or an optionally substituted heterocyclic group, or $R^7$ and $R^8$ together with the nitrogen to which they are attached form an optionally substituted heterocyclic ring which may contain additional heteroatoms, and may further comprise bridging groups;

q is 0, 1 or 2, and each $R^4$ is independently selected from halogen or optionally substituted $C_{1-6}$alkyl, with the proviso that where p is 0, q is 0, m is 0, n is 0, X is NHC(O), Y is nitrogen, Z is $CR^3$ and $R^3$ is methyl, $R^2$ is not a cyclopropyl group Certain compounds of formula (IB) are capable of existing in stereoisomeric forms. It will be understood that the invention encompasses all geometric and optical isomers of the compounds of formula (IB) and mixtures thereof including racemates. Tautomers and mixtures thereof also form an aspect of the present invention.

For the avoidance of doubt, it is hereby noted that the numbering and definition of groups and substituents provided herein in respect of formula (IB) is distinct and separate from that provided herein above in respect of formula (IA).

In an embodiment of the invention, in formula (IB) Y is nitrogen and Z is a group $CR_3$.

In an embodiment of the invention, in formula (IB) p is 0 or 1. Where p is 1, $R^1$ is preferably arranged ortho to group —$(CH^2)_mX(CH_2)_nR^2$ on the ring.

Preferred groups $R^1$ in formula (IB) include halogen, such as chloro, fluoro or $C_1$-$C_6$ alkyl such as methyl, optionally substituted by a substituent selected from hydroxyl, halogen and $C_1$-$C_6$ alkoxy. Preferably $R^1$ is chloro or methyl.

In an embodiment of the invention, in formula (IB) m is 0 or 1 and preferably m is 0.

In an embodiment of the invention, in formula (IB) n is 0, 1 or 2, and preferably n is 1.

In formula (IB), where $R^5$ and $R^6$ together with the carbon atom to which they are both attached forms a cycloalkyl ring, it is preferably a cyclopropyl ring.

In an embodiment of the invention, in formula (IB) each $R^5$ and $R^6$ is hydrogen.

In an embodiment of the invention, in formula (IB) $R^2$ represents a $C_{3-8}$cycloalkyl group, more preferably a $C_{5-7}$ cycloalkyl ring, e.g. a $C_5$ or $C_6$ cycloalkyl ring. Most preferably $R^2$ is an optionally substituted cyclohexyl ring.

Optional substituents for the ring $R^2$ in formula (IB) include one or more groups selected from halogen, halo$C_{1-6}$ alkyl, $C_{1-6}$ alkyl or $S(O)_fR^{50}$, where f is 0, 1 or 2 and $R^{50}$ is $C_{1-6}$alkyl. In particular, $R^2$ may carry one or two substitutents which are in particular, fluoro, methyl or trifluoromethyl.

In formula (IB), where $R^2$ is cyclohexyl, substitutents where present are preferably situated at the 1 and/or 4 positions of the ring.

Preferred optional substitutents for $C_{1-6}$alkyl groups $R^4$ in formula (IB) include halogen, hydroxy and $C_{1-6}$alkoxy, such as methoxy.

In an embodiment of the invention, in formula (IB) q is 0.

In an embodiment of the invention, the compounds of formula (IB) are selected from compounds of formula (IIIB)

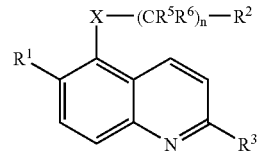

(III)

where $R^1$, X, $R^5$, $R^6$, n, $R^2$ and $R^3$ are as defined above with respect to formula (IB).

In an embodiment of the invention, in formula (IB) $R^3$ is a group $R^7$, $OR^7$, $SR^7$, $NR^7R^8$, where $R^7$ and $R^8$ are as defined above with respect to formula (IB).

In an embodiment of the invention, in formula (IB) where $R^7$ and $R^8$ includes bridging groups, these preferably form a fused 5/6 membered ring system, for example a diazabicyclo [2.2.1]hept-2-yl group.

In formula (IB), optional substitutents for $C_{1-10}$alkyl groups $R^7$ and $R^8$, include halogen, nitro, cyano, $OR^{13}$, $OC(O)R^{13}$, $C(O)R^{13}$, $C(O)OR^{13}$, $C(O)NR^{13}$, $SR^{13}$, $S(O)R^{13}$, $S(O_2)R^{13}$, $NR^{13}R^{14}$, $NR^{13}C(O)$—, —$NR^{13}S(O)_rR^{14}$, —$S(O)_r$ $NR^{13}R^{14}$, $NR^{15}C(O)NR^{13}R^{14}$, or $NR^{13}C(O)NR^{14}S(O)_rR^{15}$, optionally substituted cycloalkyl, optionally substituted aryl, optionally substituted aryloxy or optionally substituted heterocyclic groups, where r is 0, 1 or 2, and preferably 2, and $R^{13}$, $R^{14}$ and $R^{15}$ are independently selected from hydrogen or $C_{1-7}$ alkyl, aryl, cycloalkyl or a heterocyclic group, any of which may be optionally substituted, and where appropriatae, $R^{13}$ and $R^{14}$ together with the nitrogen atom to which they are attached may form an optionally subsituted heterocyclic ring, which may contain additional heteroatoms.

In formula (IB), optional substituents for cycloalkyl or heterocyclic groups $R^7$ and $R^8$, as well as for rings formed by $R^7$ and $R^8$ include those groups listed above for $C_{1-10}$alkyl groups, as well as alkyl substituted by any of said groups, and in particular by groups of formula $-(CH_2)_d R^{30}$ where d is 1 to 10, and preferably 1-6 and $R^{30}$ is halogen, nitro, cyano, $OR^{13}$, $OC(O)R^{13}$, $C(O)OR^{13}$, $C(O)NR^{13}$, $SR^{13}$, $S(O)R^{13}$, $S(O_2)R^{13}$, $NR^{13}R^{14}$, $-NR^{13}C(O)-$, $-NR^{13}S(O)_rR^{14}$, $-S(O)_rNR^{13}R^{14}$, $NR^{15}C(O)NR^{13}R^{14}$, or $NR^{13}C(O)NR^{14}S(O)_rR^{15}$ where r is 0, 1 or 2, where $R^{13}$, $R^{14}$ and $R^{15}$ are as defined above. A particular group $R^{30}$ is $NR^{13}R^{14}$.

In formula (IB), optional substitutents for alkyl groups $R^{13}$, $R^{14}$ and $R^{15}$ include halogen, nitro, cyano, $OR^{16}$, $OC(O)R^{16}$, $C(O)OR^{16}$, $SR^{16}$, $S(O)R^{16}$, $S(O_2)R^{16}$, $NR^{16}R^{17}$, $-NR^{16}C(O)-$, $-NR^{16}S(O)_rR^{17}$, $-S(O)_rNR^{16}R^{17}$, $NR^{18}C(O)NR^{16}R^{17}$, or $NR^{16}C(O)NR^{17}S(O)_rR^{18}$ where $R^{16}$, $R^{17}$ and $R^{18}$ are independently selected from hydrogen or $C_{1-7}$ alkyl, aryl, cycloalkyl or heterocyclic groups, or where appropriate, $R^{16}$ and $R^{17}$ together with the nitrogen atom to which they are attached form a heterocyclic group, which optionally contains further heteroatoms.

In formula (IB), where $R^{13}$, $R^{14}$ and $R^{15}$ are aryl, cycloalkyl or heterocyclic groups, or where $R^{13}$ and $R^{14}$ together with the nitrogen atom to which they are attached form a heterocyclic group, they may be optionally substituted by a groups $-(CH_2)_e R^{31}$ where e is 0 or an integer of from 1 to 10, preferably from 1-6, and $R^{31}$ is halogen, nitro, cyano, $OR^{16}$, $OC(O)R^{16}$, $C(O)OR^{16}$, $C(O)NR^{16}$, $SR^{16}$, $S(O)R^{16}$, $S(O_2)R^{16}$, $NR^{16}R^{17}$, $-NR^{16}C(O)-$, $-NR^{16}S(O)_rR^{17}$, $-S(O)_rNR^{16}R^{17}$, $NR^{18}C(O)NR^{16}R^{17}$, or $NR^{16}C(O)NR^{17}S(O)_rR^{18}$, cycloalkyl, aryl, aryloxy or heterocyclic groups, where r is as defined above, and $R^{16}$, $R^{17}$ and $R^{18}$ are as defined above. A particular group for $R^{31}$ is $NR^{16}R^{17}$.

In an embodiment of the invention, in formula (IB) preferred substitutents for $R^7$ or $R^8$ include halogen, hydroxy and $C_{1-6}$alkoxy.

In formula (IB), suitable substituents for aryl groups $R^{13}$, $R^{14}$ or $R^{15}$ include halogen, hydroxy or $C_{1-6}$alkylsulphonylamino.

In formula (IB), preferred examples of $R^3$ include groups of formula (IIB)

(IIB)

where $X^1$ represents an oxygen or sulphur atom or a group $>N-R^{11}$ and $R^{11}$ is hydrogen or a $C_{1-5}$alkyl group which may be optionally substituted by one or more substituents selected from hydroxy, halogen or $C_{1-6}$alkoxy;

s is 0 or 1;

$R^9$ represents a bond or a $C_1$-$C_5$ alkylene group, which may be optionally substituted, $R^{10}$ represents hydrogen, hydroxyl, carboxy, a group $-NR^{19}R^{20}$, an optionally substituted carbocyclic or an optionally substituted heterocyclic ring, either or which may include bridging groups, where $R^{19}$ and $R^{20}$ are independently selected from hydrogen, pyrrolidine, piperazine, piperidine, $C_{1-6}$alkylcarbonyl, $C_{2-7}$alkenyl, optionally substituted $C_{1-7}$alkyl, or C(O)NHS$(O^2)R^{21}$ where $R^{21}$ is $C_{1-5}$alkyl, provided that when s is 1 and $R^9$ is a bond, $R^{10}$ is other than hydroxy, carboxy or a group $-NR^{19}R^{20}$.

In formula (IIB), optional substituents for $C_{1-7}$ alkyl groups $R^{19}$ and $R^{20}$ include at least one substituent selected from halogen, carboxyl, hydroxyl, $C_1$-$C_6$ alkylamino, di-$C_1$-$C_6$ alkylamino, $-NH(CH_2)_{2-4}OH$, $C_1$-$C_6$ alkoxy, $C_1$-$C_6$ alkylthio, $C_1$-$C_6$ alkoxycarbonyl, $-NR^{37}R^{38}$ and $-CONR^{38}R^{37}$, $-NR^{37}COR^{38}$ and an optionally substituted saturated or unsaturated 3- to 10-membered ring system which may comprise at least one ring heteroatom selected from nitrogen, oxygen and sulphur; where $R^{37}$ and $R^{38}$ are independently selected from hydrogen atom or a $C_1$-$C_6$ alkyl, $C_2$-$C_6$ hydroxyalkyl or $C_3$-$C_8$ cycloalkyl group, or $R^{37}$ and $R^{38}$ together with the nitrogen atom to which they are attached form a 3- to 8-membered saturated heterocyclic ring;

In formula (IIB), where $R^{19}$ and $R^{20}$ carries a substituent which is a ring system as described above, this is suitably optionally substituted by at least one substituent selected from halogen, hydroxyl, oxo, carboxyl, cyano, $C_1$-$C_6$ alkyl, $C_1$-$C_6$ hydroxyalkyl, $-(CH_2)_t NR^{22}R^{23}$, $-(CH_2)_t CONR^{24}R^{25}$, $-(CH_2)_t NR^{26}COR^{27}$, or $-(CH_2)_t R^{29}$ where $R^{22}$ and $R^{23}$ each independently represent a hydrogen atom or a $C_1$-$C_6$ alkyl, $C_2$-$C_6$ hydroxyalkyl or $C_3$-$C_8$ cycloalkyl group, or $R^{22}$ and $R^{23}$ together with the nitrogen atom to which they are attached form a 3- to 8-membered saturated heterocyclic ring;

$R^{24}$ and $R^{25}$ each independently represent a hydrogen atom or a $C_1$-$C_6$ alkyl, $C_2$-$C_6$ hydroxyalkyl or $C_3$-$C_8$ cycloalkyl group, or $R^{24}$ and $R^{25}$ together with the nitrogen atom to which they are attached form a 3- to 8-membered saturated heterocyclic ring;

$R^{26}$ and $R^{27}$ each independently represent a hydrogen atom or a $C_1$-$C_6$ alkyl, $C_2$-$C_6$ hydroxyalkyl or $C_3$-$C_8$ cycloalkyl group;

$R^{29}$ is aryl such as phenyl, and t is 0, 1, 2, 3, 4, 5 or 6.

In formula (IIB), where $R^{10}$ is an optionally substituted carbocyclic or an optionally substituted heterocyclic ring, suitable substituents include those listed above for ring substitutents on $R^{19}$ and $R^{20}$ as described in the paragraph above.

In formula (IIB), optional substituents for $C_{1-5}$alkylene groups $R^9$ include one or more substituents selected from hydroxyl, halogen, $C_1$-$C_6$ alkoxy, $C_1$-$C_6$ alkylthio, $C_1$-$C_6$ hydroxyalkyl, $C_1$-$C_6$ hydroxyalkyloxy, $C_1$-$C_6$ alkoxycarbonyl, $C_3$-$C_8$ cycloalkyl, phenyl (optionally substituted by at least one substituent selected from halogen, hydroxyl and $C_1$-$C_6$ alkylsulphonylamino), benzyl, indolyl (optionally substituted by at least one substituent selected from $C_1$-$C_6$ alkoxy), oxopyrrolidinyl, phenoxy, benzodioxolyl, phenoxyphenyl, piperidinyl and benzyloxy.

In formula (IIB), any hydroxyl groups will not normally be attached to a carbon atom adjacent a nitrogen atom. Further, when $R^9$ is other than a bond, the group $R^{10}$ may be attached to the $C_1$-$C_5$ alkyl moiety of $R^9$ at any suitable point; thus $R^{10}$ may be attached to an internal or terminal carbon atom of the $C_1$-$C_5$ alkyl moiety of $R^9$.

In formula (IIB), $R^{11}$ represents a hydrogen atom or a $C_1$-$C_5$ alkyl group which may be optionally substituted by at least one substituent (e.g. one, two or three substituents independently) selected from hydroxyl, halogen (e.g. fluorine, chlorine, bromine or iodine) and $C_1$-$C_6$, or $C_1$-$C_4$, alkoxy.

In an embodiment of the invention, in formula (IIB) $R^{11}$ represents a hydrogen atom or a $C_1$-$C_5$ alkyl group which may be optionally substituted by at least one hydroxyl group.

In formula (IIB), s is preferably 0.

In an embodiment of the invention, in formula (IIB) where s is 0, $R^9$ is a $C_{1-5}$ alkylene group such as methylene, and $R^{10}$ is a heterocyclic group such as a saturated nitrogen containing ring, for instance piperidine. In an alternative embodiment, in formula (IIB) s is 1 and $X^1$ is a group >$NR^{11}$ where $R^{11}$ is hydrogen or a $C_{1-5}$alkyl group such as methyl.

In formula (IIB), preferred groups $R^9$ include a bond or a $C_1$-$C_5$ alkyl group which may be optionally substituted by at least one substituent (e.g. one, two or three substituents independently) selected from hydroxyl, halogen (e.g. fluorine, chlorine, bromine or iodine), $C_1$-$C_6$, or $C_1$-$C_4$, alkoxy, $C_1$-$C_6$, or $C_1$-$C_4$, alkylthio, $C_1$-$C_6$, or $C_1$-$C_4$, hydroxyalkyl, $C_1$-$C_6$, or $C_1$-$C_4$, hydroxyalkyloxy, $C_1$-$C_6$, or $C_1$-$C_4$, alkoxycarbonyl, $C_3$-$C_8$ cycloalkyl, phenyl (optionally substituted by at least one substituent, e.g. one, two or three substituents independently, selected from halogen, hydroxyl and $C_1$-$C_6$, or $C_1$-$C_4$, alkylsulphonylamino), benzyl, indolyl (optionally substituted by at least one substituent, e.g. one, two or three substituents independently, selected from $C_1$-$C_6$, or $C_1$-$C_4$, alkoxy), oxopyrrolidinyl, phenoxy, 1,3-benzodioxolyl, phenoxyphenyl, piperidinyl and benzyloxy.

In an embodiment of the invention, in formula (IIB) $R^9$ represents a bond or a $C_1$-$C_4$ alkyl group which may be optionally substituted by one, two or three substituents independently selected from hydroxyl, $C_1$-$C_2$ alkoxy, methylthio, $C_1$-$C_2$ hydroxyalkyl, $C_1$-$C_2$ hydroxyalkyloxy, methoxycarbonyl, $C_3$-$C_6$ cycloalkyl, phenyl (optionally substituted by at least one substituent selected from halogen, hydroxyl and methylsulphonylamino), benzyl, indolyl (optionally substituted by at least one methoxy), oxopyrrolidinyl, phenoxy, benzodioxolyl, phenoxyphenyl, piperidinyl and benzyloxy.

In another embodiment of the invention, in formula (IIB) $R^9$ represents a bond or a $C_1$-$C_4$ alkyl group which may be optionally substituted by one, two or three substituents independently selected from hydroxyl, $C_1$-$C_2$ alkoxy, methylthio, $C_1$-$C_2$ hydroxyalkyl, $C_1$-$C_2$ hydroxyalkyloxy, methoxycarbonyl, cyclopropyl, phenyl (optionally substituted by at least one substituent selected from chlorine, hydroxyl and methylsulphonylamino), benzyl, indolyl (optionally substituted by at least one methoxy), oxopyrrolidinyl, phenoxy, benzodioxolyl, phenoxyphenyl, piperidinyl and benzyloxy.

In a preferred embodiment of the invention, in formula (IIB) $R^9$ represents a bond or a $C_{1-4}$alkyl group which is unsubstituted.

In an embodiment of the invention, in formula (IIB) $R^{10}$ represents hydrogen, hydroxyl, carboxy or a group —$NR^{19}R^{20}$.

In formula (IIB), preferably $R^{19}$ and $R^{20}$ each independently represent hydrogen, pyrrolidinyl, $C_1$-$C_6$, or $C_1$-$C_4$, alkylcarbonyl, $C_2$-$C_7$ alkenyl, or $C_1$-$C_7$ alkyl optionally substituted with at least one substituent (e.g. one, two, three or four substituents independently) selected from carboxyl, hydroxyl, $NR^{45}R^{46}$, $OR^{45}$, $SR^{45}$, $OC(O)R^{45}$ and $C(O)OR^{45}$ (where $R^{45}$ and $R^{46}$ are independently selected from hydrogen or $C_{1-6}$alkyl, and preferably $C_{1-4}$alkyl,) and a saturated or unsaturated 3- to 10-membered ring system which may comprise at least one ring heteroatom (e.g. one, two, three or four ring heteroatoms independently) selected from nitrogen, oxygen and sulphur, the ring system being optionally substituted by at least one substituent (e.g. one, two, three or four substituents independently) selected from halogen (e.g. fluorine, chlorine, bromine or iodine), hydroxyl, oxo, carboxyl, cyano, $C_1$-$C_6$, or $C_1$-$C_4$, alkyl, $C_1$-$C_6$, or $C_1$-$C_4$, hydroxyalkyl, —$NR^{22}R^{23}$, —$(CH_2)_tNR^{24}R^{25}$ and —$CONR^{26}R^{27}$, where $R^{22}$, $R^{23}$, $R^{24}$, $R^{25}$, $R^{26}$, $R^{27}$ and t are as defined above.

For instance, in formula (IIB) $R^{19}$ and $R^{20}$ each independently represent hydrogen, pyrrolidinyl, $C_1$-$C_2$ alkylcarbonyl, $C_5$-$C_7$ alkenyl, or $C_1$-$C_7$ alkyl optionally substituted with one or two substituents independently selected from carboxyl, hydroxyl, amino, $C_1$-$C_2$ alkylamino, di-$C_1$-$C_2$ alkylamino, —$NH(CH_2)_{2-4}OH$, $C_1$-$C_2$ alkoxy, $C_1$-$C_2$ alkylthio, $C_1$-$C_2$ alkoxycarbonyl, and a saturated or unsaturated 3- to 10-membered ring system which may comprise at least one ring heteroatom (e.g. one, two, three or four ring heteroatoms independently) selected from nitrogen, oxygen and sulphur, the ring system being optionally substituted by at least one substituent (e.g. one, two, three or four substituents independently) selected from fluorine, hydroxyl, oxo, carboxyl, cyano, $C_1$-$C_2$ alkyl, $C_1$-$C_2$ hydroxyalkyl, —$NR^{22}R^{23}$, —$(CH_2)_tNR^{24}R^{25}$ and —$CONR^{26}R^{27}$ where $R^{22}$, $R^{23}$, $R^{24}$, $R^{25}$, $R^{26}$, $R^{27}$ and t are as defined above.

Specific examples of $R^{19}$ and $R^{20}$ in formula (IIB) include hydrogen, pyrrolidinyl, methylcarbonyl, $C_7$ alkenyl, or $C_1$-$C_7$ alkyl optionally substituted with one or two substituents independently selected from carboxyl, hydroxyl, methylamino, di-methylamino, —$NH(CH_2)_2OH$, methylthio, $C_1$-$C_2$ alkoxycarbonyl, and a saturated or unsaturated 3- to 10-membered ring system which may comprise one, two or three ring heteroatoms independently selected from nitrogen, oxygen and sulphur, the ring system being optionally substituted by one or two substituents independently selected from fluorine, hydroxyl, oxo, $C_1$-$C_2$ alkyl and hydroxymethyl.

The saturated or unsaturated 3- to 10-membered ring system defined above in respect of $R^{19}$ and $R^{20}$ in formula (IIB), may be monocyclic or polycyclic (e.g. bicyclic) and may have alicyclic or aromatic properties. An unsaturated ring system will be partially or fully unsaturated. Examples of ring systems that may be used include cyclopropyl, cyclobutyl, cyclopentyl, cyclohexyl, cycloheptyl, cyclopentenyl, cyclohexenyl, bicyclo[2.2.1]hept-2-yl, bicyclo[2.2.1]hept-5-en-2-yl, homopiperazinyl, phenyl, 3,4-dihydro-2H-pyranyl, pyrrolidinyl, piperidinyl, piperazinyl, phenyl, pyrazolyl, thiazolidinyl, indanyl, thienyl, isoxazolyl, thiadiazolyl, pyrrolyl, furyl, thiazolyl, indolyl, imidazolyl, benzimidazolyl, triazolyl, tetrazolyl and pyridinyl.

In one aspect of the invention, the saturated or unsaturated 3- to 10-membered ring system of $R^{19}$ and $R^{20}$ in formula (IIB) is selected from cyclopropyl, cyclohexenyl, phenyl, thienyl, pyridinyl, furyl, bicyclo[2.2.1]hept-5-en-2-yl, 3,4-dihydro-2H-pyranyl, thiazolyl, pyrrolyl, pyrazolyl, imidazolyl and thiadiazolyl.

In formula (IIB), where $R^{10}$ is an optionally substituted carbocyclic or heterocyclic ring, it is preferably a saturated or unsaturated 4- to 9-membered ring system which is optionally substituted.

Optional substituents for where $R^{10}$ in formula (IIB) is an optionally substituted carbocyclic or heterocyclic ring, include those listed above for ring substituents on $R^{19}$ and $R^{20}$ i.e. at least one substituent selected from halogen, hydroxyl, oxo, carboxyl, cyano, $C_1$-$C_6$ alkyl, $C_1$-$C_6$ hydroxyalkyl, —$(CH_2)_tNR^{22}R^{23}$, —$(CH_2)_tCONR^{24}R^{25}$, —$(CH_2)_tNR^{26}COR^{27}$ or —$(CH_2)_tR^{29}$ where $R^{22}$ and $R^{23}$ each independently represent a hydrogen atom or a $C_1$-$C_6$ alkyl, $C_2$-$C_6$ hydroxyalkyl or $C_3$-$C_8$ cycloalkyl group, or $R^{22}$ and $R^{23}$ together with the nitrogen atom to which they are attached form a 3- to 8-membered saturated heterocyclic ring;

$R^{24}$ and $R^{25}$ each independently represent a hydrogen atom or a $C_1$-$C_6$ alkyl, $C_2$-$C_6$ hydroxyalkyl or $C_3$-$C_8$ cycloalkyl group, or $R^{24}$ and $R^{25}$ together with the nitrogen atom to which they are attached form a 3- to 8-membered saturated heterocyclic ring; $R^{26}$ and $R^{27}$ each independently represent a hydrogen atom or a $C_1$-$C_6$ alkyl, $C_2$-$C_6$ hydroxyalkyl or $C_3$-$C_8$ cycloalkyl group;

$R^{29}$ is aryl such as phenyl; and t is 0, 1, 2, 3, 4, 5 or 6.

Preferred optional substituents for $R^{10}$ in formula (IIB) include one or more groups selected from, amino, $C_1$-$C_6$ alkyl, $C_1$-$C_6$ alkylamino, —NH(CH$_2$)$_2$OH, —NH(CH$_2$)$_3$OH, $C_1$-$C_6$ hydroxyalkyl, benzyl and

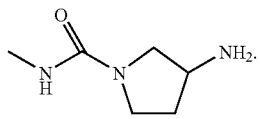

In formula (IIB) preferred rings $R^{10}$ are saturated or unsaturated 4- to 9-membered ring systems which may comprise one or two ring heteroatoms independently selected from nitrogen, oxygen and sulphur, the ring system being optionally substituted by at least one substituent (e.g. one, two, three or four substituents independently) selected from hydroxyl, amino (—NH$_2$), $C_1$-$C_2$ alkyl, $C_1$-$C_2$ alkylamino, —NH(CH$_2$)$_2$ OH, —NH(CH$_2$)$_3$OH, $C_1$-$C_2$ hydroxyalkyl, benzyl and

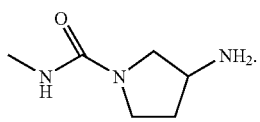

In formula (IIB), when $R^{10}$ represents a saturated or unsaturated 4- to 9-membered ring system, the ring system may be monocyclic or polycyclic (e.g. bicyclic) and may have alicyclic or aromatic properties. An unsaturated ring system will be partially or fully unsaturated. Examples of ring systems that may be used include cyclobutyl, cyclopentyl, cyclohexyl, cycloheptyl, cyclopentenyl, cyclohexenyl, bicyclo[2.2.1]hept-2-yl, bicyclo[2.2.1]hept-5-en-2-yl, 2,3-dihydro-1H-indenyl, homopiperazinyl, phenyl, pyrrolidinyl, piperidinyl, piperazinyl, pyrazolyl, thiazolidinyl, indanyl, thienyl, isoxazolyl, thiadiazolyl, pyrrolyl, furyl, thiazolyl, indolyl, imidazolyl, benzimidazolyl, triazolyl, tetrazolyl and pyridinyl.

In one embodiment of the invention, in formula (IIB) the saturated or unsaturated 4- to 9-membered ring system $R^{10}$ is selected from cyclobutyl, cyclohexyl, bicyclo[2.2.1]hept-2-yl, 2,3-dihydro-1H-indenyl, pyrrolidinyl, piperidinyl and piperazinyl.

Particular examples of heterocyclic rings $R^{10}$ in formula (IIB) are groups of formula NR$^{33}$R$^{34}$ where R$^{33}$ and R$^{34}$ together with the nitrogen atom to which they are attached forms a $C_{4-9}$ heterocyclic ring which may contain additional heteroatoms and which may be optionally substituted, and may optionally contain bridging groups. Examples of such groups $R^{10}$ in formula (IIB) are groups of formula (iii), (iv), (v) and (vi)

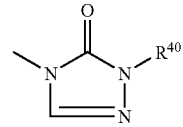

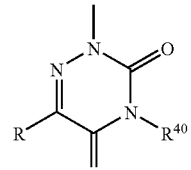

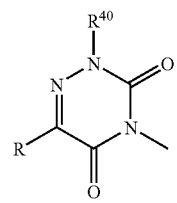

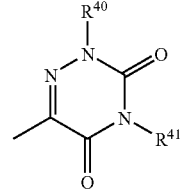

where $R^{40}$ and $R^{41}$ are hydrogen or substituent groups as defined herein, and in particular are independently selected from hydrogen and $C_{1-6}$alkyl.

In formula (IIB), when $R^{10}$ is a group NR$^{33}$R$^{34}$, it is preferably a saturated five or six-membered heterocyclic ring which may comprise a second ring heteroatom selected from nitrogen and oxygen. The ring is optionally substituted for example with at least one substituent selected from those listed above for ring substitutents on $R^{19}$ and $R^{20}$.

Particular substituents however include hydroxyl, halogen, $C_1$-$C_6$ alkyl, amino, mono or di-$C_{1-4}$alkylamino and hydroxy$C_1$-$C_6$alkyl.

In another embodiment of the invention, when $R^{10}$ in formula (IIB) is NR$^{33}$R$^{34}$, R$^{33}$ and R$^{34}$ together with the nitrogen atom to which they are attached may form a saturated five or six-membered heterocyclic ring which may comprise a second ring heteroatom selected from nitrogen and oxygen, and may further comprise bridging groups; the ring being optionally substituted by at least one substituent (e.g. one, two, three or four substituents independently) selected from hydroxyl, amino, mono- or di-$C_{1-4}$alkylamino, hydroxy$C_{1-3}$alkylamino, halogen (e.g. fluorine, chlorine, bromine or iodine), $C_1$-$C_6$, or $C_1$-$C_4$, alkyl and $C_1$-$C_6$, or $C_1$-$C_4$, hydroxyalkyl. Examples of heterocyclic rings that may be formed include piperidinyl, piperazinyl and morpholinyl.

Where in formula (IIB) is $R^{10}$ is a group NR$^{33}$R$^{34}$ wherein R$^{33}$ and R$^{34}$ together with the nitrogen atom to which they are attached may form a saturated five or six-membered heterocyclic ring which includes bridging groups, these preferably form a fused 5/6 membered ring system such as a diazabicyclo[2.2.1]hept-2-yl group.

For instance, where in formula (IIB) is $R^{10}$ is a group NR$^{33}$R$^{34}$, R$^{33}$ and R$^{34}$ together with the nitrogen atom to which they are attached may form a saturated five or six-membered heterocyclic ring which may comprise a second ring heteroatom selected from nitrogen and oxygen, the ring being optionally substituted by one or two substituents independently selected from, amino, hydroxy, hydroxy$C_{1-3}$alkylamino, $C_1$-$C_2$ alkyl and $C_1$-$C_2$ hydroxyalkyl.

In a preferred embodiment of the invention, in formula (IIB) where s is 0, $R^9$ is a bond and $R^{10}$ is a group $NR^{33}R^{34}$ where $R^{33}$ and $R^{34}$ together with the nitrogen atom to which they are attached form a saturated five or six-membered heterocyclic ring optionally substituted as described above.

In formula (IB), preferred $R^{22}$ and $R^{23}$ groups are independently hydrogen atom or a $C_1$-$C_6$, or $C_1$-$C_4$, alkyl, $C_2$-$C_6$, or $C_2$-$C_4$, hydroxyalkyl or $C_3$-$C_8$, or $C_5$-$C_6$, cycloalkyl group, or $R^{22}$ and $R^{23}$ together with the nitrogen atom to which they are attached form a 3- to 8-membered saturated heterocyclic ring (e.g. pyrrolidinyl or piperidinyl).

In formula (IIB), $R^{24}$ and $R^{25}$ preferably each independently represent a hydrogen atom or a $C_1$-$C_6$, or $C_1$-$C_4$, alkyl, $C_2$-$C_6$, or $C_2$-$C_4$, hydroxyalkyl or $C_3$-$C_8$, or $C_5$-$C_6$, cycloalkyl group, or $R^{24}$ and $R^{25}$ together with the nitrogen atom to which they are attached form a 3- to 8-membered saturated heterocyclic ring (e.g. pyrrolidinyl or piperidinyl).

In formula (IIB), $R^{26}$ and $R^{27}$ each independently represent a hydrogen atom or a $C_1$-$C_6$, or $C_1$-$C_4$, alkyl, $C_2$-$C_6$, or $C_2$-$C_4$, hydroxyalkyl or $C_3$-$C_8$, or $C_5$-$C_6$, cycloalkyl group, or $R^{26}$ and $R^{27}$ together with the nitrogen atom to which they are attached form a 3- to 8-membered saturated heterocyclic ring (e.g. pyrrolidinyl or piperidinyl).

In a preferred embodiment of the present invention, $R^3$ in formula (IB) is a group of sub-formula (ii) or (ii)

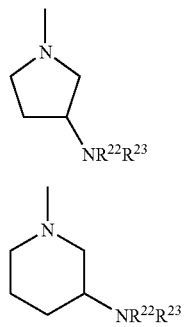

Particular compounds of the present invention according to formula (IB) are as follows:

N-[6-Chloro-2-(4-piperidinylmethyl)-5-quinolinyl]-cyclohexaneacetamide, dihydrochloride;
N-[6-Chloro-2-(1-piperazinyl)-5-quinolinyl]-cyclohexaneacetamide, dihydrochloride;
N-[6-Chloro-2-[methyl[3-(methylamino)propyl]amino]-5-quinolinyl]-cyclohexaneacetamide, dihydrochloride;
6-Chloro-N-(cyclohexylmethyl)-2-methyl-5-quinolinecarboxamide, hydrochloride;
N-[6-Chloro-2-[(3-hydroxypropyl)amino]-5-quinolinyl]-cyclohexaneacetamide, hydrochloride;
N-[6-Chloro-2-[[(2R)-2,3-dihydroxypropyl]amino]-5-quinolinyl]-cyclohexaneacetamide;
4-[[6-Chloro-5-[(cyclohexylacetyl)amino]-2-quinolinyl]amino]-butanoic acid;
N-[6-Chloro-2-[methyl[3-(methylamino)propyl]amino]-5-quinolinyl]-4-(trifluoromethyl)-cyclohexaneacetamide, dihydrochloride;
N-[6-Chloro-2-(1-piperazinyl)-5-quinolinyl]-4-(trifluoromethyl)-cyclohexaneacetamide;
N-[6-Chloro-2-(hexahydro-1H-1,4-diazepin-1-yl)-5-quinolinyl]-cyclohexaneacetamide;
N-[6-Chloro-2-[(cis-3,5-dimethyl-1-piperazinyl]-5-quinolinyl]-cyclohexaneacetamide;
N-[6-Chloro-2-(4-methyl-1-piperazinyl)-5-quinolinyl]-cyclohexaneacetamide, dihydrochloride;
N-[6-Chloro-2-[(1S,4S)-2,5-diazabicyclo[2.2.1]hept-2-yl]-5-quinolinyl]-cyclohexaneacetamide, acetate;
N-[6-Chloro-2-[(3R)-3-pyrrolidinylamino]-5-quinolinyl]-cyclohexaneacetamide, dihydrochloride;
N-[2-[3-(Ethylamino)propyl]-6-methyl-5-quinolinyl]-cyclohexaneacetamide, dihydrochloride;
N-[6-Chloro-2-[3-(ethylamino)propyl]-5-quinolinyl]-cyclohexaneacetamide, dihydrochloride;
N-[6-Chloro-2-[[2-[(2-hydroxyethyl)amino]ethyl]amino]-5-quinolinyl]-cyclohexaneacetamide, dihydrochloride;
N-5-Quinolinyl-cyclohexaneacetamide;
1-Methyl-N-5-quinolinyl-cyclohexaneacetamide;
4-Methyl-N-5-quinolinyl-cyclohexaneacetamide;
N-5-Quinolinyl-cyclopentanepropanamide;
N-[6-Chloro-2-[3-[(3-hydroxypropyl)amino]propyl]-5-quinolinyl]-cyclohexaneacetamide;
N-[2-(3-Aminopropyl)-6-chloro-5-quinolinyl]-cyclohexaneacetamide;
N-[6-Chloro-2-[3-[[[(methylsulfonyl)amino]carbonyl]amino]propyl]-5-quinolinyl]-cyclohexaneacetamide;
N-[2-[3-(Butylamino)propyl]-6-chloro-5-quinolinyl]-cyclohexaneacetamide dihydrochloride;
N-[6-Chloro-2-[methyl[3-(methylamino)propyl]amino]-5-quinolinyl]-1-cyclohexyl-cyclopropanecarboxamide, hydrochloride;
N-[6-Chloro-2-(1-piperazinyl)-5-quinolinyl]-1-cyclohexyl-cyclopropanecarboxamide;
N-[6-Chloro-2-[(3R)-3-hydroxy-1-pyrrolidinyl]-5-quinolinyl]-cyclohexaneacetamide;
N-[6-Chloro-2-[(3S)-3-hydroxy-1-pyrrolidinyl]-5-quinolinyl]-cyclohexaneacetamide;
N-[2-[(3R)-3-Amino-1-pyrrolidinyl]-6-chloro-5-quinolinyl]-cyclohexaneacetamide;
N-[2-[(3S)-3-Amino-1-pyrrolidinyl]-6-chloro-5-quinolinyl]-cyclohexaneacetamide;
N-[2-(4-Amino-1-piperidinyl)-6-chloro-5-quinolinyl]-cyclohexaneacetamide;
N-[6-Chloro-2-[(3R)-3-(methylamino)-1-pyrrolidinyl]-5-quinolinyl]-cyclohexaneacetamide;
N-[6-Chloro-2-[(3R)-3-[(2-hydroxyethyl)amino]-1-pyrrolidinyl]-5-quinolinyl]-cyclohexaneacetamide;
N-[6-Chloro-2-[(3S)-3-(methylamino)-1-pyrrolidinyl]-5-quinolinyl]-cyclohexaneacetamide;
N-[6-Chloro-2-[(3S)-3-[(2-hydroxyethyl)amino]-1-pyrrolidinyl]-5-quinolinyl]-cyclohexaneacetamide;
N-[6-Chloro-2-[(3R)-3-hydroxy-1-piperidinyl]-5-quinolinyl]-cyclohexaneacetamide;
N-[2-[(3S)-3-Amino-1-pyrrolidinyl]-6-methyl-5-quinolinyl]-cyclohexaneacetamide;
N-[6-Methyl-2-(1-piperazinyl)-5-quinolinyl]-cyclohexaneacetamide;
N-[6-Chloro-5-[(cyclohexylacetyl)amino]-2-quinolinyl]-glycine;
N-[6-Chloro-5-[(cyclohexylacetyl)amino]-2-quinolinyl]-β-alanine; and
6-Chloro-N-(cyclohexylmethyl)-2-(1-piperazinyl)-5-quinolinecarboxamide, dihydrochloride.

Suitable pharmaceutically acceptable salts of compounds of formula (IB) include base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulphonate, fumarate, hydrochloride, hydrobromide, citrate, maleate and salts formed with phosphoric and sulphuric acid. There may be more than one cation or anion depending on the number of charged functions and the valency of the cations or anions. A preferred pharmaceutically acceptable salt is a hydrochloride salt.

Suitable prodrugs of compounds of formula (IB) are compounds which are hydrolysed in vivo to form compounds of formula (IB). Thus for example where compounds of formula (IB) include a carboxy group, these may be in the form of pharmaceutically acceptable esters or amides.

Suitable pharmaceutically acceptable esters of formula (IB) for carboxy groups include $C_{1-6}$alkyl esters, for example methyl or ethyl; $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; $C_{1-6}$alkoxycarbonyloxyethyl esters, for example 1-methoxycarbonyloxyethyl; aminocarbonylmethyl esters and mono- or di-N—($C_{1-6}$alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include $C_{1-6}$alkanoyl esters, for example acetyl esters; and benzoyl esters wherein the phenyl group may be substituted with aminomethyl or N-substituted mono- or di-$C_{1-6}$alkyl aminomethyl, for example 4-aminomethylbenzoyl esters and 4-N,N-dimethylaminomethylbenzoyl esters.

Pharmaceutically acceptable amides are similarly in-vivo hydrolysable to yield the parent acid, and include $C_{1-6}$alkylamides such as acetamide.

The present invention further provides a process for the preparation of a compound of formula (IB) as defined above, or a pharmaceutically acceptable salt, prodrug or solvate thereof, which comprises either:

(a) reacting a compound of formula (IVB)

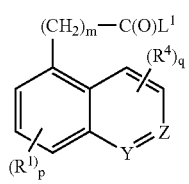

(IVB)

wherein $L^1$ represents a leaving group (e.g. hydroxyl or halogen) and Y, Z, $R^1$, $R^4$, m, p and q are as defined in formula (IB), with a compound of formula (VB), $$H_2N—(CR^5R^6)_n—R^2 \quad (VB)$$

$R^2$, $R^5$, $R^6$ and n are as defined in formula (IB); or (b) reacting a compound of formula (VIB)

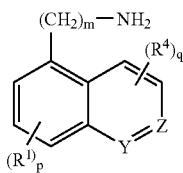

(VIB)

wherein Y, Z, $R^1$, $R^4$, m, p and q are as defined in formula (IB), with a compound of formula (VIIB)

$$L^2C(O)—(CR^5R^6)_n—R^2 \quad (VIIB)$$

wherein $L^2$ represents a leaving group (e.g. hydroxyl or halogen) and $R^2$, $R^5$, $R^6$ and n are as defined in formula (IB); or (c) when Y is N and Z is $CR^3$, and $R^3$ represents a group of formula (IIB) above where s is 1 and X is $>NR^{11}$, reacting a compound of formula (VIIIB)

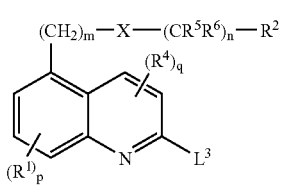

(VIIIB)

wherein $L^3$ is a leaving group (e.g. halogen, paratoluene sulphonate or methane sulphonate), and all other variables are as defined in relation to formula (IB), with a compound of formula (IXB), H—N($R^{11}$)—$R^9$-$R^{10}$, wherein $R^9$, $R^{10}$ and $R^{11}$ are as defined in formula (IIB); or (d) when Y is N and Z is $CR^3$, and $R^3$ is a group $R^7$ where $R^7$ is optionally substituted $C_3$-$C_{10}$ alkyl group, reacting a compound of formula (VIIIB) as defined in (c) above with a compound of formula (XB) or (XIB)

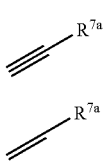

(X)

(XI)

wherein $R^{7a}$ represents a $C_1$-$C_7$ alkyl group optionally substituted as defined for $R^7$ in formula (IB), optionally followed by a hydrogenation reaction; or (e) when Y is N and Z is $CR^3$, and $R^3$ is a group of formula (IIB) where s is 0, $R^9$ is $(CH_2)_2$ and $R^{10}$ is —$NR^{19}R^{20}$, reacting a compound of formula (VIIB) as defined in (c) above with a compound of formula (XIIB)

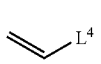

(XIIB)

wherein L⁴ is a leaving group (eg. trialkyltin, dialkylboron or zinc), followed by reaction with a compound of formula (XIIIB), HNR¹⁹R²⁰, wherein R¹⁹ and R²⁰ are as defined above;

(f) when Y is N and Z is CR³, and R³ is a group of formula (IIB) where s is 0, R⁹ is (CH₂) and R¹⁰ is —NR¹⁹R²⁰, reacting a compound of formula (VIIIB) as defined in (c) above with a compound of formula (XIIB) as defined in (e) above, followed by an oxidation reaction and then by reaction with a compound of formula (XIIIB) as defined in (e) above under reductive amination conditions; or (g) when Y is N and Z is CR³, and R³ is a group of formula (IIB) where s is 0, reacting a compound of formula (VIIIB) as defined in (c) above with a compound of formula (XIVB)

(XIVB)

wherein R⁹' is suitably defined such that saturation of the alkene and combination with R⁹' gives a group of formula R⁹ as defined in formula (IIB) and R¹⁰ is as defined in formula (IIB), followed by removal of any protecting groups;

and optionally after (a), (b), (c), (d), (e), (f) or (g) carrying out one or more of the following:
  converting the compound obtained to a further compound of the invention
  forming a pharmaceutically acceptable salt, prodrug or solvate of the compound.

In processes (a) and (b) the coupling reaction is conveniently carried out in an organic solvent such as dichloromethane, N,N-dimethylformamide or 1-methyl-2-pyrrolidinone. If L¹ or L² represent a hydroxyl group, it may be necessary or desirable to use a coupling agent such as bromo-tris-pyrrolidino-phosphonium hexafluorophosphate (PyBroP).

In process (c) the reaction may be performed in an organic solvent such as acetonitrile, N,N-dimethylformamide or 1-methyl-2-pyrrolidinone, and in the presence of a suitable base such as sodium hydride, triethylamine or potassium carbonate.

In process (d), if the compound of formula (VIIIB) is reacted with a compound of formula (XB), then the reaction is conveniently carried out in an organic solvent such as acetonitrile, e.g. at ambient temperature (20° C.), in the presence of catalytic bistriphenylphosphine dichloride palladium (0), copper (I) iodide and a base (e.g. triethylamine). The subsequent hydrogenation reaction may use hydrogen gas with a catalyst such as 5% rhodium on carbon in a solvent, for example, ethyl acetate or ethanol, and at a pressure of 3 bar.

Alternatively, if the compound of formula (VIIIB) is reacted with a compound of formula (XIB), then it is preferred if the compound of formula (XIB) is pre-treated by reaction with a hydroborating reagent (e.g. 9-borabicyclo [3.3.1]nonane or catecholborane) in an organic solvent such as diethyl ether or tetrahydrofuran at a temperature in the range from, e.g. 0° C. to 80° C., in particular from 60° C. to 70° C., for about 2 to 3 hours. The pre-treated compound is then reacted with the compound of formula (VIIIB) in the presence of a suitable base (e.g. sodium hydroxide or tri-potassium orthophosphate) and a palladium catalyst (e.g. dichloro[1,1'-bis(diphenylphosphino)ferrocene]palladium (II) dichloromethane adduct), typically at a temperature in the range from 25° C. to 90° C., particularly from 60° C. to 70° C., for about 2 to 24 hours.

In process (e), the reaction with the vinyl compound of formula (XIIB) may conveniently be carried out in a solvent such as N,N-dimethylformamide and in the presence of catalytic dichlorobis(triphenylphosphine)palladium, at elevated temperature, e.g. at about 70° C. The subsequent addition reaction with the compound of formula (XIIIB) may be performed under acidic or basic conditions, for example, in acetic acid in a solvent such as methanol or isopropanol at elevated temperature, e.g. at about 100° C.

In process (f), the reaction of the vinyl compound of formula (XVIIIB) may be performed by procedures analogous to those outlined in the previous paragraph on process (e). The subsequent oxidation reaction may be carried out under standard conditions, for example, by using ozone followed by treatment with dimethylsulfide or triphenylphosphine in a suitable solvent such as dichloromethane, or, by using osmium tetroxide and sodium periodate in a suitable solvent such as 1,4-dioxane and water. The reductive amination step may be conveniently carried out in the presence of a reducing agent such as sodium cyanoborohydride, triacetoxyborohydride or sodium borohydride, in a polar solvent such as methanol, ethanol or dichloromethane either alone or in combination with acetic acid.

In process (g), the compound of formula (XIVB) is pre-treated by reaction with a hydroborating reagent (such as 9-borabicyclo[3.3.1]nonane or catecholborane) in a solvent (such as diethyl ether or tetrahydrofuran) at a temperature in the range from 0° C. to 80° C. (in particular from 60° C. to 70° C.) for about 2 to 3 hours, then cooling the reaction mixture to room temperature and adding a solution of a base (such as sodium hydroxide in water or tri-potassium orthophosphate in water) followed by a solution of the compound of formula (VIII) in a solvent (such as N,N-dimethylformamide) and a palladium catalyst (such as tetrakis(triphenylphosphine)palladium (II)). The resulting reaction mixture is stirred at a temperature in the range from 25° C. to 90° C. (particularly from 60° C. to 70° C.) for about 2 to 24 hours to yield the desired compounds of formula (IB).

Compounds of formulae (IVB), (VB), (VIB), (VIIB), (IXB), (XB), (XIB), (XIIB), (XIIIB) and (XIVB) are either commercially available, are known in the literature or may be prepared using known techniques.

Compounds of formula (VIIIB) are novel compounds and form a further aspect of the invention. Examples of preparation methods for certain of these compounds are given hereinafter in the examples. Other examples can be prepared by analogous methods. In particular, compounds of formula (VIIIB) or analogues where Y is CL³ and Z is N can be prepared by either (i) reacting a compound of formula (XVB)

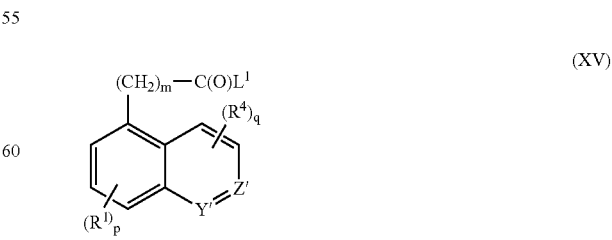

(XV)

wherein L¹ represents a leaving group (e.g. hydroxyl or halogen) and R¹, R⁴, m, p and q are as defined in formula (IB), and one of Y' or Z' is N and the other is a group CL³ where L³ is as defined in relation to formula (VIIIB), with a compound of formula (VB) as defined above;

(ii) reacting a compound of formula (XVIB)

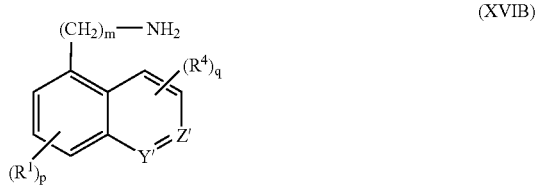

wherein $R^1$, $R^4$, m, p and q are as defined in formula (IB), Y' and Z' are as defined in relation to formula (XVB) with a compound of formula (VIIB) as defined above. Reaction conditions analogous to those described above in relation to steps (a) and (b) are suitably employed.

Compounds of formula (XVB) and (XVIB) are either commercially available, are known in the literature or may be prepared using known techniques.

Compounds of formula (IB) can be converted into further compounds of formula (IB) using standard procedures. For example, compounds of formula (IB) in which $R^2$ represents a halogen atom may be converted to a corresponding compound of formula (IB) in which $R^2$ represents a $C_1$-$C_6$ alkyl group by reaction with an alkyl Grignard reagent (e.g. methyl magnesium bromide) in the presence of a catalyst such as [1,3-bis(diphenylphosphino)propane]dichloronickel (II) in a solvent such as tetrahydrofuran.

In a further example of the conversion of a compound of formula (IB) to another compound of formula (IB); a compound of formula (IB) where the group $NR^{13}R^{14}$ represents $NH_2$ may be converted into another compound of formula (IB) wherein $R^{13}$ represents H and $R^{14}$ is as defined in formula (IIIB), by treatment with an appropriate aldehyde (for example a suitably protected hydroxyl-acetaldehyde) in a reductive amination reaction. Suitable reducing agents include sodium cyanoborohydride, triacetoxyborohydride or sodium borohydride and the reaction may be carried out in a polar solvent such as methanol, ethanol or dichloromethane either alone or in combination with acetic acid.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (IB) above may involve, at various stages, the addition and removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (IB) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt. Other pharmaceutically acceptable salts, as well as prodrugs such as pharmaceutically acceptable esters and pharmaceutically acceptable amides may be prepared using conventional methods.

The compounds of the present invention are advantageous in that they possess pharmacological activity. They are therefore indicated as pharmaceuticals for use in the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, inflammatory bowel disease, Crohn's disease, ulcerative colitis, atherosclerosis, growth and metastases of malignant cells, myoblastic leukaemia, diabetes, Alzheimer's disease, meningitis, osteoporosis, burn injury, ischaemic heart disease, stroke, varicose veins, sarcoidosis, rhinitis, acute and chronic pain, multiple sclerosis, myeloma, bone loss associated with malignancy and inflammatory and neurodegenerative diseases of the eye such as scleritis, episcleritis, uveitis, Sjogrens syndrome-keratoconjuctivitis, sclerokeratitis, optic neuritis, diabetic retinopathy, retinitis pigmentosa, antimalarial-induced retinopathy.

Accordingly, the present invention provides a compound of formula (IA) and/or (IB) or a pharmaceutically acceptable salt, prodrug or solvate thereof, as hereinbefore defined for use in therapy.

In another aspect, the invention provides the use of a compound of formula (IA) and/or (IB) or a pharmaceutically acceptable salt, prodrug or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of effecting immunosuppression (e.g. in the treatment of rheumatoid arthritis, osteoarthritis, irritable bowel disease, atherosclerosis or psoriasis) which comprises administering a therapeutically effective amount of a compound of formula (IA) and/or (IB) or a pharmaceutically acceptable salt or solvate thereof, as hereinbefore defined to a patient.

The invention also provides a method of treating an obstructive airways disease (e.g. asthma or COPD) which comprises administering to a patient a therapeutically effective amount of a compound of formula (IA) and/or (IB) or a pharmaceutically acceptable salt or solvate thereof, as hereinbefore defined to a patient.

For the above-mentioned therapeutic uses the dosage administered will, of course, vary with the compound employed, the mode of administration, the treatment desired and the disorder indicated. The daily dosage of the compound of formula (IA) and/or (IB))/salt/solvate (active ingredient) may be in the range from 0.001 mg/kg to 30 mg/kg.

The compounds of formula (IA) and/or (IB) and pharmaceutically acceptable salts, prodrug and solvates thereof may be used on their own but will generally be administered in the form of a pharmaceutical composition in which the formula (IA) and/or (IB) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (IA) and/or (IB) or a pharmaceutically acceptable salt or solvate thereof, as hereinbefore defined in association with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention further relates to combination therapies for the treatment of any one of rheumatoid arthritis, osteoarthritis, osteoporosis, psoriasis, inflammatory bowel diseases, COPD, asthma, allergic rhinitis or cancer or the neurodegenerative diseases such as multiple sclerosis, Alzheimer's disease or stroke.

For the treatment of rheumatoid arthritis, the compounds of the invention may be combined with "biological agents" such as TNF-α inhibitors such as anti-TNF monoclonal antibodies (such as Remicade, CDP-870 and Humira) and TNF receptor immunoglobulin molecules (such as Enbrel.reg.). IL-1 receptor antagonist (such as Anakinra) and IL-1 trap, IL-18 receptor, anti-IL-6 Ab, anti-CD20 Ab, anti-IL-15 Ab and CTLA4Ig.

Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin. The COX-2 inhibitors (such as meloxicam, celecoxib, rofecoxib, valdecoxib and etoricoxib) and the cylco-oxygenase inhibiting nitric oxide donors (CINOD's) and the "disease modifying agents" (DMARDs) such as methotrexate, sulphasalazine, cyclosporine A, lefunomide; ciclesonide; hydroxychloroquine, d-penicillamine, auranofin or parenteral or oral gold.

The present invention still further relates to the combination of a compound of the invention together with a leukotriene biosynthesis inhibitor, 5-lipoxygenase (5-LO) inhibitor or 5-lipoxygenase activating protein (FLAP) antagonist selected from the group consisting of zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2n cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonists for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic $H_1$ receptor antagonists including cetirizine, loratadine, desloratadine, fexofenadine, astemizole, azelastine, and chlorpheniramine.

The present invention still further relates to the combination of a compound of the invention together with a gastroprotective $H_2$ receptor antagonist or the proton pump inhibitors (such as omeprazole)

The present invention still further relates to the combination of a compound of the invention together with an $\alpha_1$- and $\alpha_2$-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents including ipratropium bromide; tiotropium bromide; oxitropium bromide; pirenzepine; and telenzepine.

The present invention still further relates to the combination of a compound of the invention together with a $\beta_1$- to $\beta_4$-adrenoceptor agonists including metaproterenol isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the invention together with an insulin-like growth factor type I (IGF-1) mimetic.

The present invention still further relates to the combination of compound of the invention together with an inhaled glucocorticoid with reduced systemic side effects, including prednisone, prednisolone, flunisolide, triamcinolone acetonide, beclomethasone dipropionate, budesonide, fluticasone propionate, and mometasone furoate.

The present invention still further relates to the combination of a compound of the invention together with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; (j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists selected from the group consisting of NKP-608C; SB-233412 (talnetant); and D-4418; and (t) elastase inhibitors selected from the group consisting of UT-77 and ZD-0892 (u) induced nitric oxide synthase inhibitors (iNOS) or (v) chemoattractant receptor-homologous molecule expressed on TH2 cells, (CRTH2 antagonists).

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, induced nitric oxide synthase inhibitors (iNOS inhibitors), COX-2 inhibitors such as celecoxib, valdecoxib, rofecoxib and etoricoxib, and the cylco-oxygenase inhibiting nitric oxide donors (CINOD's) analgesics (such as paracetamol and tramadol), cartilage sparing agents such as diacerein, doxycyline and glucosamine, and intra-articular therapies such as corticosteroids and hyaluronic acids such as hyalgan and synvisc.

The compounds of the invention can also be used in combination with existing therapeutic agents for the treatment of inflammatory bowel diseases (Ulcerative colitis and Crohn's disease). Suitable agents to be used include sulphasalazine, 5-amino-salicylates, the thiopurines, azathioprine and 6-mecaptorurine and corticosteroids such as budesonide.

The compounds of the present invention may also be used in combination with anticancer agents such as endostatin and angiostatin or cytotoxic drugs such as adriamycin, daunomycin, cis-platinum, etoposide, taxol, taxotere and farnesyl transferase inhibitors, VegF inhibitors, COX-2 inhibitors and antimetabolites such as methotrexate, antineoplastic agents, especially antimitotic drugs including the vinca alkaloids such as vinblastine and vincristine.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The present invention will now be further explained by reference to the following illustrative examples. In the examples the NMR spectra were measured on a Varian Unity spectrometer at a proton frequency of either 300 or 400 MHz. The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® column using 0.1% aqueous trifluoroacetic acid:acetonitrile, 0.1% aqueous ammonia:acetonitrile or 0.1% ammonium acetate:acetonitrile as the eluent.

The present invention will now be further explained by reference to the following illustrative examples. In the examples the NMR spectra were measured on a Varian Unity spectrometer at a proton frequency of either 300 or 400 MHz. The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® column using 0.1% aqueous trifluoroacetic acid:acetonitrile, 0.1% aqueous ammonia:acetonitrile or 0.1% ammonium acetate:acetonitrile as the eluent. Microwave reactions were performed in a CEM Discover single mode microwave.

EXAMPLE 1

N-[6-Chloro-2-(4-piperidinylmethyl)-5-quinolinyl]-cyclohexaneacetamide, Dihydrochloride

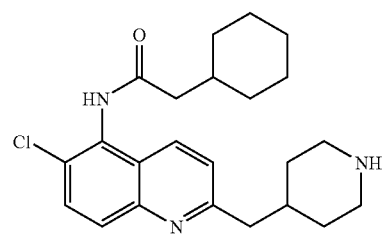

a)
N-(2,6-Dichloro-5-quinolinyl)-cyclohexaneacetamide

To a stirred solution of 2,6-dichloroquinolin-5-amine (prepared as described in (d) below) (1 g) in N-methylpyrrolidinone (12 mL) was added 4-N,N-dimethylaminopyridine (1.2 g), cyclohexaneacetic acid (1 g) and PyBroP (4.4 g). The reaction mixture was heated to 50° C. for 10 hours. The mixture was cooled to room temperature and poured into water (10 mL) which was subsequently acidified to pH1 with aqueous 2M hydrochloric acid. The resulting solution was extracted with dichloromethane (3×20 mL). The combined organic extracts were dried, filtered and partially concentrated to give a white precipitate which was removed by filtration. Purification by chromatography ($SiO_2$, methanol:dichloromethane 1:10 as eluant) gave the sub-title compound (490 mg).

$^1$H NMR (400 MHz, $d_6$-DMSO) δ 10.07 (1H, s), 8.25 (1H, d), 7.94 (2H, s), 7.70 (1H, d), 2.37 (2H, d), 1.83-1.63 (6H, m), 1.33-1.00 (5H, m).

MS: APCI(+ve) 337/339 (M+H$^+$).

b) 4-[[6-Chloro-5-[(cyclohexylacetyl)amino]-2-quinolinyl]methyl]-1-piperidinecarboxylic acid, 1,1-dimethylethyl Ester 9-Borabicyclo[3.3.1]nonane dimer solution (3.5 mL, 2M in tetrahydrofuran) was added to 4-methylene-1-piperidinecarboxylic acid, 1,1-dimethylethyl ester (prepared according to the method of Journal of Medicinal Chemistry 2002, 45, 3143) (345 mg) at room temperature under nitrogen. The mixture was refluxed for 3 hours after which it was cooled to room temperature. Potassium phosphate (1 g) in water (1 mL) was added and the mixture stirred for 30 minutes. N-(2,6-Dichloro-5-quinolinyl)-cyclohexaneacetamide (Example 1 (a)) (300 mg) in N,N-dimethylformamide (2 mL) was added followed by tetrakis(triphenylphosphine)palladium(0) (20 mg). The reaction mixture was heated to 80-90° C. for 4 hours under nitrogen. On cooling to room temperature the reaction mixture was filtered through diatomaceous earth and the tetrahydrofuran removed under vacuum. The resulting mixture was poured into water and extracted with ethyl acetate. The combined organic extracts were dried, filtered and evaporated. Purification ($SiO_2$, ethyl acetate:isohexane 20:80 as eluant) gave the sub-titled compound (200 mg).

MS: APCI(+ve) 500/502 (M+H$^+$).

c) N-[6-Chloro-2-(4-piperidinylmethyl)-5-quinolinyl]-cyclohexaneacetamide, Dihydrochloride 4-[[6-Chloro-5-[(cyclohexylacetyl)amino]-2-quinolinyl]methyl]-1-piperidinecarboxylic acid, 1,1-dimethylethyl ester (Example 1(b)) was dissolved in methanol (0.5 mL) and dichloromethane (3 mL). HCl in 1,4-dioxane (4M, 1 mL) was added and the mixture stirred for 1 hour. The resultant suspension was evaporated to dryness and recrystallised from methanol/ethyl acetate to give the title compound as a colourless solid (120 mg).

$^1$H NMR (400 MHz, CD$_3$OD) δ 8.89 (1H, d), 8.25 (2H, s), 8.08 (1H, d), 3.42 (2H, m), 3.01 (2H, dt), 2.52 (2H, d), 2.35 (1H, m), 2.00-1.84 (6H, m), 1.82-1.60 (6H, m), 1.43-1.09 (5H, m).

MS: APCI(+ve) 400/402 (M+H$^+$).

m.p. 170-175° C.

d) 2,6-Dichloroquinolin-5-amine

6-Chloro-5-nitroquinoline 1-oxide (4 g) was added to phosphorus oxychloride (15 mL) at 0° C. The solution was allowed to warm to room temperature and stirred for 12 hours. The excess phosphorus oxychloride was evaporated in vacuo and the residue dissolved in water (100 mL)/dichloromethane (100 mL). The layers were separated and the aqueous layer extracted with dichloromethane (2×50 mL). The combined extracts were dried over anhydrous magnesium sulfate, filtered and concentrated to give an oil. The residue was dissolved in ethanol/water (1:1, 80 mL), ammonium chloride (2.8 g) and iron (2.8 g) added. The mixture was stirred at 65° C. for 4 hours, cooled to room temperature and filtered. The resulting solid was suspended in dimethylsulfoxide (50 mL), methanol (50 mL) and aqueous hydrochloric acid added (2M, 100 mL). The resulting solid was removed by filtration and then treated with ether (50 mL) and isohexane (50 mL). Evaporation of the mixture afforded the sub-title compound as a solid (1 g).

$^1$H NMR (400 MHz, DMSO-d$_6$) δ 8.73 (1H, dd,); 7.62 (1H, d); 7.51 (1H, d); 7.13 (1H, dd); 6.36 (2H, s).

MS: APCI(+ve) 213/215 (M+H$^+$)

EXAMPLE 2

N-[6-Chloro-2-(1-piperazinyl)-5-quinolinyl]-cyclohexaneacetamide, Dihydrochloride

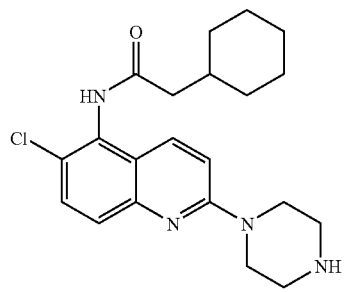

To a stirred solution of N-(2,6-dichloro-5-quinolinyl)-cyclohexaneacetamide (Example 1 (a)) (170 mg) and potassium carbonate (350 mg) in N-methylpyrrolidinone (4 mL) was added piperazine (600 mg). The mixture was heated at 120° C. for 3 hours after which it was cooled and poured into water. The mixture was extracted with dichloromethane and the combined extracts evaporated to give a residue which was then partitioned between water and ethyl acetate. The organic layer was separated and the aqueous layer further extracted with ethyl acetate. The combined organic extracts were concentrated to give a residue which was purified by chromatography (SiO$_2$, methanol:dichloromethane:ammonium hydroxide solution 19:80:1 as eluant) and the resultant product was converted to its hydrochloride salt by treatment with hydrochloric acid (4M in 1,4-dioxane). Recrystallisation (methanol/ethyl acetate) afforded the title compound as a solid (80 mg).

$^1$H NMR (400 MHz, d$_6$-DMSO) δ 9.92 (1H, s), 9.30 (2H, s), 7.97 (1H, d), 7.70-7.59 (2H, m), 7.41 (1H, d), 4.01-3.92 (4H, m), 3.27-3.17 (4H, m), 2.35 (2H, d), 1.89-1.60 (6H, m), 1.33-0.98 (5H, m).

MS: APCI(+ve) 387/389 (M+H$^+$).

m.p.>250° C.

EXAMPLE 3

N-[6-Chloro-2-[methyl[3-(methylamino)propyl]amino]-5-quinolinyl]-cyclohexaneacetamide, Dihydrochloride

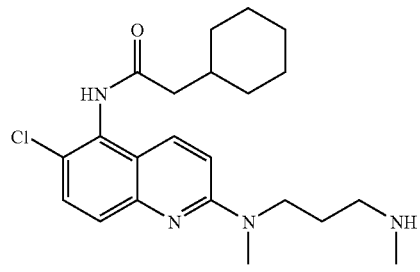

Prepared according to the method of example 2, using N-(2,6-dichloro-5-quinolinyl)-cyclohexaneacetamide (Example 1 (a)) (100 mg) and N,N'-dimethyl-1,3-propanediamine (300 mg). Further purification by HPLC (Symmetry—0.1% aqueous trifluoroacetic acid/acetonitrile) followed by conversion to its hydrochloride salt as described in example 2, afforded the title compound as a solid (56 mg).

$^1$H NMR (400 MHz, CD$_3$OD) δ 7.95 (1H, d), 7.61 (2H, s), 7.17 (1H, d), 3.63 (1H, t), 3.16 (3H, s), 2.93 (2H, t), 2.81 (2H, t), 2.58 (3H, s), 2.34 (2H, d), 2.02 (2H, t), 1.80-1.77 (1H, m), 1.70 (2H, d), 1.62 (1H, d), 1.30-1.13 (4H, m), 1.04 (2H, q).

MS: APCI(+ve) 403/405 (M+H$^+$).

m.p. 231-233° C.

EXAMPLE 4

6-Chloro-N-(cyclohexylmethyl)-2-methyl-5-quinolinecarboxamide, Hydrochloride

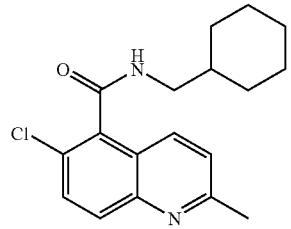

a) 6-Chloro-N-(cyclohexylmethyl)-2-methyl-5-quinolinecarboxamide, Hydrochloride To a stirred solution of 6-chloro-2-methyl-5-quinolinecarboxylic acid (prepared as described in example 4 (b)) (250 mg) in dichloromethane (5 mL) at 0° C. under nitrogen, was added N,N-dimethylformamide (1 drop) and oxalyl chloride (0.4 mL). The reaction mixture was stirred at room temperature for 1 hour, then evaporated to dryness and redissolved in dichloromethane (3 mL). This solution was cooled to 0° C. and a mixture of cyclohexanemethylamine (128 mg) and triethylamine (1 mL) in dichloromethane (2 mL) was added dropwise. The reaction mixture was stirred at room temperature for 1 hour then poured into saturated aqueous sodium hydrogen carbonate (20 mL). The mixture was extracted with dichloromethane (3×20 mL) and the combined extracts were dried, filtered and evaporated. Purification ($SiO_2$, ethyl acetate:isohexane 3:2 as eluant) gave the title compound as a solid (35 mg).

$^1$H NMR (400 MHz, $d_6$-DMSO) δ 8.85 (1H, t), 8.33 (1H, d), 8.23 (1H, d), 7.99 (1H, d), 7.80 (1H, d), 3.22 (2H, t), 2.84 (3H, s), 1.85-1.52 (6H, m,), 1.30-1.10 (3H, m), 1.06-0.93 (2H, m).

MS: APCI(+ve) 317/319 (M+H$^+$).
m.p. 210-213° C.

(b) 6-Chloro-2-methyl-5-quinolinecarboxylic Acid

Crotonaldehyde (1.5 mL) was added dropwise over a period of 1 hour to a mixture of 5-amino-2-chlorobenzoic acid (1.7 g), ferrous sulphate heptahydrate (0.77 g), sodium m-nitrobenzenesulphonate (1.2 g) and concentrated hydrochloric acid (11 mL) at 95° C. The reaction mixture was heated for a further 15 minutes then filtered whilst still hot. The collected solid was extracted with boiling 2M aqueous hydrochloric acid solution (20 mL) and the extract combined with the filtrate. Ammonium acetate was then added to give a solution of pH 4, which was cooled in ice and the resultant precipitate collected by filtration and washed with water. The product was converted to its hydrochloride salt by treatment with hydrochloric acid (4M in 1,4-dioxane) and the solid dried in vacuo to give the sub-title compound (0.5 g) as a solid.

MS: APCI(+ve) 222/224 (M+1)

EXAMPLE 5

N-[6-Chloro-2-[(3-hydroxypropyl)amino]-5-quinolinyl]-cyclohexaneacetamide, Hydrochloride

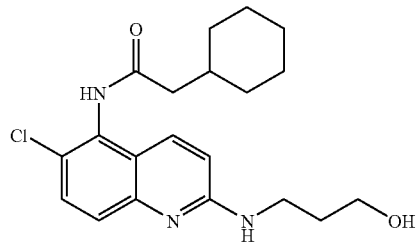

Prepared according to the method of example 2, using N-(2,6-dichloro-5-quinolinyl)-cyclohexaneacetamide (Example 1 (a)) (200 mg) and 3-amino-1-propanol (540 mg). Water was added to the residue and the product was collected by filtration. The product was converted to its hydrochloride salt by treatment with hydrochloric acid (4M in 1,4-dioxane). Recrystallisation (methanol/ethyl acetate) afforded the title compound as a solid (98 mg).

$^1$H NMR (400 MHz, $d_6$-DMSO) δ 10.10 (1H, s), 8.11-7.97 (2H, m), 7.86 (1H, d), 7.22 (1H, d), 3.64 (2H, d), 3.56 (2H, t), 2.35 (2H, d), 1.91-1.57 (8H, m), 1.34-1.13 (3H, m), 1.04 (2H, q).

MS: APCI(+ve) 376/378 (M+H$^+$).
m.p. 240-244° C.

EXAMPLE 6

N-[6-Chloro-2-[[(2R)-2,3-dihydroxypropyl]amino]-5-quinolinyl]-cyclohexaneacetamide

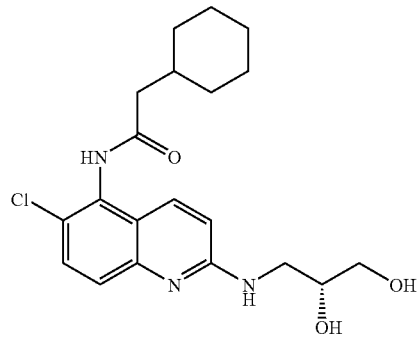

Prepared according to the method of example 2, using N-(2,6-dichloro-5-quinolinyl)-cyclohexaneacetamide (Example 1 (a)) (200 mg) and 3-amino-(2R)-1,2-propanediol (655 mg). Purification ($SiO_2$, dichloromethane:methanol 9:1 as eluant) gave the title compound (20 mg).

$^1$H NMR (400 MHz, $d_6$-DMSO) δ 9.74 (1H, s), 7.72 (1H, d), 7.54 (1H, d), 7.40 (1H, d), 6.91 (1H, d), 3.71-3.64 (1H, m), 3.59-3.50 (1H, m), 3.43-3.27 (3H, m), 2.31 (2H, d), 1.89-1.76 (3H, m), 1.75-1.58 (3H, m), 1.32-1.11 (3H, m), 1.10-0.97 (2H, m).

MS: APCI(+ve) 392/394 (M+H$^+$).
m.p. 155-159° C.

EXAMPLE 7

4-[[6-Chlor-5-[(cyclohexylacetyl)amino]-2-quinolinyl]amino]-butanoic Acid

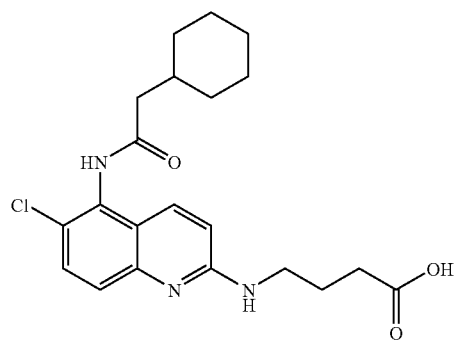

a) 4-[[6-Chloro-5-[(cyclohexylacetyl)amino]-2-quinolinyl]amino]-butanoic Acid, 1,1-dimethylethyl Ester To a stirred solution of N-(2,6-dichloro-5-quinolinyl)-cyclohexaneacetamide (Example 1 (a)) (200 mg), potassium carbonate (410 mg) and tetrabutylammonium bromide (2 mg) in N-methylpyrrolidinone (5 mL) was added 4-amino-butanoic acid 1,1-dimethylethyl ester (1 g). The mixture was heated at 130° C. for 72 hours after which it was cooled and poured into water. The mixture was extracted with dichloromethane (3×20 mL) and the combined extracts dried, filtered and evaporated. Purification (SiO$_2$, ethyl acetate:isohexane 3:7 as eluant) gave the sub-title compound (200 mg).

$^1$H NMR (400 MHz, d$_6$-DMSO) 59.71 (1H, s), 7.71 (1H, d), 7.52 (1H, d), 7.41 (1H, d), 6.80 (1H, d), 3.48-3.24 (2H, m), 2.38-2.23 (4H, m), 1.96-1.55 (8H, m), 1.40 (9H, s), 1.33-0.97 (5H, m).

b) 4-[[6-Chloro-5-[(cyclohexylacetyl)amino]-2-quinolinyl]amino]-butanoic Acid 4-[[6-Chloro-5-[(cyclohexylacetyl)amino]-2-quinolinyl]amino]-butanoic acid 1,1-dimethylethyl ester (Example 7 (a)) (200 mg) was dissolved in dichloromethane (3 mL). Trifluoroacetic acid (1 mL) was added and the mixture stirred for 3 hours. The resultant suspension was evaporated to dryness and recrystallised from acetonitrile to give the title compound (20 mg).

$^1$H NMR (400 MHz, d$_6$-DMSO) δ 12.06 (1H, s), 9.72 (1H, s), 7.71 (1H, d), 7.51 (1H, d), 7.42 (1H, d), 7.21 (1H, t), 6.80 (1H, d), 3.48-3.23 (2H, m), 2.37-2.27 (4H, m), 1.87-1.58 (8H, m), 1.33-1.12 (3H, m), 1.09-0.97 (2H, m).

MS: APCI(+ve) 404/406 (M+H$^+$).

m.p. 248-250° C.

EXAMPLE 8

N-[6-Chloro-2-[methyl[3-(methylamino)propyl]amino]-5-quinolinyl]-4-(trifluoromethyl)-cyclohexaneacetamide, Dihydrochloride

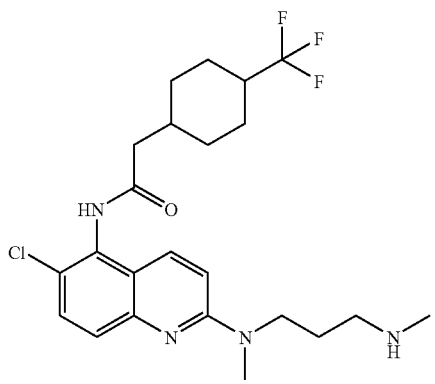

a) [4-(Trifluoromethyl)cyclohexylidene]-acetic Acid, Ethyl Ester

A suspension of sodium hydride (60% in oil, 277 mg) in hexane was stirred under nitrogen for 10 minutes and the solvent was decanted. The residue was then suspended in tetrahydrofuran (10 mL) and cooled to 0° C. Triethyl phosphonoacetate (1.5 mL) in tetrahydrofuran (10 mL) was added dropwise and the reaction mixture stirred at room temperature for 30 minutes. The mixture was then cooled to 0° C. and 4(trifluoromethyl)-cyclohexanone (1 g) in tetrahydrofuran (2 mL) was added dropwise. The reaction was stirred at room temperature for 16 hours. The mixture was then quenched by careful addition of saturated aq. NH$_4$Cl solution. The resulting solution was extracted with ether (3×15 mL). The combined organic extracts were washed with brine (2×10 mL), dried, filtered and evaporated. Purification (SiO$_2$, ethyl acetate:isohexane 2:98 as eluant) gave the sub-title compound as a colourless oil (1 g).

$^1$H NMR (400 MHz, d$_6$-DMSO) δ 5.70 (1H, s), 4.07 (2H, q), 3.84-3.73 (1H, m), 2.70-2.48 (1H, m), 2.38 (1H, d), 2.26 (1H, td), 2.08-1.92 (3H, m), 1.42-1.22 (2H, m), 1.19 (3H, t).

b) 4-(Trifluoromethyl)-cyclohexaneacetic Acid

To a stirred solution of [4-(trifluoromethyl)cyclohexylidene]-acetic acid, ethyl ester (Example 8 (a)) (1 g) in ethyl acetate (20 mL) was added 5% palladium on carbon (450 mg). The mixture was stirred at room temperature under a 2 bar atmosphere of hydrogen. The reaction mixture was then filtered through diatomaceous earth and concentrated. Purification (SiO$_2$, ethyl acetate:isohexane 1:19 as eluant) gave 4-(trifluoromethyl)-cyclohexaneacetic acid, ethyl ester (800 mg), which was dissolved in methanol (3 mL). Potassium hydroxide (1 g) in water (3 mL) was added and the mixture was stirred at room temperature for 16 hours. The reaction mixture was concentrated and subsequently acidified to pH1 with aqueous 2M hydrochloric acid. The resulting solution was extracted with dichloromethane (3×10 mL) and the combined organic extracts dried, filtered and evaporated to give the sub-title compound as an oil (660 mg).

GCMS: 210 (M$^+$)

c) N-(2,6-Dichloro-5-quinolinyl)-4-(trifluoromethyl)-cyclohexaneacetamide

Prepared according to the method of example 1(a), using 2,6-dichloroquinolin-5-amine (prepared as described in Example 1(d) above) (400 mg) and 4-(trifluoromethyl)-cyclohexaneacetic acid (Example 8 (b)) (436 mg). Purification (SiO$_2$, dichloromethane:methanol 99:1 as eluant) gave the sub-title compound (350 mg).

$^1$H NMR (400 MHz, d$_6$-DMSO) δ 10.11 (1H, s), 8.27 (1H, d), 7.94 (2H, s), 7.70 (1H, d), 3.36-3.28 (1H, m), 2.40 (2H, d), 1.98-1.56 (5H, m), 1.38-1.06 (4H, m).

d) N-[6-Chloro-2-[methyl[3-(methylamino)propyl]amino]-5-quinolinyl]-4-(trifluoromethyl)-cyclohexaneacetamide, Dihydrochloride Prepared according to the method of example 2 using N-(2,6-dichloro-5-quinolinyl)-4-(trifluoromethyl)-cyclohexaneacetamide (Example 8 (c)) (150 mg) and N,N'-dimethyl-1,3-propanediamine (450 mg). The product was converted to its hydrochloride salt by treatment with hydrochloric acid (4M in 1,4-dioxane). Recrystallisation (methanol/ethyl acetate) afforded the title compound as a solid (40 mg).

$^1$H NMR (400 MHz, d$_6$-DMSO) δ 8.12 (1H, d), 7.88 (1H, s), 7.79 (1H, d), 7.42 (1H, s), 3.85 (2H, t), 3.35 (3H, s), 3.04 (2H, t), 2.64 (3H, s), 2.40 (2H, d), 2.10-1.98 (2H, m), 1.98-1.86 (3H, m), 1.86-1.75 (1H, m), 1.70-1.61 (1H, m), 1.36-1.04 (5H, m).

MS: APCI(+ve) 471/473 (M+H$^+$).

m.p. 250° C. dec.

EXAMPLE 9

N-[6-Chloro-2-(1-piperazinyl)-5-quinolinyl]-4-(trifluoromethyl)-cyclohexaneacetamide

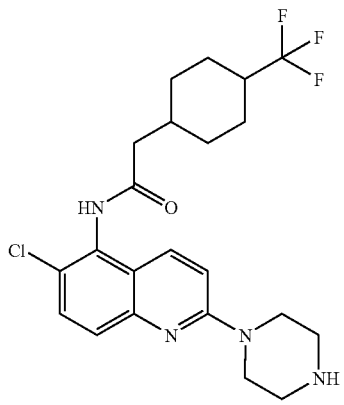

Prepared according to the method of example 2 using N-(2, 6-dichloro-5-quinolinyl)-4 (trifluoromethyl)-cyclohexaneacetamide (Example 8 (c)) (200 mg) and piperazine (420 mg). Purification (SiO$_2$, dichloromethane:methanol 95:5 as eluant) afforded the title compound as a solid (55 mg).

$^1$H NMR (400 MHz, d$_6$-DMSO) δ 9.82 (1H, s), 7.85 (1H, d), 7.57 (1H, d), 7.48 (1H, d), 7.28 (1H, d), 3.66-3.56 (4H, m), 2.85-2.73 (4H, m), 2.35 (2H, d), 2.30-2.15 (1H, m), 1.98-1.55 (5H, m), 1.36-1.04 (4H, m).

MS: APCI(+ve) 455/457 (M+H$^+$).

m.p. 186-190° C.

EXAMPLE 10

N-[6-Chlor-2-(hexahydro-1H-1,4-diazepin-1-yl)-5-quinolinyl]-cyclohexaneacetamide

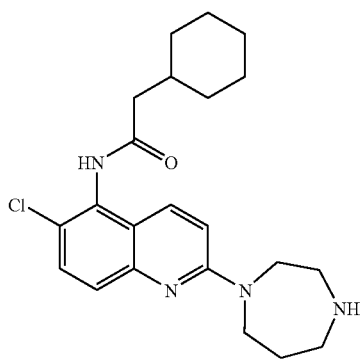

Prepared according to the method of example 2 using N-(2, 6-dichloro-5-quinolinyl)-cyclohexaneacetamide (Example 1 (a)) (200 mg) and homopiperazine (600 mg). Recrystallisation from acetonitrile afforded the title compound as a solid (96 mg).

$^1$H NMR (400 MHz, d$_6$-DMSO) δ 9.75 (1H, s), 7.81 (1H, d), 7.53 (1H, d), 7.44 (1H, d), 7.14 (1H, d), 3.94-3.65 (4H, m), 2.87 (2H, t), 2.65 (2H, t), 2.32 (2H, d), 1.92-1.59 (8H, m), 1.34-0.97 (5H, m).

MS: APCI(+ve) 401/403 (M+H$^+$).

m.p. 186-188° C.

EXAMPLE 11

N-[6-Chloro-2-[(cis-3,5-dimethyl-1-piperazinyl]-5-quinolinyl]-cyclohexaneacetamide

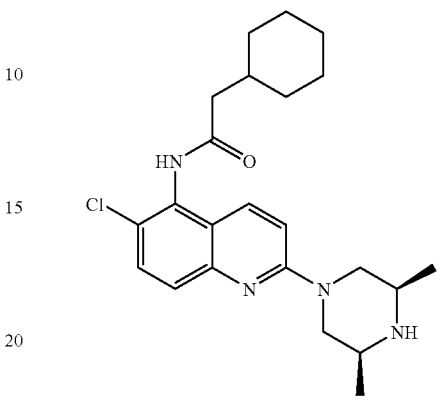

Prepared according to the method of example 2 using N-(2, 6-dichloro-5-quinolinyl)-cyclohexaneacetamide (Example 1 (a)) (150 mg) and cis-2,6-dimethylpiperazine (500 mg). Purification (SiO$_2$, dichloromethane:methanol 95:5 as eluant) and recrystallisation from methanol afforded the title compound as a solid (32 mg).

$^1$H NMR (400 MHz, d$_6$-DMSO) δ 9.77 (1H, s), 7.83 (1H, d), 7.56 (1H, d), 7.48 (1H, d), 7.31 (1H, d), 4.40 (2H, d), 2.80-2.69 (2H, m), 2.42-2.27 (4H, m), 1.90-1.58 (6H, m), 1.34-0.95 (11H, m).

MS: APCI(+ve) 415/417 (M+H$^+$).

m.p. 250-252° C.

EXAMPLE 12

N-[6-Chloro-2-(4-methyl-1-piperazinyl)-5-quinolinyl]-cyclohexaneacetamide, Dihydrochloride

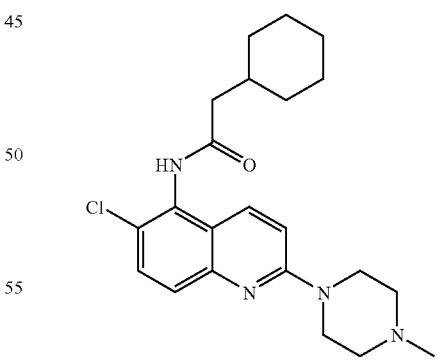

Prepared according to the method of example 2 using N-(2, 6-dichloro-5-quinolinyl)-cyclohexaneacetamide (Example 1 (a)) (150 mg) and 1-methyl-piperazine (380 mg). The product was purified by chromatography (SiO$_2$, dichloromethane: methanol 95:5 as eluant), converted to its hydrochloride salt by treatment with hydrochloric acid (4M in 1,4-dioxane) and recrystallised (methanol/ethyl acetate) to give the title compound as a solid (40 mg).

¹H NMR (400 MHz, d₆-DMSO) δ 11.14 (1H, s), 9.97 (1H, s), 8.02 (1H, d), 7.83-7.65 (2H, m), 7.47 (1H, d), 4.71 (2H, d), 3.51 (4H, t), 3.20-3.05 (2H, m), 2.79 (3H, d), 2.35 (2H, d), 1.90-1.59 (6H, m), 1.34-0.99 (5H, m).
MS: APCI(+ve) 401/403 (M+H⁺).
m.p. 270° C. dec.

EXAMPLE 13

N-[6-Chloro-2-[(1S,4S)-2,5-diazabicyclo[2.2.1]hept-2-yl]-5-quinolinyl]-cyclohexaneacetamide, Acetate

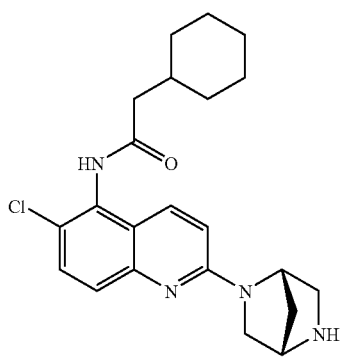

Prepared according to the method of example 2 using N-(2,6-dichloro-5-quinolinyl)-cyclohexaneacetamide (Example 1 (a)) (200 mg) and (1S,4S)-2,5-diazabicyclo[2.2.1]heptane (540 mg). Purification by chromatography (SiO₂, dichloromethane:methanol 90:10 as eluant) and further purification by HPLC (Symmetry—0.1% aqueous ammonium acetate/acetonitrile) afforded the title product (12 mg).
¹H NMR (400 MHz, d₆-DMSO) δ 9.43 (1H, s), 7.82 (1H, d), 7.50 (1H, d), 7.43 (1H, d), 6.89 (1H, d), 4.85 (1H, s), 3.70 (1H, s), 3.54 (1H, dd), 3.35 (1H, d), 2.97 (1H, d), 2.83 (1H, d), 2.36-2.27 (2H, m), 1.92-1.59 (8H, m), 1.34-0.99 (5H, m).
MS: APCI(+ve) 399/401 (M+H⁺).
m.p. 120° C. dec.

EXAMPLE 14

N-[6-Chloro-2-[(3R)-3-pyrrlidinylamino]-5-quinolinyl]-cyclohexaneacetamide, Dihydrochloride

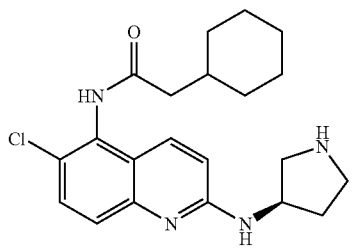

To a stirred solution of N-(2,6-dichloro-5-quinolinyl)-cyclohexaneacetamide (Example 1 (a)) (200 mg) and tetrabutylammonium bromide (750 mg) in N-methylpyrrolidinone (2 mL) was added 1-(phenylmethyl)-(3R)-3-pyrrolidinamine (1 g). The mixture was heated at 130° C. for 72 hours before being cooled to room temperature and partitioned between water and ethyl acetate. The aqueous layer was further extracted with ethyl acetate. The combined organic extracts were concentrated and the residue was purified (SiO₂, methanol:dichloromethane 7:93 as eluant) to give a brown oil containing N-[6-chloro-2-[[(3R)-1-(phenylmethyl)-3-pyrrolidinyl]amino]-5-quinolinyl]-cyclohexaneacetamide. The oil was dissolved in dichloroethane (2 mL). 1-Chloroethyl chloroformate (0.03 mL) was added and the reaction heated to reflux for 6 hours. The mixture was then allowed to cool and evaporated to dryness. The residue was dissolved in methanol and heated to reflux for 2 hours. The solution was cooled, filtered through sodium hydrogen carbonate and concentrated. Purification by chromatography (SiO₂, dichloromethane:methanol:ammonium hydroxide solution 80:20:1 as eluant) and then by HPLC (Symmetry—0.1% aqueous ammonium acetate/acetonitrile) afforded the product which was converted to its hydrochloride salt by treatment with hydrochloric acid (4M in 1,4-dioxane) and recrystallised (methanol/ethyl acetate) to give the title product (18 mg).
¹H NMR (400 MHz, d₆-DMSO) δ 9.62 (1H, s), 9.36 (1H, s), 7.92 (1H, d), 7.87-7.76 (1H, m), 7.66 (1H, d), 7.03 (1H, d), 4.86 (1H, s), 3.66-3.17 (6H, m), 2.40-2.27 (2H, m), 2.12-2.00 (1H, m), 1.93-1.57 (5H, m), 1.43-0.98 (5H, m).
MS: APCI(+ve) 387/389 (M+H⁺).
m.p. 193-198° C.

EXAMPLE 15

N-[2-[3-(Ethylamino)propyl]-6-methyl-5-quinolinyl]-cyclohexaneacetamide, Dihydrochloride

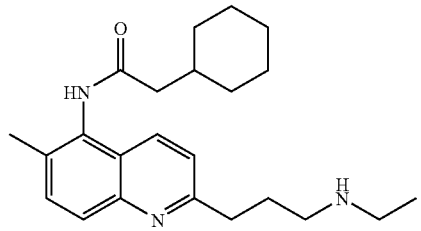

a) N-(2-Chloro-6-methyl-5-quinolinyl)-cyclohexaneacetamide

To a solution of cyclohexaneacetyl chloride (prepared according to the method of J. Am. Chem. Soc. 1986, 108, 7686) (560 mg) in dichloromethane (5 mL) was added a mixture of 2-chloro-6-methyl-5-quinolinamine (prepared according to the method of Journal of the American Chemical Society 1947, 69, 179) (350 mg) and triethylamine (1 mL) in dichloromethane (5 mL) at 0° C. The mixture was allowed to warm to room temperature and stirred overnight. The mixture was poured into saturated sodium bicarbonate solution and extracted with dichloromethane (3×20 mL). The combined organic extracts were dried, filtered and evaporated to afford the sub-title compound (400 mg).
MS: APCI(+ve) 317/319 (M+H⁺).

b) Ethyl-(2-propenyl)-carbamic Acid, 1,1-dimethylethyl Ester

Sodium hydride (60%, 0.25 g) was added to tert-butyl allylcarbamate (1.0 g) in anhydrous N-methylpyrrolidinone (4 ml) followed by ethyl iodide (1.6 ml). The crude product was purified by chromatography (SiO$_2$, isohexane:ethyl acetate 19:1 as eluant) to afford the sub-title compound (0.53 g) as a colourless oil.

$^1$H NMR (400 MHz, CDCl$_3$) δ 5.78 (1H, m); 5.12 (2H, m); 3.80 (2H, s); 3.22 (2H, d); 1.46 (9H, s); 1.08 (3H, t).

c) [3-[5-[(Cyclohexylacetyl)amino]-6-methyl-2-quinolinyl]propyl]ethyl-carbamic Acid, 1,1-dimethylethyl Ester Prepared according to the method of example 1(b), using N-(2-chloro-6-methyl-5-quinolinyl)-cyclohexaneacetamide (Example 15 (a)) (400 mg) and ethyl(2-propenyl)-carbamic acid, 1,1-dimethylethyl ester (Example 15 (b)) (277 mg). Purification (SiO$_2$, ethyl acetate:isohexane 20:80 as eluant) gave the sub-title compound (260 mg).

MS: APCI(+ve) 468 (M+H$^+$).

d) N-[2-[3-(Ethylamino)propyl]-6-methyl-5-quinolinyl]-cyclohexaneacetamide, Dihydrochloride Prepared according to the method of example 1(c), using [3-[5-[(cyclohexylacetyl)amino]-6-methyl-2-quinolinyl]propyl]ethyl-carbamic acid, 1,1-dimethylethyl ester (Example 15 (c)) (250 mg) to afford the title compound (260 mg).

$^1$H NMR (400 MHz, d$_6$-DMSO) δ 9.70 (1H, s), 8.86 (2H, s), 8.38 (1H, d), 8.00 (1H, d), 7.75 (1H, d), 7.63 (1H, d), 3.18 (2H, t), 3.05-2.90 (4H, m), 2.47-2.39 (2H, m), 2.36 (3H, s), 2.21 (2H, quint.), 1.93-1.59 (6H, m), 1.39-1.06 (8H, m).

MS: APCI(+ve) 368 (M+H$^+$).

m.p. 231-234° C.

EXAMPLE 16

N-[6-Chloro-2-[3-(ethylamino)propyl]-5-quinolinyl]-cyclohexaneacetamide, Dihydrochloride

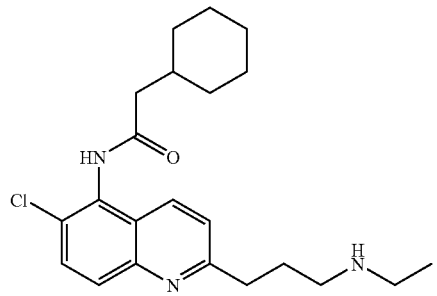

Prepared according to the method of example 15, using N-(2,6-dichloro-5-quinolinyl)-cyclohexaneacetamide (Example 1(a)) (500 mg) and ethyl(2-propenyl)carbamic acid 1,1-dimethylethyl ester (330 mg). Recrystallisation (methanol/ethyl acetate) afforded the title compound as a solid (195 mg).

$^1$H NMR (400 MHz, d$_6$-DMSO) δ 10.18 (1H, s), 8.92 (2H, s), 8.37 (1H, d), 8.08 (1H, d), 7.96 (1H, d), 7.73 (1H, d), 3.21-3.09 (2H, m), 3.03-2.85 (4H, m), 2.39 (2H, d), 2.17 (2H, quint.), 1.94-1.55 (6H, m), 1.35-0.99 (8H, m).

MS: APCI(+ve) 388/390 (M+H$^+$).

m.p. 152-155° C.

EXAMPLE 17

N-[6-Chloro-2-[[2-[(2-hydroxyethyl)amino]ethyl]amino]-5-quinolinyl]-cyclohexaneacetamide, Dihydrochloride

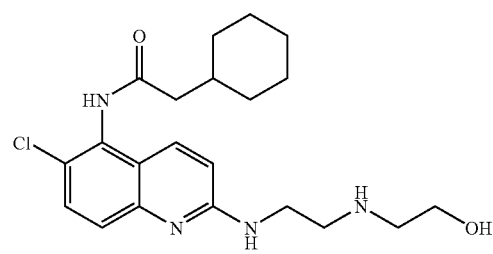

To a stirred solution of N-(2,6-dichloro-5-quinolinyl)-cyclohexaneacetamide (Example 1 (a)) (170 mg) and potassium carbonate (350 mg) in N-methylpyrrolidinone (4 mL) was added 2-[(2-aminoethyl)amino]-ethanol (500 μL). The mixture was heated at 120° C. for 5 hours after which it was cooled and poured into water. The resulting solid was isolated by filtration, dried and suspended in dichloromethane (5 mL). The suspension was then treated with di-tert-butyl dicarbonate (220 mg) and triethylamine (200 μL) and stirred for 2 hours. The mixture was poured into water and extracted with dichloromethane (3×20 mL). The combined organic layers were dried, filtered and concentrated. Purification (SiO$_2$, methanol:dichloromethane solution 2.5:97.5 as eluant) yielded the desired isomer which was then dissolved in dichloromethane (5 mL) and methanol (0.5 mL), and treated with hydrochloric acid in 1,4-dioxane (4M, 1 mL) for 1 hour. The resultant suspension was evaporated to dryness and recrystallised from methanol/ethyl acetate to give the title compound as a colourless solid (65 mg).

$^1$H NMR (400 MHz, d$_6$-DMSO/D$_2$O) δ 8.04 (1H, d), 7.94 (1H, d), 7.86 (1H, d), 7.16 (1H, d), 3.91 (2H, t), 3.75-3.65 (2H, m), 3.32 (2H, t), 3.11 (2H, t), 2.37 (2H, d), 1.90-1.60 (6H, m), 1.35-0.95 (5H, m).

MS: APCI(+ve) 405/407 (M+H$^+$).

m.p. 238-240° C.

EXAMPLE 18

N-5-Quinolinyl-cyclohexaneacetamide

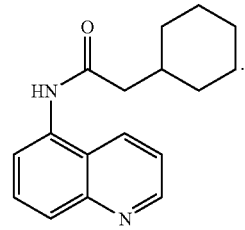

To a stirred solution of cyclohexaneacetic acid (250 mg) in dichloromethane (5 mL) at 0° C. under nitrogen, was added N,N-dimethylformamide (1 drop) and oxalyl chloride (1 mL). The reaction mixture was stirred at room temperature for 1 hour, then evaporated to dryness and redissolved in dichloromethane (3 mL). This solution was cooled to 0° C.

and a mixture of 5-quinolinamine (200 mg) and triethylamine (1 mL) in dichloromethane (2 mL) was added dropwise. The reaction mixture was stirred at room temperature for 1 hour then poured into saturated NaHCO₃ aq. (20 mL). The mixture was extracted with dichloromethane (3×10 mL) and the combined extracts were dried, filtered and evaporated. Purification (SiO₂, ethyl acetate:isohexane 3:2 as eluant) gave the title compound (30 mg).

¹H NMR (400 MHz, d₆-DMSO) δ 9.97 (1H, s), 8.92 (1H, dd), 8.45 (1H, m), 7.85 (1H, m), 7.79-7.70 (2H, m), 7.57 (1H, dd), 2.37 (2H, d), 1.92-1.58 (6H, m), 1.35-0.95 (5H, m).
MS: APCI(+ve) 269 (M+H⁺).
m.p. 183-184° C.

EXAMPLE 19

1-Methyl-N-5-quinolinyl-cyclohexaneacetamide

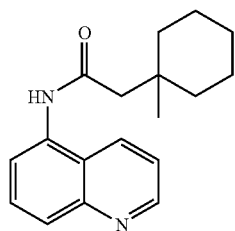

Prepared according to the method of example 18, using 5-quinolinamine (230 mg) and 1-methyl-cyclohexaneacetic acid (250 mg). Purification (SiO₂, methanol:dichloromethane 1:9 as eluant) followed by recrystallisation from methanol/ethyl acetate gave the title compound as a colourless solid (80 mg).

¹H NMR (400 MHz, d₆-DMSO) δ 9.93 (1H, s), 8.91 (1H, dd), 8.45 (1H, d), 7.85 (1H, d), 7.78-7.70 (2H, m), 7.57 (1H, dd), 2.41 (2H, s), 1.60-1.30 (10H, m), 1.10 (3H, s).
MS: APCI(+ve) 283 (M+H⁺).
m.p. 133-135° C.

EXAMPLE 20

4-Methyl-N-5-quinolinyl-cyclohexaneacetamide

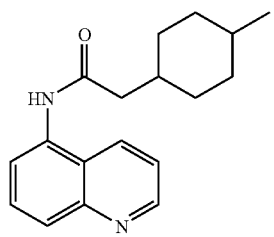

Prepared according to the method of example 18, using 5-quinolinamine (250 mg) and 4-methyl-cyclohexaneacetic acid (270 mg). Purification (HPLC, Symmetry—0.1% aqueous trifluoroacetic acid/acetonitrile) followed by recrystallisation from methanol/ethyl acetate gave the title compound as a colourless solid (84 mg).

¹H NMR (300 MHz, d₆-DMSO) δ 9.97 (1H, m), 8.80 (1H, dd), 8.44 (1H, d), 7.85 (1H, m), 7.80-7.68 (2H, m), 7.57 (1H, ddd), 2.50-2.35 (2H, m), 1.85-1.20 (6H, m), 1.17-0.90 (4H, m), 0.87 (3H, d).

MS: APCI(+ve) 283 (M+H⁺).
m.p. 181-183° C.

EXAMPLE 21

N-5-Quinolinyl-cyclopentanepropanamide

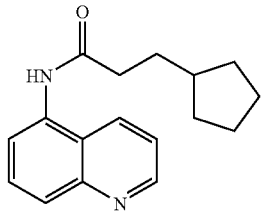

Prepared according to the method of example 18, using 5-quinolinamine (250 mg) and cyclopentanepropanoic acid (270 mg). Purification (HPLC, Symmetry—0.1% aqueous trifluoroacetic acid/acetonitrile) followed by recrystallisation from methanol/ethyl acetate gave the title compound as a colourless solid (112 mg).

¹H NMR (400 MHz, d₆-DMSO) δ 10.13 (1H, s), 9.05 (1H, dd), 8.71 (1H, d), 7.94-7.82 (3H, m), 7.74 (1H, dd), 2.53 (2H, m), 1.90-1.45 (9H, m), 1.15 (2H, m).
MS: APCI(+ve) 269 (M+H⁺).
m.p. 135-138° C.

EXAMPLE 22

N-[6-Chloro-2-[3-[(3-hydroxypropyl)amino]propyl]-5-quinolinyl]-cyclohexaneacetamide

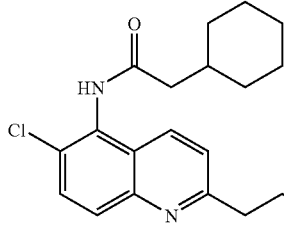

a) [3-[[(1,1-dimethylethyl)dimethylsilyl]oxy]propyl] 2-propenyl-carbamic acid, 1,1-dimethylethyl ester Prepared according to the method of example 15(b) using (2-bromopropoxy)-tert-butyldimethylsilane.
MS: APCI(+ve) 230 ((M-boc)+H⁺).

b) N-[6-Chloro-2-[3-[(3-hydroxypropyl)amino]propyl]-5-quinolinyl]-cyclohexaneacetamide Prepared according to the method of example 1(b)/(c), using N-(2,6-dichloro-5-quinolinyl)-cyclohexaneacetamide (Example 1(a)) (130 mg) and [3-[[(1,1-dimethylethyl)dimethylsilyl]oxy]propyl]-2-propenyl-carbamic acid, 1,1-dimethylethyl ester (example 22(a)) (152 mg). Purification (SiO₂, methanol:dichloromethane 1:9 as eluant) gave the title compound as a colourless solid (21 mg).

¹H NMR (400 MHz, CD₃OD) δ 8.12 (1H, d), 7.87 (1H, d), 7.74 (1H, d), 7.44 (1H, d), 3.60 (2H, t), 3.05-3.01 (6H, m), 2.36 (2H, d), 2.15-2.09 (2H, m), 1.84-1.78 (4H, m), 1.69 (2H, d), 1.62 (1H, d), 1.32-1.02 (6H, m).

MS: APCI(+ve) 418/420 (M+H+).

m.p. 159-163° C.

EXAMPLE 23

N-[2-(3-Aminopropyl)-6-chloro-5-quinolinyl]-cyclohexaneacetamide

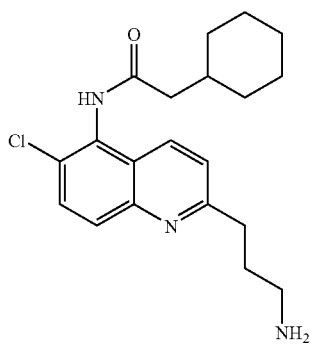

a) [3-[6-Chloro-5-[(cyclohexylacetyl)amino]-2-quinolinyl]propyl]-carbamic Acid 1,1-dimethylethyl Ester To 2-propenyl-carbamic acid 1,1-dimethylethyl ester under nitrogen was added 9-borabicyclo[3.3.1]nonane (0.5M in tetrahydrofuran, 7.1 mL) and the mixture refluxed for 2 hours. The reaction was allowed to cool to room temperature and potassium phosphate (1.02 g) in water (1.8 mL) added. The resultant mixture was stirred for 15 minutes. N-(2,6-Dichloro-5-quinolinyl)-cyclohexaneacetamide (prepared as described in Example 1a) (0.5 g) was added followed by tetrakis(triphenylphosphine)palladium(0) (17 mg) in dimethylformamide (2.8 mL). The reaction was heated at 70° C. under nitrogen for 4 hours. To the cooled solution was added brine (30 mL) and the mixture extracted with ethyl acetate (3×30 mL). The combined organics were dried, filtered and concentrated to give the sub-title compound (0.9 g).

MS: APCI(−ve) 458 (M−H+).

b) N-[2-(3-Aminopropyl)-6-chloro-5-quinolinyl]-cyclohexaneacetamide

Trifluoroacetic acid (5 mL) was added to a solution of [3-[6-chloro-5-[(cyclohexylacetyl)amino]-2-quinolinyl]propyl]carbamic acid, 1,1-dimethylethyl ester (Example 23(a)) (0.9 g) in dichloromethane (15 mL). After stirring for 2 hours the solvent was removed under reduced pressure and the resulting residue was purified (Varian Chem elute cartridge with dichloromethane as eluant). Further purification (Varian SCX cartridge using methanol (100 mL) and then 10% ammonia in methanol (100 mL) as eluant) afforded the title compound (300 mg).

$^1$H NMR (400 MHz, CD$_3$OD) δ 8.21 (1H, d), 7.95 (1H, d), 7.82 (1H, d), 7.54 (1H, d), 3.04 (2H, t), 2.83 (2H, t), 2.46 (2H, d), 2.04 (2H, quint.), 1.99-1.89 (3H, m), 1.83-1.76 (2H, m), 1.75-1.68 (1H, m), 1.43-1.22 (3H, m), 1.21-1.09 (2H, m).

MS: APCI(+ve) 360 (M+H+).

m.p. 121-130° C.

EXAMPLE 24

N-[6-Chloro-2-[3-[[[(methylsulfonyl)amino]carbonyl]amino]propyl]-5-quinolinyl]-cyclohexaneacetamide

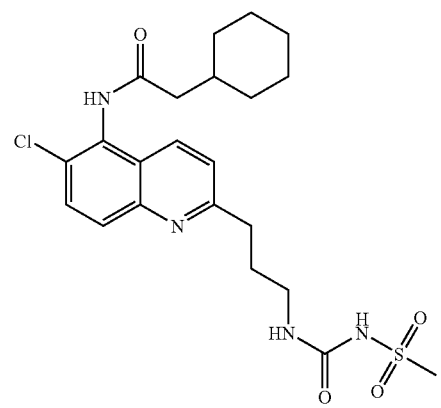

To a stirred solution of para-nitrophenylchloroformate (0.050 g) in dichloromethane was added dimethylaminopyridine (0.031 g), the mixture was stirred under nitrogen for 5 minutes and then triethylamine (0.035 mL) and methanesulphonamide (0.024 g) were added. The reaction was stirred for 1 hour before N-[2-(3-aminopropyl)-6-chloro-5-quinolinyl]-cyclohexaneacetamide (Example 23 (b)) (0.080 g) was added and the mixture was stirred for 1 hour under nitrogen. The solvent was removed under reduced pressure and the residue purified (MAX Waters cartridge, using methanol (30 mL) and 10% acetic acid in methanol (50 mL) as eluant). Removal of the solvent afforded the title compound (0.020 g).

$^1$H NMR (400 MHz, CD$_3$OD) δ 8.31 (1H, d), 7.67 (2H, s), 7.42 (1H, d), 3.19 (2H, t), 2.99-2.92 (5H, m), 2.37-2.31 (2H, m), 2.02-1.88 (4H, m), 1.81-1.74 (2H, m), 1.73-1.66 (1H, m), 1.41-1.20 (4H, m), 1.20-1.06 (2H, m).

MS: APCI(−ve) 479 (M−H+).

m.p. 151-152° C.

EXAMPLE 25

N-[2-[3-(Butylamino)propyl]-6-chloro-5-quinolinyl]-cyclohexaneacetamide Dihydrochloride

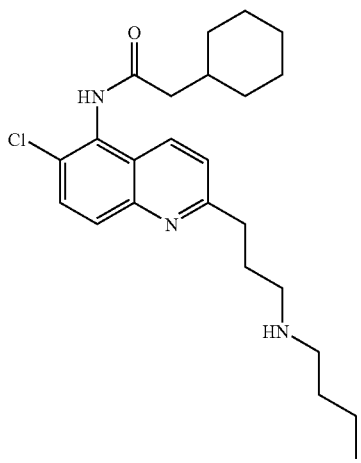

A solution of N-[2-(3-aminopropyl)-6-chloro-5-quinolinyl]-cyclohexaneacetamide (0.2 g) (Example 23), acetic acid (1 drop) and butanal (0.074 mL) in tetrahydrofuran was placed in a 10 mL vial and heated at 100° C. for 30 minutes within a microwave. Once the reaction had cooled to room temperature sodium triacetoxyborohydride (0.236 g) was added and the mixture stirred for 12 hours. The solvent was removed and the residue taken up in dimethylsulfoxide (3 mL). The residue was purified by HPLC (Waters Symmetry column using 25% to 95% acetonitrile in 0.1% aqueous trifluoroacetic acid). Further purification (SiO$_2$, ammonia:methanol:dichloromethane, 1:4:95 as eluant) followed by removal of solvent and conversion to its hydrochloride salt with 4M hydrogen chloride in 1,4-dioxane (5 mL) afforded the title product (0.021 g).

$^1$H NMR (400 MHz, d$_6$-DMSO) δ 10.08 (1H, s), 8.73 (2H, s), 8.25 (1H, d), 7.98 (1H, d), 7.89 (1H, d), 7.63 (1H, d), 3.08 (2H, t), 3.03-2.94 (2H, m), 2.93-2.84 (2H, m), 2.38 (2H, d), 2.16 (2H, quintet), 1.90-1.77 (3H, m), 1.76-1.68 (2H, m), 1.67-1.54 (3H, m), 1.38-1.14 (6H, m), 1.13-1.00 (2H, m), 0.89 (3H, t).

MS: APCI(+ve) 416 (M+H$^+$).

m.p. 219-221° C.

EXAMPLE 26

N-[6-Chloro-2-[methyl[3-(methylamino)propyl]amino]-5-quinolinyl]-1-cyclohexyl-cyclopropanecarboxamide, Hydrochloride

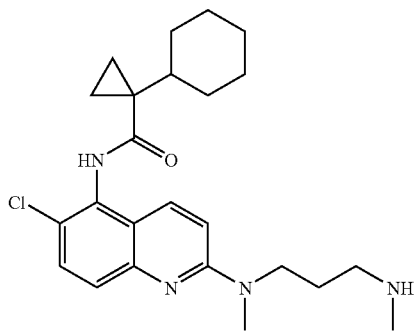

a) 1-Cyclohexyl Cyclopropanecarboxylic Acid

To 1-phenyl-cyclopropanecarboxylic acid (0.500 g) in acetic acid (2 mL) was added Adams catalyst (0.050 g) in ethanol (0.3 mL). The reaction was left to stir for 48 hours under 5 bar of hydrogen. The reaction was filtered, washing with ethanol (10 mL) and water (10 mL). The resulting solid was collected by filtration and subsequently washed with water (10 mL) to afford the sub-titled compound (0.3 g).

$^1$H NMR (400 MHz, CD$_3$OD) δ 1.77-1.71 (2H, m), 1.68-1.62 (3H, m), 1.43-1.12 (6H, m), 1.07 (2H, q), 0.73 (2H, q).

MS: APCI(-ve) 167 (M-H$^+$).

b) 1-Cyclohexyl-N-(2,6-dichloro-5-quinolinyl)-cyclopropanecarboxamide

Prepared according to the method of example 1(a), using 2,6-dichloro-5-quinolinamine (prepared as described in Example 1(d)) (0.3 g) and 1-cyclohexyl cyclopropanecarboxylic acid (Example 26(a)) (0.28 g) at 100° C. for 15 hours. Purification by chromatography (SiO$_2$, dichloromethane as eluant) afforded the sub-title compound (0.26 g).

$^1$H NMR (400 MHz, CD$_3$OD) δ 8.15 (1H, d), 7.91 (1H, d), 7.87 (1H, d), 7.59 (1H, d), 1.95-1.88 (2H, m), 1.87-1.75 (2H, m), 1.74-1.68 (1H, m), 1.42-1.17 (6H, m), 1.14 (2H, dd), 0.89 (2H, dd).

MS: APCI(-ve) 361 (M-H$^+$).

c) N-[6-Chloro-2-[methyl[3-(methylamino)propyl]amino]-5-quinolinyl]-1-cyclohexyl-cyclopropanecarboxamide, Hydrochloride To a 10 mL vial was added 1-cyclohexyl-N-(2,6-dichloro-5-quinolinyl)-cyclopropanecarboxamide (example 26 (b)) (0.13 g), N,N-dimethyl-1,3-propanediamine (0.13 mL) and acetonitrile (3 mL). The vial was sealed and heated at 100° C. in a microwave for 20 minutes followed by 30 minutes at 110° C. The solvent was removed from the cooled reaction under reduced pressure, saturated aqueous sodium hydrogen carbonate solution (30 mL) was added and the mixture was extracted with dichloromethane (3×50 mL). The combined organics were washed with water (50 mL) and brine (50 mL) before being dried, filtered and concentrated. Purification (Varian SCX cartridge, using methanol and 10% ammonia in methanol as eluant) gave a crude product which was further purified by chromatography (SiO$_2$, ammonia:methanol:dichloromethane, 1:2.5:96.5 as eluant). The product was converted to its hydrochloride salt by dissolution in dichloromethane and treatment with 4M hydrogen chloride in 1,4 dioxane (5 mL). Removal of volatiles and recrystallisation from methanol/acetonitrile afforded the title compound (0.075 g).

$^1$H NMR (400 MHz, CD$_3$OD) δ 8.03 (1H, d), 7.94 (1H, s), 7.81 (1H, d), 7.47 (1H, d), 3.86 (2H, t), 3.38 (3H, s), 3.06 (2H, t), 2.65 (3H, s), 2.06 (2H, quint.), 1.80 (2H, d), 1.76-1.65 (2H, m), 1.62 (2H, d), 1.33-1.19 (3H, m), 1.18-1.06 (2H, m), 1.04 (2H, dd), 0.82 (2H, dd).

MS: APCI(+ve) 428 (M+H$^+$).

m.p. 215-218° C.

EXAMPLE 27

N-[6-Chloro-2-(1-piperazinyl)-5-quinolinyl]-1-cyclohexyl-cyclopropanecarboxamide

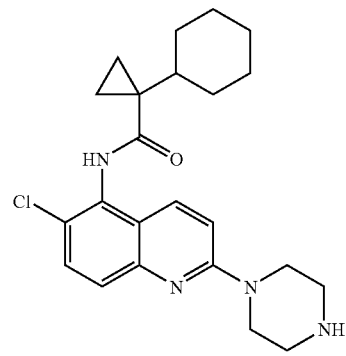

To a 10 mL vial was added 1-cyclohexyl-N-(2,6-dichloro-5-quinolinyl)-cyclopropanecarboxamide (Example 26 (b)) (0.13 g), piperazine (0.091 g) and acetonitrile (3 mL). The vial was sealed and heated in a microwave at 110° C. for 40 minutes. The solvent was removed from the cooled reaction and the residue taken up in dichloromethane and purified (SiO$_2$, ammonia:methanol:dichloromethane, 1:2:97 as eluant). The solvent was removed from the combined fractions and the product recrystallised from ethanol to afford the title compound (0.050 g).

$^1$H NMR (400 MHz, CD$_3$OD) δ 7.77 (1H, d), 7.48 (2H, d), 7.12 (1H, d), 3.63 (4H, t), 2.83 (4H, t), 1.85-1.78 (2H, m), 1.76-1.69 (2H, m), 1.66-1.58 (2H, m), 1.31-1.04 (5H, m), 1.00 (2H, dd), 0.77-0.73 (2H, m).

MS: APCI(+ve) 413 (M+H$^+$).

m.p. 219° C.

EXAMPLE 28

N-[6-Chloro-2-[(3R)-3-hydroxy-1-pyrrolidinyl]-5-quinolinyl]-cyclohexaneacetamide

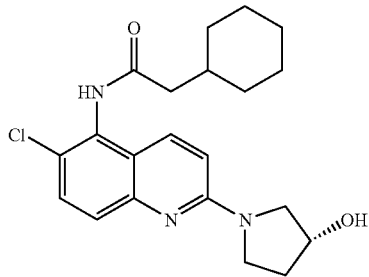

Prepared according to the method of example 27, using N-(2,6-dichloro-5-quinolinyl)-cyclohexaneacetamide (Example 1(a)) (0.05 g) and (3R)-3-pyrrolidinol (0.052 g) to afford the title compound (0.01 g).

$^1$H NMR (400 MHz, d$_6$-DMSO) δ 9.76 (1H, s), 7.84 (1H, d), 7.51 (2H, dd), 6.95 (1H, d), 5.01-4.97 (1H, m), 4.42 (1H, s), 3.67-3.53 (3H, m), 3.52-3.42 (1H, m), 2.32 (2H, d), 2.09-1.98 (1H, m), 1.97-1.88 (1H, m), 1.87-1.77 (3H, m), 1.75-1.67 (2H, m), 1.67-1.60 (1H, m), 1.33-1.12 (3H, m), 1.11-0.99 (2H, m).

MS: APCI(+ve) 388 (M+H$^+$).

m.p. 226-227° C.

EXAMPLE 29

N-[6-Chloro-2-[(3S)-3-hydroxy-1-pyrrolidinyl]-5-quinolinyl]-cyclohexaneacetamide

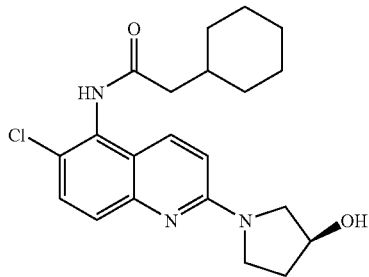

Prepared according to the method of example 27, using N-(2,6-dichloro-5-quinolinyl)-cyclohexaneacetamide (Example 1(a)) (0.533 g) and (3S)-3-pyrrolidinol (0.365 g) to afford the title compound (0.48 g).

$^1$H NMR (400 MHz, d$_6$-DMSO) δ 9.76 (1H, s), 7.84 (1H, d), 7.54 (1H, d), 7.47 (1H, d), 6.94 (1H, d), 5.02-4.96 (1H, m), 4.42 (1H, s), 3.69-3.53 (3H, m), 3.52-3.41 (1H, m), 2.32 (2H, d), 2.10-1.99 (1H, m), 1.98-1.88 (1H, m), 1.87-1.76 (3H, m), 1.75-1.67 (2H, m), 1.67-1.60 (1H, m), 1.33-1.13 (3H, m), 1.12-0.99 (2H, m).

MS: APCI(+ve) 388 (M+H$^+$).

m.p. 219-221° C.

EXAMPLE 30

N-[2-[(3R)-3-Amino-1-pyrrolidinyl]-6-chloro-5-quinolinyl]-cyclohexaneacetamide

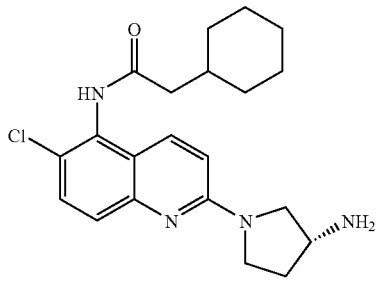

To a 10 mL vial was added N-(2,6-dichloro-5-quinolinyl)-cyclohexaneacetamide (Example 1(a)) (0.166 g), (3R)-3-pyrrolidinamine (0.127 g), triethylamine (0.083 mL) and acetonitrile (5 mL). The vial was sealed and heated at 100° C. for 30 minutes within a microwave. The reaction was cooled to room temperature and the resulting solid removed by filtration. This solid was purified (Varian SCX cartridge, using methanol and 10% ammonia in methanol as eluant) to afford the title compound (0.102 g).

$^1$H NMR (400 MHz, d$_6$-DMSO) δ 9.75 (1H, s), 7.83 (1H, d), 7.54 (1H, d), 7.46 (1H, d), 6.92 (1H, d), 3.70-3.48 (4H, m), 3.26-3.18 (1H, m), 2.32 (2H, d), 2.11-2.02 (1H, m), 1.89-1.60 (9H, m), 1.33-1.13 (3H, m), 1.11-0.97 (2H, m).

MS: APCI(+ve) 387 (M+H$^+$).

m.p. 201-206° C.

EXAMPLE 31

N-[2-[(3S)-3-Amino-1-pyrrolidinyl]-6-chloro-5-quinolinyl]-cyclohexaneacetamide

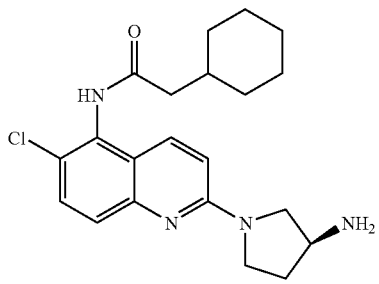

Prepared according to the method of example 30, using N-(2,6-dichloro-5-quinolinyl)-cyclohexaneacetamide (Example 1(a)) (0.166 g) and (3S)-3-pyrrolidinamine (0.127 g) to afford the title compound (0.113 g).

$^1$H NMR (400 MHz, d$_6$-DMSO) δ 9.76 (1H, s), 7.84 (1H, d), 7.54 (1H, d), 7.46 (1H, d), 6.93 (1H, d), 3.70-3.58 (3H, m), 3.58-3.49 (1H, m), 3.28-3.21 (1H, m), 2.32 (2H, d), 2.14-2.04 (1H, m), 1.88-1.76 (4H, m), 1.76-1.67 (4H, m), 1.67-1.60 (1H, m), 1.32-1.11 (3H, m), 1.11-0.99 (2H, m).

MS: APCI(+ve) 387 (M+H$^+$).

m.p. 219-226° C.

EXAMPLE 32

N-[2-(4-Amino-1-piperidinyl)-6-chloro-5-quinolinyl]-cyclohexaneacetamide

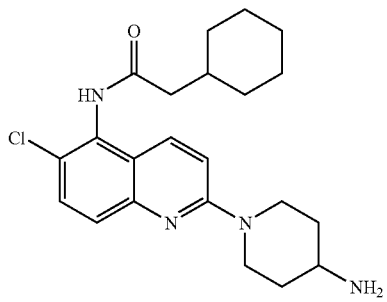

Prepared according to the method of example 30, using N-(2,6-dichloro-5-quinolinyl)-cyclohexaneacetamide (Example 1(a)) (0.113 g) and 4-piperidinamine (0.152 mL) to afford the title compound (0.109 g).

$^1$H NMR (400 MHz, $d_6$-DMSO) δ 9.82 (1H, s), 7.87 (1H, d), 7.59 (1H, d), 7.49 (1H, d), 7.35 (1H, d), 4.57-4.49 (2H, m), 3.27-3.18 (2H, m), 3.08-2.99 (3H, m), 2.35-2.31 (2H, m), 1.97-1.90 (2H, m), 1.84-1.77 (4H, m), 1.75-1.67 (2H, m), 1.67-1.61 (1H, m), 1.48-1.33 (3H, m), 1.32-1.15 (2H, m), 1.11-0.99 (1H, m).

MS: APCI(+ve) 401 (M+H$^+$).

m.p. 333-334° C.

EXAMPLE 33

N-[6-Chloro-2-[(3R)-3-(methylamino)-1-pyrrolidinyl]-5-quinolinyl]-cyclohexaneacetamide

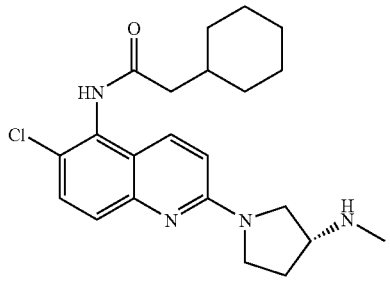

a) N-[6-Chloro-2-[(3S)-3-[(methylsulfonyl)oxy]-1-pyrrolidinyl]-5-quinolinyl]-cyclohexaneacetamide To a stirred solution of N-[6-chloro-2-[(3S)-3-hydroxy-1-pyrrolidinyl]-5-quinolinyl]-cyclohexaneacetamide (Example 29) (0.4 g) in dichloromethane was added methanesulphonyl chloride (0.104 mL) and triethylamine (0.215 mL). The reaction was stirred for 12 hours under nitrogen and then purified (Varian Chem elute cartridge, saturated sodium hydrogen carbonate solution and dichloromethane as eluant) to afford the sub-title compound (0.45 g).

MS: APCI(+ve) 466 (M+H$^+$).

b) N-[6-Chloro-2-[(3R)-3-(methylamino)-1-pyrrolidinyl]-5-quinolinyl]Cyclohexaneacetamide To a 10 mL vial was added N-[6-Chloro-2-[(3S)-3-[(methylsulfonyl)oxy]-1-pyrrolidinyl]-5-quinolinyl]-cyclohexaneacetamide (Example 33(a)) (225 mg) and 8M methylamine in ethanol (6 mL). The vial was sealed and heated at 80° C. for 120 minutes within a microwave. The solvent was removed under vacuum and purified (SiO$_2$, ammonia:methanol:dichloromethane, 1:2:97 as eluant) to afford the titled compound (0.033 g).

$^1$H NMR (400 MHz, $d_6$-DMSO) δ 9.75 (1H, s), 7.83 (1H, d), 7.54 (1H, d), 7.46 (1H, d), 6.93 (1H, d), 3.69-3.63 (1H, m), 3.63-3.48 (2H, m), 3.36-3.23 (4H, m), 2.30 (3H, s), 2.14-2.04 (1H, m), 1.89-1.75 (4H, m), 1.75-1.67 (2H, m), 1.67-1.59 (1H, m), 1.32-1.12 (3H, m), 1.11-0.97 (2H, m).

MS: APCI(+ve) 401 (M+H$^+$).

m.p. 169° C.

EXAMPLE 34

N-[6-Chloro-2-[(3R)-3-[(2-hydroxyethyl)amino]-1-pyrrolidinyl]-5-quinolinyl]-cyclohexaneacetamide

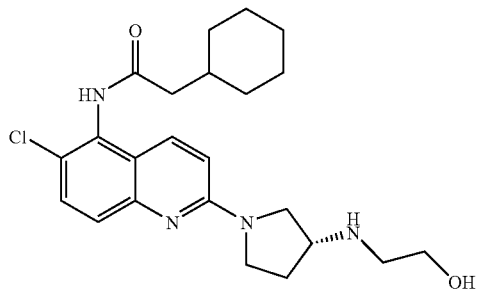

Prepared according to the method of example 33(b), using N-[6-Chloro-2-[(3S)-3-[(methylsulfonyl)oxy]-1-pyrrolidinyl]-5-quinolinyl]-cyclohexaneacetamide (Example 33(a)) (0.225 g) and ethanolamine (2 mL) to afford the title compound (0.052 g).

$^1$H NMR (400 MHz, $d_6$-DMSO) δ 9.75 (1H, s), 7.83 (1H, d), 7.54 (1H, d), 7.46 (1H, d), 6.93 (1H, d), 3.72-3.66 (1H, m), 3.66-3.57 (1H, m), 3.57-3.49 (1H, m), 3.48-3.44 (2H, m), 3.42-3.36 (2H, m), 2.69-2.59 (2H, m), 2.32 (2H, d), 2.16-2.07 (1H, m), 1.88-1.76 (4H, m), 1.75-1.67 (2H, m), 1.67-1.60 (1H, m), 1.33-1.13 (3H, m), 1.10-0.99 (2H, m).

MS: APCI(+ve) 431 (M+H$^+$).

m.p. 197-199° C.

EXAMPLE 35

N-[6-Chloro-2-[(3S)-3-(methylamino)-1-pyrrolidinyl]-5-quinolinyl]-cyclohexaneacetamide

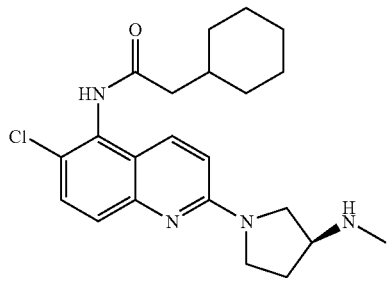

a) N-[6-Chloro-2-[(3R)-3-[(methylsulfonyl)oxy]-1-pyrrolidinyl]-5-quinolinyl]-cyclohexaneacetamide Prepared according to the method of example 33(a), using N-[6-chloro-2-[(3R)-3-hydroxy-1-pyrrolidinyl]-5-quinolinyl]-cyclohexaneacetamide (Example 28) (0.46 g) and methanesulphonyl chloride (0.183 mL) to afford the sub-title compound (0.47 g).

MS: APCI(+ve) 466 (M+H$^+$).

b) N-[6-Chloro-2-[(3S)-3-(methylamino)-1-pyrrolidinyl]-5-quinolinyl]-cyclohexaneacetamide Prepared according to the method of example 33(b), using N-[6-Chloro-2-[(3R)-3-[(methylsulfonyl)oxy]-1-pyrrolidinyl]-5-quinolinyl]-cyclohexaneacetamide (Example 35(a)) (0.2 g) and 8M methylamine in ethanol (3 mL) to afford the title compound (0.063 g).

$^1$H NMR (400 MHz, d-DMSO) δ 9.75 (1H, s), 7.83 (1H, d), 7.54 (1H, d), 7.46 (1H, d), 6.93 (1H, d), 3.66 (1H, dd), 3.63-3.48 (2H, m), 3.4-3.22 (4H, m), 2.31 (3H, s), 2.15-2.04 (1H, m), 1.88-1.76 (4H, m), 1.75-1.67 (2H, m), 1.67-1.60 (1H, m), 1.32-1.12 (3H, m), 1.10-0.99 (2H, m).

MS: APCI(+ve) 401 (M+H$^+$).

m.p. 164-165° C.

EXAMPLE 36

N-[6-Chloro-2-[(3S)-3-[(2-hydroxyethyl)amino]-1-pyrrolidinyl]-5-quinolinyl]-cyclohexaneacetamide

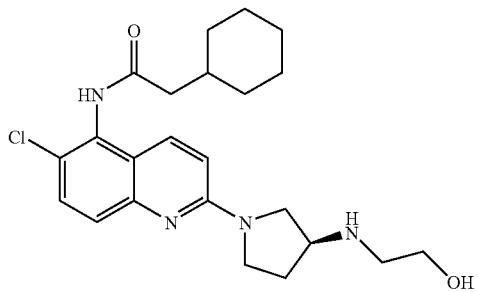

Prepared according to the method of example 33(b), using N-[6-Chloro-2-[(3R)-3-[(methylsulfonyl)oxy]-1-pyrrolidinyl]-5-quinolinyl]-cyclohexaneacetamide (Example 35(a)) (0.2 g) and ethanolamine (0.8 mL) to afford the title compound (0.068 g).

$^1$H NMR (400 MHz, d$_6$-DMSO) δ 9.75 (1H, d), 7.83 (1H, d), 7.54 (1H, d), 7.46 (1H, d), 6.93 (1H, d), 4.48 (1H, t), 3.72-3.57 (2H, m), 3.56-3.49 (1H, m), 3.49-3.36 (4H, m), 2.68-2.62 (2H, m), 2.32 (2H, d), 2.17-2.07 (1H, m), 1.87-1.77 (4H, m), 1.75-1.67 (2H, m), 1.67-1.60 (1H, m), 1.33-1.12 (3H, m), 1.10-0.98 (2H, m).

MS: APCI(+ve) 431 (M+H$^+$).

m.p. 194-196° C.

EXAMPLE 37

N-[6-Chloro-2-[(3R)-3-hydroxy-1-piperidinyl]-5-quinolinyl]-cyclohexaneacetamide

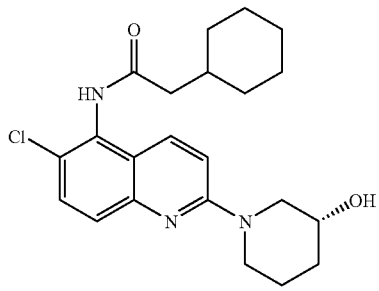

N-(2,6-Dichloro-5-quinolinyl)-cyclohexaneacetamide (Example 1(a)) (1 g), (3R)-3-piperidinol hydrochloride (0.424 g) and triethylamine (1.2 mL) were placed into a 10 mL microwave vial followed by the addition of acetonitrile (3 mL). The vial was sealed and heated at 120° C. in a single mode microwave for 45 minutes. On cooling a solid crystallised from the reaction mixture which was filtered and washed with acetonitrile (10 mL) to afford the sub-title compound (0.7 g).

$^1$H NMR (400 MHz, d$_6$-DMSO) δ 9.77 (1H, s), 7.83 (1H, d), 7.56 (1H, d), 7.46 (1H, d), 7.29 (1H, d), 4.89 (1H, s), 4.33 (1H, d), 4.12 (1H, d), 3.52 (1H, s), 3.21-3.11 (1H, m), 2.94 (1H, t), 2.32 (2H, d), 1.96-1.88 (1H, m), 1.87-1.75 (4H, m), 1.75-1.67 (2H, m), 1.67-1.59 (1H, m), 1.50-1.38 (2H, m), 1.33-1.11 (3H, m), 1.10-0.98 (2H, m).

MS: APCI(+ve) 402 (M+H$^+$).

m.p. 209-214° C.

EXAMPLE 38

N-[2-[(3S)-3-Amino-1-pyrrolidinyl]-6-methyl-5-quinolinyl]-cyclohexaneacetamide

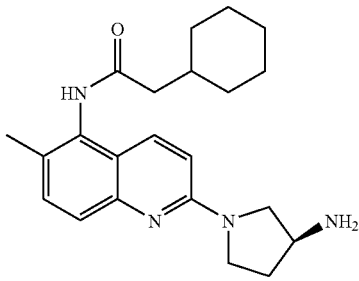

Prepared according to the method of example 30, using N-(2-Chloro-6-methyl-5-quinolinyl)-cyclohexaneacetamide (Example 15(a)) (0.2 g) and (3S)-3-pyrrolidinamine (0.163 g) which after recrystallisation from ethanol afforded the title compound (0.159 g).

$^1$H NMR (400 MHz, d$_6$-DMSO) δ 9.53 (1H, s), 7.85 (1H, d), 7.42-7.32 (2H, m), 6.83 (1H, d), 3.69-3.56 (3H, m), 3.55-3.40 (2H, m), 3.25-3.18 (1H, m), 2.31 (2H, d), 2.20 (3H, s), 2.12-2.03 (1H, m), 1.88-1.60 (8H, m), 1.33-1.13 (3H, m), 1.11-0.98 (2H, m).

MS: APCI(+ve) 367 (M+H$^+$).

m.p. 223-224° C.

EXAMPLE 39

N-[6-Methyl-2-(1-piperazinyl)-5-quinolinyl]-cyclohexaneacetamide

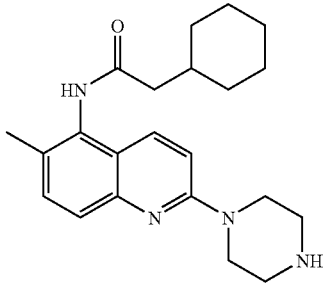

Prepared according to the method of example 2, using N-(2-Chloro-6-methyl-5-quinolinyl)-cyclohexaneacetamide (Example 15(a)) (0.2 g) and piperazine (0.163 g). The reaction was cooled to room temperature, the resulting solid collected by filtration and recrystallised from methanol to afford the title compound (0.102 g).

$^1$H NMR (400 MHz, CD$_3$OD/TFA) δ 8.35 (1H, d), 7.81 (2H, dd), 7.54 (1H, d), 4.25-4.14 (4H, m), 3.56-3.46 (4H, m), 2.46 (2H, d), 2.40 (3H, s), 1.99-1.67 (6H, m), 1.43-1.08 (5H, m).

MS: APCI(+ve) 367 (M+H$^+$).

EXAMPLE 40

N-[6-Chloro-5-[(cyclohexylacetyl)amino]-2-quinolinyl]-glycine

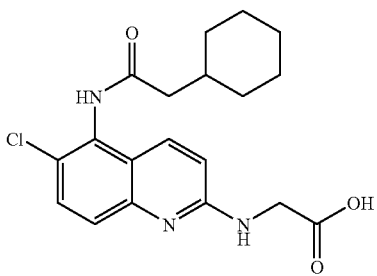

a) N-[6-Chlor-5-[(cyclhexylacetyl)amino]-2-quinolinyl]-glycine, 1,1-dimethylethyl Ester Prepared according to the method of example 7 (a), using N-(2,6-dichloro-5-quinolinyl)-cyclohexaneacetamide (Example 1 (a)) (400 mg) and glycine tert-butyl ester hydrochloride (1.5 g) to afford the sub-title compound (63 mg).

MS: APCI(+ve) 432/434 (M+H$^+$).

b) N-[6-Chloro-5-[(cyclohexylacetyl)amino]-2-quinolinyl]-glycine

Prepared according to the method of example 7 (b), using N-[6-chloro-5-[(cyclohexylacetyl)amino]-2-quinolinyl]-glycine, 1,1-dimethylethyl ester (Example 40(a)) (63 mg) and trifluoroacetic acid (2 mL). Purification by HPLC (Symmetry—0.1% aqueous ammonium acetate/acetonitrile) afforded the title product (27 mg).

$^1$H NMR (400 MHz, d$_6$-DMSO) δ 9.42 (1H, br s), 7.77 (1H, d), 7.50 (1H, d), 7.42 (1H, d), 7.09 (1H, br s), 6.92 (1H, d), 4.08 (2H, br s), 2.31 (2H, br m), 1.91-1.59 (6H, m), 1.34-1.00 (5H, m).

MS: APCI(-ve) 374/376 (M-H$^+$).

m.p. 222-225° C. dec.

EXAMPLE 41

N-[6-Chloro-5-[(cyclohexylacetyl)amino]-2-quinolinyl]-β-alanine

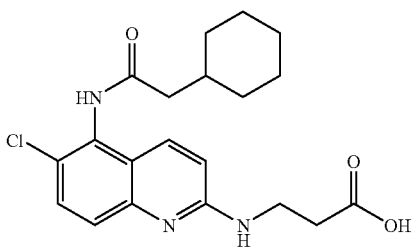

a) N-[6-Chloro-5-[(cyclohexylacetyl)amino]-2-quinolinyl]-β-alanine, 1,1-dimethylethyl Ester Prepared according to the method of example 7 (a), using N-(2,6-dichloro-5-quinolinyl)-cyclohexaneacetamide (Example 1 (a)) (400 mg) and β-alanine tert-butyl ester hydrochloride (1.6 g) to afford the sub-title compound (150 mg).

MS: APCI(+ve) 446/448 (M+H$^+$).

b) N-[6-Chloro-5-[(cyclohexylacetyl)amino]-2-quinolinyl]-β-alanine

Prepared according to the method of example 7 (b), using N-[6-chloro-5-[(cyclohexylacetyl)amino]-2-quinolinyl]-β-alanine, 1,1-dimethylethyl ester (Example 41 (a)) (150 mg) and trifluoroacetic acid (2 mL). Purification by HPLC (Symmetry—0.1% aqueous ammonium acetate/acetonitrile) afforded the title product (39 mg).

$^1$H NMR (400 MHz, d$_6$-DMSO) δ 12.23 (1H, s), 9.73 (1H, s), 7.71 (1H, d), 7.53 (1H, d), 7.45 (1H, d), 7.27 (1H, t), 6.82 (1H, d), 3.59 (2H, td), 2.58 (2H, t), 2.31 (2H, d), 1.89-1.59 (6H, m), 0.97-1.33 (5H, m).

MS: APCI(-ve) 388/390 (M-H$^+$).

m.p. 222-224° C. dec.

EXAMPLE 42

6-Chloro-N-(cyclohexylmethyl)quinoline-5-carboxamide

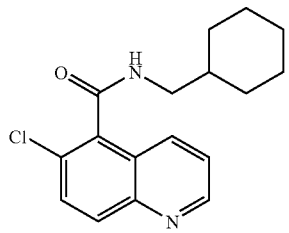

To a solution of 5-bromo-6-chloroquinoline (prepared according to the method of Journal of Heterocyclic Chemistry 1967, 4, 410) (4.0 g), cyclohexanemethylamine (4.2 mL) and triethylamine (2.4 mL) in N-methylpyrrolidinone (40 mL) was added dichlorobis(triphenylphosphine)palladium (II) (1.6 g). The mixture was heated with stirring at 100° C. under a 6 bar pressure of carbon monoxide for 18 hours after which it was cooled and filtered through diatomaceous earth, washing with methanol. The combined organics were concentrated to give a residue which was purified (SiO$_2$, isohexane:ethyl acetate:ammonia in methanol (7 M) 49:49:2 as eluant) to yield the title compound as a solid (4.6 g).

$^1$H NMR (300 MHz, d$_6$-DMSO) δ 8.97 (1H, dd), 8.75 (1H, t), 8.10 (1H, dd), 8.07 (1H, d), 7.82 (1H, d), 7.65 (1H, dd), 3.21 (2H, dd), 1.50-1.86 (6H, m), 0.91-1.32 (5H, m).

MS: APCI(+ve) 303/305 (M+H$^+$).

m.p. 193-194° C.

EXAMPLE 43

6-Chloro-N-(cyclohexylmethyl)-2-(1-piperazinyl)-5-quinolinecarboxamide, Dihydrochloride

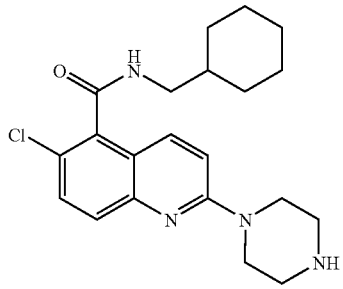

a) 2,6-Dichloro-N-(cyclohexylmethyl)quinoline-5-carboxamide

To a solution of 6-chloro-N-(cyclohexylmethyl)quinoline-5-carboxamide (Example 42) (1.0 g) was added a mixture of aqueous hydrogen peroxide (5 mL, 27%) and glacial acetic acid (8 mL) over 10 minutes. The mixture was heated with stirring at 65° C. for 3 hours after which it was cooled to room temperature and partitioned between dichloromethane and water. The organic layer was separated and the aqueous layer was further extracted with dichloromethane. The combined organic extracts were washed with aqueous saturated sodium bicarbonate before being dried, filtered and evaporated to give a residue to which phosphorous oxychloride (5 mL) was added over 10 minutes. The mixture was heated with stirring at 120° C. under an atmosphere of nitrogen for 3 hours after which it was cooled to room temperature and the volatile components were removed in vacuo to leave a residue which was partitioned between dichloromethane and water. The organic layer was separated, the aqueous layer was further extracted with dichloromethane and the combined organic extracts were washed with aqueous saturated sodium bicarbonate before being dried, filtered and evaporated to yield the subtitled compound as a solid (0.90 g).

MS: APCI(+ve) 337/339 (N+H$^+$).

b) 6-Chloro-N-(cyclohexylmethyl)-2-(1-piperazinyl)-5-quinolinecarboxamide, Dihydrochloride A stirred solution of 2,6-dichloro-N-(cyclohexylmethyl)quinoline-5-carboxamide (Example 43 (a)) (200 mg) and piperazine (160 mg) in acetonitrile (2 mL) was heated at 80° C. in a CEM Discover microwave for 1 hour after which it was cooled to room temperature and concentrated. The residue was purified (Waters' SCX resin, ammonia in methanol (7 M) as eluant) and the resultant product was converted to the dihydrochloride salt by treatment with hydrochloric acid (4M in 1,4-dioxane). Recrystallisation (methanol/ethyl acetate) afforded the title compound as a solid (110 mg).

$^1$H NMR (300 MHz, d$_6$-DMSO) δ 9.35 (1H, br s), 8.72 (1H, t), 7.87 (1H, d), 7.75 (1H, br d), 7.65 (1H, d), 7.46 (1H, d), 4.00 (4H, br s), 3.23-3.19 (6H, m), 1.81-1.65 (6H, m), 1.24-0.92 (5H, m).

MS: APCI(+ve) 387/389 (M+H$^+$).

m.p. 305-306° C.

EXAMPLE 44

2-[(3S)-3-Amino-1-pyrrolidinyl]-6-chloro-N-(cyclohexylmethyl)-5-quinolinecarboxamide

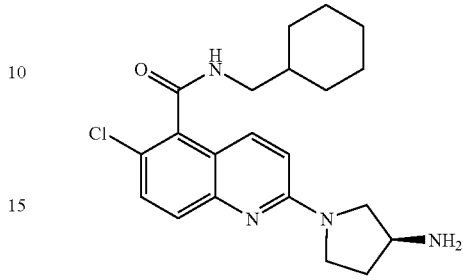

A stirred suspension of 2,6-dichloro-N-(cyclohexylmethyl)quinoline-5-carboxamide (Example 43(a)) (500 mg) and (3S)-3-pyrrolidinamine (0.60 mL) in acetonitrile (3 mL) was heated at 100° C. in a microwave for 40 minutes after which it was cooled to room temperature and concentrated. Purification by chromatography (SiO$_2$, dichloromethane:methanol:ammonia in methanol (7 M) 95:5:0.5 as eluant) and subsequent recrystallisation (acetonitrile) afforded the title compound as a solid (280 mg).

$^1$H NMR (400 MHz, d$_6$-DMSO, 90° C.) δ 8.26 (1H, br s), 7.74 (1H, d), 7.51 (1H, d), 7.44 (1H, d), 6.90 (1H, d), 3.72-3.59 (3H, m), 3.58-3.49 (1H, m), 3.26-3.16 (3H, m), 2.15-2.06 (1H, m), 1.83-1.56 (7H, m), 1.30-1.12 (3H, m), 1.08-0.96 (2H, m).

MS: APCI(+ve) 387/389 (M+H$^+$).

EXAMPLE 45

6-Chloro-N-(cyclohexylmethyl)-2-[methyl[3-(methylamino)propyl]amino]-5-quinoline Carboxamide, Dihydrochloride

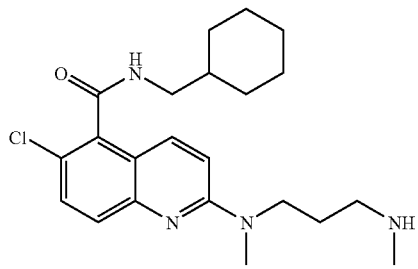

A stirred suspension of 2,6-dichloro-N-(cyclohexylmethyl)quinoline-5-carboxamide (Example 43 (a)) (250 mg) and N,N'-dimethyl-1,3-propanediamine (0.80 mL) in acetonitrile (3 mL) was heated at 100° C. in a microwave for 2 hours after which it was cooled to room temperature and concentrated. The residue was purified by recrystallisation (methanol:ethyl acetate). The resultant product was converted to the dihydrochloride salt by treatment with hydrochloric acid (4M in 1,4-dioxane). Recrystallisation (methanol/ethyl acetate) afforded the title compound as a solid (110 mg).

$^1$H NMR (400 MHz, d$_6$-DMSO, 90° C.) δ 9.09 (2H, br), 8.44 (1H, br), 8.07 (1H, br), 7.88 (1H, d), 7.64 (1H, d), 7.39

(1H, d), 3.90 (2H, t), 3.30 (3H, s), 3.22-3.19 (2H, m), 3.01-2.92 (2H, m), 2.55-2.50 (3H, m), 2.08-2.00 (2H, quin), 1.83-1.54 (6H, m), 1.31-0.97 (5H, m).

MS: APCI(+ve) 403/405 (M+H$^+$).

EXAMPLE 46

6-Chloro-N-(cyclohexylmethyl)-2-[methyl[2-(methylamino)ethyl]amino]-5-quinolinecarboxamide, Dihydrochloride

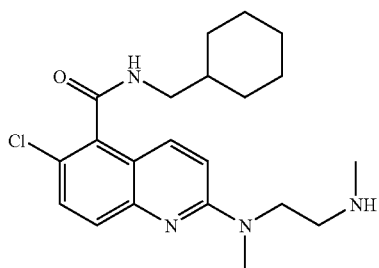

A stirred suspension of 2,6-dichloro-N-(cyclohexylmethyl)quinoline-5-carboxamide (Example 43 (a)) (200 mg) and N,N'-dimethyl-1,2-ethanediamine (0.30 mL) in acetonitrile (2 mL) was heated at 100° C. in a microwave for 90 minutes after which it was cooled to room temperature and concentrated. Purification (SiO$_2$, dichloromethane:methanol:ammonia in methanol (7 M) 95:5:0.5), conversion to the dihydrochloride salt by treatment with hydrochloric acid (4M in 1,4-dioxane) and recrystallisation (methanol/ethyl acetate) afforded the title compound as a solid (160 mg).

$^1$H NMR (400 MHz, d$_6$-DMSO, 90° C.) δ 9.23 (2H, br), 8.42 (1H, br), 7.95 (1H, br d), 7.88 (1H, d), 7.62 (1H, d), 7.39 (1H, d), 4.09 (2H, t), 3.28 (3H, s), 3.22-3.19 (4H, m), 2.59 (3H, s), 1.83-1.55 (6H, m), 1.31-0.96 (5H, m).

MS: APCI(+ve) 389/391 (M+H$^+$).

EXAMPLE 47

6-Chloro-N-(cyclohexylmethyl)-2-[3-[(3-hydroxypropyl)amino]propyl]-5-quinolinecarboxamide

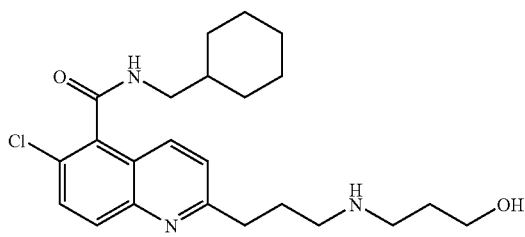

a) [3-[6-Chloro-5-[[(cyclohexylmethyl)amino]carbonyl]-2-quinolinyl]propyl][3-[[(1,1-dimethylethyl) dimethylsilyl]oxy]propyl]-carbamic Acid, 1,1-dimethyl Ester Prepared according to the method of Example 1 (b), using 2,6-dichloro-N-(cyclohexylmethyl)quinoline-5-carboxamide (Example 43 (a)) (300 mg) and [3-[[(1,1-dimethylethyl) dimethylsilyl]oxy]propyl]2-propenyl-carbamic acid, 1,1-dimethylethyl ester (Example 22(a)) (600 mg). Purification (SiO$_2$, methanol:dichloromethane 1:9) gave the title compound as a colourless oil (510 mg).

MS: APCI(+ve) 633/635 (M+H$^+$).

b) 6-Chloro-N-(cyclohexylmethyl)-2-[3-[(3-hydroxypropyl)amino]propyl]-5-quinolinecarboxamide HCl in 1,4-dioxane (4M, 3 mL) was added to 3-[6-chloro-5-[[(cyclohexylmethyl)amino]carbonyl]-2-quinolinyl]propyl][3-[[(1,1-dimethylethyl)dimethylsilyl]oxy]propyl]-carbamic acid, 1,1-dimethyl ester (Example 47(a)) (500 mg) and the mixture was stirred for 4 hours at room temperature before being concentrated. Purification (SiO$_2$, dichloromethane:methanol:ammonia in methanol (7 M) 97:3:0.5) and recrystallisation (methanol/ethyl acetate) afforded the title compound as a solid (90 mg).

$^1$H NMR (400 MHz, d$_6$-DMSO) δ 8.72 (1H, t), 8.00 (1H, d), 7.97 (1H, d), 7.76 (1H, d), 7.56 (1H, d), 3.46 (2H, t), 3.22-3.18 (2H, m), 2.97 (2H, t), 2.68-2.62 (4H, m), 1.93 (2H, quin), 1.83-1.67 (4H, m), 1.66-1.53 (4H, m), 1.29-0.93 (5H, m).

MS: APCI(+ve) 418/420 (M+H$^+$).

EXAMPLE 48

2-[(3R)-3-Amino-1-pyrrolidinyl]-6-chloro-N-(cyclohexylmethyl)-5-quinolinecarboxamide, Dihydrochloride

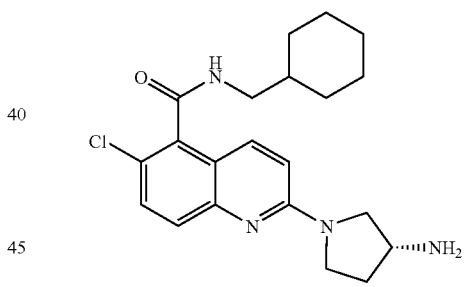

A stirred suspension of 2,6-dichloro-N-(cyclohexylmethyl)quinoline-5-carboxamide (Example 43(a)) (200 mg) and (3R)-3-pyrrolidinamine (0.20 mL) in acetonitrile (2 mL) was heated at 100° C. in a microwave for 1 hour after which it was cooled to room temperature and concentrated. The residue was purified by chromatography (SiO$_2$, dichloromethane:methanol:ammonia in methanol (7 M) (95:5:1), and then by HPLC (Symmetry—0.1% aqueous trifluoroacetic acid/acetonitrile). Conversion to the dihydrochloride salt by treatment with hydrochloric acid (4M in 1,4-dioxane) and subsequent recrystallisation (methanol/ethyl acetate) afforded the title compound as a solid (46 mg).

$^1$H NMR (400 MHz, d$_6$-DMSO, 90° C.) δ 8.70-8.29 (3H, m), 8.04 (1H, d), 7.92 (1H, d), 7.67 (1H, d), 7.18 (1H, d), 4.07-3.87 (4H, m), 3.85-3.75 (1H, m), 3.24-3.18 (2H, m), 2.46-2.35 (1H, m), 2.33-2.23 (1H, m), 1.85-1.54 (6H, m), 1.33-0.95 (5H, m).

MS: APCI(+ve) 387/389 (M+H$^+$).

EXAMPLE 49

N-(2-Amino-6-chloro-5-quinolinyl)-cyclohexaneacetamide, Trifluoroacetate

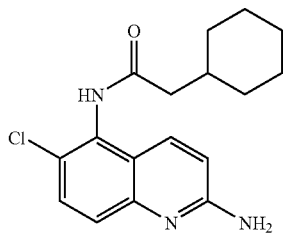

A stirred suspension of N-(2,6-dichloro-5-quinolinyl)-cyclohexaneacetamide (Example 1 (a)) (200 mg) and tetrabutylammonium bromide (20 mg) in ammonium hydroxide (28% $NH_3$ in water) (1.0 mL) was heated at 180° C. in a microwave for 3 hours after which it was cooled to room temperature and concentrated. Purification by HPLC (Symmetry—0.1% aqueous trifluoroacetic acid/acetonitrile) gave the title compound as a solid (44 mg).

$^1$H NMR (400 MHz, $d_6$-DMSO) δ 10.03 (2H, s), 8.60 (1H, br), 8.10 (1H, d), 7.86 (1H, d), 7.59 (1H, d), 7.10 (1H, d), 2.35 (2H, d), 1.88-1.57 (6H, m), 1.31-0.97 (5H, m).

MS: APCI(+ve) 318/320 (M+H$^+$).

EXAMPLE 50

6-Chloro-N-(cyclohexylmethyl)-2-[(3S)-3-[(2-hydroxyethyl)amino]-1-pyrrolidinyl]-5-quinolinecarboxamide, Hydrochloride

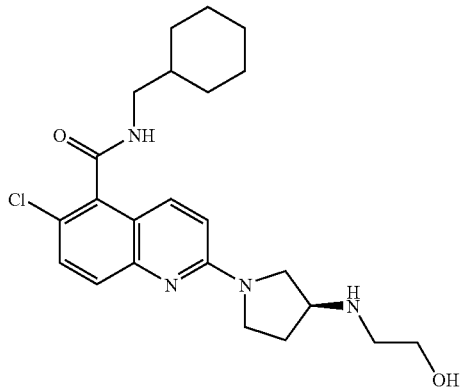

a) 6-Chloro-N-(cyclohexylmethyl)-2-[(3S)-3-[[2-[[(1,1-dimethylethyl)dimethylsilyl]oxy]ethyl]amino]-1-pyrrolidinyl]-5-quinolinecarboxamide A suspension of 2-[(3S)-3-amino-1-pyrrolidinyl]-6-chloro-N-(cyclohexylmethyl)-5-quinolinecarboxamide (example 44) (0.16 g) and activated 3 Å molecular sieves (0.16 g) in anhydrous, degassed dichloromethane (7 mL) was treated with (tert-butyldimethylsilyloxy)acetaldehyde (0.078 mL) and the resulting mixture stirred at room temperature for 6 hours. To this mixture was added sodium triacetoxyborohydride (0.17 g) and stirring continued for 16 hours. The reaction mixture was filtered and concentrated to dryness. Purification (SiO$_2$, Ethyl acetate:isohexane 4:1 as eluant) gave the sub-titled compound (0.17 g).

$^1$H NMR (300 MHz, $d_6$-DMSO, 120° C.) δ 8.05 (1H, s), 7.76 (1H, d), 7.51 (1H, d), 7.42 (1H, d), 6.89 (1H, d), 3.66 (2H, t), 3.76-3.42 (3H, m), 3.33-3.27 (1H, m), 3.21 (2H, t), 2.72 (2H, t), 2.19-2.08 (1H, m), 1.91-1.58 (8H, m), 1.33-0.98 (5H, m), 0.88 (9H, s), 0.05 (6H, s).

b) 6-Chloro-N-(cyclohexylmethyl)-2-[(3S)-3-[(2-hydroxyethyl)amino]-1-pyrrolidinyl]-5-quinolinecarboxamide, Hydrochloride A mixture of 6-Chloro-N-(cyclohexylmethyl)-2-[(3S)-3-[[2-[[(1,1-dimethylethyl)dimethylsilyl]oxy]ethyl]amino]-1-pyrrolidinyl]-5-quinolinecarboxamide (Example 50(a)) (0.16 g) in 1,4-dioxane (1 mL) was treated with 4M HCl in 1,4-dioxane (1 mL) and stirred at room temperature for 16 hours. The reaction mixture was concentrated to dryness. Purification (HPLC, Symmetry—0.1% aqueous trifluoroacetic acid/acetonitrile) followed by conversion of the resultant product to its hydrochloride salt by treatment with hydrochloric acid (4M in 1,4-dioxane) afforded the title product (0.05 g).

$^1$H NMR (300 MHz, $d_6$-DMSO, 120° C.) δ 7.76 (1H, d), 7.52 (1H, d), 7.43 (1H, d), 6.90 (1H, d), 3.77-3.28 (6H, m), 3.20 (2H, d), 2.72-2.66 (2H, m), 2.20-2.08 (1H, m), 1.89-1.56 (8H, m), 1.32-0.96 (5H, m).

MS: APCI(+ve) 431/433 (M+H$^+$).

m.p. 211-220° C.

EXAMPLE 51

2-[(3S)-3-Amino-1-piperidinyl]-6-chloro-N-(cyclohexylmethyl)-5-quinolinecarboxamide

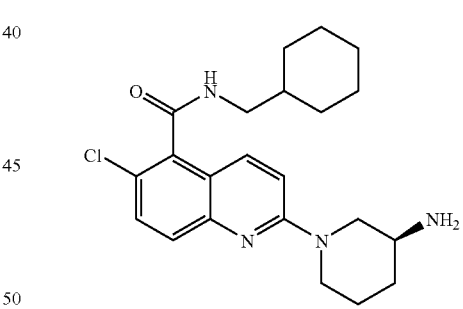

A stirred suspension of 2,6-dichloro-N-(cyclohexylmethyl)quinoline-5-carboxamide (Example 43(a)) (250 mg), (3S)-3-piperidinamine dihydrochloride (260 mg) and tetrabutylammonium bromide (20 mg) in acetonitrile (2 mL) was heated at 130° C. in a microwave for 90 minutes after which it was cooled to room temperature and concentrated. The residue was purified by chromatography (SiO$_2$, dichloromethane:methanol:ammonia in methanol (7 M) 96:3:1 as eluant) and subsequent recrystallisation (acetonitrile) gave the title compound as a solid (120 mg).

$^1$H NMR (400 MHz, $d_6$-DMSO) δ 8.64 (1H, t), 8.19 (2H, br s), 7.80 (1H, d), 7.57 (2H, s), 7.37 (1H, d), 4.55-4.47 (1H, m), 4.12-4.05 (1H, m), 3.30-3.14 (5H, m), 2.09-2.00 (1H, m), 1.89-1.49 (9H, m), 1.29-1.11 (3H, m), 1.04-0.91 (2H, m).

MS: APCI(+ve) 401/403 (M+H$^+$).

EXAMPLE 52

6-Chloro-N-(cyclohexylmethyl)-2-[(3S)-3-[(2-hydroxyethyl)amino]-1-piperidinyl]-5-quinolinecarboxamide, Hydrochloride

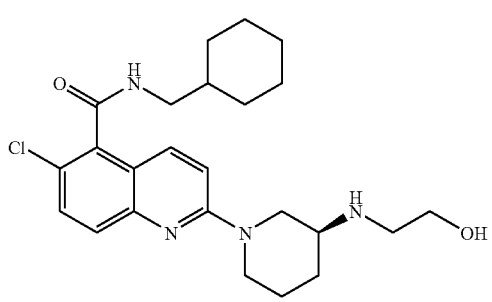

a) 6-Chloro-N-(cyclohexylmethyl)-2-[(3S)-3-[[2-[[(1,1-dimethylethyl)dimethylsilyl]oxy]ethyl]amino]-1-piperidinyl]-5-quinolinecarboxamide Prepared according to the method of example 50(a) using 2-[(3S)-3-amino-1-piperidinyl]-6-chloro-N-(cyclohexylmethyl)-5-quinolinecarboxamide Example 51) (200 mg), activated 3 Å molecular sieves (0.20 g), (tert-butyldimethylsilyloxy)acetaldehyde (0.085 mL), dichloromethane (5.0 mL) and sodium triacetoxyborohydride (210 mg). Purification (SiO$_2$, ethyl acetate:isohexane 1:1) gave the sub-titled compound (190 mg).

MS: APCI(+ve) 560/562 (M+H$^+$).

b) 6-Chloro-N-(cyclohexylmethyl)-2-[(3S)-3-[(2-hydroxyethyl)amino]-1-piperidinyl]-5-quinolinecarboxamide Prepared according to the method of example 50(b) using 6-chloro-N-(cyclohexylmethyl)-2-[(3S)-3-[[2-[[(1,1-dimethylethyl)dimethylsilyl]oxy]ethyl]amino]-1-piperidinyl]-5-quinolinecarboxamide Example 52(a)) (190 mg) and hydrochloric acid (4M in 1,4-dioxane) (2.0 mL). Purification (SiO$_2$, dichloromethane:methanol:ammonia in methanol (7 M) 96:3:1) and subsequent recrystallisation (acetonitrile) gave the title compound as a solid (53 mg).

$^1$H NMR (400 MHz, d$_6$-DMSO) δ 8.61 (1H, t), 7.72 (1H, d), 7.52-7.50 (2H, m), 7.34 (1H, d), 4.50 (1H, t), 4.46-4.37 (1H, d), 4.30-4.22 (1H, d), 3.45 (2H, app q), 3.19-3.14 (2H, m), 3.13-3.04 (1H, m), 2.90-2.82 (1H, m), 2.73-2.65 (2H, m), 2.58-2.52 (1H, m), 1.95 (1H, m), 1.83-1.29 (9H, m), 1.28-1.09 (3H, m), 1.04-0.91 (2H, m).

MS: APCI(+ve) 445/447 (M+H$^+$).

EXAMPLE 53

6-Chloro-N-(cyclohexylmethyl)-2-(3-hydroxy-1-azetidinyl)-5-quinolinecarboxamide

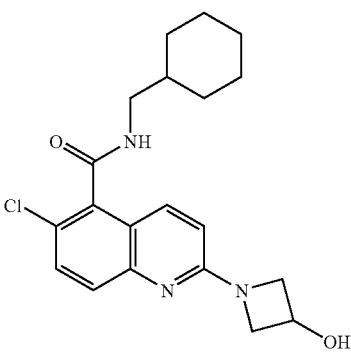

Prepared according to the method of example 30, using 2,6-dichloro-N-(cyclohexylmethyl)quinoline-5-carboxamide (Example 43 (a)) (0.10 g), and hydroxy azetidine hydrochloride (0.30 g). Purification (HPLC, Symmetry—0.1% aqueous trifluoroacetic acid/acetonitrile) afforded the title compound (0.04 g).

$^1$H NMR (400 MHz, CD$_3$OD) δ 7.76 (1H, d), 7.56 (1H, d), 7.44 (1H, d), 6.70 (1H, d), 4.63 (1H, tt), 4.32 (2H, dd), 3.87 (2H, dd), 3.19 (2H, d), 1.82-1.49 (6H, m), 1.28-0.91 (5H, m).

MS: APCI(+ve) 374/376 (M+H$^+$).

m.p. 206-208° C.

EXAMPLE 54

2-[(3S)-3-Amino-1-pyrrolidinyl]-N-(cyclohexylmethyl)-5-quinolinecarboxamide

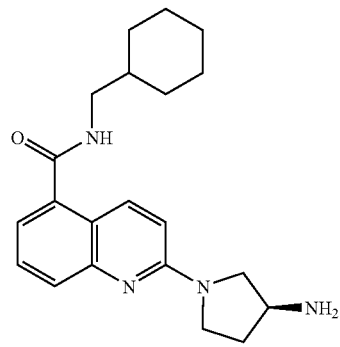

A suspension of 2-[(S)-3-amino-1-pyrrolidinyl]-6-chloro-N-(cyclohexylmethyl)-5-quinolinecarboxamide (Example 44) (0.10 g) and triethylamine (0.04 mL) in ethanol (20 mL) was treated with 5% palladium on charcoal (0.05 g) and stirred under 2 atmospheres of hydrogen at ambient temperature for 16 hours. The reaction mixture was filtered through Celite and the liquors concentrated to dryness. Recrystallisation from methanol/ethyl acetate afforded to title compound (0.05 g).

$^1$H NMR (300 MHz, CD$_3$OD) δ 8.28 (1H, dd), 7.78 (1H, d), 7.47 (1H, dt), 7.26 (1H, d), 6.89 (1H, dd), 4.02-3.94 (1H, m), 3.91-3.85 (1H, m), 3.77-3.61 (3H, m), 3.18 (2H, d), 2.50-2.37 (1H, m), 2.19-2.08 (1H, m), 1.82-1.49 (6H, m), 1.32-0.88 (5H, m).

MS: APCI(+ve) 353 (M+H⁺).

m.p. 127-128° C.

EXAMPLE 55

6-Chloro-N-(cyclohexylmethyl)-2-[3-[(2-hydroxyethyl)amino]-1-azetidinyl]-5-quinolinecarboxamide

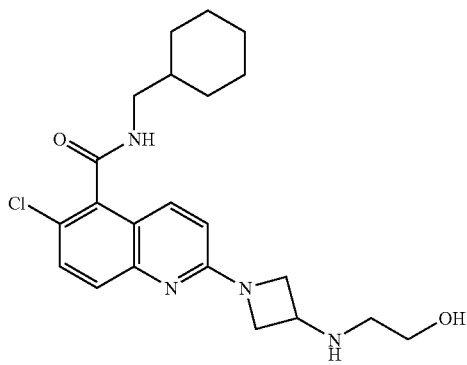

a) 6-Chloro-N-(cyclohexylmethyl)-2-[3-[[2-[(methylsulfonyl)oxy]ethyl]amino]-1-azetidinyl]-5-quinolinecarboxamide Prepared according to the method of example 33(a), using 6-chloro-N-(cyclohexylmethyl)-2-(3-hydroxy-1-azetidinyl)-5-quinolinecarboxamide (Example 53) (0.55 g) to afford the title compound (0.18 g).

MS: APCI(+ve) 453/455 (M+H⁺).

b) 6-Chloro-N-(cyclohexylmethyl)-2-[3-[(2-hydroxyethyl)amino]-1-azetidinyl]-5-quinolinecarboxamide Prepared according to the method of example 33(b), using 6-chloro-N-(cyclohexylmethyl)-2-[3-[[2-[(methylsulfonyl)oxy]ethyl]amino]-1-azetidinyl]-5-quinolinecarboxamide (Example 55(a)) (0.10 g) and ethanolamine (0.3 mL) to afford the title compound (0.03 g).

¹H NMR (300 MHz, CD₃OD) δ 7.76 (1H, d), 7.56 (1H, d), 7.44 (1H, d), 6.70 (1H, d), 4.29 (2H, t), 3.84 (2H, dd), 3.76 (1H, tt), 3.56 (2H, t), 3.22 (2H, d), 2.65 (2H, t), 1.83-1.48 (6H, m), 1.31-0.89 (5H, m).

MS: APCI(+ve) 417/419 (M+H⁺).

m.p. 150-151° C.

EXAMPLE 56

[1-[6-Chlor-5-[(cyclohexylacetyl)amino]-2-quinolinyl]-3-pyrrolidinyl](2-hydroxyethyl)-carbamic Acid 1,1-dimethylethyl Ester

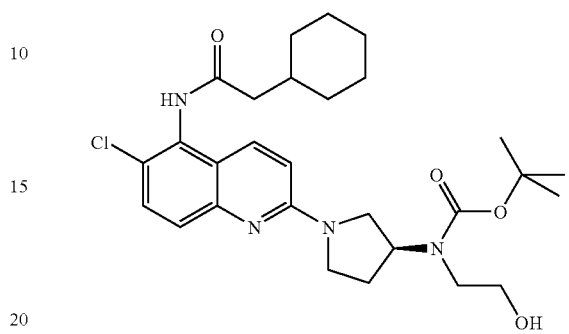

To a stirred solution of N-[6-chloro-2-[(3S)-3-[(2-hydroxyethyl)amino]-1-pyrrolidinyl]-5-quinolinyl]-cyclohexaneacetamide (Example 36) (1 g) in dichloromethane (5 mL) and methanol (2 mL) was added di-tert-butyl-carbonate (1 g). The mixture was stirred at room temperature for 18 hours and absorbed onto silica. Purification (SiO₂, methanol:dichloromethane 5:95 as eluant) gave the title compound as a solid (400 mg).

¹H NMR (300 MHz, d₆-DMSO/CD₃OD, major rotamer) δ 7.84 (1H, d), 7.60 (1H, d), 7.53 (1H, d), 6.76 (1H, d), 4.68 (1H, m), 3.90-3.75 (2H, m), 3.74-3.63 (2H, m), 3.59-3.49 (4H, m), 3.42-3.27 (2H, m), 2.40 (2H, d), 2.31-2.18 (2H, m), 2.00-1.87 (2H, m), 1.71-1.65 (2H, m), 1.49 (9H, s), 1.40-1.01 (5H, m).

MS: APCI(+ve) 531.5/533.5 (M+H⁺).

m.p. 115-120° C.

EXAMPLE 57

N-(Cyclohexylmethyl)-6-methyl-5-quinolinecarboxamide

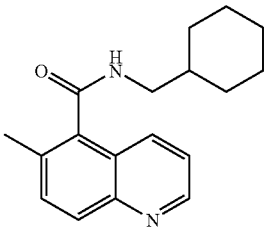

Prepared according to the method of example 42, using 5-bromo-6-methylquinoline (prepared according to the method of Khimiya Geterotsiklicheskikh Soedinenii 1988, 8, 1084) (4.0 g), cyclohexanemethylamine (4.2 mL), triethylamine (2.4 mL), dichlorobis(triphenylphosphine)palladium (II) (1.6 g) in N-methylpyrrolidinone (40 mL) to afford the title compound (3.9 g)

¹H NMR (300 MHz, d₆-DMSO) δ 8.86 (1H, dd), 8.58 (1H, t), 8.07 (1H, d), 7.95 (1H, d), 7.64 (1H, d), 7.54 (1H, dd), 3.21 (2H, t), 2.43 (3H, s), 1.83-1.52 (6H, m), 1.31-1.09 (3H, m), 1.05-0.91 (2H, m).

MS: APCI(+ve) 283.1 (M+H⁺).

m.p. 165° C.

EXAMPLE 58

2-[(3S)-3-Amino-1-pyrrolidinyl]-N-(cyclohexylmethyl)-6-methyl-5-quinolinecarboxamide, Acetate

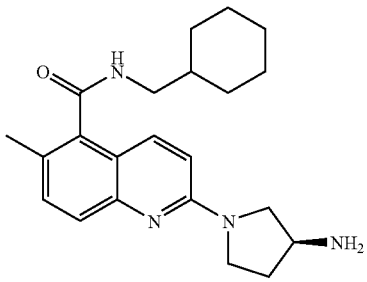

a) 2-Chloro-N-(cyclohexylmethyl)-6-methyl-5-quinolinecarboxamide

Prepared according to the method of example 43(a), using N-(cyclohexylmethyl)-6-methyl-5-quinolinecarboxamide (Example 57) (3 g), peracetic acid (3.3 g, 45% in acetic acid), glacial acetic acid (20 mL) and subsequently phosphorous oxychloride (20 mL) to afford the sub-titled compound (1.5 g).

MS: APCI(+ve) 317.3/319.1 (M+H$^+$).

b) 2-[(3S)-3-Amino-1-pyrrolidinyl]-N-(cyclohexylmethyl)-6-methyl-5-quinolinecarboxamide, Acetate Prepared according to the method of example 30, using 2-chloro-N-(cyclohexylmethyl)-6-methyl-5-quinolinecarboxamide Example 58(a)) (0.450 g) and (3S)-3-pyrrolidinamine (0.500 g). Purification (HPLC, Symmetry—0.1% aqueous ammonium acetate/acetonitrile) afforded the title compound (0.110 g).

$^1$H NMR (400 MHz, d$_6$-DMSO) δ 8.43 (1H, t), 7.73 (1H, d), 7.45 (1H, d), 7.32 (1H, d), 6.84 (1H, d), 3.69-3.56 (3H, m), 3.51 (1H, m), 3.22 (1H, m), 3.16 (2H, t), 2.30 (3H, s), 2.08 (1H, m), 1.87 (3H, s), 1.81-1.66 (5H, m), 1.66-1.49 (2H, m), 1.30-1.08 (3H, m), 1.04-0.89 (2H, m).

MS: APCI(+ve) 367.3 (M+H$^+$).

m.p. 154-155° C.

EXAMPLE 59

N-[2-[[(3S)-3-Amino-1-pyrrolidinyl]methyl]-6-chloro-5-quinolinyl]-cyclohexaneacetamide

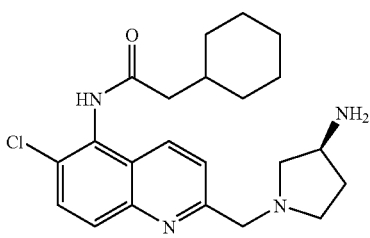

a) N-(6-Chloro-2-ethenyl-5-quinolinyl)-cyclohexaneacetamide

To a solution of N-(2,6-dichloro-5-quinolinyl)-cyclohexaneacetamide (Example 1(a)) (2 g) in dimethylformamide (6 mL) was added tributyl(vinyl)tin (3.63 g), 2,6-di-tert-butyl-4-methylphenol (50 mg) and dichlorobis(triphenylphosphine)palladium (0.25 g). The reaction was heated at 80° C. under nitrogen for 6 hours and then cooled to room temperature. The mixture was filtered through diatomaceous earth and poured into water and dichloromethane. The organic layer was separated and the aqueous was further extracted with dichloromethane. The combined organic layers were dried, filtered and evaporated. Purification (SiO$_2$, methanol: dichloromethane 5:95 as eluant) gave the sub-titled compound (1.2 g).

MS: APCI(+ve) 329.4/331.2 (M+H$^+$).

b) N-(6-Chloro-2-formyl-5-quinolinyl)-cyclohexaneacetamide

Ozone was bubbled through a solution of N-(6-chloro-2-ethenyl-5-quinolinyl)-cyclohexaneacetamide (example 59(a)) (1.2 g) in dichloromethane (40 mL) and acetic acid (1 mL) at −78° C. for 2 hours. Dimethylsulfide (2 mL) was added and the solution allowed to warm to room temperature overnight. Saturated aqueous sodium bicarbonate was added and the mixture stirred rapidly. The aqueous phase was separated and further extracted with dichloromethane. The combined organic extracts were dried, filtered and evaporated to yield the sub-titled compound (0.7 g).

MS: APCI(+ve) 331/333 (M+H$^+$).

c) N-[2-[[(3S)-3-Amino-1-pyrrolidinyl]methyl]-6-chloro-5-quinolinyl]-cyclohexaneacetamide To a solution of N-(6-chloro-2-formyl-5-quinolinyl)-cyclohexaneacetamide (Example 59 (b)) (0.68 g) in dichloromethane (10 mL) and methanol (1 mL) was added (3S)-3-pyrrolidinyl-carbamic acid, 1,1-dimethylethyl ester (1.1 g). The mixture was stirred for 2 hours and then sodium triacetoxyborohydride (1.2 g) added. The mixture was stirred overnight and then poured into water. The product was filtered off and suspended in methanol (2 mL). Treatment with hydrochloric acid (4M in 1,4-dioxane) yielded the crude product which was purified by HPLC (Symmetry—0.1% aqueous ammonium acetate/acetonitrile) to afford the titled product (29 mg).

$^1$H NMR (400 MHz, d$_6$-DMSO) δ 11.31 (1H, s), 10.14 (1H, s), 8.64 (3H, s), 8.33 (1H), 8.04 (1H, d), 7.96 (1H, d), 7.78 (1H, d), 4.9 (2H, s), 4.12-3.50 (5H, m), 2.40 (2H, d), 2.19 (1H, m), 1.93-1.58 (7H, m), 1.35-1.00 (5H, m).

MS: APCI(+ve) 401.2/403.2 (M+H$^+$).

m.p. 160° C. dec

EXAMPLE 60

N-[2-[(3S)-3-Amino-1-piperidinyl]-6-chloro-5-quinolinyl]-cyclohexaneacetamide

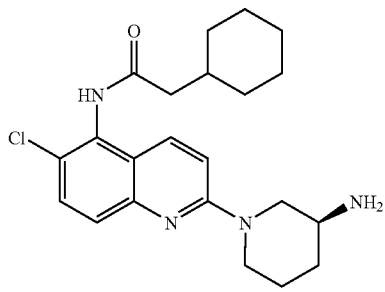

N-(2,6-Dichloro-5-quinolinyl)-cyclohexaneacetamide (Example 1(a)) (0.2 g), (3S)-3-piperidinamine (0.089 g) and triethylamine (0.25 mL) were placed into a 10 mL microwave vial followed by the addition of acetonitrile (5 mL). The vial was sealed and heated at 120° C. in a single mode microwave for 30 minutes, and a further 60 minutes at 150° C. The product crystallised from the reaction on cooling and was subsequently filtered and washed with acetonitrile (10 mL). Purification (SiO$_2$, 7M ammonia in methanol:methanol:dichloromethane 1:4:95) gave the title compound (0.055 g).

$^1$H NMR (400 MHz, CD$_3$OD) δ 7.91 (1H, d), 7.56 (2H, s), 7.22 (1H, d), 4.47-4.42 (1H, m), 4.33-4.25 (1H, m), 3.14-3.06 (1H, m), 2.92-2.78 (2H, m), 2.41 (2H, d), 2.07-1.99 (1H, m), 1.98-1.88 (3H, m), 1.87-1.75 (3H, m), 1.75-1.67 (1H, m), 1.66-1.53 (1H, m), 1.47-1.21 (4H, m), 1.19-1.08 (2H, m).

MS: APCI(+ve) 401.2 (M+H$^+$).

m.p. 173-176° C.

EXAMPLE 61

N-[6-Chloro-2-[(3S)-3-[(2-hydroxyethyl)amino]-1-piperidinyl]-5-quinolinyl]-cyclohexaneacetamide

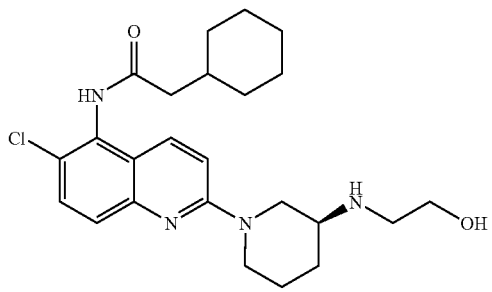

a) N-[6-Chloro-2-[(3S)-3-[[2-[[(1,1-dimethylethyl) dimethylsilyl]oxy]ethyl]amino]-1-piperidinyl]-5-quinolinyl]-cyclohexaneacetamide Prepared according to the method of example 50(a), using N-[2-[(3S)-3-amino-1-piperidinyl]-6-chloro-5-quinolinyl]-cyclohexaneacetamide (Example 60) (200 mg), (tert-butyldimethylsilyloxy)acetaldehyde (0.086 mL) and sodium triacetoxyborohydride (0.212 g) to afford the sub-title compound (0.2 g).

MS: APCI(+ve) 559.5/561.5 (M+H$^+$).

b) N-[6-Chloro-2-[(3S)-3-[(2-hydroxyethyl)amino]-1-piperidinyl]-5-quinolinyl]-cyclohexaneacetamide Prepared according to the method of example 50(b), using N-[6-chloro-2-[(3S)-3-[[2-[[(1,1-dimethylethyl)dimethylsilyl]oxy]ethyl]amino]-1-piperidinyl]-5-quinolinyl]-cyclohexaneacetamide (Example 61(a)) (200 mg) and 4M hydrogen chloride in 1,4-dioxane (2 mL). Purification (SiO$_2$, methanol:dichloromethane 5:95 as eluant) gave the title compound as a solid (56 mg).

$^1$H NMR (400 MHz, CD$_3$OD) δ 7.96 (1H, d), 7.60 (2H, s), 7.27 (1H, d), 4.54 (1H, d), 4.02 (1H, d), 3.77 (2H, t), 3.58-3.49 (1H, m), 3.42-3.31 (2H, m), 3.24-3.16 (3H, m), 2.34 (2H, d), 2.23-2.14 (1H, m), 1.93-1.57 (8H, m), 1.33-0.98 (5H, m).

MS: APCI(+ve) 445.2/447.1 (M+H$^+$).

m.p. 182-183° C.

EXAMPLE 62

N-[2-[(3S)-3-Amin-1-pyrrolidinyl]-6-chloro-5-quinlinyl]-cyclopentanepropanamide

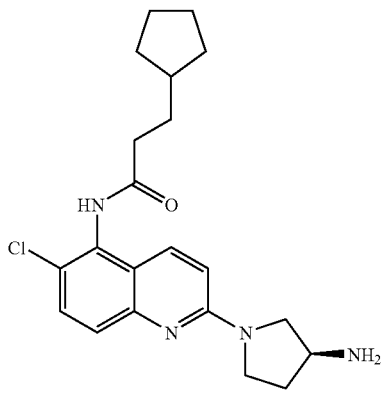

a) N-(2,6-Dichloro-5-quinolinyl)-cyclopentanepropanamide

To a stirred solution of cyclopentanepropanoic acid (1 g) in dichloromethane (5 mL) at 0° C. under nitrogen, was added N,N-dimethylformamide (1 drop) and oxalyl chloride (2 mL). The reaction mixture was stirred at room temperature for 2 hours, then evaporated to dryness and redissolved in dichloromethane (2 mL). The solution was added to a mixture of 2,6-dichloroquinolin-5-amine (Example 1(d)) (500 mg) and potassium carbonate (650 mg) in acetone (10 mL). The reaction mixture was stirred at room temperature for 16 hours. The resulting solid was collected by filtration and subsequently washed with water (10 mL) to afford the sub-title compound (530 mg).

$^1$H NMR (400 MHz, d$_6$-DMSO) δ 8.27 (1H, d), 7.96-7.85 (2H, m), 7.66 (1H, d), 2.57-2.40 (2H, m), 1.93-1.44 (9H, m), 1.21-1.07 (2H, m).

MS: APCI(+ve) 337.2/339.2 (M+H$^+$).

b) N-[2-[(3S)-3-Amino-1-pyrrolidinyl]-6-chloro-5-quinolinyl]-cyclopentanepropanamide Prepared according to the method of example 30, using N-(2,6-dichloro-5-quinolinyl)-cyclopentanepropanamide (Example 62(a)) (500 mg) and (3S)-3-pyrrolidinamine (390 mg). Purification (SiO$_2$, methanol:dichloromethane:ammonium hydroxide solution 7:93:1 as eluant) gave the title compound as a solid (400 mg).

$^1$H NMR (400 MHz, d$_6$-DMSO) δ 9.76 (1H, s), 7.83 (1H, d), 7.54 (1H, d), 7.46 (1H, d), 6.90 (1H, d), 3.74-3.45 (4H, m), 3.39-3.15 (1H, m), 2.44 (2H, t), 2.07 (1H, td), 1.92-1.45 (12H, m), 1.22-1.07 (2H, m).

MS: APCI(+ve) 387.1/389.1 (M+H$^+$).
m.p. 192-194° C.

EXAMPLE 63

N-[6-Chloro-2-[(3S)-3-[(2-hydroxyethyl)amino]-1-pyrrolidinyl]-5-quinolinyl]-cyclopentanepropanamide

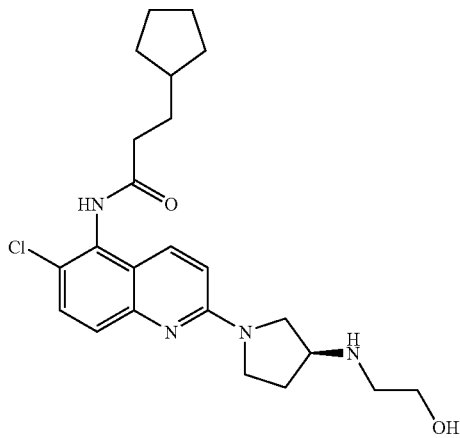

a) N-[6-Chloro-2-[(3S)-3-[[2-[[(1,1-dimethylethyl)dimethylsilyl]oxy]ethyl]amino]-1-pyrrolidinyl]-5-quinolinyl]-cyclopentanepropanamide Prepared according to the method of example 50(a), using N-[2-[(3S)-3-amino-1-pyrrolidinyl]-6-chloro-5-quinolinyl]-cyclopentanepropanamide (Example 62) (300 mg) and [[(1,1-dimethylethyl)dimethylsilyl]oxy]-acetaldehyde (133 μl). Purification (SiO$_2$, methanol:dichloromethane 3:97 as eluant) gave the sub-title compound as a solid (200 mg).

$^1$H NMR (400 MHz, d$_6$-DMSO) δ 9.80 (1H, s), 7.88 (1H, d), 7.58 (1, d), 7.50 (1H, d), 6.96 (1H, d), 3.85-3.16 (9H, m), 2.77-2.68 (2H, m), 2.48 (2H, t), 2.22-2.10 (1H, m), 1.95-1.48 (9H, m), 1.24-1.12 (2H, m), 0.90 (9H, s), 0.08 (6H, s).

MS: APCI(+ve) 545.5/547.5 (M+H$^+$).

b) N-[6-Chloro-2-[(3S)-3-[(2-hydroxyethyl)amino]-1-pyrrolidinyl]-5-quinolinyl]-cyclopentanepropanamide To a stirred solution of N-[6-chloro-2-[(3S)-3-[[2-[[(1,1-dimethylethyl)dimethylsilyl]oxy]ethyl]amino]-1-pyrrolidinyl]-5-quinolinyl]-cyclopentanepropanamide (Example 63(a)) (200 mg) in dichloromethane:methanol 1:1 (3 mL) under nitrogen, was added HCl (1 mL, 4M solution in dioxane). The reaction mixture was stirred at room temperature for 30 minutes, then evaporated to dryness. Purification (HPLC, Symmetry—0.1% aqueous trifluoroacetic acid/acetonitrile) gave the title compound as a solid (35 mg).

$^1$H NMR (400 MHz, d$_6$-DMSO) δ 9.77 (1H, s), 7.84 (1H, d), 7.54(1H, d), 7.47(1H, d), 6.92 (1H, d), 4.54 (1H, s), 3.75-3.40 (6H, m), 2.72-2.61 (2H, m), 2.44 (2H, t), 2.20-2.06 (1H, m), 1.92-1.74 (4H, m), 1.71-1.45 (6H, m), 1.22-1.06 (2H, m).

MS: APCI(+ve) 431.2/433.2 (M+H$^+$).
m.p. 186-188° C.

EXAMPLE 64

N-[6-Chloro-2-[4-(1,5-dihydro-5-oxo-4H-1,2,4-triazol-4-yl)-1-piperidinyl]-5-quinolinyl]-cyclohexaneacetamide

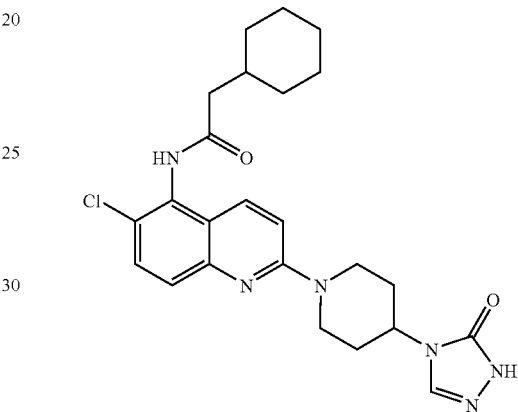

a) 2-Formyl-N-[1-(phenylmethyl)-4-piperidinyl]-hydrazinecarboxamide 1-(Phenylmethyl)$_4$-piperidinamine (3 g) in dichloromethane (10 mL) and triethylamine (4.5 mL) were added dropwise to a stirred solution of triphosgene (1.55 g) in dichloromethane (20 mL) at 0° C. under nitrogen. The reaction mixture was allowed to warm to room temperature and stirred for 30 minutes. The mixture was cooled to 0° C. and formyl hydrazine (1.4 g) and triethylamine (4.5 mL) were added. The reaction was stirred at room temperature for 1 hour and then evaporated to dryness. Purification (SiO$_2$, methanol:dichloromethane:ammonium hydroxide solution 5:95:1 as eluant) gave the sub-title compound (2.5 g).

MS: APCI(+ve) 277.2 (M+H$^+$).

b) 2,4-Dihydro-4-[1-(phenylmethyl)-4-piperidinyl]-3H-1,2,4-triazol-3-one

2-Formyl-N-[1-(phenylmethyl)-4-piperidinyl]-hydrazinecarboxamide (Example 64(a)) (2.5 g) was divided between S x 10 mL vials. Potassium hydroxide (5 mL, 1 M solution in methanol) was added to each vial and the reactions were heated at 90° C. for 35 minutes within a microwave. The combined products were acidified to pH6 with aqueous 2M hydrochloric acid and were then evaporated to dryness. Purification (SiO$_2$, methanol:dichloromethane:acetic acid 15:85:1 as eluant) gave the sub-title compound as an oil (2.2 g).

MS: APCI(+ve) 259.2 (M+H$^+$).

c) 2,4-Dihydro-4-(4-piperidinyl)-3H-1,2,4-triazol-3-one 2,4-Dihydro-4-[1-(phenylmethyl)-4-piperidinyl]-3H-1,2,4-triazol-3-one (Example 64(b)) (2.2 g) was divided between 2, 10 mL vials. 1,4-Cyclohexadiene (5 mL) and palladium hydroxide (270 mg, 20 wt. % on carbon) were added to each vial and the reactions were heated at 100° C. for 30 minutes within a microwave. The reaction mixtures were combined, ethanol (50 mL) and water (50 mL) were added and the mixture was filtered through diatomaceous earth and evaporated to give the sub-title compound as a solid (720 mg).

MS: APCI(+ve) 169.2 (M+H$^+$).

d) N-[6-Chloro-2-[4-(1,5-dihydro-5-oxo-4H-1,2,4-triazol-4-yl)-1-piperidinyl]-5-quinolinyl]-cyclohexaneacetamide Prepared according to the method of example 30, using N-(2,6-dichloro-5-quinolinyl)-cyclohexaneacetamide (Example 1(a)) (150 mg) and 2,4-dihydro-4(4-piperidinyl)-3H-1,2,4-triazol-3-one Example 64 (c)) (225 mg). Methanol (10 mL) and dichloromethane (10 mL) were added to the reaction mixture and the solid was collected by filtration to afford the title compound (40 mg).

$^1$H NMR (400 MHz, d$_6$-DMSO) 11.64 (1H, s), 9.80 (1H, s), 7.99 (1H, s), 7.87 (1H, d), 7.59 (1H, d), 7.50 (1, d), 7.39 (1H, d), 4.71 (2H, d), 4.13-4.01 (1H, m), 3.05 (2H, t), 2.33 (2H, d), 1.99-1.59 (10H, m), 1.34-0.98 (5H, m).

MS: APCI(+ve) 469.1/471.1 (M+H$^+$).
m.p. 310-313° C.

EXAMPLE 65

1-[6-Chloro-5-[(cyclohexylacetyl)amino]-2-quinolinyl]-D-proline, Trifluoroacetate

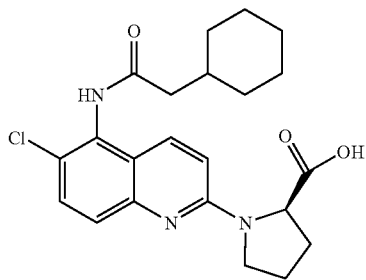

a) 1-[6-Chloro-5-[(cyclohexylacetyl)amino]-2-quinolinyl]-D-proline, 1,1-dimethylethyl Ester Prepared according to the method of example 30, using N-(2,6-dichloro-5-quinolinyl)-cyclohexaneacetamide (Example 1 (a)) (200 mg) and 1,1-dimethylethyl ester D-proline (308 mg). Purification (SiO$_2$, ethyl acetate:isohexane 25:75 as eluant) gave the sub-title compound as an oily solid (200 mg).

MS: APCI(+ve) 472.5/474.5 (M+H$^+$).

b) 1-[6-Chloro-5-[(cyclohexylacetyl)amino]-2-quinolinyl]-D-proline, Trifluoroacetate Trifluoroacetic acid (1 mL) was added to a stirred solution of 1-[6-chloro-5-[(cyclohexylacetyl)amino]-2-quinolinyl]-D-proline 1,1-dimethylethyl ester (Example 65(a)) (200 mg) in dichloromethane (3 mL). The reaction was stirred at room temperature for 3 hours and then evaporated to dryness. Purification (SiO$_2$, methanol:dichloromethane 10:90 as eluant) gave the title compound as a solid (150 mg).

$^1$H NMR (400 MHz, d$_6$-DMSO) 9.58 (1H, s), 7.97 (1H, d), 7.67-7.56 (2H, m), 7.02 (1H, d), 4.74 (1H, dd), 3.78-3.62 (2H, m), 2.42-2.26 (3H, m), 2.22-1.96 (3H, m), 1.93-1.57 (6H, m), 1.36-1.01 (5H, m).

MS: APCI(+ve) 416.1/418.1 (M+H$^+$).
m.p. 170-173° C.

EXAMPLE 66

1-[6-Chloro-5-[(cyclohexylacetyl)amino]-2-quinolinyl]-4-piperidinecarboxylic Acid, Lithium Salt

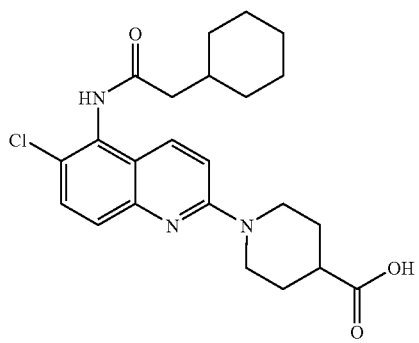

a) 1-[6-Chloro-5-[(cyclohexylacetyl)amino]-2-quinolinyl]-4-piperidine Carboxylic Acid, Ethyl Ester Prepared according to the method of example 30, using N-(2,6-dichloro-5-quinolinyl)-cyclohexaneacetamide (Example 1(a)) (200 mg) and 4-piperidinecarboxylic acid, ethyl ester (280 mg). Purification (SiO$_2$, ethyl acetate:isohexane 25:75 as eluant) gave the sub-title compound as an oil (200 mg).

MS: APCI(+ve) 458.5/460.5 (M+H$^+$).

b) 1-[6-Chloro-5-[(cyclohexylacetyl)amino]-2-quinolinyl]-4-piperidinecarboxylic Acid, Lithium Salt To a stirred suspension of 1-[6-chloro-5-[(cyclohexylacetyl)amino]-2-quinolinyl]4-piperidinecarboxylic acid ethyl ester (Example 66(a)) (200 mg) in methanol (2 mL) was added lithium hydroxide (30 mg) in water (2 mL). The mixture was stirred at 50° C. for 6 hours and then allowed to cool to room temperature. The solid was collected by filtration and subsequently washed with water (10 mL) to afford the titled compound (40 mg).

$^1$H NMR (400 MHz, d$_6$-DMSO)δ 9.78 (1H, s), 7.85 (1H, d), 7.57 (1H, d), 7.48 (1H, d), 7.32 (1H, d), 4.41 (2H, d), 3.08 (2H, t), 2.58-2.45 (1H, m), 2.32 (2H, d), 1.97-1.46 (10H, m), 1.35-0.95 (5H, m).

MS: APCI(+ve) 430.2/432.2 (M+H$^+$).

EXAMPLE 67

6-Chloro-5-[(cyclohexylacetyl)amino]-2-quinolinebutanoic Acid

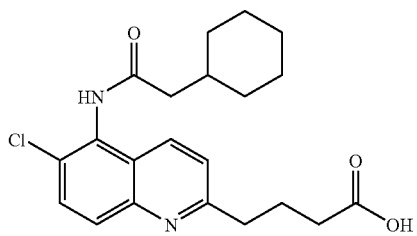

a) N-[6-chloro-2-(3-cyanopropyl)-5-quinolinyl]-cyclohexaneacetamide

Bromo(3-cyanopropyl)-zinc (30 mL, 0.5 M in tetrahydrofuran) and tetrakis(triphenylphosphine)palladium(0) (86 mg) were added to N-(2,6-dichloro-5-quinolinyl)-cyclohexaneacetamide (Example 1(a)) (500 mg). The reaction mixture was heated to reflux for 30 minutes. The mixture was cooled to room temperature and then poured into aqueous saturated ammonium chloride solution (50 mL) and extracted with ethyl acetate (3×50 mL). The combined organic extracts were dried, filtered and evaporated. Purification (SiO$_2$, methanol: dichloromethane 3:97 as eluant) gave the sub-title compound as a solid (490 mg).

$^1$H NMR (500 MHz, d$_6$-DMSO) δ 9.96 (1H, s), 8.13 (1H, d), 7.92 (1H, d), 7.82 (1H, d), 7.56 (1H, d), 3.04 (2H, t), 2.61 (2H, t), 2.37 (2H, d), 2.09 (2H, quintet), 1.90-1.78 (2H, m), 1.76-1.60 (4H, m), 1.33-1.12 (3H, m), 1.11-1.01 (2H, m).

MS: APCI(+ve) 370.4/372.4 (M+H$^+$).

b) 6-Chloro-5-[(cyclohexylacetyl)amino]-2-quinolinebutanoic Acid

Potassium hydroxide (2 mL, 50% solution in water) was added to a stirred solution of N-[6-chloro-2-(3-cyanopropyl)-5-quinolinyl]-cyclohexaneacetamide (Example 67(a)) (190 mg) in methanol (2 mL). The reaction mixture was heated to 50° C. for 6 hours then allowed to cool. The mixture was acidified with aqueous 2M hydrochloric acid until a precipitate formed which was collected by filtration. Purification by HPLC (Symmetry—0.1% aqueous ammonium acetate/acetonitrile) afforded the title compound as a solid (45 mg).

$^1$H NMR (400 MHz, d$_6$-DMSO) δ 9.99 (1H, s), 8.11 (1H, d), 7.90 (1H, d), 7.80 (1H, d), 7.51 (1H, d), 2.92 (2H, t), 2.36 (2H, d), 2.20 (2H, t), 1.96 (2H, quintet), 1.90-1.58 (6H, m), 1.34 0.98 (5H, m).

MS: APCI(+ve) 389.1/391.1 (M+H$^+$).

m.p. 216-220° C.

EXAMPLE 68

1-[6-Chloro-5-[(cyclohexylacetyl)amino]-2-quinolinyl]-4-piperidineacetic Acid

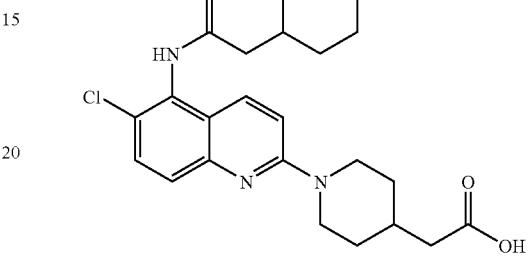

a) 1-[6-Chloro-5-[(cyclohexylacetyl)amino]-2-quinolinyl]-4-piperidineacetic Acid, Ethyl Ester Prepared according to the method of example 30, using N-(2,6-dichloro-5-quinolinyl)-cyclohexaneacetamide (prepared as in Example 1(a)) (200 mg) and 4-piperidineacetic acid, ethyl ester (305 mg). The reaction mixture was evaporated to dryness, the residue was suspended in methanol and the solid collected by filtration to afford the sub-title compound (150 mg).

$^1$H NMR (400 MHz, d$_6$-DMSO) δ 9.77 (1H, s), 7.83 (1H, d), 7.56 (1H, d), 7.47 (1H, d), 7.31 (1H, d), 4.52 (2H, d), 4.07 (2H, q), 2.94 (2H, t), 2.36-2.19 (4H, m), 2.07-1.94 (1H, m), 1.89-1.58 (8H, m), 1.37-0.97 (10H, m).

MS: APCI(+ve) 472.5/474.5 (M+H$^+$).

b) 1-[6-Chlro-5-[(cyclohexylacetyl)amino]-2-quinolinyl]-4-piperidineacetic Acid Prepared according to the method of Example 66(b), using 1-[6-chloro-5-[(cyclohexylacetyl)amino]-2-quinolinyl]4-piperidineacetic acid, ethyl ester (Example 68(a)) (150 mg). Purification by HPLC (Symmetry—0.1% aqueous ammonium acetate/acetonitrile) afforded the title compound as a solid (15 mg).

$^1$H NMR (400 MHz, d$_6$-DMSO) δ 9.78 (1H, s), 7.83 (1H, d), 7.56 (1H, d), 7.47 (1H, d), 7.30 (1H, d), 4.52 (2H, d), 2.93 (2H, t), 2.32 (2H, d), 2.14 (2H, d), 2.04-1.58 (9H, m), 1.35-0.95 (7H, m).

MS: APCI(+ve) 444.1/446.1 (M+H$^+$).

m.p 242-244° C.

EXAMPLE 69

4-[6-Chloro-5-[(cyclohexylacetyl)amino]-2-quinolinyl]-1-piperazineacetic Acid, Lithium Salt

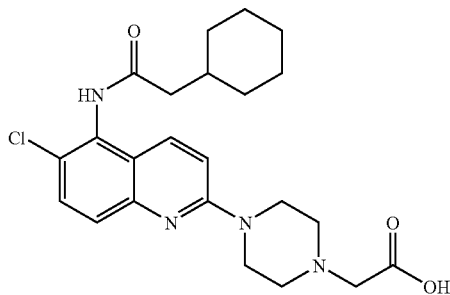

a) 4-[6-Chloro-5-[(cyclohexylacetyl)amino]-2-quinolinyl]-1-piperazineacetic Acid, Ethyl Ester Prepared according to the method of example 30, using N-(2,6-dichloro-5-quinolinyl)-cyclohexaneacetamide (Example 1 (a)) (200 mg) and 1-piperazineacetic acid, ethyl ester (310 mg) to afford the sub-title compound as a solid (180 mg).

$^1$H NMR (400 MHz, d$_6$-DMSO) δ 9.48 (1H, s), 7.88 (1H, d), 7.55 (1H, d), 7.48 (1H, d), 7.24 (1H, d), 4.11 (2H, q), 3.71 (4H, t), 3.27 (2H, s), 2.65 (4H, t), 2.37-2.26 (2H, m), 1.94-1.57 (6H, m), 1.35-0.97 (8H, m).

MS: APCI(+ve) 473.5/475.5 (M+H$^+$).

b) 4-[6-Chloro-5-[(cyclohexylacetyl)amino]-2-quinolinyl]-1-piperazineacetic Acid, Lithium Salt Prepared according to the method of Example 66(b), using 4-[6-chloro-5-[(cyclohexylacetyl)amino]-2-quinolinyl]-1-piperazineacetic acid ethyl ester (Example 69(a)) (180 mg) to afford the title compound as a solid (80 mg).

$^1$H NMR (400 MHz, d$_6$-DMSO) δ 8.02 (1H, d), 7.28 (1H, d), 6.97 (1H, d), 6.91 (1H, d), 3.61 (4H, s), 2.75 (2H, s), 2.51 (4H, s), 1.99 (2H, d), 1.91-1.55 (6H, m), 1.30-1.05 (3H, m), 0.99-0.85 (2H, m).

MS: APCI(+ve) 445.1/447.1 (M+H$^+$).
m.p. 320-326° C.

EXAMPLE 70

6-Chloro-5-[(cyclohexylacetyl)amino]-2-quinolinepentanoic Acid

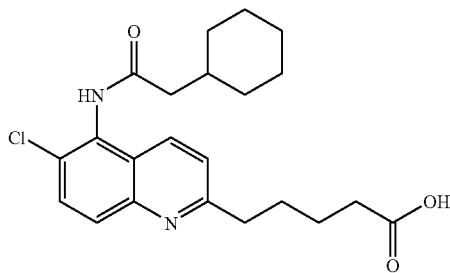

a) N-[6-Chloro-2-(4-cyanobutyl)-5-quinolinyl]-cyclohexaneacetamide

Prepared according to the method of example 67(a), using N-(2,6-dichloro-5-quinolinyl)-cyclohexaneacetamide (Example 1 (a)) (500 mg) and bromo(4-cyanobutyl)-zinc (30 mL, 0.5 M solution in tetrahydrofuran). Purification (SiO$_2$, methanol:dichloromethane 1:99 as eluant) gave the sub-title compound (600 mg).

$^1$H NMR (400 MHz, d$_6$-DMSO) δ 9.95 (1H, s), 8.12 (1H, d), 7.91 (1H, d), 7.81 (1H, d), 7.54 (1H, d), 2.96 (2H, t), 2.56 (2H, t), 2.36 (2H, d), 1.91-1.54 (10H, m), 1.34-0.98 (5H, m).

MS: APCI(+ve) 384.5/386.5 (M+H$^+$).

b) 6-Chloro-5-[(cyclohexylacetyl)amino]-2-quinolinepentanoic Acid

Prepared according to the method of example 67(b), using N-[6-chloro-2-(4-cyanobutyl)-5-quinolinyl]-cyclohexaneacetamide (Example 70(a)) (200 mg). Purification by HPLC (Symmetry—0.1% aqueous ammonium acetate/acetonitrile) afforded the title compound as a solid (25 mg).

$^1$H NMR (400 MHz, d$_6$-DMSO) δ 9.96 (1H, s), 8.11 (1H, d), 7.90 (1H, d), 7.80 (1H, d), 7.52 (1H, d), 2.92 (2H, t), 2.36 (2H, d), 2.23 (2H, t), 1.93-1.50 (10H, m), 1.34-0.98 (5H, m).

MS: APCI(-ve) 401.2/403.2 (M-H$^+$).
m.p. 199-201° C.

EXAMPLE 71

1-[6-Chloro-5-[[(cyclohexylmethyl)amino]carbonyl]-2-quinolinyl]-D-proline

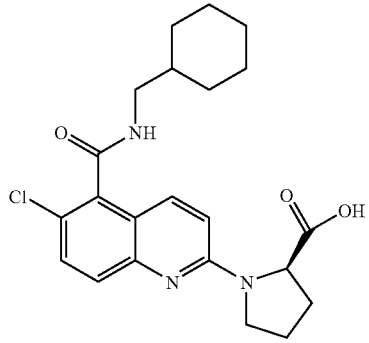

a) 1-[6-Chloro-5-[[(cyclohexylmethyl)amino]carbonyl]-2-quinolinyl]-D-proline 1,1-dimethylethyl Ester Prepared according to the method of example 30, using 2,6-dichloro-N-(cyclohexylmethyl)-5-quinolinecarboxamide (Example 43(a)) (200 mg) and D-proline, 1,1-dimethylethyl ester (310 mg). Purification (SiO$_2$, ethyl acetate:isohexane 30:70 as eluant) gave the sub-title compound as an oil (250 mg).

MS: APCI(+ve) 472.5/474.5 (M+H$^+$).

b) 1-[6-Chloro-5-[[(cyclohexylmethyl)amino]carbonyl]-2-quinolinyl]-D-proline Prepared according to the method of example 65(b), using 1-[6-chloro-5-[[(cyclohexylmethyl)amino]carbonyl]-2-quinolinyl]-D-proline 1,1-dimethylethyl ester (Example 71(a)) (250 mg). Purification (SiO₂, methanol:dichloromethane 5:95 as eluant) gave the title compound as a solid (144 mg).

¹H NMR (300 MHz, d₆-DMSO) δ 8.66 (1H, t), 7.80 (1H, d), 7.56 (2H, s), 7.05 (1H, d), 4.67 (1H, d), 3.83-3.50 (2H, m), 3.17 (2H, t), 2.40-2.23 (1H, m), 2.18-1.90 (3H, m), 1.85-1.46 (6H, m), 1.34-0.86 (5H, m).

MS: APCI(+ve) 416.1/418.1 (M+H⁺).

m.p. 157-160° C.

EXAMPLE 72

1-[6-Chloro-5-[[(cyclohexylmethyl)amino]carbonyl]-2-quinolinyl]-L-proline, Trifluoroacetate

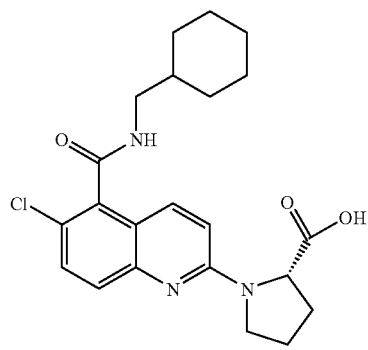

a) 1-[6-Chloro-5-[[(cyclohexylmethyl)amino]carbonyl]-2-quinolinyl]-L-proline 1,1-dimethylethyl Ester Prepared according to the method of example 30, using 2,6-dichloro-N-(cyclohexylmethyl)-5-quinolinecarboxamide Example 43(a)) (200 mg) and L-proline, 1,1-dimethylethyl ester (305 mg). Purification (SiO₂, ethyl acetate:isohexane 20:80 as eluant) gave the sub-title compound as an oil (200 mg).

MS: APCI(+ve) 472.5/474.5 (M+H⁺).

b) 1-[6-Chloro-5-[[(cyclohexylmethyl)amino]carbonyl]-2-quinolinyl]-L-proline, Trifluoroacetate Prepared according to the method of example 65(b), using 1-[6-chloro-5-[[(cyclohexylmethyl)amino]carbonyl]-2-quinolinyl]-L-proline 1,1-dimethylethyl ester (Example 72(a)) (200 mg) Purification (SiO₂, methanol:dichloromethane 5:95 as eluant followed by HPLC—Symmetry—0.1% aqueous trifluoroacetic acid/acetonitrile) gave the title compound as a solid (85 mg).

¹H NMR (400 MHz, d₆-DMSO) δ 8.32 (1H, s), 7.81 (1H, d), 7.56-7.46 (2H, m), 6.98 (1H, d), 4.65 (1H, dd), 3.72-3.59 (2H, m), 3.19 (2H, t), 2.36-2.25 (1H, m), 2.16-1.98 (3H, m), 1.84-1.54 (6H, m), 1.34-0.93 (5H, m).

MS: APCI(+ve) 416.1/418.1 (M+H⁺).

m.p. 168-170° C.

EXAMPLE 73

4-[6-Chloro-5-[[(cyclohexylmethyl)amino]carbonyl]-2-quinolinyl]-1-piperazineacetic acid, Acetate

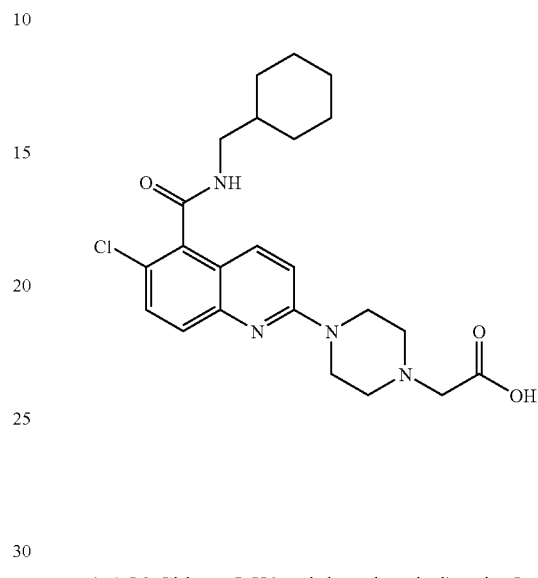

a) 4-[6-Chloro-5-[[(cyclohexylmethyl)amino]carbonyl]-2-quinolinyl]-1-piperazineacetic Acid, Ethyl Ester Prepared according to the method of example 30, using 2,6-dichloro-N-(cyclohexylmethyl)-5-quinolinecarboxamide Example 43(a)) (200 mg) and 1-piperazineacetic acid, ethyl ester (500 mg) to afford the subtitle compound as a solid (200 mg).

¹H NMR (400 MHz, d₆-DMSO) δ 8.63 (1H, t), 7.75 (1H, d), 7.58-7.52 (2H, m), 7.35 (1H, d), 4.15-4.04 (2H, m), 3.77-3.65 (4H, m), 3.20-3.14 (4H, m), 2.66-2.58 (4H, m), 1.84-1.51 (6H, m), 1.29-1.09 (6H, m), 1.05-0.90 (2H, m).

MS: APCI(+ve) 473.5/475.5 (M+H⁺).

b) 4-[6-Chloro-5-[[(cyclohexylmethyl)amino]carbonyl]-2-quinolinyl]-1-piperazineacetic acid, acetate To a stirred suspension of 4-[6-chloro-5-[[(cyclohexylmethyl)amino]carbonyl]-2-quinolinyl]-1-piperazineacetic acid, ethyl ester (Example 73(a)) (200 mg) in methanol (2 mL) was added sodium hydroxide (2 mL, 1 M solution in water). The mixture was stirred at 50° C. for 3 hours and then allowed to cool to room temperature. Reaction mixture was concentrated and then acidified to pH7 with aqueous 2M hydrochloric acid. The resulting precipitate was collected by filtration. Purification (Varian NH₂ cartridge using methanol (100 mL) and then 10% acetic acid in methanol (100 mL) as eluant) afforded the title compound as a solid (18 mg).

¹H NMR (400 MHz, d₆-DMSO) δ 8.63 (1H, t), 7.75 (1H, d), 7.59-7.50 (2H, m), 7.34 (1H, d), 3.71 (4H, s), 3.22-3.07 (4H, m), 2.63 (4H, s), 1.84-1.50 (6H, m), 1.30-1.10 (3H, m), 1.04-0.90 (2H, m).

MS: APCI(−ve) 443.2/445.2 (M−H⁺).

m.p. 185-190° C.

EXAMPLE 74

1-[6-Chloro-5-[[(cyclohexylmethyl)amino]carbonyl]-2-quinolinyl]-4-piperidinecarboxylic Acid, Sodium Salt

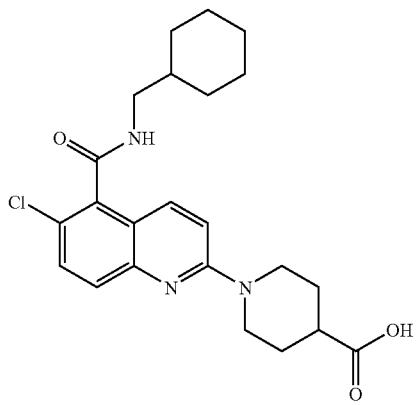

a) 1-[6-Chloro-5-[[(cyclohexylmethyl)amino]carbonyl]-2-quinolinyl]-4-piperidinecarboxylic Acid, Ethyl Ester Prepared according to the method of example 30, using 2,6-dichloro-N-(cyclohexylmethyl)-5-quinolinecarboxamide (Example 43(a)) (200 mg) and 4-piperidinecarboxylic acid, ethyl ester (470 mg) to afford the sub-titled compound as a solid (200 mg).

$^1$H NMR (400 MHz, d$_6$-DMSO) δ 8.62 (1H, t), 7.75 (1H, d), 7.57-7.50 (2H, m), 7.36 (1H, d), 4.43 (2H, d), 4.07 (2H, q), 3.21-3.05 (4H, m), 2.72-2.61 (1H, m), 1.92 (2H, d), 1.85-1.39 (8H, m), 1.28-1.12 (6H, m), 1.03-0.91 (2H, m).

MS: APCI(+ve) 458.5/460.5 (M+H$^+$).

b) 1-[6-Chloro-5-[[(cyclohexylmethyl)amino]carbonyl]-2-quinolinyl]-4-piperidinecarboxylic Acid, Sodium Salt Prepared according to the method of example 73(b), using 1-[6-chloro-5-[[(cyclohexylmethyl)amino]carbonyl]-2-quinolinyl]-4-piperidinecarboxylic acid ethyl ester (Example 74(a)) (200 mg). The reaction mixture was concentrated and the precipitate was collected by filtration and washed with water to afford the title compound as a solid (130 mg).

$^1$H NMR (400 MHz, d$_6$-DMSO) δ 8.62 (1H, t), 7.70 (1H, d), 7.55-7.45 (2H, m), 7.31 (1H, d), 4.29 (2H, d), 3.16 (2H, t), 3.07 (2H, t), 2.12-2.00 (1H, m), 1.85-1.43 (10H, m), 1.28-1.10 (3H, m), 1.04-0.91 (2H, m).

MS: APCI(−ve) 428.2/430.2 (M−H$^+$).

m.p. 320-324° C.

EXAMPLE 75

1-[6-Chloro-5-[[(cyclohexylmethyl)amino]carbonyl]-2-quinolinyl]-4-piperidineacetic Acid, Trifluoroacetate

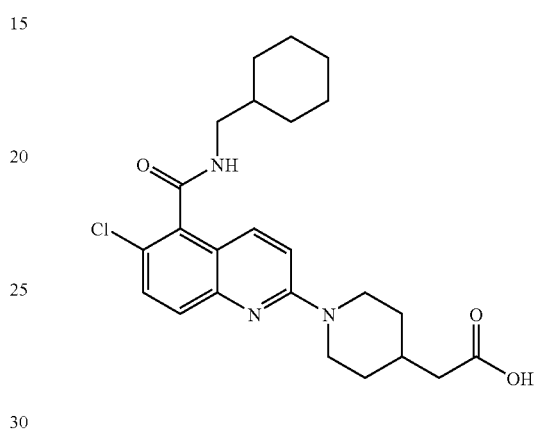

a) 1-[6-Chloro-5-[[(cyclohexylmethyl)amino]carbonyl]-2-quinolinyl]-4-piperidineacetic Acid Ethyl Ester Prepared according to the method of example 30, using 2,6-dichloro-N (cyclohexylmethyl)-5-quinolinecarboxamide (Example 43(a)) (200 mg) and 4 piperidineacetic acid, ethyl ester (470 mg) to afford the sub-titled compound as a solid (200 mg).

$^1$H NMR (300 MHz, d$_6$-DMSO) δ 8.61 (1H, t), 7.72 (1H, d), 7.52 (2H, s), 7.34 (1H, d), 4.52 (2H, d), 4.07 (2H, q), 3.21-3.12 (2H, m), 2.95 (2H, t), 2.26 (2H, d), 2.09-1.93 (1H, m), 1.87-1.48 (8H, m), 1.32-0.88 (10H, m).

MS: APCI(+ve) 472.5/474.5 (M+H$^+$).

b) 1-[6-Chloro-5-[[(cyclohexylmethyl)amino]carbonyl]-2-quinlinyl]-4-piperidineacetic Acid, Trifluoroacetate Prepared according to the method of example 73(b), using 1-[6-chloro-5-[[(cyclohexylmethyl)amino]carbonyl]-2-quinolinyl]4-piperidineacetic acid ethyl ester (Example 75(a)) (200 mg). Purification by HPLC (Symmetry—0.1% aqueous trifuoroacetic acid/acetonitrile) afforded the title compound as a solid (90 mg).

$^1$H NMR (400 MHz, d$_6$-DMSO) δ 8.71 (1H, t), 7.82 (1H, d), 7.77-7.60 (2H, m), 7.50 (1H, d), 4.48 (2H, d), 3.27-3.05 (4H, m), 2.20 (2H, d), 2.11-1.96 (1H, m), 1.88-1.51 (8H, m), 1.35-1.08 (5H, m), 1.05-0.90 (2H, m).

MS: APCI(−ve) 442.2/444.2 (M−H$^+$).

m.p. 79-83° C.

EXAMPLE 76

1-[6-Chloro-5-[[(2-cyclohexylethyl)amino]carbonyl]-2-quinolinyl]-4-piperidinecarboxylic Acid

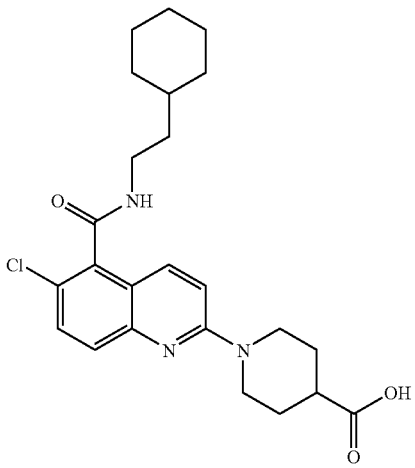

a) 5-Bromo-2,6-dichloro-quinoline 2,6-Dichloroquinoline (30 g) and aluminium trichloride (60 g) were heated to 120° C. with stirring under a nitrogen atmosphere. Bromine (9.2 mL) was added dropwise over 1 hour and the mixture was then stirred at 120° C. for 1 hour before being cooled to room temperature. A methanol/deionised water mixture (150 mL, 1:1) was then slowly added and the mixture was concentrated in vacuo. Dichloromethane (500 mL) and deionised water (250 mL) were added, the layers were separated and the aqueous fraction was extracted with dichloromethane (2×250 mL). The combined organic extracts were washed with saturated aqueous sodium hydrogen carbonate (250 mL) before being dried, filtered and concentrated. Purification by chromatography (SiO$_2$, isohexane: dichloromethane 7:3 as eluant) gave the title compound as a solid (27 g).

$^1$H NMR (400 MHz, CDCl$_3$) δ 8.53 (1H, d), 7.94 (1H, d), 7.78 (1H, d), 7.50 (1H, d).

MS: APCI(+ve) 276/278/280/282 (M+H$^+$).

b) 2,6-Dichloro-5-quinolinecarboxylic Acid

To a stirred solution of 5-bromo-2,6-dichloro-quinoline (23 g) in tetrahydrofuran (300 mL) at 0° C. was added isopropylmagnesium chloride (2M in tetrahydrofuran, 42 mL) over 2 hours. CO$_2$ was bubbled through the solution for 20 minutes and then methanol (20 mL) was added. The mixture was poured into water (500 mL) and extracted with ethyl acetate. The aqueous layer was acidified with hydrochloric acid (2M in water) to pH2-3 and the resulting solid collected by filtration. The solid was washed with water and dried to afford the sub-titled compound (11.5 g).

$^1$H NMR (400 MHz, d$_6$-DMSO) δ 8.29 (1H, d), 8.07 (1H, d), 7.94 (1H, d), 7.74 (1H, d).

c) 6-Chloro-2-[4-(ethoxycarbonyl)-1-piperidinyl]-5-quinolinecarboxylic Acid

Prepared according to the method of example 30, using 2,6-dichloro-5-quinolinecarboxylic acid (Example 76(b)) (800 mg) and 4-piperidinecarboxylic acid, ethyl ester (2.7 g). Purification (Varian NH$_2$ cartridge using methanol (100 mL) and then 2% acetic acid in methanol (100 mL) as eluant) afforded the title compound as a solid (900 mg).

MS: APCI(+ve) 363.2/365.2 (M+H$^+$).

d) 1-[6-Chloro-5-[[(2-cyclohexylethyl)amino]carbonyl]-2-quinolinyl]-4 Piperidinecarboxylic Acid Ethyl Ester Prepared according to the method of example 4(a), using 6-chloro-2-[4-(ethoxycarbonyl)-1-piperidinyl]-5-quinolinecarboxylic acid (example 76(c)) (217 mg) and cyclohexaneethanamine (277 mg). Purification (SiO$_2$, methanol:dichloromethane 1:99 as eluant) gave the title compound as a solid (200 mg).

MS: APCI(+ve) 472.3/474.3 (M+H$^+$).

e) 1-[6-Chloro-5-[[(2-cyclohexylethyl)amino]carbonyl]-2-quinolinyl]-4-piperidinecarboxylic Acid To a 10 mL vial was added 1-[6-chloro-5-[[(2-cyclohexylethyl)amino]carbonyl]-2-quinolinyl]-4-piperidinecarboxylic acid ethyl ester (Example 76(d)) (200 mg), methanol (2 mL) and potassium hydroxide (100 mg) in water (1 mL)). The vial was sealed and heated at 70° C. in a microwave for 10 minutes. The mixture was concentrated and the residue was acidified to pH 5 with aqueous 2 M hydrochloric acid. The resulting solid was collected by filtration. Purification (Varian NH$_2$ cartridge using methanol:dichloromethane 1:1 (100 mL) and then 2% acetic acid in methanol:dichloromethane 1:1 (100 mL) as eluant) afforded the title compound (150 mg).

$^1$H NMR (400 MHz, d$_6$-DMSO) δ 8.58 (1H, s), 7.75 (1H, d), 7.61-7.47 (2H, m), 7.35 (1H, d), 4.41 (2H, d), 3.35 (2H, d), 3.09 (2H, t), 2.61-2.41 (1H, m), 1.98-1.85 (2H, m), 1.81-1.33 (10H, m), 1.30-1.06 (3H, m), 1.01-0.82 (2H, m).

MS: APCI(+ve) 444.1/446.1 (M+H$^+$).

m.p. 253-256° C.

EXAMPLE 77

1-[6-Chloro-5-[(3-cyclopentyl-1-oxopropyl)amino]-2-quinolinyl]-4-piperidinecarboxylic Acid

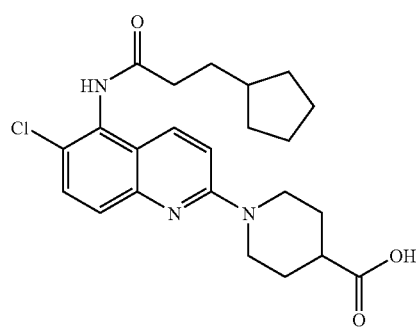

a) 1-(5-Amino-6-chloro-2-quinolinyl)-4-piperidinecarboxylic Acid, Ethyl Ester Prepared according to the method of example 30, using 2,6-dichloroquinolin-5-amine (Example 1(d)) (800 mg) and 4-piperidinecarboxylic acid, ethyl ester (1.8 g). Purification (SiO$_2$, miethanol:dichloromethane 1:99 as eluant) gave the sub-title compound as a solid (900 mg).

$^1$H NMR (400 MHz, d$_6$-DMSO) δ 8.34 (1H, d), 7.29 (1H, d), 7.14 (1H, d), 6.78 (1H, d), 5.84 (2H, s), 4.40 (2H, d), 4.07 (2H, q), 3.03 (2H, t), 2.69-2.58 (1H, m), 1.90 (2H, d), 1.55 (2H, q), 1.19 (3H, t).

MS: APCI(+ve) 334.2/336.2 (M+H$^+$).

b) 1-[6-Chloro-5-[(3-cyclopentyl-1-oxopropyl)amino]-2-quinolinyl]-4-piperidinecarboxylic Acid, Ethyl Ester Prepared according to the method of example 62(a), using cyclopentanepropanoic acid (256 mg) and 1-(5-amino-6-chloro-2-quinolinyl)-4-piperidinecarboxylic acid, ethyl ester Example 77(a)) (200 mg), to afford the sub-titled compound (240 mg).

$^1$H NMR (400 MHz, d$_6$-DMSO) δ 9.80 (1H, s), 7.86 (1H, d), 7.58 (1H, d), 7.49 (1H, d), 7.32 (1H, d), 4.43 (2H, d), 4.08 (2H, q), 3.10 (2H, t), 2.72-2.61 (1H, m), 2.45 (2H, t), 1.98-1.44 (13H, m), 1.24-1.08 (5H, m).

c) 1-[6-Chlor-5-[(3-cyclopentyl-1-oxopropyl)amino]-2-quinolinyl]-4-piperidinecarboxylic Acid Prepared according to the method of example 73(b), using 1-[6-chloro-5-[(3-cyclopentyl-1-oxopropyl)amino]-2-quinolinyl]-4-piperidinecarboxylic acid, ethyl ester Example 77(b)) (240 mg), to afford the titled compound (160 mg).

$^1$H NMR (400 MHz, d$_6$-DMSO) δ 9.83 (1H, s), 7.84 (1H, d), 7.55 (1H, d), 7.47 (1H, d), 7.29 (1H, d), 4.37 (2H, d), 3.05 (2H, t), 2.45 (2H, t), 2.41-2.32 (1H, m), 1.92-1.75 (5H, m), 1.72-1.45 (8H, m), 1.22-1.08 (2H, m).

MS: APCI(−ve) 428.2/430.2 (M−H$^+$).

EXAMPLE 78

1-[6-Chloro-5-[(3-cyclohexyl-1-oxopropyl)amino]-2-quinolinyl]-4-piperidinecarboxylic Acid, Potassium Salt

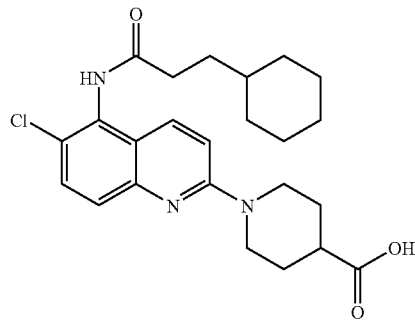

a) 1-[6-Chloro-5-[(3-cyclohexyl-1-oxopropyl)amino]-2-quinolinyl]-4-piperidinecarboxylic Acid, Ethyl Ester Prepared according to the method of example 62(a), using cyclohexanepropanoic acid (280 mg) and 1-(5-amino-6-chloro-2-quinolinyl)-4-piperidinecarboxylic acid, ethyl ester (Example 77(a)) (200 mg), to afford the sub-titled compound (240 mg).

$^1$H NMR (400 MHz, d$_6$-DMSO) δ 9.87 (1H, s), 7.98-7.83 (1H, m), 7.72-7.51 (2H, m), 7.43-7.30 (1H, m), 4.43 (2H, d), 4.08 (2H, q), 3.16 (2H, s), 2.76-2.63 (1H, m), 2.46 (2H, t), 1.95 (2H, d), 1.82-1.50 (9H, m), 1.38-1.07 (7H, m), 0.92 (2H, q).

MS: APCI(+ve) 458.2/460.2 (M+H$^+$).

b) 1-[6-Chlor-5-[(3-cyclohexyl-1-oxopropyl)amin]-2-quinolinyl]-4-piperidinecarbxylic Acid, Potassium Salt Prepared according to the method of example 76(e), using 1-[6-chloro-5-[(3-cyclohexyl-1-oxopropyl)amino]-2-quinolinyl]4-piperidinecarboxylic acid, ethyl ester (Example 78(b)) (240 mg). The reaction mixture was concentrated, water was added to the residue and the solid was collected by filtration and washed with water to afford the titled compound (160 mg).

$^1$H NMR (300 MHz, d$_6$-DMSO) δ 9.95 (1H, s), 7.82 (1H, d), 7.53 (1H, d), 7.44 (1H, d), 7.24 (1H, d), 4.27 (2H, d), 3.03 (2H, t), 2.48-2.40 (1H, m), 2.04-1.91 (1H, m), 1.86-1.40 (12H, m), 1.39-1.11 (4H, m), 0.92 (2H, q).

MS: APCI(−ve) 442.2/444.2 (M−H$^+$).

EXAMPLE 79

1-[6-Chloro-5-[[(1-methylcyclohexyl)acetyl]amino]-2-quinolinyl]-4-piperidinecarboxylic Acid

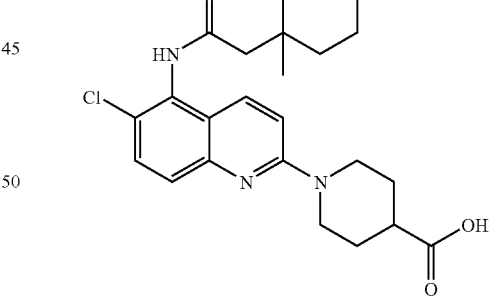

a) 1-[6-Chloro-5-[[(1-methylcyclohexyl)acetyl]amino]-2-quinolinyl]-4-piperidinecarboxylic Acid, Ethyl Ester Prepared according to the method of example 62(a), using 1-methyl-cyclohexaneacetic acid (280 mg) and 1-(5-amino-6-chloro-2-quinolinyl)-4-piperidinecarboxylic acid, ethyl ester (Example 77(a)) (200 mg), to afford the sub-titled compound (200 mg).

MS: APCI(+ve) 472.2/474.2 (M+H$^+$).

b) 1-[6-Chloro-5-[[(1-methylcyclohexyl)acetyl]amino]-2-quinolinyl]-4-piperidinecarboxylic Acid Prepared according to the method of example 76 (e), using 1-[6-chloro-5-[[(1-methylcyclohexyl)acetyl]amino]-2-quinolinyl]-4-piperidinecarboxylic acid, ethyl ester (Example 79(b)) (200 mg). Recrystallisation (ethanol/water) afforded the title compound (160 mg).

$^1$H NMR (300 MHz, $d_6$-DMSO) δ 9.43 (1H, s), 7.91 (1H, d), 7.61-7.45 (2H, m), 7.26 (1H, d), 4.35 (2H, d), 3.17 (2H, t), 2.64-2.52 (H, m), 2.38 (2H, s), 2.00-1.88 (2H, m), 1.73-1.29 (12H, m), 1.13 (3H, s).

MS: APCI(−ve) 442.2/444.2 (M−H$^+$).

m.p. 210-212° C.

EXAMPLE 80

N-[6-Chloro-2-[3-[(2-hydroxyethyl)amino]-1-piperidinyl]-5-quinolinyl]-cyclohexaneacetamide

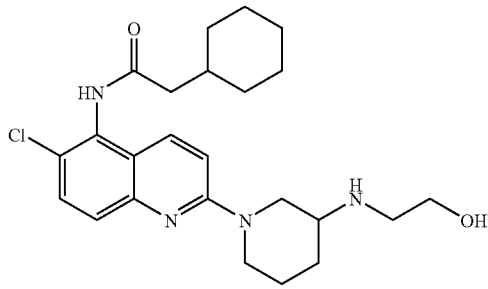

a) N-[6-Chloro-2-[(3R)-3-[(methylsulfonyl)oxy]-1-piperidinyl]-5-quinolinyl]Cyclohexaneacetamide To a stirred solution of N-[6-chloro-2-[(3R)-3-hydroxy-1-piperidinyl]-5-quinolinyl]-cyclohexaneacetamide (Example 37) (0.715 g) in dichloromethane (10 mL) was added triethylamine (0.99 mL) followed by methanesulfonyl chloride (0.275 mL). The reaction was stirred under nitrogen for 24 hours followed by the removal of volatiles under vacuum. The resulting mixture was taken up in methanol (20 mL) and placed down a Varian® SCX cartridge, washed with methanol (50 mL) and eluted with ammonia in methanol (0.7M, 50 mL). The solvent was removed to afford the sub-titled compound (0.64 g).

MS: APCI(+ve) 480.4 (M+H$^+$).

b) N-[6-Chloro-2-[3-[(2-hydroxyethyl)amino]-1-piperidinyl]-5-quinolinyl]-cyclohexaneacetamide N-[6-Chloro-2-[(3R)-3-[(methylsulfonyl)oxy]-1-piperidinyl]-5-quinolinyl]-cyclohexaneacetamide (Example 80(a)) (0.2 g), 2-amino-ethanol (0.075 ml) and acetonitrile (3 ml) were loaded into a 10 ml microwave reaction vial, capped and heated at 80° C. for 90 minutes within a single mode microwave. The solvent was removed under vacuum and the residue was purified by chromatography (SiO$_2$, 7M ammonia in methanol:dichloromethane 1:99 as eluant) to give the title compound as a solid (0.018 g).

$^1$H NMR (400 MHz, CD$_3$OD) δ 7.91 (1H, d), 7.56 (2H, s), 7.23 (1H, d), 4.60-4.54 (1H, m), 4.31-4.24 (1H, m), 3.68 (2H, t), 3.18-3.10 (1H, m), 2.99-2.92 (1H, m), 2.87-2.82 (2H, m), 2.75-2.67 (1H, m), 2.41 (2H, d), 2.12-2.03 (1H, m), 1.98-1.88 (3H, m), 1.87-1.75 (3H, m), 1.75-1.67 (1H, m), 1.67-1.54 (1H, m), 1.53-1.44 (1H, m), 1.42-1.21 (3H, m), 1.20-1.08 (2H, m).

MS: APCI(+ve) 445 (M+H$^+$).

m.p. 185-186° C.

EXAMPLE 81

N-[6-Chloro-2-[2-[[(2-hydroxyethyl)amino]methyl]-1-pyrrolidinyl]-5-quinolinyl]-cyclohexaneacetamide

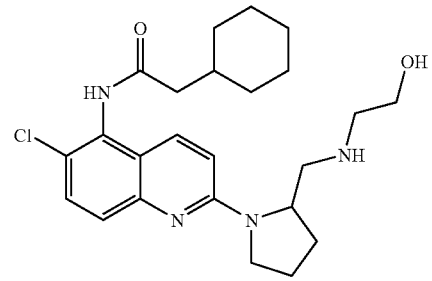

The title compound was isolated from the previous reaction mixture (Example 80(b)) as a late eluting by-product (30 mg).

$^1$H NMR (400 MHz, CD$_3$OD) δ 7.93 (1H, d), 7.64 (1H, d), 7.56 (1H, d), 6.99 (1H, d), 4.48-4.41 (1H, m), 3.72-3.66 (3H, m), 3.55-3.47 (1H, m), 3.04-2.98 (1H, m), 2.89-2.76 (3H, m), 2.42 (2H, d), 2.18-1.99 (4H, m), 1.98-1.88 (3H, m), 1.82-1.75 (2H, m), 1.75-1.68 (1H, m), 1.42-1.20 (3H, m), 1.21-1.08 (2H, m).

MS: APCI(+ve) 445 (M+H$^+$).

m.p. 157-158° C.

EXAMPLE 82

N-[6-Chloro-2-[3-(methylamino)-1-piperidinyl]-5-quinolinyl]-cyclohexaneacetamide

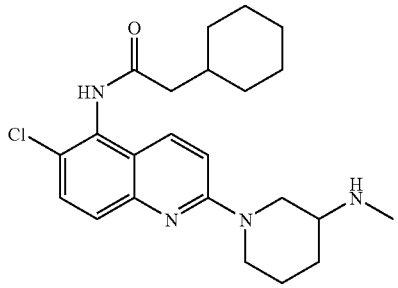

N-[6-Chloro-2-[(3R)-3-[(methylsulfonyl)oxy]-1-piperidinyl]-5-quinolinyl]-cyclohexaneacetamide (Example 80(a)) (0.2 g) and 8M methylamine in ethanol (5 ml) were placed into a 10 ml microwave vial and heated at 80° C. for 60 minutes within a single mode microwave. The reaction was pre-absorbed onto silica and purified (SiO$_2$, 7M ammonia in methanol:methanol:dichloromethane 1:3:96 as eluant). The resulting product was recrystallised from acetonitrile to afford the title compound (0.007 g).

$^1$H NMR (400 MHz, CD$_3$OD) δ 7.91 (1H, d), 7.56 (2H, s), 7.22 (1H, d), 4.56-4.50 (1H, m), 4.28-4.21 (1H, m), 3.20-3.12 (1H, m), 3.02-2.95 (1H, m), 2.63-2.55 (1H, m), 2.46 (3H, s), 2.41 (2H, d), 2.12-2.04 (1H, m), 1.96-1.88 (3H, m), 1.86-1.75 (3H, m), 1.75-1.67 (1H, m), 1.66-1.52 (1H, m), 1.51-1.21 (4H, m), 1.21-1.08 (2H, m).

MS: APCI(+ve) 415.2 (M+H$^+$).

m.p. 158-159° C.

EXAMPLE 83

N-[6-Chloro-2-[2-[(methylamino)methyl]-1-pyrrolidinyl]-5-quinolinyl]-cyclohexaneacetamide

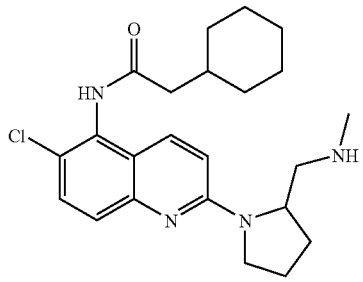

The title compound was isolated from the previous reaction mixture Example 82) as a late eluting by-product (36 mg).

$^1$H NMR (400 MHz, CD$_3$OD) δ 7.94 (1H, d), 7.59 (2H, d), 6.99 (1H, d), 4.48-4.41 (1H, m), 3.72-3.67 (1H, m), 3.55-3.47 (1H, m), 2.96 (1H, dd), 2.79 (1H, dd), 2.53 (3H, s), 2.42 (2H, d), 2.17-2.03 (3H, m), 2.03-1.97 (1H, m), 1.97-1.88 (3H, m), 1.83-1.75 (2H, m), 1.75-1.67 (1H, m), 1.42-1.21 (3H, m), 1.20-1.08 (2H, m).

MS: APCI(+ve) 415.2 (M+H$^+$).

m.p. 138-145° C.

EXAMPLE 84

N-[2-[(3R)-3-Hydrxy-1-pyrrolidinyl]-6-methyl-5-quinolinyl]-cyclohexaneacetamide

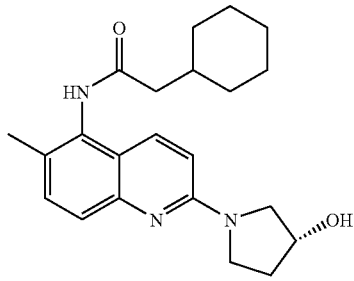

Prepared according to the method of example 27, using N-(2-chloro-6-methyl-5-quinolinyl)-cyclohexaneacetamide (Example 15(a)) (0.7 g), (3R)-3-pyrrolidinol (0.577 g) and acetonitrile (6 mL). Purification (SiO$_2$, 7M ammonia in methanol:methanol:dichloromethane 1:3:96 as eluant) gave the title compound (0.57 g)

$^1$H NMR (400 MHz, CD$_3$OD) δ 7.95 (1H, d), 7.59 (1H, d), 7.43 (1H, d), 6.89 (1H, d), 4.58-4.53 (1H, m), 3.75-3.68 (3H, m), 3.63-3.57 (1H, m), 2.42 (2H, d), 2.30 (3H, s), 2.22-2.12 (1H, m), 2.11-2.03 (1H, m), 1.99-1.86 (3H, m), 1.83-1.76 (2H, m), 1.75-1.68 (1H, m), 1.43-1.22 (3H, m), 1.22-1.09 (2H, m).

MS: APCI(+ve) 386.2 (M+H$^+$).

m.p. 248-249° C.

EXAMPLE 85

N-[(3S)-1-[6-Chloro-5-[(cyclohexylacetyl)amino]-2-quinolinyl]-3-pyrrolidinyl]-glycine a) N-[(3S)-1-[6-Chloro-5-[(cyclohexylacetyl)amino]-2-quinlinyl]-3-pyrrolidinyl]-glycine, Ethyl Ester N-[2-[(3S)-3-Amino-1-pyrrolidinyl]-6-chloro-5-quinolinyl]-cyclohexaneacetamide (Example 31) (0.25 g), 3 Å molecular sieves (0.2 g) and oxo-acetic acid, ethyl ester (4.9M in toluene) (0.131 mL) were stirred in dichloromethane (5 mL) under nitrogen for 2 hours followed by the addition of sodium triacetoxyborohydride (0.27 g). After 24 hours 1M sodium hydroxide (20 mL) was added with the formation of a precipitate which was filtered and washed with dichloromethane. The organic layer was separated and the aqueous phase extracted twice with dichloromethane. The combined organic phases were washed with brine, dried, filtered and solvent removed under vacuum to afford the sub titled compound (0.1 g).

MS: APCI(+ve) 473 (M+H$^+$).

b) N-[(3S)-1-[6-Chloro-5-[(cyclohexylacetyl)amino]-2-quinolinyl]-3-pyrrolidinyl]-glycine N-[(3S)-1-[6-Chloro-5-[(cyclohexylacetyl)amino]-2-quinolinyl]-3-pyrrolidinyl]-glycine ethyl ester (Example 85(a)) (100 mg), 1M sodium hydroxide (0.422 mL) and methanol (5 mL) were stirred for 12 hours before reaction was acidified with 1M hydrochloric acid and volatiles removed under vacuum. Purification (SiO$_2$, 7M ammonia in methanol: methanol:dichloromethane 1:4:95) gave the title compound (0.028 g)

$^1$H NMR (400 MHz, CD$_3$OD plus 1 drop of NaOD (40% in D$_2$O)) δ 7.95 (1H, d), 7.57 (1H, d), 7.52 (1H, d), 6.91 (1H, d), 3.85-3.73 (2H, m), 3.65-3.57 (1H, m), 3.55-3.43 (2H, m), 3.24 (2H, s), 2.40 (2H, d), 2.32-2.23 (1H, m), 2.01-1.89 (4H, m), 1.82-1.74 (2H, m), 1.74-1.67 (1H, m), 1.42-1.20 (3H, m), 1.19-1.08 (2H, m).

MS: APCI(-ve) 443.4 (M-H$^+$).

m.p. 257-259° C.

EXAMPLE 86

N-[2-[(3S)-3-[(2-Hydroxyethyl)amino]-1-pyrrolidinyl]-6-methyl-5-quinolinyl]-cyclohexaneacetamide

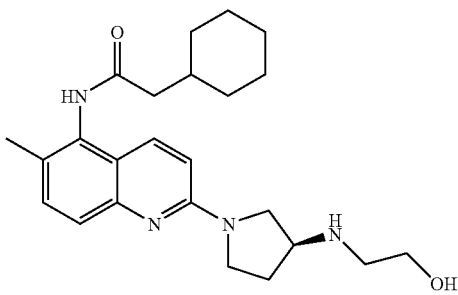

a) N-[6-Methyl-2-[(3R)-3-[(methylsulfonyl)oxy]-1-pyrrolidinyl]-5-quinolinyl]-cyclohexaneacetamide Prepared according to the method of example 33(a), using N-[2-[(3R)-3-hydroxy-1-pyrrolidinyl]-6-methyl-5-quinolinyl]-cyclohexaneacetamide (Example 84) (0.545 g), methanesulfonyl chloride (0.23 mL), triethylamine (0.62 mL) and dichloromethane (20 mL) to afford the sub-title compound (0.4 g).

MS: APCI(+ve) 446 (M+H$^+$).

b) N-[2-[(3S)-3-[(2-Hydroxyethyl)amino]-1-pyrrolidinyl]-6-methyl-5-quinolinyl]-cyclohexaneacetamide Prepared according to the method of example 33(b), using N-[6-methyl-2-[(3R)-3-[(methylsulfonyl)oxy]-1-pyrrolidinyl]-5-quinolinyl]-cyclohexaneacetamide (Example 86(a)) (0.16 g), 2-amino-ethanol (0.065 mL), and acetonitrile (4 mL). Purification (SiO$_2$, 7M ammonia in methanol:methanol:dichloromethane 1:2:99 as eluant) gave the title compound (0.06 g).

$^1$H NMR (400 MHz, CD$_3$OD) δ 7.95 (1H, d), 7.59 (1H, d), 7.43 (1H, d), 6.89 (1H, d), 3.87 (1H, dd), 3.80-3.73 (1H, m), 3.69 (2H, t), 3.64-3.57 (1H, m), 3.53 (1H, quintet), 3.46-3.41 (1H, m), 2.82 (2H, td), 2.41 (2H, d), 2.36-2.26 (1H, m), 2.30 (3H, s), 2.00-1.86 (4H, m), 1.83-1.76 (2H, m), 1.75-1.68 (1H, m), 1.43-1.22 (3H, m), 1.22-1.09 (2H, m)

MS: APCI(+ve) 411.2 (M+H$^+$).

m.p. 204-207° C.

EXAMPLE 87

N-[(3S)-1-[6-Chloro-5-[(cyclohexylacetyl)amino]-2-quinolinyl]-3-pyrrolidinyl]-β-alanine

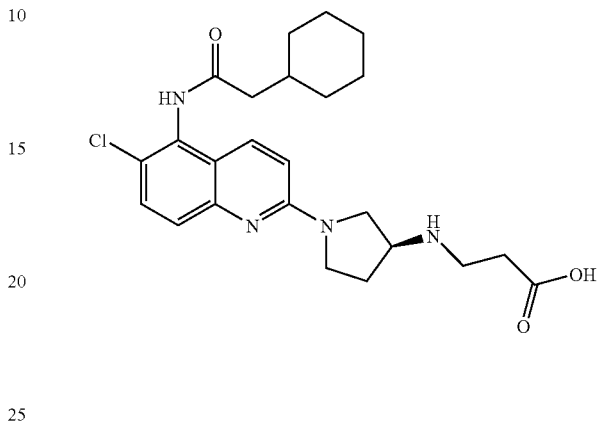

a) 3-[(3S)-3-Pyrrolidinylamino]-propanenitrile

3-[[(3S)-1-(Phenylmethyl)-3-pyrrolidinyl]amino]-propanenitrile (as described in WO2000075137) (0.6 g), 20% palladium hydroxide on carbon (0.15 g), 1,4 cyclohexadiene (3 mL) and ethanol (2 mL) were loaded into a 10 mL microwave vial, capped and heated at 100° C. for 90 minutes within a single mode microwave. The reaction mixture was filtered and the volatiles removed under vacuum to afford the sub-title compound (0.304 g).

MS: APCI(+ve) 140.3 (M+H$^+$).

b) N-[6-Chloro-2-[(3S)-3-[(2-cyanoethyl)amino]-1-pyrrolidinyl]-5-quinolinyl]-cyclohexaneacetamide N-(2,6-Dichloro-5-quinolinyl)-cyclohexaneacetamide (Example 1 (a)) (0.4 g), 3-[(3S)-3-pyrrolidinylamino]-propanenitrile (Example 87(a)) (0.3 g) and triethylamine (0.6 mL) were heated within a microwave in a sealed 10 mL vial for 60 minutes at 120° C. The volatiles were removed under vacuum and the mixture purified (SiO$_2$, methanol:dichloromethane 1:99 as eluant) to give the sub-titled compound (0.25 g).

MS: APCI(+ve) 440.5 (M+H$^+$).

c) N-[(3S)-1-[6-Chloro-5-[(cyclohexylacetyl)amino]-2-quinolinyl]-3-pyrrolidinyl]-β-alanine N-[6-Chloro-2-[(3S)-3-[(2-cyanoethyl)amino]-1-pyrrolidinyl]-5-quinolinyl]-cyclohexaneacetamide (0.1 g), potassium hydroxide (0.051 g), water (1 mL) and methanol (2 mL) were heated within a single mode microwave in a sealed 10 mL vial for 100 minutes at 90° C. The resulting mixture was dissolved in methanol (20 mL) and purified on a Varian® SCX cartridge, washed with methanol (50 mL) and eluted with ammonia in methanol (0.7M, 50 mL). The residue was further purified on a Varian® NH$_2$ cartridge washed with methanol (50 mL) and eluted with acetic acid:methanol (10:90). The solvent was removed under vacuum and the residue triturated with hot methanol, cooled and filtered to afford the title compound (7 mg).

¹H NMR (400 MHz, d₆-DMSO) δ 9.76 (1H, s), 7.84 (1H, d), 7.55 (1H, d), 7.47 (1H, d), 6.95 (1H, d), 3.75-3.68 (1H, m), 3.67-3.58 (1H, m), 3.57-3.49 (1H, m), 3.48-3.41 (2H, m), 2.85-2.80 (2H, m), 2.36-2.30 (4H, m), 2.19-2.10 (1H, m), 1.91-1.77 (4H, m), 1.74-1.67 (2H, m), 1.67-1.60 (1H, m), 1.32-1.13 (4H, m), 1.10-0.99 (2H, m).

MS: APCI(-ve) 457.2 (M-H⁺).

EXAMPLE 88

N-[6-Chloro-2-[(3S)-3-[[(trifluoromethyl)sulfonyl]amino]-1-pyrrolidinyl]-5-quinolinyl]-cyclohexaneacetamide

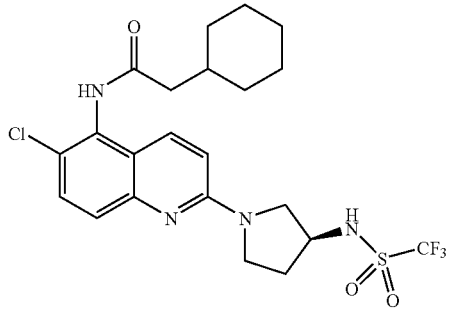

N-[2-[(3S)-3-Amino-1-pyrrolidinyl]-6-chloro-5-quinolinyl]-cyclohexaneacetamide (Example 31) (0.15 g), triethylamine (0.108 mL) and dichloromethane (15 mL) were cooled to 0° C. followed by the addition of trifluoroacetic anhydride (0.078 mL). The reaction was allowed to warm to room temperature and stirred for 1 hour. Water (10 mL) was added and the organic phase separated. The combined organic layers were concentrated and the residue purified by HPLC (Symmetry—0.1% aqueous ammonium acetate/acetonitrile). Further purification on a Varian® NH₂ cartridge, eluting with methanol (50 mL) and then with acetic acid:methanol (10:90), afforded the title product (0.018 g).

¹H NMR (400 MHz, d₆-DMSO) δ 9.77 (1H, s), 7.85 (1H, d), 7.56 (1H, d), 7.49 (1H, d), 6.96 (1H, d), 4.21-4.13 (1H, m), 3.83-3.75 (1H, m), 3.71-3.63 (1H, m), 3.58-3.50 (1H, m), 3.43-3.35 (1H, m), 2.32 (2H, d), 2.27-2.17 (1H, m), 2.00-1.89 (1H, m), 1.86-1.77 (3H, m), 1.75-1.67 (2H, m), 1.67-1.60 (1H, m), 1.32-1.11 (4H, m), 1.10-0.98 (2H, m).

MS: APCI(+ve) 519.1 (M+H⁺).
m.p. 178-200° C.

EXAMPLE 89

N-[6-Chloro-2-[(3S)-3-[[[(methylsulfonyl)amino]carbonyl]amino]-1-pyrrolidinyl]-5-quinolinyl]-cyclohexaneacetamide

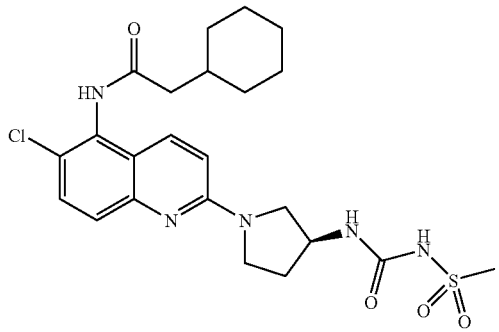

N-[2-[(3S)-3-Amino-1-pyrrolidinyl]-6-chloro-5-quinolinyl]-cyclohexaneacetamide (Example 31) (0.15 g) and (methylsulfonyl)-carbamic acid ethyl ester (0.065 g) were heated with a single mode microwave in a sealed 10 mL vial for 30 minutes at 130° C. The residue was purified on a Varian® NH₂ cartridge washed with methanol (50 mL) and eluted with acetic acid:methanol (10:90) to afford the title product (0.016 g).

¹H NMR (400 MHz, d₆-DMSO) δ 9.77 (1H, s), 7.86 (1H, d), 7.56 (1H, d), 7.49 (1H, d), 6.97 (1H, d), 6.83-6.76 (1H, m), 4.33-4.25 (1H, m), 3.80-3.74 (1H, m), 3.66-3.55 (2H, m), 3.47-3.39 (1H, m), 3.18 (3H, s), 2.32 (2H, d), 2.27-2.17 (1H, m), 2.01-1.90 (1H, m), 1.88-1.77 (3H, m), 1.75-1.67 (2H, m), 1.67-1.60 (1H, m), 1.32-1.14 (4H, m), 1.13-0.98 (2H, m).

MS: APCI(+ve) 508.1 (M+H⁺).
m.p. 303-307° C.

EXAMPLE 90

N-[2-[(3S)-3-Amino-1-pyrrolidinyl]-6-chloro-5-quinolinyl]-cyclohexanepropanamide

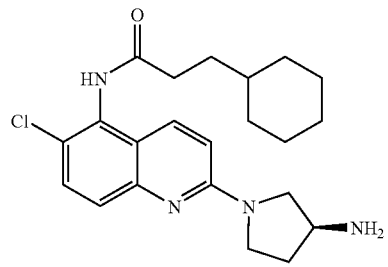

a) N-(2,6-dichloro-5-quinolinyl)-cyclohexanepropanamide

Prepared according to the method of example 62(a), using 2,6-dichloroquinolin-5-amine (example 1(d)) (0.5 g) and cyclohexanepropionic acid (1.2 mL). The resulting precipitate was filtered and washed with acetone. The precipitate was further washed with water and then ether to give the sub-title compound as a solid (0.248 g)

¹H NMR (300 MHz, DMSO) δ 8.28-8.25 (1H, d), 7.93 (2H, s), 7.69-7.66 (1H, d), 1.78-1.53 (8H, m), 1.31-1.12 (5H, m), 0.98-0.86 (2H, m).

MS: APCI(+ve) 351.2 (M+H⁺).

b) N-[2-(3-Amino-1-pyrrolidinyl)-6-chloro-5-quinolinyl]-cyclohexanepropanamide N-(2,6-Dichloro-5-quinolinyl)-cyclohexanepropanamide (Example 90(a)) (0.24 g), (S)-3-aminopyrrolidine (0.18 g) and triethylamine (0.1 mL) were suspended in acetonitrile and heated at 100° C. in a microwave for 1 hour. The resulting precipitate was filtered and then washed with acetonitrile to give a brown solid. Purification (SiO₂, methanol:dichloromethane:triethylamine 3:97:0.5) gave the title compound as a colourless solid (230 mg).

¹H NMR (400 MHz, DMSO) δ 9.77 (1H, s), 7.86-7.83 (1H, d), 7.56-7.54 (1H, d), 7.48-7.46 (1H, d), 6.93-6.91 (1H, d), 3.70-3.64 (3H, m), 3.56-3.55 (1H, m), 2.46-2.42 (2H, t), 2.16-2.14 (1H, m), 1.85-1.53 (8H, m), 1.32-1.1 (5H, m), 0.96-0.85 (2H, m).

MS: APCI(+ve) 401.2 (M+H⁺)

EXAMPLE 91

N-[6-Chloro-2-[methyl[3-(methylamino)propyl]amino]-5-quinolinyl]-cyclohexanepropanamide

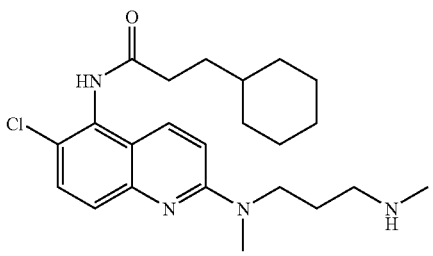

Prepared according to the method of example 90(b), using N-(2,6-dichloro-5-quinolinyl)-cyclohexanepropanamide (Example 90(a)) (0.16 g), N,N'-dimethylpropanediamine (0.3 mL) and triethylamine (0.1 mL). Purification (SiO$_2$, methanol:dichloromethane:triethylamine 5:95:0.5 followed by HPLC, Symmetry—0.1% aqueous trifluoroacetic acid:acetonitrile) gave the title compound as a solid (70 mg).

$^1$H NMR (400 MHz, d$_6$-DMSO) δ 9.85(1H, s), 8.43 (2H, bs), 7.91-7.89 (1H, d), 7.65-7.63 (1H, d), 7.59 (1H, bs), 7.22-7.2 (1H, d), 3.77-3.74 (1H, t), 2.93-2.91 (1H,), 2.58-2.55 (2H, t), 2.52 (6H, m), 2.48-2.44 (2H, t), 1.96-1.93 (2H, t), 1.89-1.62(5H, m), 1.59-1.53 (2H, q), 1.33-1.10(4H, m), 0.96-0.85 (2H, m).

MS: APCI(+ve) 417.2 (M+H$^+$).

EXAMPLE 92

N-[6-Chloro-2-(1-piperazinyl)-5-quinolinyl]-cyclohexanepropanamide

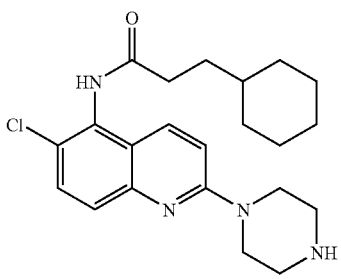

N-(2,6-Dichloro-5-quinolinyl)-cyclohexanepropanamide (Example 90(a)) (0.16 g), 1-piperazinecarboxylic acid, 1,1-dimethylethyl ester (0.34 g,), triethylamine (0.15 mL) and tetra-butylammonium bromide (80 mg) were heated at 140° C. for 1 hour in a microwave. The resulting precipitate was filtered and then washed with acetonitrile to give a solid. This solid was dissolved in dichloromethane and trifluoroacetic acid (1 mL) was added. The reaction mixture was stirred at room temperature for 3 hours, then concentrated under vacuum to dryness. Purification (HPLC, Symmetry—0.1% aqueous trifluoroacetic acid:acetonitrile followed by Varian SCX cartridge using methanol and then 10% ammonia in methanol as eluant) gave the title compound as a white solid (30 mg).

$^1$H NMR (400 MHz, DMSO) δ 9.79 (1H, s), 7.86-7.83 (1H, d), 7.58-7.56 (1H, d), 7.48-7.46 (2H, d), 7.28-7.26 (1H, d), 3.61 (4H, t), 2.8 (4H, m), 2.49-2.42 (2H, t), 1.79-1.53 (7H, m), 1.36-1.1 (4H, m), 0.96-0.85 (2H, m).

MS: APCI(+ve) 401.2 (M+H$^+$).

EXAMPLE 93

N-[6-Chloro-2-[(3S)-3-[(2-hydrxyethyl)amino]-1-pyrrolidinyl]-5-quinolinyl]-cyclohexanepropanamide

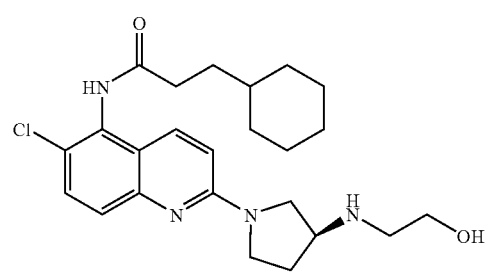

Prepared according to method of example 50(a), using N-[2-(3-amino-1-pyrrolidinyl)-6-chloro-5-quinolinyl]-cyclohexanepropanamide (Example 90(b)) (0.12 g), (tert-butyldimethylsilyloxy)acetaldehyde (51 μL) and sodium triacetoxyborohydride (0.13 g). The crude mixture was purified (SiO$_2$, methanol:dichloromethane 2:98) and the product dissolved in dichloromethane. Trifluoroacetic acid (0.2 mL) was added and the reaction mixture stirred at room temperature for 48 hours. The reaction mixture was concentrated under vacuum and the residue purified (Varian SCX cartridge using methanol and then 10% ammonia in methanol, HPLC Symmetry, 0.1% aqueous ammonium acetate:acetonitrile) to give the title compound as a solid (0.018 g).

$^1$H NMR (400 MHz, d$_6$-DMSO) δ 9.76 (1H, s), 7.84-7.82 (1H, d), 7.55-7.52 (1H, d), 7.47-7.45 (1H, d), 6.92-6.90 (1H, d), 3.6-3.4 (6H, m), 2.6 (2H, m), 2.46-2.42 (2H, t,), 2.15-2.07 (1H, m), 1.89-1.53 (8H, m), 1.36-1.1(5H, m), 0.96-0.83(2H, m).

MS: APCI(+ve) 445.2 (M+H$^+$).

EXAMPLE 94

2-[(3S)-3-Amino-1-pyrrolidinyl]-6-chloro-N-(2-cyclohexylethyl)-5-quinolinecarboxamide, Ditrifluoroacetate

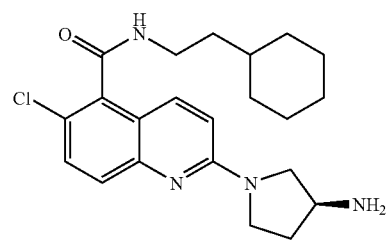

a) 6-Chloro-5-quinolinecarboxylic Acid tert-Butyllithium (1.6 mL, 1.7 M in pentane) was added to a solution of 5-bromo-6-chloro-quinoline (prepared according to the method of Journal of Heterocyclic Chemistry 1967, 4, 410) (0.3 g) in dry tetrahydrofuran at −78° C. under nitrogen. The reaction mixture was stirred at −78° C. for 10 minutes and then carbon dioxide bubbled through for one minute. The reaction mixture was stirred at −78° C. for another 10 minutes and then water (3 mL) added. The reaction mixture was allowed to warm up to room temperature, concentrated under vacuum and the residue was partitioned between water and ethyl acetate. The aqueous layer was freeze dried to give the sub-titled compound as a solid (0.3 g).

$^1$H NMR (300 MHz, $d_6$-DMSO) δ 8.84-8.82 (1H, d), 8.29-8.27 (1H, d), 7.77-7.74 (1H, d), 7.61-7.58 (1H, d), 7.51-7.47 (1H, m).

MS: APCI(+ve) 208 (M+H$^+$).

b) 6-Chloro-N-(2-cyclohexylethyl)-5-quinolinecarboxamide

Oxalyl chloride (0.3 mL) was added to a suspension of 6-chloro-5-quinolinecarboxylic acid (example 94(a)) (0.3 g) in dichloromethane and 2 drops of N,N-dimethylformamide. The reaction mixture was stirred at room temperature for 1 hour then evaporated to an oil. The residue was added to cyclohexylethylamine hydrochloride (0.33 g) and triethylamine (0.6 mL) in dichloromethane and then stirred at room temperature for 1 hour. Water was added and the reaction mixture was extracted with dichloromethane. The combined organics were dried and concentrated. Purification (SiO$_2$, ethyl acetate:isohexane 50:50) gave the sub titled compound as a solid (0.115 g).

$^1$H NMR (300 MHz, $d_6$-DMSO) δ 8.97-8.96 (1H, m), 8.73-8.70 (1H, t), 8.11-8.04 (2H, m), 7.84-7.81 (1H, d), 7.67-7.63 (1H, m), 3.39-3.36 (2H, q), 1.76-1.62 (5H, m), 1.50-1.35 (3H, m), 1.30-1.07 (3H, m), 0.96-0.85 (2H, m).

MS: APCI(+ve) 317.3 (M+H$^+$).

c) 6-Chloro-5-[[(2-cyclohexylethyl)amino]carbonyl]-1-hydroxy-quinolinium

Peracetic acid (1.3 mL, 36-40% in acetic acid) was added to 6-chloro-N-(2-cyclohexylethyl)-5-quinolinecarboxamide (Example 94(b)) (0.115 g) in acetic acid and the reaction mixture stirred at room temperature overnight. The reaction mixture was washed with a 10% sodium sulfite solution and then extracted with dichloromethane. The organics were washed with water, dried and concentrated. Purification (SiO$_2$, methanol:ethylacetate 5:95) gave the sub titled compound as a solid (0.05 g).

$^1$H NMR (300 MHz, $d_6$-DMSO) δ 8.80-8.77 (1H, t), 8.64-8.63 (1H, d), 8.57-8.55 (1H, d), 7.89-7.86 (1H, d), 7.61-7.55 (2H, m), 3.4 (2H, q), 1.90-1.62 (5H, m), 1.50-1.35 (3H, m), 1.25-1.09 (3H, m), 0.96-0.85 (2H, m).

MS: APCI(+ve) 333.3 (M+H$^+$).

d) 2,6-Dichloro-N-(2-cyclohexylethyl)-5-quinolinecarboxamide

Phosphorous oxychloride (2 mL) was added to 6-chloro-5-[[(2-cyclohexylethyl)amino]carbonyl]-1-hydroxy-quinolinium Example 94(c)) (0.089 g) and the mixture heated at 60° C. for 2 hours. The reaction mixture was concentrated under reduced pressure and added to water. The aqueous was extracted with ethyl acetate and the combined organics dried filtered and evaporated give the sub titled compound as a solid (0.079 g).

MS: APCI(+ve) 351.4 (M+H$^+$).

e) 2-[(3S)-3-Amino-1-pyrrolidinyl]-6-chloro-N-(2-cyclohexylethyl)-5-quinolinecarboxamide, Ditrifluoroacetate Prepared according to the method of example 90(b), using 2,6-dichloro-N-(2-cyclohexylethyl)-5-quinolinecarboxamide (Example 94(d)) (0.079 g), (S)-3-aminopyrrolidine (0.05 g) and triethylamine (0.031 mL). The reaction mixture was concentrated under reduced pressure and purified (HPLC Symmetry, 0.1% aqueous trifluoroacetic acid:acetonitrile as eluant) to give the title compound (0.014 g).

$^1$H NMR (300 MHz, $d_6$-DMSO) δ 8.65 (1H, bs), 8.11 (3H, bs), 7.84-7.82(1H, d), 7.65-7.62 (2H, m), 7.11-7.09 (1H, d), 4.12-3.56(4H, range of ppm), 3.36-3.34(2H, d), 2.38-2.32 (1H, m), 2.14(1H, m), 1.76-1.64(5H, m), 1.46-1.4(3H, m), 1.23-1.12(4H, m), 0.93-0.90(2H, m).

MS: APCI(+ve) 401.2 (M+H$^+$).

EXAMPLE 95

N-[6-Chloro-2-[(3S)-3-[(2-hydroxyethyl)sulfonyl]-1-pyrrolidinyl]-5-quinolinyl]

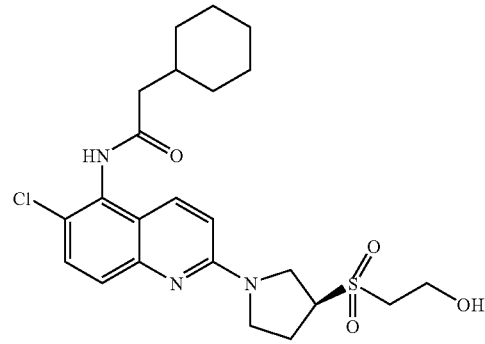

a) N-[6-Chloro-2-[(3S)-3-[(2-hydroxyethyl)thio]-1-pyrrolidinyl]-5-quinolinyl]-cyclohexaneacetamide Mercaptoethanol (0.073 mL) was added to N-[6-chloro-2-[(3S)-3-[(methylsulfonyl)oxy]-1-pyrrolidinyl]-5-quinolinyl]-cyclohexaneacetamide (Example 33(a)) (0.1 g) and potassium carbonate (0.24 g) in dry N,N-dimethylformamide. The reaction mixture was heated at 60° C. in a microwave for 2 hours and then partitioned between water and ethyl acetate. The combined organics were washed with brine, dried and concentrated. Purification (SiO$_2$, methanol:dichloromethane 3:97 as eluant) gave the sub-titled compound as a solid (0.05 g).

MS: APCI(+ve) 448.1 (M+H$^+$).

b) N-[6-Chloro-2-[(3S)-3-[(2-hydroxyethyl)sulfonyl]-1-pyrrlidinyl]-5-quinolinyl]-cyclohexaneacetamide Hydrogen peroxide (0.57 mL, 1.25M in methanol) and p-toluenesulfonylimidazole (0.081 g) were added to N-[6-chloro-2-[(3S)-3-[(2-hydroxyethyl)thio]-1-pyrrolidinyl]-5-quinolinyl]-cyclohexaneacetamide (Example 95(a)) (0.034 g) in methanol. The reaction mixture was cooled down to 0° C. and 1M sodium hydroxide (0.36 mL) was carefully added. The reaction mixture was allowed to warm up to room temperature overnight and 10 mL of 10% sodium metabisulfite solution added. Methanol was removed under reduced pressure and the aqueous layer extracted with dichloromethane. The combined organics were concentrated under vacuum.

Purification (SiO$_2$, methanol-dichloromethane 2:98 as eluant) gave the title compound as a solid (0.004 g).

$^1$H NMR (300 MHz, d$_6$-DMSO) δ 9.78 (1H, s), 7.90-7.87 (1H, d), 7.60-7.57 (1H, d), 7.53-7.50 (1H, d), 7.04-7.00 (1H, d), 5.22-5.18 (1H, t), 4.19-4.14 (1H, q), 3.87-3.60 (7H, m), 3.37-3.33 (1H, m), 2.4 (2H, m), 2.33-2.31 (2H, d), 1.83-1.62 (6H, m), 1.29-1.02 (5H, m).

MS: APCI(+ve) 480.1 (M+H$^+$).

EXAMPLE 96

N-[6-Chloro-2-[(3S)-3-cyano-1-pyrrolidinyl]-5-quinolinyl]-cyclohexaneacetamide

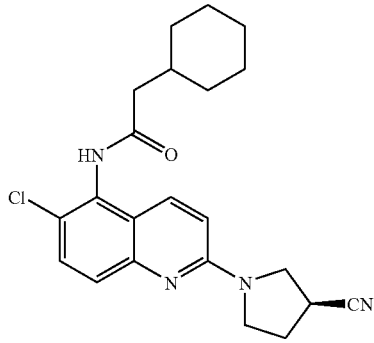

Lithium cyanide (4 mL, 0.5M in DMF) was added to N-[6-chloro-2-[(3R)-3-hydroxy-1-pyrrolidinyl]-5-quinolinyl]-cyclohexaneacetamide (Example 33(a)) (0.21 g) in N,N'-dimethylformamide. The reaction mixture was heated at 60° C. for 10 hours. A saturated solution of sodium bicarbonate was added and the reaction mixture extracted with ethyl acetate. The combined organics were washed with brine, dried and concentrated. Purification (SiO$_2$, iso-hexane:ethyl acetate 1:1 as eluant) gave the title compound as a solid (0.066 g).

$^1$H NMR (300 MHz, d$_6$-DMSO) a 9.78 (1H, s), 7.90-7.87 (1H, d), 7.60-7.57 (1H, d), 7.53-7.50 (1H, d), 7.02-6.99 (1H, d), 3.92-3.57 (5H, m), 2.44-2.25 (4H, m), 1.83-1.62 (6H, m), 1.29-1.02 (5H, m).

MS: APCI(+ve) 397.1 (M+H$^+$).

EXAMPLE 97

N-[1-[6-Chloro-5-[[(cyclohexylmethyl)amino]carbonyl]-2-quinolinyl]-3-azetidinyl]-β-alanine

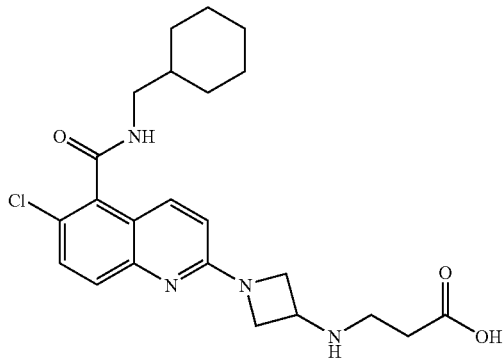

a) 2-(3-Amino-1-azetidinyl)-6-chloro-N-(cyclohexylmethyl)-5-quinolinecarboxamide 3-Azetidinyl-carbamic acid, 1,1-dimethylethyl ester (0.5 g) was added to 2,6-dichloro-N-(cyclohexylmethyl)quinoline-5-carboxamide (Example 43(a)) (0.28 g), tetra-butylammonium bromide (0.28 g) and triethylamine (0.5 mL) in acetonitrile (4 mL). The reaction mixture was heated at 120° C. in a microwave for 1 hour, concentrated under reduced pressure and purified (SiO$_2$, methanol:dichloromethane 4:96 as eluant). The residue (0.24 g) was dissolved in dichloromethane and trifluoroacetic acid (1 mL) added. The reaction mixture was stirred at room temperature for 1 hour, concentrated and then treated with 7M ammonia in methanol. Purification (Varian SCX cartridge using methanol and then 10% ammonia in methanol) gave the sub-titled compound as a solid (0.1 g).

$^1$H NMR (400 MHz, d$_6$-DMSO) δ 8.64-8.60 (1H, t), 7.73-7.70 (1H, d), 7.57-7.57 (2H, m), 6.82-6.79 (1H, d), 4.28-4.23 (2H, t), 3.89-3.80 (1H, q), 3.71-3.66 (2H, m), 3.18-3.14 (2H, t), 1.80-1.34 (6H, m), 1.28-0.91 (5H, m).

b) N-[1-[6-Chloro-5-[[(cyclohexylethyl)amino]carbonyl]-2-quinolinyl]-3-azetidinyl]-β-alanine To a stirred solution of 2-(3-amino-1-azetidinyl)-6-chloro-N-(cyclohexylmethyl)-5-quinolinecarboxamide (Example 97(a)) (0.1 g) in methanol (1 mL) was added ethyl acrylate (0.032 mL). The mixture was stirred at room temperature for 20 hours. Sodium hydroxide (1 mL, 1M) was added and the reaction mixture was stirred for 72 hours. Hydrochloric acid (0.5 mL, 2M) was added and the reaction mixture was concentrated under vacuum. Purification (HPLC—Symmetry, 0.1% aqueous ammonium acetate:acetonitrile as eluant) gave the title compound as a solid (0.026 g).

$^1$H NMR (400 MHz, d$_6$-DMSO) δ 8.64-8.60 (1H, t), 7.74-7.71 (1H, d), 7.57-7.49 (2H, m), 6.82-6.79 (1H, d), 4.26-4.21 (2H, t), 3.78-3.68 (3H, m), 3.18-3.13 (2H, t), 2.74-2.69 (2H, t), 2.34-2.27 (2H, m), 1.80-1.60 (6H, m), 1.23-0.85 (5H, m).

MS: APCI(-ve) 443.2 (M-H$^+$).

EXAMPLE 98

6-Chloro-N-(cyclohexylmethyl)-2-[3-(1H-tetrazol-5-yl)-1-azetidinyl]-5-quinolinecarboxamide

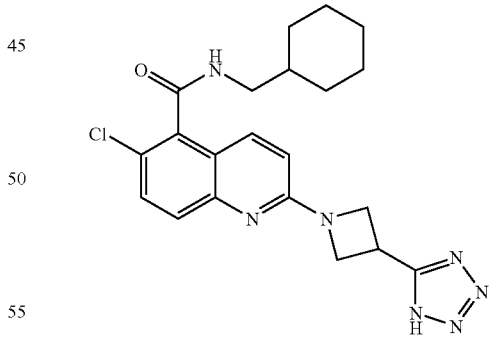

a) 6-Chlor-2-(3-cyano-1-azetidinyl)-N-(cyclohexylmethyl)-5-quinolinecarboxamide

A mixture of 2,6-dichloro-N-(cyclohexylmethyl)-5-quinolinecarboxamide (example 43(a)) (0.25 g, 0.74 mmol), 3-azetidinecarbonitrile (prepared according to the method of JP 2001172257A), tetra-butylammonium bromide (0.25 g) and potassium carbonate (0.2 g) in N-methylpyrrolidinone were heated at 130° C. in a microwave for 2 hours. Water was added and the reaction mixture was extracted with dichloromethane. The organic fraction was washed with water, dried over magnesium sulfate and concentrated. The residue was purified firstly by C18 cartridge (eluting with 10 to 100% methanol in water) and then by chromatography (SiO$_2$, ethyl acetate: methanol 100:0 to 50:50 as eluant) to give the sub-title compound as a solid (0.082 g).

MS: APCI(+ve) 383.2 (M+H$^+$).

b) 6-Chloro-N-(cyclohexylmethyl)-2-[3-(1H-tetrazol-5-yl)-1-azetidinyl]-5-quinolinecarboxamide To a stirred solution of 6-chloro-2-(3-cyano-1-azetidinyl)-N-(cyclohexylmethyl)-5-quinoilnecarboxamide Example 98(a)) (0.08 g) and dibutyltin oxide (0.017 g) in toluene (5 mL) was added azidotrimethylsilane (0.08 mL). The mixture was heated at 100° C. for 20 hours after which it was cooled and then methanol added. The solvent was evaporated under reduced pressure, methanol was added and the mixture stirred for 5 minutes before being concentrated under vacuum. The residue was purified (HPLC, Symmetry—0.1% aqueous trifluoroacetic acid:acetonitrile) to give the title compound as a solid (0.033 g).

$^1$H NMR (400 MHz, d$_6$-DMSO) δ 10.51 (1H, s), 8.88-8.87 (1H, t), 8.06-8.03 (1H, d), 7.95-7.91 (2H, m), 7.18 (1H, d), 4.80 (2H, m), 4.20 (1H, m), 4.00 (1H, m), 3.85-3.81 (1H, m), 3.19-3.16 (2H, q), 1.79-1.54 (6H, m), 1.24-0.93 (5H, m).

MS: APCI(+ve) 426.1 (M+H$^+$).

EXAMPLE 99

N-[6-Chlor-2-[(3S)-3-(1H-tetrazol-5-yl)-1-pyrrolidinyl]-5-quinolinyl]-cyclohexaneacetamide

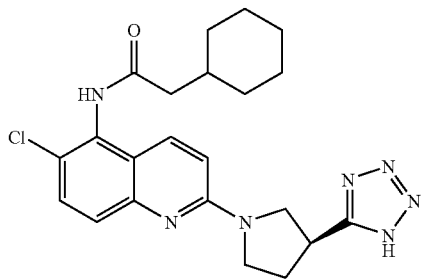

Prepared according to the method of example 98(b), using N-[6-chloro-2-[(3S)-3-cyano-1-pyrrolidinyl]-5-quinolinyl]-cyclohexaneacetamide (example 96) (0.036 g). Purification -(Varian NH$_2$ cartridge, methanol then 2% acetic acid in methanol as eluant) gave the title compound as a solid (0.028 g).

$^1$H NMR (300 MHz, d$_6$-DMSO) δ 9.77 (1H, s), 7.88-7.85 (1H, d), 7.58-7.55 (1H, d), 7.50-7.47 (1H, d), 7.01-6.98 (1H, d), 4.10-3.61 (5H, m), 2.33-2.25 (3H, m), 1.91-0.98 (11H, m), 0.87-0.82 (1H, t).

MS: APCI(+ve) 440.1 (M+H$^+$).

EXAMPLE 100

N-[6-Chloro-2-[(3R)-3-(1H-tetrazol-5-yl)-1-pyrrolidinyl]-5-quinolinyl]-cyclohexaneacetamide

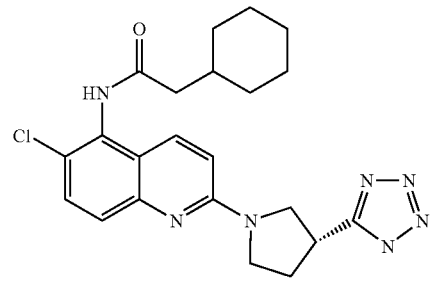

a) N-[6-Chloro-2-[(3R)-3-cyano-1-pyrrolidinyl]-5-quinolinyl]-cyclohexaneacetamide Prepared according to the method of example 96, using N-[6-chloro-2-[(3S)-3-[(methylsulfonyl)oxy]-1-pyrrolidinyl]-5-quinolinyl]-cyclohexaneacetamide (example 33 (a)) (0.33 g) and lithium cyanide in N,N-dimethylformamide (6 mL, 0.5M). Purification (SiO$_2$, isohexane:ethyl acetate 60:40, as eluant) gave the sub-title compound as a solid (0.066 g).

$^1$H NMR (300 MHz, d$_6$-DMSO) δ 9.79 (1H, d), 7.91-7.88 (1H, d), 7.61-7.58 (1H, d), 7.53-7.55 (1H, d), 7.03-7.00 (1H, d), 3.90-3.57 (5H, m), 2.44-2.20 (4H, m), 1.83-1.63 (6H, m), 1.29-0.90 (5H, m).

MS: APCI(+ve) 397.5 (M+H$^+$).

b) N-[6-Chloro-2-[(3R)-3-(1H-tetrazol-5-yl)-1-pyrrolidinyl]-5-quinolinyl]-cyclohexaneacetamide Prepared according to the method of example 98 (b), using N-[6-chloro-2-[(3R)-3-cyano-1-pyrrolidinyl]-5-quinolinyl]-cyclohexaneacetamide (example 100 (a)) (66 mg), dibutyltin oxide (9 mg) and azidotrimethylsilane (0.06 mL). The residue was purified by ion exchange column (Varian NH$_2$ cartridge, methanol then 3% acetic acid in methanol as eluant). Further purification by ion exchange column (Varian SCX cartridge, methanol then 7N ammonia in methanol as eluant) gave the title compound as a solid (11 mg).

$^1$H NMR (400 MHz, CD$_3$OD) δ 9.78 (1H, s), 7.89-7.86 (1H, d), 7.58-7.56 (1H, d), 7.50-7.49 (1H, d), 7.01-6.99 (1H, d), 4.20-3.60 (5H, m), 2.29-2.25 (3H, m), 1.86-1.57 (6H, m), 1.31-0.99 (6H, m).

MS: APCI(+ve) 440.1 (M+H$^+$).

EXAMPLE 101

N-[6-Chloro-2-[(3S)-3-[[2-(2H-tetrazol-5-yl)ethyl]amino]-1-pyrrolidinyl]-5-quinolinyl]-cyclohexaneacetamide

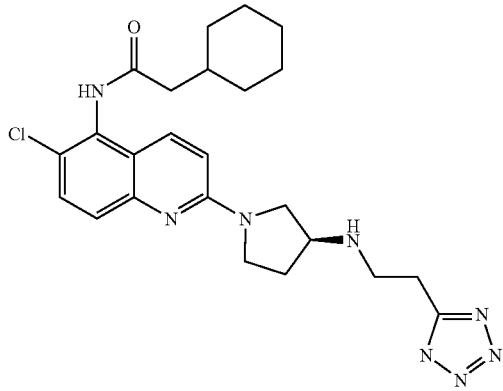

N-[6-Chloro-2-[(3S)-3-[(2-cyanoethyl)amino]-1-pyrrolidinyl]-5-quinolinyl]-cyclohexaneacetamide (example 87(b)) (0.15 g), trimethylsilylazide (0.091 ml), dibutyltin oxide (0.009 g) and toluene (5 ml) were heated within a single mode microwave in a sealed 10 ml vial at 100° C. for 30 minutes and then at 120° C. for 120 minutes. The reaction was cooled to room temperature, filtered and washed with toluene. The solid was then triturated with methanol and filtered before being dissolved in hot methanol and purified by Varian SCX cartridge (methanol (50 ml) and then ammonia in methanol (0.7M, 50 ml) as eluant). to afford the title compound (0.025 g).

$^1$H NMR (400 MHz, d$_6$-DMSO) δ 9.78 (1H, s), 7.86 (1H, d), 7.57 (1H, d), 7.49 (1H, d), 6.98 (1H, d), 3.85-3.62 (3H, m), 3.61-3.49 (2H, m), 3.19-3.12 (2H, m), 3.07-3.00 (2H, m), 2.32 (2H, d), 2.30-2.19 (1H, m), 2.09-1.96 (1H, m), 1.89-1.76 (3H, m), 1.76-1.59 (3H, m), 1.35-1.13 (3H, m), 1.12-0.97 (2H, m).

MS: APCI(+ve) 483.5 (M+H$^+$).

m.p. 220-221° C.

EXAMPLE 102

N-[6-Chloro-2-[4-(4,5-dihydro-5-oxo-1,2,4-oxadiazol-3-yl)-1-piperidinyl]-5-quinolinyl]-cyclohexaneacetamide

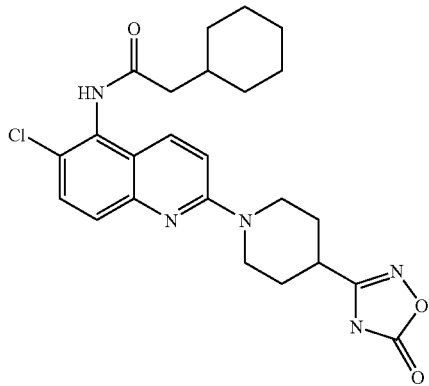

a) N-[2-[4-[Amino(hydroxyimino)methyl]-1-piperidinyl]-6-chloro-5-quinolinyl]-cyclohexaneacetamide N-[6-Chloro-2-(4-cyano-1-piperidinyl)-5-quinolinyl]-cyclohexaneacetamide (Example 113) (0.2 g), hydroxylamine (50% w/v in H$_2$O) (0.23 mL) and ethanol (2.5 mL) were heated within a microwave in a sealed 10 mL vial at 90° C. for 100 minutes. The reaction was cooled to room temperature and the resulting precipitate was filtered and washed with ethanol to afford the subtitle compound as a solid (0.18 g).

$^1$H NMR (400 MHz, d$_6$-DMSO) δ 9.77 (1H, s), 8.79 (1H, s), 7.84 (1H, d), 7.56 (1H, d), 7.48 (1H, d), 7.33 (1H, d), 5.33 (2H, s), 4.58 (2H, d), 2.93 (2H, t), 2.36-2.27 (3H, m), 1.87-1.76 (5H, m), 1.75-1.67 (2H, m), 1.66-1.53 (3H, m), 1.32-1.12 (3H, m), 1.10-0.98 (2H, m).

MS: APCI(+ve) 444 (M+H$^+$).

m.p. 246-247° C.

b) N-[6-Chloro-2-[4-(4,5-dihydro-5-oxo-1,2,4-oxadiazol-3-yl)-1-piperidinyl]-5-quinolinyl]-cyclohexaneacetamide To a stirred solution of N-[2-[4[amino(hydroxyimino)methyl]-1-piperidinyl]-6-chloro-5-quinolinyl]-cyclohexaneacetamide (example 102(a)) (0.1 g) and pyridine (0.02 mL) in dichloromethane (5 mL) at 0° C. was added 2-ethylhexylchloroformate (0.064 mL). After 10 minutes the reaction was allowed to warm to room temperature and was then stirred for 2 hours. The solvent was removed under vacuum and the resulting solid was transferred to a 10 mL microwave vial with isohexane (3 mL) and heated within a microwave at 140° C. for 20 minutes. The reaction mixture was filtered and the solid was taken up in boiling methanol (20 mL) and purified by Varian NH$_2$ cartridge (methanol (50 mL) and then acetic acid:methanol 10:90 as eluant) to afford the title product (0.042 g).

$^1$H NMR (400 MHz, d$_6$-DMSO), 9.79 (s, 1H), 7.86 (1H, d), 7.58 (1H, d), 7.50 (1H, d), 7.36 (1H, d), 4.55 (2H, d), 3.12 (2H, t), 3.00-2.91 (1H, m), 2.33 (2H, d), 1.95 (2H, d), 1.81 (3H, d), 1.75-1.57 (5H, m), 1.32-1.13 (3H, m), 1.12-0.97 (2H, m).

MS: APCI(+ve) 470.2 (M+H$^+$).

m.p. 233-235° C.

EXAMPLE 103

N-[6-Chloro-2-[4-(4,5-dihydro-5-oxo-1,2,4-thiadiazol-3-yl)-1-piperidinyl]-5-quinolinyl]-cyclohexaneacetamide

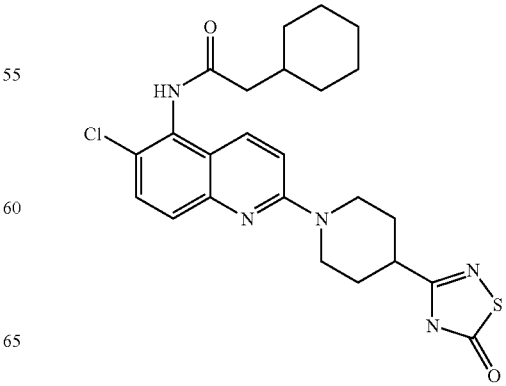

To a stirred solution of N-[2-[4[amino(hydroxyimino)methyl]-1-piperidinyl]-6-chloro-5-quinolinyl]-cyclohexaneacetamide (Example 102(a)) (0.1 g) in tetrahydrofuran (2 mL) was added 1,1'-thiocarbonyldiimidazole (0.042 g). After stirring for 1 hour, silica (1 g) in chloroform:methanol (5:1) (12 mL) was added and the mixture was stirred for a further 12 hours. The solvent was removed under vacuum, the resulting solid was taken up in methanol (20 mL) and was purified by Varian $NH_2$ cartridge (methanol (50 mL) and then acetic acid:methanol 10:90 as eluant) to afford the title product (0.041 g).

$^1$H NMR (400 MHz, $d_6$-DMSO) δ 9.79 (1H, s), 7.86 (1H, d), 7.58 (1H, d), 7.49 (1H, d), 7.35 (1H, d), 4.57 (2H, d), 3.06 (2H, t), 2.96-2.86 (1H, m), 2.33 (2H, d), 2.02-1.94 (2H, m), 1.88-1.77 (3H, m), 1.75-1.60 (5H, m), 1.32-1.11 (3H, m), 1.11-0.99 (2H, m).

MS: APCI(+ve) 486.2 (M+H$^+$).

m.p. 275° C.

EXAMPLE 104

N-[6-Chloro-2-[3-(1H-tetrazol-5-yl)propyl]-5-quinolinyl]-cyclohexaneacetamide, Trifluoroacetate

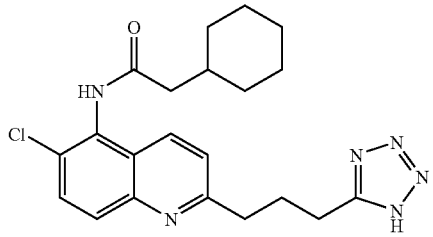

To a stirred solution of N-[6-chloro-2-(3-cyanopropyl)-5-quinolinyl]-cyclohexaneacetamide (prepared as in example 67 (a)) (100 mg) in toluene (2 mL) was added trimethylsilyl azide (0.07 mL) and dibutyltin oxide (6 mg). The mixture was heated to 100° C. for 6 hours then allowed to cool and evaporated. Purification (HPLC, Symmetry—0.1% aqueous trifluoroacetic acid/acetonitrile) gave the title compound as a solid (35 mg).

$^1$H NMR (400 MHz, $d_6$-DMSO) δ 10.00 (1H, s), 8.19 (1H, d), 7.93 (1H, d), 7.85 (1H, d), 7.59 (1H, d), 3.09-2.94 (4H, m), 2.37 (2H, d), 2.23 (2H, quintet), 1.91-1.59 (6H, m), 1.35-0.99 (5H, m).

MS: APCI(+ve) 413.1/415.1 (M+H$^+$).

m.p. 140-145° C.

EXAMPLE 105

N-[6-Chloro-2-[4-(1H-tetrazol-5-yl)butyl]-5-quinolinyl]-cyclohexaneacetamide

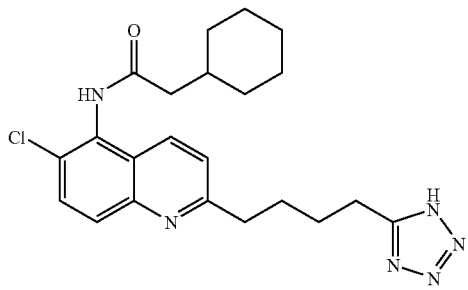

Prepared according to the method of example 104, using N-[6-chloro-2-(4-cyanobutyl)-5-quinolinyl]-cyclohexaneacetamide (prepared as in M example 70 (a)) (300 mg). Purification by HPLC (Symmetry—0.1% aqueous ammonium acetate/acetonitrile) gave the title compound as a solid (70 mg).

$^1$H NMR (400 MHz, $d_6$-DMSO) δ 9.96 (1H, s), 8.11 (1H, d), 7.89 (1H, d), 7.80 (1H, d), 7.52 (1H, d), 3.01-2.86 (4H, m), 2.36 (2H, d), 1.93-1.58 (10H, m), 1.34-0.98 (5H, m).

MS: APCI(+ve) 427.1/429.1 (M+H$^+$).

m.p. 192-195° C.

EXAMPLE 106

6-Chloro-N-(cyclohexylmethyl)-2-[4-(1H-tetrazol-5-yl)butyl]-5-quinolinecarboxamide

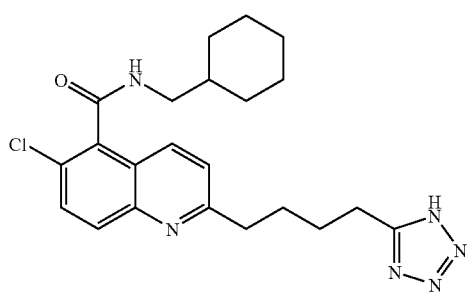

a) 6-Chloro-2-(4-cyanobutyl)-N-(cyclohexylmethyl)-5-quinolinecarboxamide

Prepared according to the method of example 67 (a) using 2,6-dichloro-N-(cyclohexylmethyl)-5-quinolinecarboxamide (prepared as in Example 43 (a)) (500 mg) and bromo(4-cyanobutyl)-zinc (30 mL, 0.5 M solution in tetrahydrofuran). Purification ($SiO_2$, methanol:dichloromethane 1:200 as eluant) gave the sub-title compound as a solid (600 mg).

MS: APCI(+ve) 384.5/386.5 (M+H$^+$).

b) 6-Chloro-N-(cyclohexylmethyl)-2-[4-(1H-tetrazol-5-yl)butyl]-5-quinolinecarboxamide Prepared according to the method of example 104, using 6-chloro-2-(4-cyanobutyl)-N-(cyclohexylmethyl)-5-quinolinecarboxamide (Example 106 (a)) (300 mg). Purification (Varian $NH_2$ cartridge using methanol (100 mL) and then 10% acetic acid in methanol (100 mL) as eluant) and further purification ($SiO_2$, methanol:dichloromethane 5:95 as eluant) gave the title compound as a solid (80 mg).

$^1$H NMR (300 MHz, $d_6$-DMSO) δ 8.71 (1H, t), 8.04-7.90 (2H, m), 7.75 (1H, d), 7.56 (1H, d), 3.20 (2H, t), 3.03-2.86 (4H, m), 1.90-1.49 (10H, m), 1.33-0.88 (5H, m).

MS: APCI(+ve) 427.1/429.1 (M+H$^+$).

m.p. 90-93° C.

EXAMPLE 107

N-[6-Chloro-2-[(3S)-3-[2-(1H-tetrazol-5-yl)ethoxy]-1-pyrrolidinyl]-5-quinolinyl]-cyclohexaneacetamide

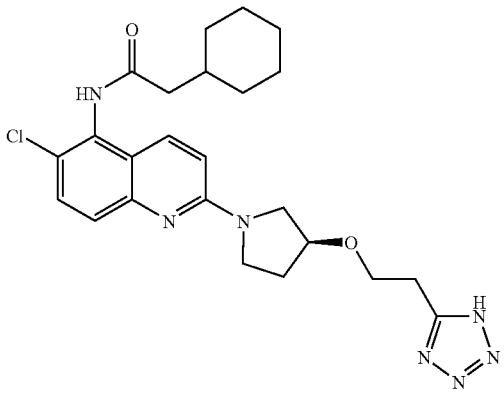

a) (3S)-3-(2-Cyan ethoxy)-1-pyrrolidinecarbxylic acid, 1,1-dimethylethyl Ester Sodium methoxide (1.2 g) was carefully added portionwise to a stirred mixture of (3S)-3-hydroxy-1-pyrrolidinecarboxylic acid, 1,1-dimethylethyl ester (prepared according to the method of Bioorganic and Medicinal Chemistry Letters 2003, 13, 3317) (2 g) and acrylonitrile (5 mL) at 0° C. under nitrogen. The reaction mixture was stirred at room temperature for 15 hours and then poured into water (50 mL). The mixture was extracted with dichloromethane (2×50 mL) and the combined extracts were washed with water (50 mL) before being dried, filtered and evaporated. Purification (SiO$_2$, methanol:dichloromethane 2:98 as eluant) gave the sub-title compound as a colourless oil (1 g).

$^1$H NMR (400 MHz, d$_6$-DMSO) δ 4.10 (1H, s), 3.70-3.51 (2H, m), 3.39-3.15 (4H, m), 2.77-2.69 (2H, m), 1.96-1.83 (2H, m), 1.42 (9H, s).

b) 3-[(3S)-3-Pyrrolidinyloxy]-propanenitrile

To a stirred solution of (3S)-3-(2-cyanoethoxy)-1-pyrrolidinecarboxylic acid, 1,1-dimethylethyl ester (Example 107 (a)) (1 g) in dichloromethane (10 mL) was added trifluoroacetic acid (3 mL). The mixture was stirred at room temperature for 30 minutes and then concentrated. Purification (Varian SCX cartridge, using methanol and then 10% ammonia in methanol as eluant) gave the sub-title compound (350 mg).

$^1$H NMR (400 MHz, d$_6$-DMSO) δ 4.04-3.94 (1H, m), 3.58-3.45 (2H, m), 2.84-2.59 (6H, m), 1.82-1.54 (2H, m), 1.23 (1H, s).

c) N-[6-Chloro-2-[(3S)-3-(2-cyanoethoxy)-1-pyrrolidinyl]-5-quinolinyl]-cyclohexaneacetamide Prepared according to the method of example 30, using N-(2,6-dichloro-5-quinolinyl)-cyclohexaneacetamide (prepared as in Example 1(a)) (400 mg) and 3-[(3S)-3-pyrrolidinyloxy]-propanenitrile (Example 107 (b)) (350 mg). The resulting precipitate was collected by filtration and washed with acetonitrile to give the sub-title compound as a solid (370 mg).

$^1$H NMR (400 MHz, d$_6$-DMSO) δ 9.77 (1H, s), 7.85 (1H, d), 7.55 (1H, d), 7.48 (1H, d), 6.97 (1H, d), 4.30 (1H, s), 3.75-3.45 (6H, m), 2.76 (2H, t), 2.32 (2H, d), 2.18-2.04 (2H, m), 1.90-1.59 (6H, m), 1.34-0.96 (5H, m).

d) N-[6-Chloro-2-[(3S)-3-[2-(1H-tetrazol-5-yl)ethoxy]-1-pyrrolidinyl]-5-quinolinyl]-cyclohexaneacetamide Prepared according to the method of example 104, using N-[6-chloro-2-[(3S)-3-(2-cyanoethoxy)-1-pyrrolidinyl]-5-quinolinyl]-cyclohexaneacetamide (Example 101 (c)) (200 mg). Purification by Varian NH$_2$ cartridge (methanol and then 10% acetic acid in methanol as eluant) and then by Varian SCX cartridge (methanol and 10% ammonia in methanol) gave the title compound as a solid (110 mg).

$^1$H NMR (400 MHz, d$_6$-DMSO) δ 9.77 (1H, s), 7.84 (1H, d), 7.55 (1H, d), 7.47 (1H, d), 6.93 (1H, d), 4.25 (1H, s), 3.87-3.74 (2H, m), 3.68-3.52 (3H, m), 3.49-3.36 (1H, m), 3.07 (2H, t), 2.32 (2H, d), 2.05 (2H, s), 1.92-1.58 (6H, m), 1.34-0.96 (5H, m).

MS: APCI(+ve) 484.2/486.2 (M+H$^+$).

m.p. 177-181° C.

EXAMPLE 108

N-[6-Chloro-2-[(3S)-3-[2-(4,5-dihydro-5-oxo-1,2,4-oxadiazol-3-yl)ethoxy]-1-pyrrolidinyl]-5-quinolinyl]-cyclohexaneacetamide

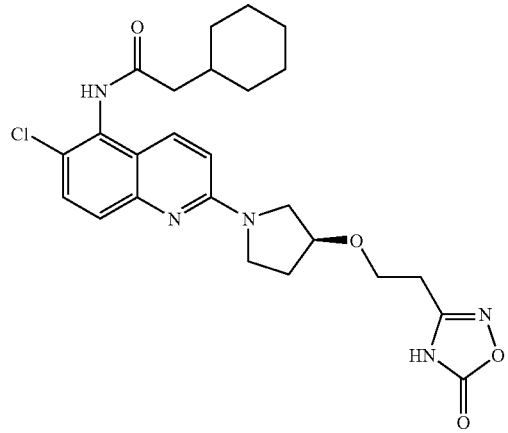

a) N-[2-[(3S)-3-[[3-amino-3-(hydroxyimino)propyl]oxy]-1-pyrrolidinyl]-6-chlro-5-quinolinyl]-cyclohexaneacetamide Prepared according to the method of example 102 (a) using N-[6-chloro-2-[(3S)-3-(2-cyanoethoxy)-1-pyrrolidinyl]-5-quinolinyl]-cyclohexaneacetamide (prepared as in Example 107 (c)) (200 mg). The reaction mixture was concentrated and water was added to the residue. Filtration of the resulting suspension gave the sub-title compound as a solid (200 mg).

$^1$H NMR (300 MHz, d$_6$-DMSO) δ 9.76 (1H, s), 8.77 (1H, s), 7.84 (1H, d), 7.55 (1H, d), 7.48 (1H, d), 6.96 (1H, d), 5.34 (2H, s), 4.23 (1H, s), 3.77-3.43 (6H, m), 2.32 (2H, d), 2.21 (2H, t), 2.15-2.03 (2H, m), 1.90-1.58 (6H, m), 1.37-0.95 (5H, m).

b) N-[6-Chloro-2-[(3S)-3-[2-(4,5-dihydro-5-oxo-1,2,4-oxadiazol-3-yl)ethoxy]-1-pyrrolidinyl]-5-quinolinyl]-cyclohexaneacetamide Prepared according to the method of Example 102 (b) using N-[2-[(3S)-3-[[3-amino-3-(hydroxyimino)propyl]oxy]-1-pyrrolidinyl]-6-chloro-5-quinolinyl]-cyclohexaneacetamide (Example 108 (a)) (200 mg). Purification (SiO$_2$, methanol:dichloromethane 2:98 as eluant) gave the title compound as a solid (20 mg).

$^1$H NMR (300 MHz, d$_6$-DMSO) δ 9.63 (1H, s), 7.99 (1H, d), 7.82 (1H, d), 7.69 (1H, d), 7.11 (1H, d), 4.38-4.30 (1H, m), 3.86-3.61 (6H, m), 2.76 (2H, t), 2.34 (2H, d), 2.21-2.10 (2H, m), 1.96-1.56 (6H, m), 1.41-0.98 (5H, m).

MS: APCI(+ve) 500.2/502.2 (M+H$^+$).

m.p. 185-190° C.

EXAMPLE 109

N-[6-Chloro-2-[4-(1H-tetrazol-5-yl)-1-piperidinyl]-5-quinolinyl]cyclohexane-acetamide

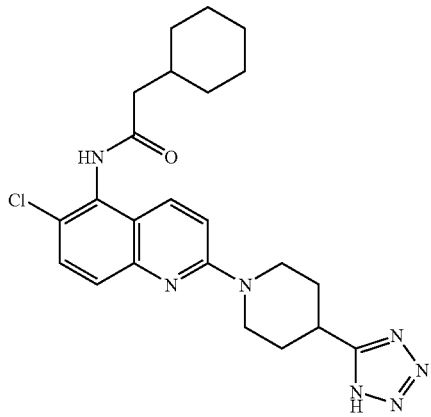

Prepared according to the method of example 98(b), using N-[6-chloro-2-(4-cyano-1-piperidinyl)-5-quinolinyl]-cyclohexaneacetamide (example 113) (0.07 g) to afford the title compound (0.02 g).

$^1$H NMR (300 MHz, CD$_3$OD) δ 7.83 (1H, d), 7.51-7.43 (2H, m), 7.17 (1H, d), 4.54 (2H, d), 3.27-3.02 (3H, m), 2.32 (2H, d), 2.06-1.57 (10H, m), 1.36-0.93 (5H, m).

MS: APCI(+ve) 454/456 (M+H$^+$).

m.p. 295-300° C.

EXAMPLE 110

6-Chloro-N-(cyclohexylmethyl)-2-[4-(1H-tetrazol-5-yl)-1-piperidinyl]-5-quinolinecarboxamide

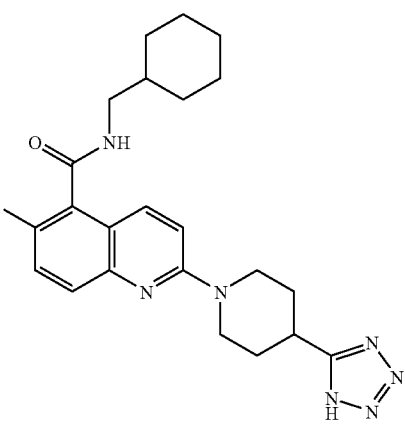

a) 6-Chloro-2-(4-cyano-1-piperidinyl)-N-(cyclohexylmethyl)-5-quinolinecarboxamide Prepared according to the method of example 51, using 2,6-dichloro-N-(cyclohexylmethyl)-5-quinolinecarboxamide Example 43(a)) (0.25 g), and 4-cyanopiperidine hydrochloride (0.25 g) to afford the title compound (0.27 g).

$^1$H NMR (300 MHz, CD$_3$OD) δ 7.78 (1H, d), 7.54 (1H, d), 7.42 (1H, d), 7.17 (1H, d), 4.00 (2H, ddd), 3.51 (2H, ddd), 3.19 (2H, s), 2.99 (1H, dt), 1.99-1.89 (2H, m), 1.82-1.49 (8H, m), 1.30-1.10 (3H, m), 1.04-0.90 (2H, m).

MS: APCI(+ve) 411/413 (M+H$^+$).

b) 6-Chloro-N-(cyclohexylmethyl)-2-[4-(1H-tetrazol-5-yl)-1-piperidinyl]-5-quinolinecarboxamide Prepared according to the method of example 98 (b), using 6-chloro-2-(4-cyano-1-piperidinyl)-N-(cyclohexylmethyl)-5-quinolinecarboxamide (Example 110 (a)) (0.25 g) to afford the title compound (0.15 g).

$^1$H NMR (300 MHz, CD$_3$OD) δ 7.79 (1H, d), 7.54 (1H, d), 7.42 (1H, d), 7.21 (1H, d), 4.57 (2H, d), 3.30 (1H, tt), 3.13 (2H, t), 2.08 (2H, d), 1.79 (4H, d), 1.73-0.89 (11H, m).

MS: APCI(+ve) 454/456 (M+H$^+$).

m.p. 255-257° C.

EXAMPLE 111

6-Chloro-N-(2-cyclohexylethyl)-2-[4-(1H-tetrazol-5-yl)-1-piperidinyl]-5-quinolinecarboxamide

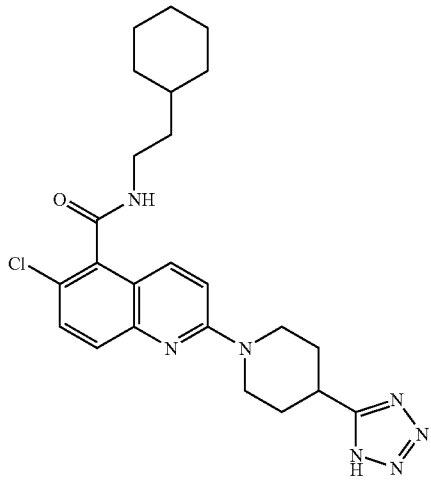

a) 6-Chloro-2-(4-cyano-1-piperidinyl)-N-(2-cyclohexylethyl)-5-quinolinecarboxamide Prepared according to the method of example 51, using 2,6-dichloro-N-(cyclohexylethyl)-5-quinolinecarboxamide (Example 94 (d)) (0.35 g), and 4-cyanopiperidine hydrochloride (0.25 g) to afford the title compound (0.12 g).

$^1$H NMR (400 MHz, d$_6$-DMSO) δ 8.59 (1H, t), 7.76 (1H, d), 7.57 (1H, d), 7.53 (1H, d), 7.37 (1H, d), 4.08-3.98 (2H, m), 3.53 (2H, t), 3.36 (2H, t), 3.21-3.13 (1H, m), 2.02-1.93 (2H, m), 1.81-1.58 (7H, m), 1.49-1.39 (3H, m), 1.27-1.11 (3H, m), 0.97-0.86 (2H, m).

MS: APCI(+ve) 425/427 (M+H$^+$).

b) 6-Chloro-N-(cyclohexylmethyl)-2-[4-(1H-tetrazol-5-yl)-1-piperidinyl]-5-quinolinecarboxamide Prepared according to the method of example 98 (b), using 6-chloro-2-(4-cyano-1-piperidinyl)-N-(2-cyclohexylethyl)-5-quinolinecarboxamide (Example 111 (a)) (0.12 g) to afford the title compound (0.07 g).

$^1$H NMR (400 MHz, dc-DMSO) δ 8.59 (1H, t), 7.77 (1H, d), 7.57 (1H, d), 7.53 (1H, d), 7.41 (1H, d), 4.57 (2H, d), 3.43-3.32 (3H, m), 3.20 (1H, t), 2.09 (2H, d), 1.79-1.59 (7H, m), 1.49-1.35 (3H, m), 1.27-1.11 (3H, m), 0.97-0.86 (2H, m).

MS: APCI(+ve) 468/470 (M+H$^+$).

m.p. 252-255° C.

EXAMPLE 112

6-Chloro-N-(cyclohexylmethyl)-2-[(3S)-3-(1,1-dioxido-4-oxo-1,2,5-thiadiazolidin-2-yl)-1-pyrrolidinyl]-5-quinolinecarboxamide

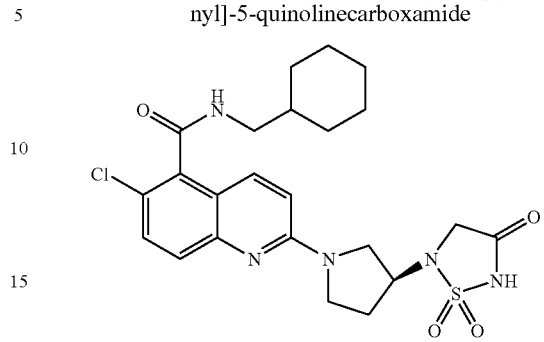

a) N-[(3S)-1-[6-chloro-5-[[(cyclohexylmethyl)amino]carbonyl]-2-quinolinyl]-3-pyrrolidinyl]-glycine, Ethyl Ester A stirred solution of 2-[(3S)-3-Amino-1-pyrrolidinyl]-6-chloro-N-(cyclohexylmethyl)-5-quinolinecarboxamide (prepared as in Example 44) (450 mg), ethyl chloroacetate (0.21 mL) and triethylamine (0.33 mL) in acetonitrile (3 mL) was heated at 100° C. in a microwave for 1 hour after which it was cooled to room temperature and concentrated. Purification by chromatography (SiO$_2$, dichloromethane:methanol:ammonia in methanol (7 M) 96:3:1 as eluant) gave the subtitle compound as a solid (490 mg).

MS: APCI(+ve) 473 (M+H$^+$).

b) N-[(3S)-1-[6-Chloro-5-[[(cyclohexylmethyl)amino]carbonyl]-2-quinolinyl]-3-pyrrolidinyl]-N-[[[(1,1-dimethylethoxy)carbonyl]amino]sulfonyl]-glycine, Ethyl Ester A solution of 2-methyl-2-propanol (140 mg) in dichloromethane 2 mL) was added over 15 minutes to a stirred solution of chlorosulfonyl isocyanate (0.17 mL) in dichloromethane (16 mL) under nitrogen at 0° C. The mixture was allowed to warm to room temperature over 2 hours and was then added over 20 minutes to a stirred solution of N-[(3S)-1-[6-chloro-5-[[(cyclohexylmethyl)amino]carbonyl]-2-quinolinyl]-3-pyrrolidinyl]-glycine, ethyl ester (Example 112 (a)) (490 mg) and triethylamine (0.25 mL) in dichloromethane (10 mL) under nitrogen at 0° C. After 3 hours, deionised water (10 mL) was added, the layers were separated and the aqueous fraction was extracted with dichloromethane (2×10 mL). The combined organic extracts were dried over anhydrous magnesium sulfate, filtered and concentrated to give an oil. Purification by chromatography (SiO$_2$, dichloromethane:methanol 99:1 as eluant) gave the sub-title compound as a solid (670 mg).

MS: APCI(+ve) 653/655 (M+H$^+$).

c) 6-Chloro-N-(cyclohexylmethyl)-2-[(3S)-3-(1,1-dioxido-4-oxo-1,2,5-thiadiazolidin-2-yl)-1-pyrrolidinyl]-5-quinolinecarboxamide N-[(3S)-1-[6-Chloro-5-[[(cyclohexylmethyl)amino]carbonyl]-2-quinolinyl]-3-pyrrolidinyl]-N-[[[(1,1-dimethylethoxy)carbonyl]amino]sulfonyl]-glycine, ethyl ester (Example 112 (b)) (670 mg) was dissolved in dichloromethane (5 mL). Trifluoroacetic acid (1 mL) was added and the mixture stirred for 3 hours before being concentrated. Sodium methoxide (25% in methanol, 3 mL) was added and the mixture was stirred under nitrogen for 2 hours. The products were concentrated onto silica gel and purified by chromatography (SiO$_2$, dichloromethane:methanol 92:8 as eluant). Further purification by HPLC (Symmetry—0.1% aqueous trifluoroacetic acid/acetonitrile) gave the title compound as a solid (20 mg).

$^1$H NMR (400 MHz, d$_6$-DMSO) δ 8.80 (1H, t), 8.01-7.88 (2H, m), 7.83-7.76 (1H, m), 7.36-7.27 (1H, m), 7.18-6.95 (1H, m), 3.89-3.68 (7H, m), 3.19 (2H, m), 2.38-2.22 (2H, m), 1.88-1.49 (6H, m), 1.35-1.11 (3H, m), 1.09-0.87 (2H, m).

MS: APCI(+ve) 506/508 (M+H$^+$).

EXAMPLE 113

N-[6-Chloro-2-(4-cyan-1-piperidinyl)-5-quinolinyl]-cyclhexaneacetamide

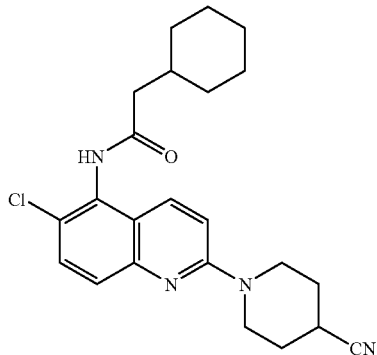

Prepared according to the method of example 51, using N-(2,6-dichloro-5-quinolinyl)-cyclohexaneacetamide (Example 1(a)) (0.10 g), and 4-cyanopiperidine hydrochloride (0.21 g) to afford the title compound (0.08 g).

$^1$H NMR (300 MHz, CD$_3$OD) δ 7.98 (1H, d), 7.62 (2H, s), 7.28 (1H, d), 4.17-4.07 (2H, m), 3.70-3.59 (2H, m), 3.17-3.07 (1H, m), 2.44 (2H, d), 2.13-1.69 (10H, m), 1.47-1.09 (5H, m).

MS: APCI(+ve) 411/413 (M+H+).

m.p.=235-237° C.

EXAMPLE 114

N-[6-Chloro-2-[4-[[(trifluoromethyl)sulfonyl]amino]-1-piperidinyl]-5-quinolinyl]-cyclohexaneacetamide

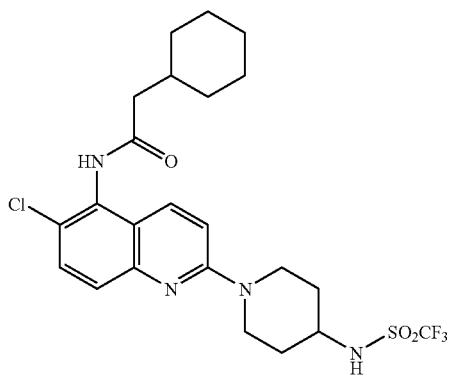

To a solution of N-(2-(amino-1-piperidinyl)-6-chloro-5-quinolinyl]-cyclohexaneacetamide (example 32) (0.05 g) in dichloromethane (5 mL) cooled to −78° C. and under a nitrogen atmosphere, was added triethylamine (0.10 mL) followed by triflic anhydride (0.12 mL). The mixture was allowed to warm to room temperature and then quenched by the addition of water (5 mL). Saturated sodium bicarbonate solution (5 mL) was added and the organics collected, dried and concentrated. Purification (NH$_2$ ion-exchange cartridge, 1% AcOH in acetonitrile as eluant), followed by trituration with diethylether gave the title compound (0.02 g).

$^1$H NMR (300 MHz, CD$_3$OD) δ 7.83 (1H, d), 7.47 (2H, s), 7.14 (1H, d), 4.45 (2H, d), 3.66-3.53 (1H, m), 3.02 (2H, t), 2.37 (2H, d), 1.97-1.44 (8H, m), 1.35-0.93 (7H, m).

MS: APCI(+ve) 533/535 (M+H$^+$).

m.p.=187-189° C.

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p. 126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of the Examples was tested for antagonist activity at the P2X$_7$ receptor. Thus, the test was performed in 96-well flat bottomed microtitre plates, the wells being filled with 250 μl of test solution comprising 200 μl of a suspension of THP-1 cells (2.5×10$^6$ cells/ml) containing 10$^{-4}$M ethidium bromide, 25 μl of a high potassium buffer solution containing 10$^{-5}$M bbATP, and 25 μl of the high potassium buffer solution containing 3×10$^{-5}$M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of the Examples demonstrated antagonist activity, having a pIC$_{50}$ figure >5.5. For example; the following table shows the pIC$_{50}$ figures for a representative selection of compounds:

| Compound of Example No. | pIC$_{50}$ |
|---|---|
| 5 | 6.9 |
| 17 | 7.6 |
| 20 | 6.9 |
| 28 | 7.4 |
| 33 | 7.6 |
| 37 | 7.3 |
| 42 | 6.5 |
| 73 | 6.4 |
| 102 | 6.7 |
| 112 | 6.5 |
| 24 | 6.3 |

The invention claimed is:
1. A compound of formula (III)

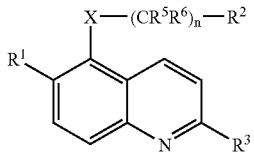

or a pharmaceutically acceptable salt thereof,
wherein
$R^1$ is selected from halogen or $C_{1-6}$ alkyl,
X is C(O)NH or NHC(O);
n is 1;
each $R^5$ and each $R^6$ are independently selected from hydrogen or $C_{1-3}$alkyl, or $R^5$ and $R^6$ together with the carbon atom to which they are both attached forms a $C_{3-6}$cycloalkcyl ring,
$R^2$ is an optionally substituted cycloalkyl group containing 5 to 7 carbon atoms; and
$R^3$ is hydrogen, or a group $R^7$, $OR^7$, $SR^7$, $NR^7R^8$, where $R^7$ and $R^8$ are independently selected from hydrogen, optionally substituted $C_{1-10}$alkyl, an optionally substituted cycloalkyl or an optionally substituted heterocyclic group, or $R^7$ and $R^8$ together with the nitrogen to which they are attached form an optionally substituted heterocyclic ring which may contain additional heteroatoms, and may further comprise bridging groups.

2. The compound of claim 1, wherein $R^3$ is a group of formula (IIB)

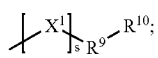

where $X^1$ represents a group >N—$R^{11}$ and $R^{11}$ is hydrogen or a $C_{1-5}$alkyl group which may be optionally substituted by one or more substituents selected from hydroxy, halogen or $C_{1-6}$alkoxy;
s is 0 or 1;
$R^9$ represents a bond or a $C_1$-$C_5$ alkylene group, which may be optionally substituted,
$R^{10}$ represents hydrogen, hydroxyl, carboxy, a group —$NR^{19}R^{20}$, an optionally substituted carbocyclic or an optionally substituted heterocyclic ring, either or which may include bridging groups,
where $R^{19}$ and $R^{20}$ are independently selected from hydrogen, pyrrolidine, piperazine, piperidine, $C_{1-6}$alkylcarbonyl, $C_{2-7}$alkenyl, optionally substituted $C_{1-7}$alkyl, or C(O)NHS(O²)$R^{21}$ where $R^{21}$ is $C_{1-5}$alkyl, provided that when s is 1 and $R^9$ is a bond, $R^{10}$ is other than hydroxy, carboxy or a group —$NR^{19}R^{20}$.

3. A compound according to claim 2, wherein in formula (IIB) $R^9$ represents a $C_{1-5}$ alkylene group which can be optionally substituted; and $R^{10}$ represents hydrogen, hydroxyl, carboxyl, or a group —$NR^{19}R^{20}$.

4. A compound according to claim 2, wherein $R^{10}$ represents a 4- to 9-menabered carbocydic or heterocyctie ring, either of which is optionally substituted by at least one substituent.

5. The compound of claim 2, wherein s is 0, $R^9$ is a bond and $R^{10}$ is a group $NR^{33}$ and $R^{34}$ where $R^{33}$ and $R^{34}$ together with the nitrogen atom to which they are attached form a saturated five or six-membered heterocyclic ring optionally substituted by one or two substituents independently selected from, amino, hydroxy, hydroxy$C_{1-3}$alkylamino, $C_1$-$C_2$ alkyl and $C_1$-$C_2$ hydroxyalkyl.

6. A compound of formula (III) according to claim 1, or pharmaceutically acceptable salt thereof, selected from the group consisting of:
N-[6-Chloro-2-(4-piperidinylmethyl)-5-quinolinyl]-cyclohexaneacetamide, dihydrochloride,
N-[6-Chloro-2-(1-piperazinyl)-5-quinolinyl]-cyclohexaneacetamide, dihydrochloride,
N-[6-Chloro-2-[methyl[3-methylamino)propyl]amino]-5-quinolinyl]-cyclohexaneacetamide, dihydrochloride,
6-Chloro-N-(cyclohexylmethyl)-2-methyl-5-quinolinecarboxamide, hydrochloride,
N-[6-Chloro-2-[(3-hydroxypropyl)amino]-5-quinolinyl]-cyclohexaneacetamide, hydrochloride,
N-[6-Chloro-2[[(2R)-2,3-dihydroxypropyl]amino]-5-quinolinyl]-cyclohexaneacetamide,
4-[[6-Chloro-5-[(cyclohexylacetyl)amino]-2-quinolinyl]amino]-butanoic acid,
N-[6-Chloro-2-[methyl[3-(methylamino)propyl]amino]-5-quinolinyl]-4-(trifluoromethyl)-cyclohexaneacetamide, dihydrochloride,
N-[6-Chloro-2-(1-piperazinyl)-5-quinolinyl]-4-(trifluoromethyl)-cyclohexaneacetamide,
N-[6-Chloro-2-(hexahydro-1H-1,4-diazepin-1-yl)-5-quinolinyl]-cyclohexaneacetamide,
N-[6-Chloro-2-[(cis-3,5-dimethyl-1-piperazinyl]-5-quinolinyl]-cyclohexaneacetamide,
N-[6-Chloro-2-(4-methyl-1-piperazinyl)-5-quinolinyl]-cyclohexaneacetamide, dihydrochloride,
N-[6-Chloro-2-[(1S,4S)-2,5-diazabicyclo[2.2.1]hept-2-yl]-5-quinolinyl]-cyclohexaneacetamide, acetate,
N-[6-Chloro-2-[(3R)-3-pyrrolidinylamino]-5-quinolinyl]-cyclohexaneacetamide, dihydrochloride,
N-[2-[3-(Ethylamino)propyl]-6-methyl-5-quinolinyl]-cyclohexaneacetamide, dihydrochloride,
N-[6-Chloro-2-[3-(ethylamino)propyl]-5-quinolinyl]-cyclohexaneacetamide, dihydrochloride,
N-[6-Chloro-2-[[2-[(hydroxyethyl)amino]ethyl]amino]-5-quinolinyl]-cyclohexaneacetamide, dihydrochloride,
N-[6-Chloro-2-[3-[(3-hydroxypropyl)amino]propyl]-5-quinolinyl]-cyclohexaneacetamide,
N-[2-(3-Aminopropyl)-6-chloro-5-quinolinyl]-cyclohexaneacetamide,
N-[6-Chloro-2-[3-[[[(methylsulfonyl)amino]carbonyl]amino]propyl]-5-quinolinyl]-cyclohexaneacetamide,
N-[2-[3-(Butylamino)propyl]-6-chloro-5-quinolinyl]-cyclohexaneacetamide dihydrochloride,
N-[6-Chloro-2-[methyl[3-(methylamino)propyl]amino]-5-quinolinyl]-1-cyclohexyl-cyclopropanecarboxamide, hydrochloride,
N-[6-Chloro-2-(1-piperazinyl)-5-quinolinyl]-1-cyclohexyl-cyclopropanecarboxamide,
N-[6-Chloro-2-[(3R)-3-hydroxy-1-pyrrolidinyl]-5-quinolinyl]-cyclohexaneacetamide,
N-[6-Chloro-2-[(3S)-3-hydroxy-1-pyrrolidinyl]-5-quinolinyl]-cyclohexaneacetamide,
N-[2-[(3R)-3-amino-1-pyrrolidinyl]-6-chloro-5-quinolinyl]-cyclohexaneacetamide,
N-[2-[(3S)-3-amino-1-pyrrolidinyl]-6-chloro-5-quinolinyl]-cyclohexaneacetamide,
N-[2-(4-amino-1-piperidinyl)-6-chloro-5-quinolinyl]-cyclohexaneacetamide,
N-[6-Chloro-2-[(3R)-3-(methylamino)-1-pyrrolidinyl]-5-quinolinyl]-cyclohexaneacetamide, N-[6-Chloro-2-[(3R)-3-[(2-hydroxyethyl)amino]-1-pyrrolidinyl]-5-quinolinyl]-cyclohexaneacetamide, N-[6-Chloro-2-[(3S)-3-(methylamino)-1-pyrrolidinyl]-5-quinolinyl]-cyclohexaneacetamide, N-[6-Chloro-2-[(3S)-3-[(2-hydroxyethyl)amino]-1-pyrrolidinyl]-5-quinolinyl]-cyclohexaneacetamide, N-[6-Chloro-2-[(3R)-3-hydroxy-1-piperidinyl]-5-quinolinyl]-cyclohexaneacetamide, N-[2-[(3S)-3-amino-1-pyrrolidinyl]-6-methyl-5-quinolinyl]-cyclohexaneacetamide, N-[6-Methyl-2-(1-piperazinyl)-5-quinolinyl]-cyclohexaneacetamide, N-[6-Chloro-5-[(cyclohexylacetyl)amino]-2-quinolinyl]-glycine, N-[6-Chloro-5-[(cyclohexylacetyl)amino]-2-quinolinyl]-β-alamine, 6-Chloro-N-(cyclohexylmethyl)quinoline-5-carboxamide, and 6-Chloro-N-(cyclohexylmethyl)-2-(1-piperazinyl)-5-quinolinecarboxamide, dihydrochloride.

7. A pharmaceutical composition comprising a compound of formula (III), or a pharmaceutically acceptable salt thereof, as claimed in claim 1 in association with a pharmaceutically acceptable adjuvant, diluent or carrier.

8. A process for the preparation of a pharmaceutical composition as claimed in claim 7 which comprises mixing a compound of formula (III), or a pharmaceutically acceptable salt thereof, as defined in claim 1 with a pharmaceutically acceptable adjuvant, diluent or carrier.

* * * * *

UNITED STATES PATENT AND TRADEMARK OFFICE
CERTIFICATE OF CORRECTION

PATENT NO. : 7,408,065 B2
APPLICATION NO. : 10/558898
DATED : August 5, 2008
INVENTOR(S) : Richard Evans et al.

It is certified that error appears in the above-identified patent and that said Letters Patent is hereby corrected as shown below:

<u>Column 129</u>

Line 62, in Claim 4, "9-menabered carbocydic or heterocyctie" should read
-- 9-membered carbocyclic or heterocyclic --

<u>Column 130</u>

Lines 12-13, in Claim 6, "N-[6-Chloro-2-[methyl[3-methylamino)propyl]amino]-5-quinolinyl]-cyclohexaneacetamide, dihydrochloride" should read -- N-[6-Chloro-2-[methyl[3-(methylamino)propyl]amino]-5-quinolinyl]cyclohexaneacetamide, dihydrochloride --

Lines 18-19, in Claim 6, "N-[6-Chloro-2[[(2R)-2,3-dihydroxypropyl]amino]-5-quinolinyl]-cyclohexaneacetamide" should read -- N-[6-Chloro-2-[[(2R)-2,3-dihydroxypropyl]amino]-5-quinolinyl]-cyclohexaneacetamide --

Lines 60-61, in Claim 6, "N-[2-[(3R)-3-amino-1-pyrrolidinyl]-6-chloro-5-quinolinyl]-cyclohexaneacetamide" should read -- N-[2-[(3R)-3-Amino-1-pyrrolidinyl]-6-chloro-5-quinolinyl]-cyclohexaneacetamide --

Lines 62-63, in Claim 6, "N-[2-[(3S)-3-amino-1-pyrrolidinyl]-6-chloro-5-quinolinyl]-cyclohexaneacetamide" should read -- N-[2-[(3S)-3-Amino-1-pyrrolidinyl]-6-chloro-5-quinolinyl]-cyclohexaneacetamide --

Lines 64-65, in Claim 6, "N-[2-(4-amino)-1-piperidinyl)-6-chloro-5-quinolinyl]-cyclohexaneacetamide" should read -- N-[2-(4-Amino)-1-piperidinyl)-6-chloro-5-quinolinyl]-cyclohexaneacetamide --

Signed and Sealed this

Eleventh Day of May, 2010

David J. Kappos
*Director of the United States Patent and Trademark Office*

CERTIFICATE OF CORRECTION (continued)
U.S. Pat. No. 7,408,065 B2

Column 131

Lines 9-10, in Claim 6, "N-[2-[(3S)-3-amino-1-pyrrolidinyl]-6-methyl-5-quinolinyl]-cyclohexaneacetamide" should read -- N-[2-[(3S)-3-Amino-1-pyrrolidinyl]-6-methyl-5-quinolinyl]-cyclohexaneacetamide --